United States Patent
Page et al.

(10) Patent No.: US 10,253,002 B2
(45) Date of Patent: Apr. 9, 2019

(54) COMPOUNDS AND METHODS OF TREATING INFECTIONS

(71) Applicant: Neoculi Pty Ltd., Burwood, Victoria (AU)

(72) Inventors: Stephen Page, Newton (AU); Sanjay Garg, South Australia (NZ); Martine Keenan, Murdoch (AU); Adam McCluskey, Charlestown (AU); Andrew Stevens, Adamstown (AU)

(73) Assignee: NEOCULI PTY LTD, Victoria (AU)

(*) Notice: Subject to any disclaimer, the term of this patent is extended or adjusted under 35 U.S.C. 154(b) by 160 days.

(21) Appl. No.: 14/888,306

(22) PCT Filed: May 1, 2014

(86) PCT No.: PCT/AU2014/000483
§ 371 (c)(1),
(2) Date: Oct. 30, 2015

(87) PCT Pub. No.: WO2014/176636
PCT Pub. Date: Nov. 6, 2014

(65) Prior Publication Data
US 2016/0075665 A1    Mar. 17, 2016

(30) Foreign Application Priority Data

May 1, 2013 (AU) .............................. 2013901516

(51) Int. Cl.
| | |
|---|---|
| *C07D 239/50* | (2006.01) |
| *C07D 239/48* | (2006.01) |
| *C07D 251/48* | (2006.01) |
| *C07D 251/54* | (2006.01) |
| *C07D 251/66* | (2006.01) |
| *C07D 281/16* | (2006.01) |
| *C07C 281/18* | (2006.01) |
| *C07C 281/16* | (2006.01) |
| *C07D 333/58* | (2006.01) |
| *A61K 31/155* | (2006.01) |
| *A61K 31/381* | (2006.01) |
| *C07D 209/14* | (2006.01) |
| *C07D 295/125* | (2006.01) |
| *C07C 281/08* | (2006.01) |
| *A61K 45/06* | (2006.01) |
| *A61K 31/14* | (2006.01) |
| *A61K 31/17* | (2006.01) |
| *A61K 31/175* | (2006.01) |
| *A61K 31/404* | (2006.01) |
| *A61K 31/505* | (2006.01) |
| *C07C 323/45* | (2006.01) |
| *C07C 337/08* | (2006.01) |
| *C07D 215/12* | (2006.01) |
| *C07D 209/40* | (2006.01) |
| *C07D 213/53* | (2006.01) |
| *C07D 307/56* | (2006.01) |

(Continued)

(52) U.S. Cl.
CPC ............ *C07D 239/50* (2013.01); *A01N 43/54* (2013.01); *A01N 47/44* (2013.01); *A61K 31/14* (2013.01); *A61K 31/155* (2013.01); *A61K 31/17* (2013.01); *A61K 31/175* (2013.01); *A61K 31/381* (2013.01); *A61K 31/404* (2013.01); *A61K 31/505* (2013.01); *A61K 45/06* (2013.01); *C07C 281/08* (2013.01); *C07C 281/16* (2013.01); *C07C 281/18* (2013.01); *C07C 323/45* (2013.01); *C07C 337/08* (2013.01); *C07D 209/14* (2013.01); *C07D 209/40* (2013.01); *C07D 213/53* (2013.01); *C07D 215/12* (2013.01); *C07D 239/48* (2013.01); *C07D 251/48* (2013.01); *C07D 251/54* (2013.01); *C07D 251/66* (2013.01); *C07D 295/125* (2013.01); *C07D 307/56* (2013.01); *C07D 333/58* (2013.01); *C07F 9/6512* (2013.01)

(58) Field of Classification Search
CPC .. C07D 239/48; C07D 239/50; C07D 251/48; C07D 251/54; C07D 251/66; C07C 281/16; C07C 281/18
See application file for complete search history.

(56) References Cited

U.S. PATENT DOCUMENTS

| | | |
|---|---|---|
| 3,419,659 A | 12/1968 | Catino et al. |
| 3,541,218 A | 11/1970 | Marshall et al. |

(Continued)

FOREIGN PATENT DOCUMENTS

| | | | | |
|---|---|---|---|---|
| GB | 1256723 A | * | 12/1971 | ........... C07C 129/12 |
| GB | 1304164 A | | 1/1973 | |

(Continued)

OTHER PUBLICATIONS

Kadatz et al. CAS Accession No. 1966:38684.*

(Continued)

*Primary Examiner* — Joseph R Kosack
(74) *Attorney, Agent, or Firm* — MH2 Technology Law Group, LLP

(57) ABSTRACT

The invention provides compounds of Formula I, and methods of treating or preventing a bacterial infection in a subject using a compound of Formula I. The invention also provides the use of a compound of Formula I in the manufacture of a medicament for the treatment of a bacterial infection in a subject. The invention further provides a medical device when used in a method of treating or preventing a bacterial infection in a subject and to a medical device comprising the composition of the invention.

9 Claims, 46 Drawing Sheets
Specification includes a Sequence Listing.

(51) Int. Cl.
  *A01N 43/54*   (2006.01)
  *A01N 47/44*   (2006.01)
  *C07F 9/6512*  (2006.01)

(56) References Cited

U.S. PATENT DOCUMENTS

| | | | |
|---|---|---|---|
| 3,897,563 A | | 7/1975 | Kulsa et al. |
| 3,941,825 A | * | 3/1976 | Tomcufcik ............ C07C 281/18 |
| | | | 558/422 |
| 3,975,533 A | | 8/1976 | Kodama et al. |
| 3,992,446 A | | 11/1976 | Tomcufcik |
| 4,575,560 A | | 3/1986 | Addor et al. |
| 4,754,067 A | | 6/1988 | Addor et al. |
| 2005/0136444 A1 | * | 6/2005 | Scully ................. A61K 31/155 |
| | | | 435/6.16 |
| 2009/0285772 A1 | | 11/2009 | Phiasivongsa et al. |
| 2010/0081661 A1 | | 4/2010 | Wilks et al. |

FOREIGN PATENT DOCUMENTS

| | | |
|---|---|---|
| JP | 2001-526648 A | 12/2001 |
| JP | 2007-506435 A2 | 3/2007 |
| SU | 414787 | 5/1974 |
| WO | 98/47869 A1 | 10/1998 |
| WO | 2005/031000 A2 | 3/2007 |
| WO | 2008/014266 A2 | 1/2008 |

OTHER PUBLICATIONS

Wong et al. CAS Accession No. 1972:136238.*
Makki et al., "Synthesis of New Bioactive Sulfur Compounds Bearing Heterocyclic Moiety and Their Analytical Applications", International Journal of Chemistry, 2011, vol. 3, No. 1, pp. 181-192.
Tehrani et al., "Synthesis and Antimycobacterial Activity of Symmetric Thiocarbohydrazone Derivatives against *Mycobacterium bovis* BCG", Iranian Journal of Pharmaceutical Research, 2013, vol. 12, No. 2 pp. 331-346.
Pelttari et al., "Carbohydrazones of Substituted Salicyladehydes as Potential Lead Compounds for the Development of Narrow-Spectrum Antimicrobials", Zeitschrift fur Naturforschung C, 2007, vol. 62, pp. 483-486.
Pandey et al., "Synthesis of Schiff Bases of 2-amino-5-aryl-1,3,4-thiadiazole and Its Analgesic, Anti-Inflammatory and Anti-Bacterial Activity", Journal of Chemistry, 2012, vol. 9, No. 4, pp. 2524-2531.
Hosny et al., "A New Type of Synthesis of 1,2,3-Thiadiazole and 1,2,3-Diazaphosphole Derivatives Via-Hurd-Mori Cyclization", Journal of Chemistry, vol. 9, No. 3, pp. 1276-1287.
Kumar et al., "Syntheses, Antibacterial and Antifungal Screening of Some 1,3,4-Oxadiazole Analogues", International Journal of Pharmacy and Pharmaceutical Sciences, 2012, vol. 4, Supplement 1, pp. 440-443.
Shi et al., "Synthesis of new deoxycholic acid bis thiocarbazones under solvent-free conditions using microwave irradiation", Journal of Chemical Research, 2011, vol. 35, No. 4, pp. 198-201.
Kumar et al., "Synthesis and biological activity of 5-substitued-2-amino-1,3,4-oxadiazole derivatives", Turkish Journal of Chemistry, 2011, vol. 35, pp. 99-108.
Oniga et al., "Synthesis of Some 2-(Acetophenon-hydrazin)-thiazoles and 2-(4-thiazolyl-methynhydrazin)-thiazoles as potential antibacterial and antifungal agents", Farmacia, 2010, vol. 58, No. 6, pp. 825-833.
Pavan et al., "Thiosemicarbazones, semicarbazones, dithiocarbazates and hydrazide/hydrazones: Anti-*Mycobacterium tuberculosis* activity and cytotoxicity", European Journal of Medicinal Chemistry, 2010, vol. 45, pp. 1898-1905.
Castillo-Garit et al., "Ligand-based discovery of novel trypanosomicidal drug-like compounds: In silico identification and experimental support", European Journal of Medicinal Chemistry, 2011, vol. 46, pp. 3324-3330.
CAS RN 1024798-17-1, STN Entry Date Jun. 3, 2008.

CAS RN 902275-25-6, STN Entry Date Aug. 17, 2006.
CAS RN 387363-92-0, STN Entry Date Jan. 28, 2002.
CAS RN 1159783-84-2, STN Entry Date Jun. 24, 2009.
CAS RN 1159808-94-2, STN Entry Date Jun. 24, 2009.
CAS RN 133476-56-9, STN Entry Date Apr. 26, 1991.
Office Action from Russian Agency for Patents and Trademarks for Russian Patent Application No. 2015150264/04 dated Jun. 30, 2017, English translation, 5 pages.
Stanley et al., "Sensitivity of *Escherichia coli* 0157:H7 strain 932 to selected anticoccidial drugs in broiler chicks", Poultry Science, 1996, vol. 75, No. 1, pp. 42-46.
Rhee, "Synthesis and evaluation of antimicrobial antitumor activities of methylthiosemicarbazones and thiocarbohydrazones", Yakhak Hoechi, 1972, vol. 16, No. 4, pp. 162-175.
Nishimura et al., "Antibacterial activities of amidinohydrazones. III. Antibacterial activities of alkoxybenzaldehyde and cinnamaldehyde amidinohydrazones", Yakugaku Zasshi, 1973, vol. 93, No. 9, pp. 1247-1250 with English abstract.
Espindola, "Evaluation of the antimicrobial activity and cytotoxicity of aryl-semicarbazones derivatives", Revista Brasileira de Farmacia, 2011, vol. 92, No. 3, pp. 171-175 with English abstract.
Fahrni et al., "Synthetic, structural and biological 13 studies of oxovanadium(V) complexes of azomethines", Indian Journal of Chemistry, Section A: Inorganic, Bio-inorganic, Physical, Theoretical & Analytical Chemistry, 1998, vol. 37A No. 12, pp. 1126-1129.
Coxon, "Synthesis, antitubercular activity and mechanism of resistance of highly effective thiacetazone analogs", PLoS One, 2013, Vo. 8, No. 1, p. e53162, 13 pages.
Sondhi et al., "Synthesis of biologically active novel bis Schiff bases, bis hydrazone and bis guanidine derivatives", Indian Journal of Chemistry, Section B: Organic Chemistry Including Medicinal Chemistry, 2009, vol. 48B, No. 8, pp. 1128-1136.
Li et al., "Green synthetic method for 1,5-disubstituted carbohydrazones", Synthetic Communications, 2006, vol. 36, No. 18, pp. 2613-2619.
Grammaticakis, "Preparation and mid-ultraviolet absorption [2000-3750 Ang.] of carbohydrazones", Comptes Rendus des Seances de l1Academie des Sciences, Serie C: Sciences Chimiques, 1970, vol. 270, No. 1, pp. 76-79 with English translation of abstract and relevance as cited on p. 7 of of Office Action dated Jan. 13, 2017 for Japanese Patent Application No. 2016-510900.
Office Action from Japanese Patent Office for Japanese Patent Application No. 2016-510900 dated Jan. 13, 2017, English translation, 29 pages.
Gautam et al., "Synthesis, antimicrobial and insecticidal activity of some 4H-1,2,4 triazole derivatives", Indian Journal of Chemistry, Section B: Organic Chemistry Including Medicinal Chemistry, 2010, vol. 49B, No. 7, pp. 956-995.
Chary et al., "Studies on antimicrobial activity of semicarbazones and their metal complexes", Oriental Journal of Chemistry, 2010, vol. 26, No. 3, pp. 1159-1162.
Grigoryan et al., "Synthesis of pyrimidylhydrazones and substituted pyrimidyl-aryl- and -cyclohexylthiosemicarbazides and study of their influence on DNA methylation", Pharmaceutical Chemistry Journal, 2012, vol. 46, No. 7, pp. 402-405.
Wang et al., "High-spin tetranuclear iron(III) grids: Synthesis, crystal structure and magnetic properties", Polyhedron, 2013, vol. 52, pp. 970-975.
Unishi et al., "Preparation of poly(Schiff base)", Kogyo Kagaku Zasshi, 1969, vol. 72, No. 12, pp. 2661-2664 with English translation of abstract.
Hansen, "Fate and antibacterial potency of anticoccidial drugs and their main abiotic degradation products", Environmental Pollution, 2009, vol. 157, No. 2, pp. 474-480.
Okajima et al., "Synthesis and reaction of 2-Imino-1,3-thiazetidines and 2-Imino-1,3-dithietanes", Journal of Heterocyclic Chemistry, 1991, vol. 28, No. 1, pp. 177-185.
Office Action from Chinese State Intellectual Property Office for Chinese Patent Application No. 2014800376130 dated Oct. 2016, English translation, 6 pages.

(56) References Cited

OTHER PUBLICATIONS

Marien et al., "In Vitro Activity of Robenidine Hydrochloride on Rabbit Clostridium Perfringens Isolates", Pathology and Hygiene, 9th World Rabbit Congress, Verona, Italy, Jun. 10-13, 2018, pp. 1005-1008.

Messeder et al., "Aromatic Guanyl Hydrazones: Synthesis, Structural Studies and in vitro Activity against Trypanosoma crizi", Bioorganic & Medicinal Chemistry Letters, 1995, vol. 5, No. 24, pp. 3079-3084.

CAS RN 28356-34-5, Accession No. 1970:121985, cited in Unishi et al., "Preparation of poly(Schiff base)", 1969, 72(12):2661-4.

Office Action dated Aug. 24, 2018 for Australian Patent Application No. 2014262129, 8 pages.

Office Action dated Aug. 24, 2018 for Chinese Application No. 2014800376130, 5 pages, English translation.

Office Action dated Mar. 20, 2018 for Russian Application No. 2015150264, 4 pages, English translation.

\* cited by examiner

| NCL Code | Compound Name | Structure |
|---|---|---|
| NCL812 | 2,2'-bis[(4-chlorophenyl)methylene]carbonimidic dihydrazide hydrochloride | 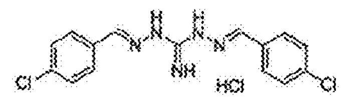 |
| NCL001 | 2,2'-bis[(4-chlorophenyl)methylene]carbonic dihydrazide | 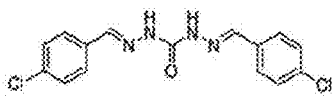 |
| NCL002 | 2,2'-bis[(2-chlorophenyl)methylene]carbonic dihydrazide | 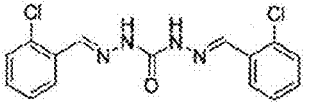 |
| NCL003 | 2,2'-bis[(4-fluorophenyl)methylene]carbonic dihydrazide | 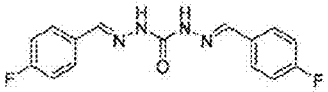 |
| NCL004 | 2,2'-bis[(3-fluorophenyl)methylene]carbonic dihydrazide | 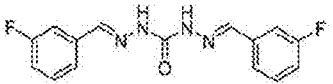 |
| NCL005 | 2,2'-bis[(2-fluorophenyl)methylene]carbonic dihydrazide | 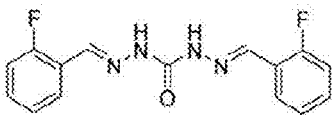 |
| NCL006 | 2,2'-bis[(4-methoxyphenyl)methylene]carbonic dihydrazide | 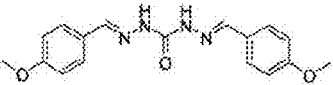 |
| NCL007 | 2,2'-bis[(4-cyanophenyl)methylene]carbonic dihydrazide | 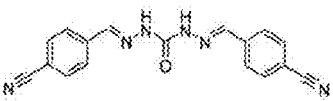 |
| NCL008 | 2,2'-bis[(2-cyanophenyl)methylene]carbonic dihydrazide | 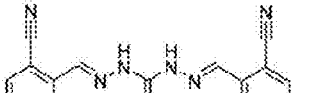 |

Figure 1

| | | |
|---|---|---|
| NCL009 | 2,2'-bis[(3-cyanophenyl)methylene]carbonic dihydrazide | 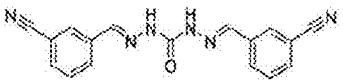 |
| NCL010 | 2,2'-bis[(3-methoxyphenyl)methylene]carbonic dihydrazide | 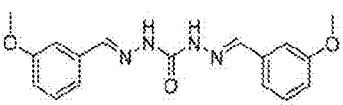 |
| NCL011 | 2,2'-bis{[3-(trifluoromethyl)phenyl]methylene}carbonic dihydrazide | 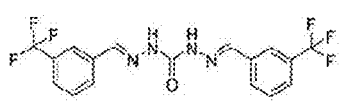 |
| NCL012 | 2,2'-bis{[4-(trifluoromethyl)phenyl]methylene}carbonic dihydrazide | 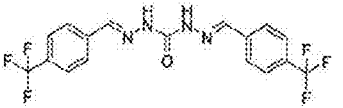 |
| NCL013 | 2,2'-bis{[2-(trifluoromethyl)phenyl]methylene}carbonic dihydrazide | 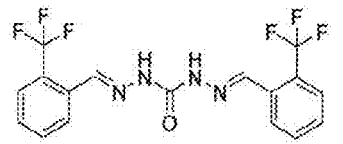 |
| NCL014 | 2-[(4-chlorophenyl)methylene]hydrazinecarboxamide | 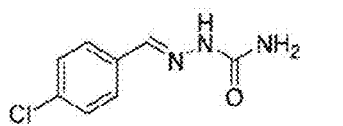 |
| NCL015 | 2-[(2-chlorophenyl)methylene]hydrazinecarboximidamide hydrochloride | 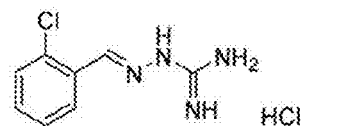 |
| NCL016 | 2-[(2-fluorophenyl)methylene]hydrazinecarboximidamide hydrochloride | 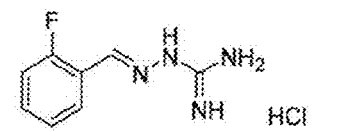 |
| NCL017 | 2-[(3-fluorophenyl)methylene]hydrazinecarboximidamide hydrochloride | 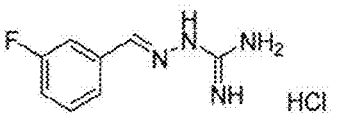 |

Figure 1 Continued...

| ID | Name |
|---|---|
| NCL018 | 2,2'-bis[(2-methylphenyl)methylene]carbonic dihydrazide |
| NCL019 | 2,2'-bis[(3-methylphenyl)methylene]carbonic dihydrazide |
| NCL020 | 2,2'-bis[(2-chlorophenyl)methylene]carbonimidic dihydrazide hydrochloride |
| NCL021 | 2,2'-bis[(4-fluorophenyl)methylene]carbonimidic dihydrazide hydrochloride |
| NCL022 | 2,2'-bis[(2-fluorophenyl)methylene]carbonimidic dihydrazide hydrochloride |
| NCL023 | 2,2'-bis[(3-fluorophenyl)methylene]carbonimidic dihydrazide hydrochloride |
| NCL024 | 2,2'-bis[(4-cyanophenyl)methylene]carbonimidic dihydrazide hydrochloride |
| NCL025 | 2,2'-bis[(2-cyanophenyl)methylene]carbonimidic dihydrazide hydrochloride |
| NCL026 | 2,2'-bis[(3-cyanophenyl)methylene]carbonimidic dihydrazide hydrochloride |

Figure 1 Continued...

| | | |
|---|---|---|
| NCL036 | 2,2'-bis{[2-(trifluoromethyl)phenyl]methylene}carbonimidic dihydrazide hydrochloride | 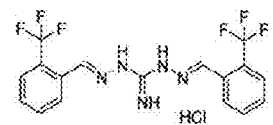 |
| NCL037 | 2,2'-bis{[3-(trifluoromethyl)phenyl]methylene}carbonimidic dihydrazide hydrochloride | 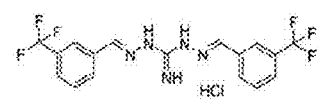 |
| NCL038 | 2,2'-bis[(4-methylphenyl)methylene]carbonimidic dihydrazide hydrochloride | 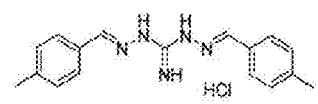 |
| NCL039 | 2,2'-bis[(2-methylphenyl)methylene]carbonimidic dihydrazide hydrochloride | 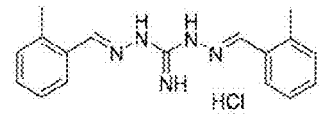 |
| NCL040 | 2,2'-bis[(3-methylphenyl)methylene]carbonimidic dihydrazide hydrochloride | 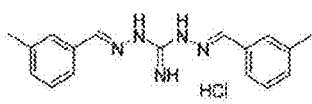 |
| NCL041 | 2-{[4-(trifluoromethyl)phenyl]methylene}hydrazinecarboximidamide hydrochloride | 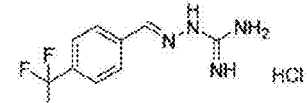 |
| NCL042 | 2-{[2-(trifluoromethyl)phenyl]methylene}hydrazinecarboximidamide hydrochloride | 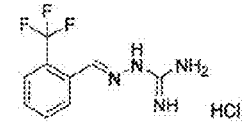 |
| NCL043 | 2-{[3-(trifluoromethyl)phenyl]methylene}hydrazinecarboximidamide hydrochloride | 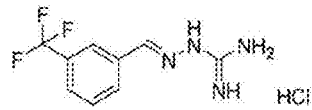 |
| NCL044 | 2-[(4-methylphenyl)methylene]hydrazinecarboximidamide hydrochloride | 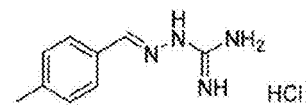 |

Figure 1 Continued...

| | | |
|---|---|---|
| NCL045 | 2-[(2-methylphenyl)methylene]hydrazinecarboximidamide hydrochloride | 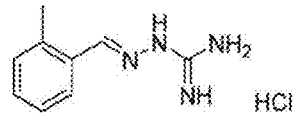 |
| NCL046 | 2-[(3-methylphenyl)methylene]hydrazinecarboximidamide hydrochloride | 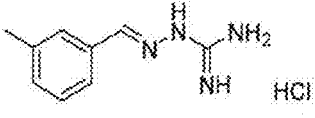 |
| NCL047 | 2-[(2-chlorophenyl)methylene]hydrazinecarboxamide | 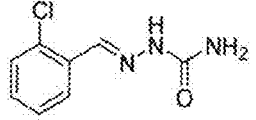 |
| NCL048 | 2-[(2-fluorophenyl)methylene]hydrazinecarboxamide | 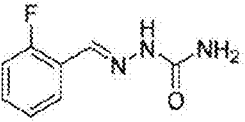 |
| NCL049 | 2-[(4-cyanophenyl)methylene]hydrazinecarboxamide | 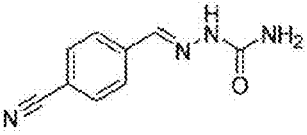 |
| NCL050 | 2-[(2-cyanophenyl)methylene]hydrazinecarboxamide | 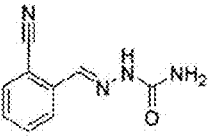 |
| NCL051 | 2-[(3-cyanophenyl)methylene]hydrazinecarboxamide | 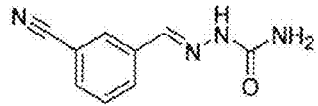 |
| NCL052 | 2-[(3-chlorophenyl)methylene]hydrazinecarboximidamide hydrochloride | 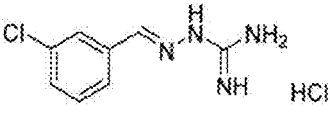 |
| NCL053 | 2-[(4-fluorophenyl)methylene]hydrazinecarboximidamide hydrochloride | 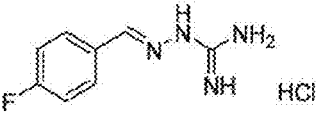 |

Figure 1 Continued...

| | | |
|---|---|---|
| NCL054 | 2,2'-bis[(3-chlorophenyl)methylene]carbonimidic dihydrazide hydrochloride | 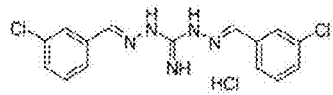 |
| NCL055 | 2-[(3-chlorophenyl)methylene]hydrazinecarboxamide | 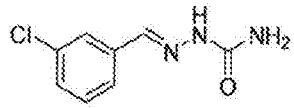 |
| NCL056 | 2-[(4-fluorophenyl)methylene]hydrazinecarboxamide | 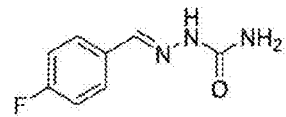 |
| NCL057 | 2-[(3-fluorophenyl)methylene]hydrazinecarboxamide | 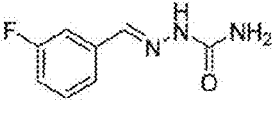 |
| NCL058 | 2-[(4-methoxyphenyl)methylene]hydrazinecarboxamide | 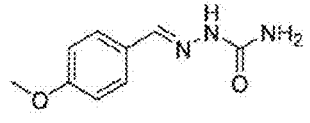 |
| NCL059 | 2-[(3-methoxyphenyl)methylene]hydrazinecarboxamide | 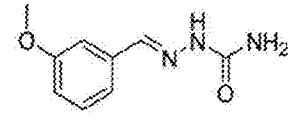 |
| NCL060 | 2-{[(2-trifluoromethyl)phenyl]methylene}hydrazinecarboxamide | 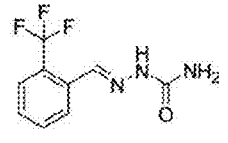 |
| NCL061 | 2,2'-bis{1-[4-(trifluoromethyl)phenyl]ethylidene}carbonimidic dihydrazide hydrochloride | 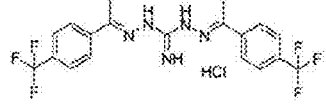 |
| NCL062 | 2,2'-bis{1-[4-chlorophenyl]ethylidene}carbonimidic dihydrazide hydrochloride | 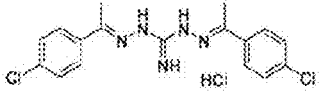 |

Figure 1 Continued...

| | | |
|---|---|---|
| NCL063 | 2,2'-bis{[4-(trifluoromethyl)phenyl]methylene} carbonothioic dihydrazide | 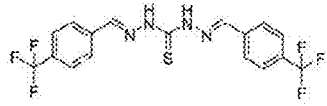 |
| NCL064 | 2,2'-bis[(2-cyanophenyl)methylene] carbonothioic dihydrazide | 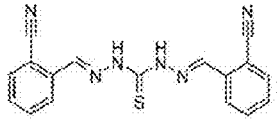 |
| NCL065 | 2,2'-bis[(3-cyanophenyl)methylene] carbonothioic dihydrazide | 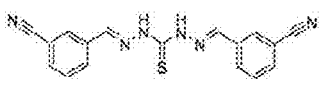 |
| NCL066 | 2,2'-bis[(3-fluorophenyl)methylene] carbonothioic dihydrazide | 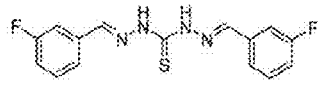 |
| NCL067 | 2-{[(3-trifluoromethyl)phenyl]methylene} hydrazinecarboxamide | 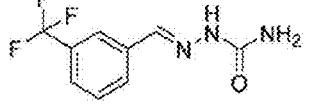 |
| NCL068 | 2-[1-(4-chlorophenyl)ethylidene]-2'-{1-[4-(trifluoromethyl)phenyl]methylene}carbonimidic dihydrazide hydrochloride | 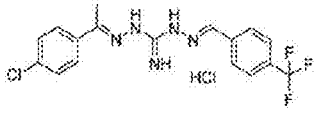 |
| NCL069 | 2-[1-(4-chlorophenyl)ethylidene] carbonimidic dihydrazide hydrochloride | 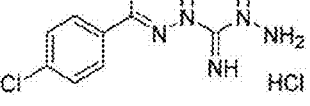 |
| NCL070 | 2,2'-bis[(3-chlorophenyl)methylene] carbonothioic dihydrazide | 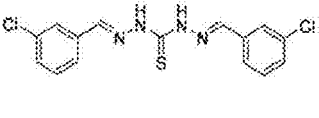 |
| NCL071 | 2-[(2-methoxyphenyl)methylene] hydrazinecarbothioamide | 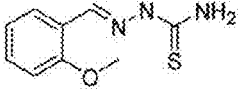 |

Figure 1 Continued...

| ID | Name | |
|---|---|---|
| NCL081 | 2-[1-(4-chlorophenyl)ethylidene]-2'-[(4-chlorophenyl)methylene]carbonimidic dihydrazide hydrochloride | |
| NCL082 | 2-[(2-chlorophenyl)methylene]-2'-[(4-chlorophenyl)methylene]carbonimidic dihydrazide hydrochloride | |
| NCL083 | 2-[(3-chlorophenyl)methylene]-2'-[(4-chlorophenyl)methylene]carbonimidic dihydrazide hydrochloride | |
| NCL084 | 2-[(2-fluoro-4-chlorophenyl)methylene]-2'-[(4-chlorophenyl)methylene]carbonimidic dihydrazide hydrochloride | |
| NCL085 | 2-[(2-cyanophenyl)methylene]-2'-[(4-chlorophenyl)methylene]carbonimidic dihydrazide hydrochloride | |
| NCL086 | 2-[(3-cyanophenyl)methylene]-2'-[(4-chlorophenyl)methylene]carbonimidic dihydrazide hydrochloride | |
| NCL087 | 2-[(4-chlorophenyl)methylene]-2'-[(4-cyanophenyl)methylene]carbonimidic dihydrazide hydrochloride | |
| NCL088 | 2-[(2-fluorophenyl)methylene]-2'-[(4-chlorophenyl)methylene]carbonimidic dihydrazide hydrochloride | |
| NCL089 | 2-[1-(4-chlorophenyl)ethylidene]-2'-{1-[4-(trifluoromethyl)phenyl]ethylidene}carbonimidic dihydrazide hydrochloride | |

Figure 1 Continued...

| | | |
|---|---|---|
| NCL090 | N-benzoyl-1-benzoyl-2-[(2-chlorophenyl)methylene]hydrazinecarboximidamide hydrochloride | 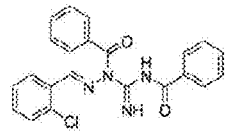 |
| NCL091 | N-(4-chlorophenyl)-3-[4-(trifluoromethyl)phenyl]-1H-1,2,4-triazol-5-amine | 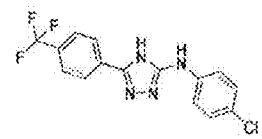 |
| NCL092 | N-(4-chlorobenzyl)-3-(4-chlorophenyl)-1H-1,2,4-triazol-5-amine | 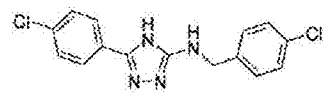 |
| NCL093 | 2,2'-bis(2-naphthalenylmethylene) carbonimidic dihydrazide hydrochloride | 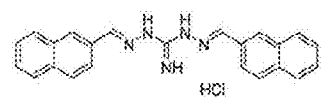 |
| NCL094 | 2,2'-bis(cyclohexylmethylene) carbonimidic dihydrazide hydrochloride | 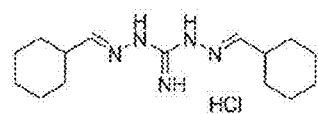 |
| NCL095 | 2,2'-bis(3-furanylmethylene) carbonimidic dihydrazide hydrochloride | 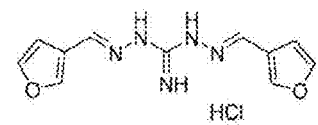 |
| NCL096 | 2,2'-bis(3-phenyl-2-propenylidene) carbonimidic dihydrazide hydrochloride | 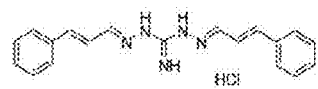 |
| NCL097 | 2,2'-bis[(3,4,5-trihydroxyphenyl)methylene] carbonimidic dihydrazide hydrochloride | 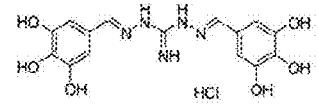 |
| NCL098 | 2,2'-bis[(3-carboxyphenyl)methylene]carbonimidic dihydrazide hydrochloride | 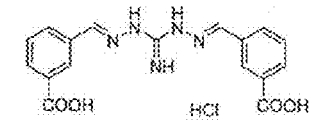 |

Figure 1 Continued...

| | | |
|---|---|---|
| NCL099 | 2,2'-bis[[4-(1,1-dimethylethyl)phenyl]methylene] carbonimidic dihydrazide hydrochloride | 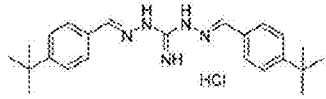 |
| NCL100 | 2,2'-bis(phenylmethylene) carbonimidic dihydrazide hydrochloride | 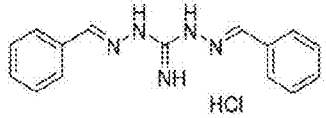 |
| NCL101 | 2,2'-bis[(2,3-dihydroxyphenyl)methylene] carbonimidic dihydrazide hydrochloride | 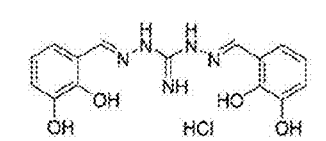 |
| NCL102 | 2,2'-bis[(2-nitrophenyl)methylene] carbonimidic dihydrazide hydrochloride | 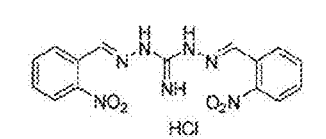 |
| NCL103 | 2,2'-bis[(2,4-dihydroxyphenyl)methylene] carbonimidic dihydrazide hydrochloride | 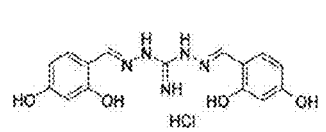 |
| NCL104 | 2,2'-bis[(2,4,5-trihydroxyphenyl)methylene] carbonimidic dihydrazide hydrochloride | 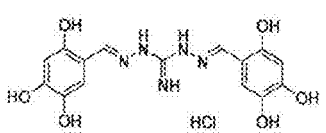 |
| NCL105 | 2,2'-bis[(2,3,4-trihydroxyphenyl)methylene] carbonimidic dihydrazide hydrochloride | 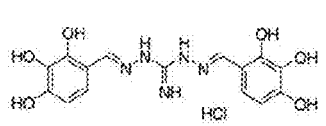 |
| NCL106 | 2,2'-bis[(4,5-dihydroxy-3-methoxyphenyl)methylene] carbonimidic dihydrazide hydrochloride | 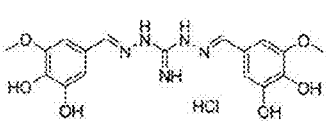 |
| NCL107 | 2,2'-bis[(2-hydroxyphenyl)methylene] carbonimidic dihydrazide hydrochloride | 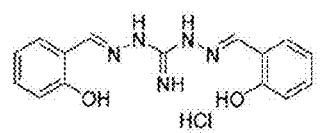 |

Figure 1 Continued...

| NCL108 | 2,2'-bis[(3-hydroxyphenyl)methylene] carbonimidic dihydrazide hydrochloride | 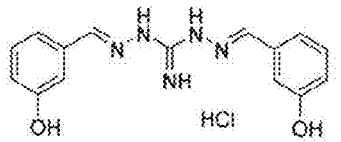 |
| NCL109 | 2,2'-bis[(3-nitrophenyl)methylene] carbonimidic dihydrazide hydrochloride | 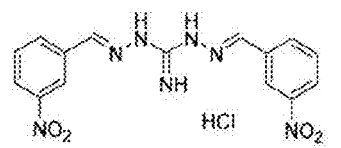 |
| NCL110 | 2,2'-bis[(4-nitrophenyl)methylene] carbonimidic dihydrazide hydrochloride | 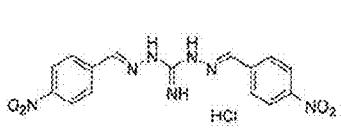 |
| NCL111 | 2,2'-bis[(3,4-dihydroxyphenyl)methylene] carbonimidic dihydrazide hydrochloride | 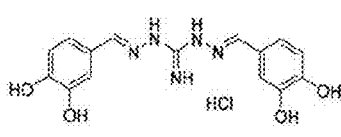 |
| NCL112 | 2,2'-bis([1,1'-biphenyl]-4-ylmethylene) carbonimidic dihydrazide hydrochloride | 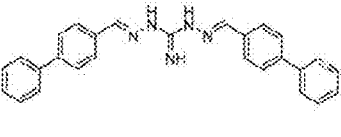 |
| NCL113 | 2,2'-bis{4-(dimethylamino)phenyl]methylene} carbonimidic dihydrazide hydrochloride | 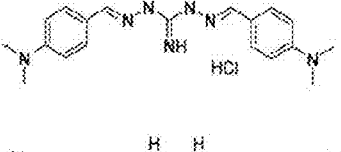 |
| NCL114 | 2,2'-bis[(3,5-dichlorophenyl)methylene] carbonimidic dihydrazide hydrochloride | 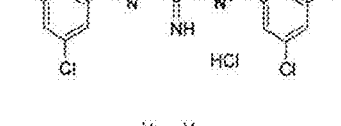 |
| NCL 115 | 2,2'-bis[(3,4-dimethoxyphenyl)methylene] carbonimidic dihydrazide hydrochloride | 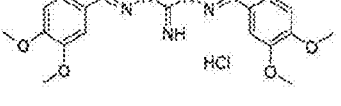 |
| NCL 116 | 2,2'-bis([1,1'-biphenyl]-2-ylmethylene) carbonimidic dihydrazide hydrochloride | 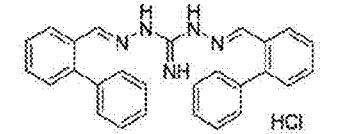 |

Figure 1 Continued...

| | | |
|---|---|---|
| NCL 117 | 2,2'-bis[(4-hydroxy-3-methoxyphenyl)methylene] carbonimidic dihydrazide hydrochloride | 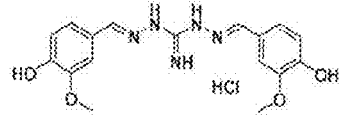 |
| NCL 118 | 2,2'-bis[(2,5-fluorophenyl)methylene] carbonimidic dihydrazide hydrochloride | 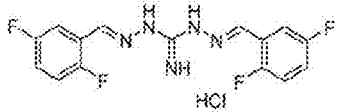 |
| NCL 119 | 2,2'-bis[(4-acetamidophenyl)methylene] carbonimidic dihydrazide hydrochloride | 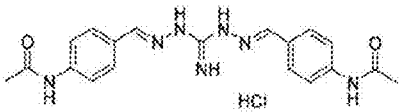 |
| NCL 120 | 2,2'-bis{[4-(1-methylethyl)phenyl]methylene} carbonimidic dihydrazide hydrochloride | 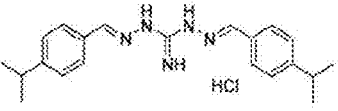 |
| NCL 121 | 2,2'-bis[(4-propylphenyl)methylene] carbonimidic dihydrazide hydrochloride | 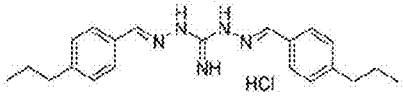 |
| NCL 122 | 2,2'-bis[(4-hydroxy-3-nitrophenyl)methylene] carbonimidic dihydrazide hydrochloride | 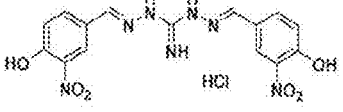 |
| NCL123 | 2,2'-bis[(3,4-difluorophenyl)methylene] carbonimidic dihydrazide hydrochloride | 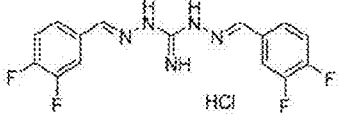 |
| NCL 124 | 2,2'-bis[(2-hydroxy-1-naphthalenyl)methylene] carbonimidic dihydrazide hydrochloride | 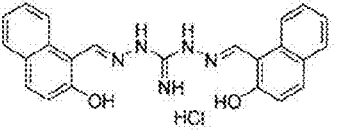 |
| NCL 125 | 2,2'-bis[(3-hydroxy-4-methoxyphenyl)methylene] carbonimidic dihydrazide hydrochloride | 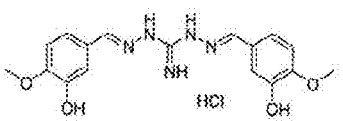 |

Figure 1 Continued...

| | | |
|---|---|---|
| NCL 126 | 2,2'-bis[(3-ethynylphenyl)methylene] carbonimidic dihydrazide hydrochloride | 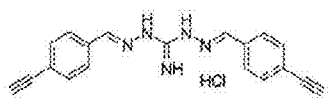 |
| NCL 127 | 2,2'-bis[(2,4-dichlorophenyl)methylene] carbonimidic dihydrazide hydrochloride | 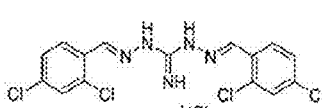 |
| NCL 128 | 2,2'-bis[(2,3,4,5,6-pentafluorophenyl)methylene] carbonimidic dihydrazide hydrochloride | 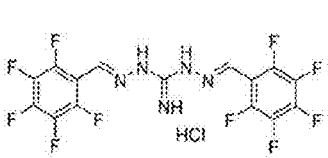 |
| NCL 129 | 2,2'-bis[(2-bromophenyl)methylene] carbonimidic dihydrazide hydrochloride | 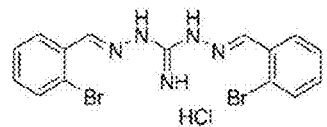 |
| NCL 130 | 2,2'-bis[(3-bromo-4,5-dimethoxyphenyl)methylene] carbonimidic dihydrazide hydrochloride | 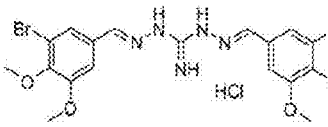 |
| NCL 131 | 2,2'-bis[(3-bromophenyl)methylene] carbonimidic dihydrazide hydrochloride | 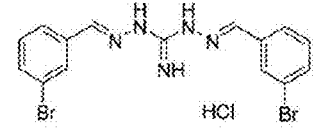 |
| NCL 132 | 2,2'-bis[(4-chloro-6-fluoro-2H-1-benzopyran-3-yl)methylene]carbonimidic dihydrazide hydrochloride | 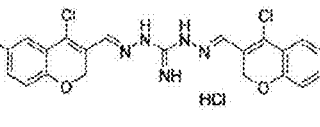 |
| NCL 133 | 2,2'-bis[(4-bromo-2-furanyl)methylene] carbonimidic dihydrazide hydrochloride | 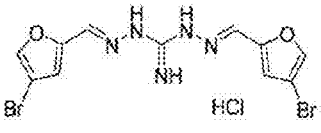 |
| NCL 134 | 2,2'-bis[(4-bromophenyl)methylene] carbonimidic dihydrazide hydrochloride | 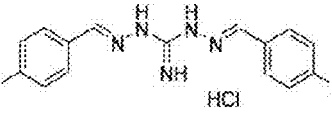 |

Figure 1 Continued...

| | | |
|---|---|---|
| NCL 135 | 2,2'-bis[(2-bromo-4,5-dimethoxyphenyl)methylene] carbonimidic dihydrazide hydrochloride | 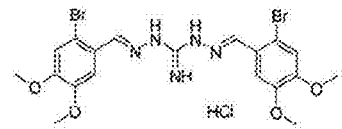 |
| NCL 136 | 2,2'-bis[(4-butylphenyl)methylene] carbonimidic dihydrazide hydrochloride | 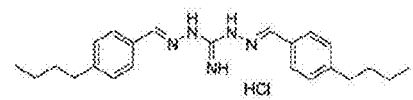 |
| NCL 137 | 2,2'-bis[(2,6-dichlorophenyl)methylene] carbonimidic dihydrazide hydrochloride | 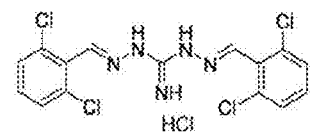 |
| NCL 138 | 2,2'-bis(2,3-diphenyl-2-propenylidene) carbonimidic dihydrazide hydrochloride | 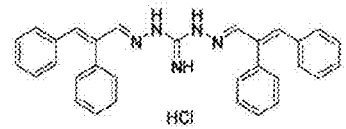 |
| NCL 139 | 2,2'-bis(3-quinolinylmethylene) carbonimidic dihydrazide hydrochloride | 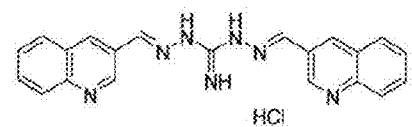 |
| NCL 140 | 2,2'-bis{[4-(methylsulfanyl)phenyl]methylene} carbonimidic dihydrazide hydrochloride | 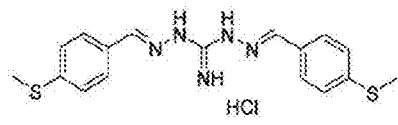 |
| NCL 141 | 2,2'-bis[(5-chlorobenzo[b]thien-3-yl)methylene]carbonimidic dihydrazide hydrochloride | 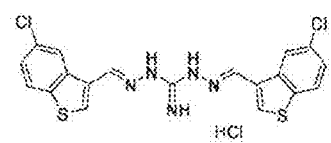 |
| NCL 142 | 1,3-bis(benzylamino)guanidine hydrochloride | 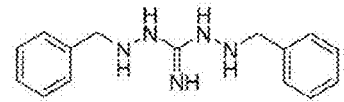 |
| NCL 143 | 2,2'-bis[1-phenylethylidene] carbonimidic dihydrazide hydrochloride | 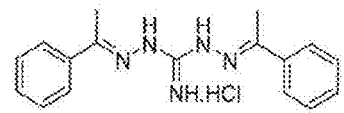 |

Figure 1 Continued...

| | | |
|---|---|---|
| NCL 144 | 2,2'-bis[(5-bromo-2-furanyl)methylene] carbonimidic dihydrazide hydrochloride | |
| NCL 145 | 2,2'-bis[(5-chloro-2-furanyl)methylene] carbonimidic dihydrazide hydrochloride | |
| NCL 146 | 2,2'-bis(1H-indol-5-ylmethylene) carbonimidic dihydrazide hydrochloride | |
| NCL 147 | 2,2'-bis(2-quinoxalinylmethylene) carbonimidic dihydrazide hydrochloride | |
| NCL 148 | 2,2'-bis{[4-(carboxypropenyl)phenyl]methylene} carbonimidic dihydrazide hydrochloride | |
| NCL 149 | 2,2'-Bis(4-pyridinylmethylene) Carbonimidic dihydrazide hydrochloride | |
| NCL 150 | 2,2'-bis[3-(4-methoxylphenyl)-2-propenylidene]carbonimidic dihydrazide hydrochloride | |
| NCL 151 | 2,2'-bis[(4-hydroxyphenyl)methylene] carbonimidic dihydrazide hydrochloride | |
| NCL 152 | 2,2'-bis[(2-hydroxy-3-methylphenyl)methylene] carbonimidic dihydrazide hydrochloride | |
| NCL 153 | 2,2'-bis[1-(4-chlorophenyl)propylidene] carbonimidic dihydrazide hydrochloride | |

Figure 1 Continued...

| | | |
|---|---|---|
| NCL 154 | 2,2'-bis[1-(4-chlorophenyl)pentylidene] carbonimidic dihydrazide hydrochloride | 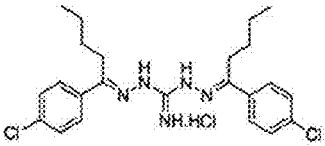 |
| NCL 155 | 2,2'-bis[1-(4-bromophenyl)ethylidene] carbonimidic dihydrazide hydrochloride | 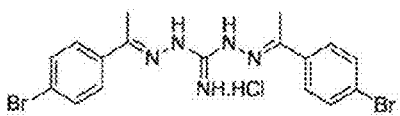 |
| NCL 156 | 2,2'-bis[1-(4-chlorophenyl)butylidene] carbonimidic dihydrazide hydrochloride | 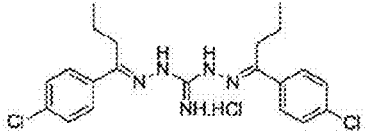 |
| NCL 157 | 2,2'-bis[(2-amino-4-chlorophenyl)methylene] carbonimidic dihydrazide hydrochloride | 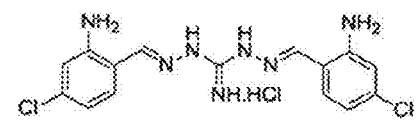 |
| NCL 158 | 2,2'-bis[1-(2-hydroxy-4-chlorophenyl)propylidene] carbonimidic dihydrazide hydrochloride | 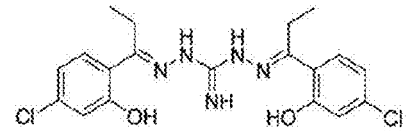 |
| NCL 159 | 2,2'-bis[(2-hydroxy-4-chlorophenyl)(cyclopentyl)methylene] carbonimidic dihydrazide hydrochloride | 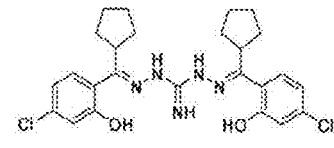 |
| NCL 160 | 2,2'-bis[[4-(trifluoromethoxy)phenyl]methylene] carbonimidic dihydrazide hydrochloride | 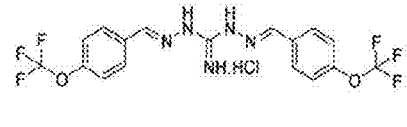 |
| NCL 161 | 2,2'-bis[1-(4-piperazinylphenyl)ethylidene] carbonimidic dihydrazide hydrochloride | 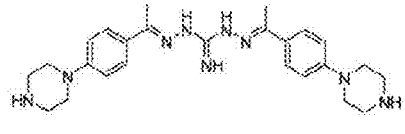 |
| NCL 162 | ethyl (E)-N'-((E)-1-(4-chlorophenyl)ethylidene) carbamohydrazonate | 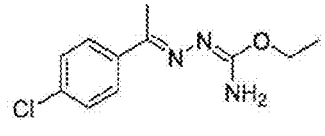 |

Figure 1 Continued...

| ID | Name |
|---|---|
| NCL 163 | 2,2'-bis(2-Oxo-1,2-dihydro-3H-indol-3-ylidene)carbonimidic dihydrazide hydrochloride |
| NCL 164 | 2,2'-bis[1-(2-amino-4-chlorophenyl)ethylidene]carbonimidic dihydrazide hydrochloride |
| NCL 165 | 2,2'-bis(1-phenyl-2-aminoethylidene)carbonimidic dihydrazide trihydrochloride |
| NCL 166 | 2,2'-bis{[4-(trifluoromethylsulfanyl)phenyl]methylene}carbonimidic dihydrazide hydrochloride |
| NCL 167 | 2,2'-bis(phenylcarboxymethylene)carbonimidic dihydrazide hydrochloride |
| NCL 168 | 2,2'-bis{[2-(1-hydroxyethylamino)-4-chlorophenyl]methylene}carbonimidic dihydrazide hydrochloride |
| NCL 169 | 2,2'-bis[(2-amino-4-chlorophenyl)methylene]carbonimidic dihydrazide |
| NCL 170 | 2,2'-bis[(2-acetamido-4-chlorophenyl)methylene]carbonimidic dihydrazide |
| NCL 171 | 2,2'-bis{[4-(dimethylamino)-2-hydroxyphenyl]methylene}carbonimidic dihydrazide |
| NCL 172 | 2,2'-Bis[1-(2-pyridinyl)ethylidene]Carbonimidic dihydrazide hydrochloride |

Figure 1 Continued...

| | | |
|---|---|---|
| NCL 173 | 2,2'-bis[1-(4-chloro-2-hydroxyphenyl)ethylidene] carbonimidic dihydrazide hydrochloride | 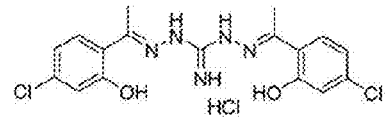 |
| NCL 174 | 2,2'-bis(4-chloro-2-hydroxyphenylmethylene) carbonimidic dihydrazide hydrochloride | 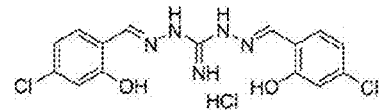 |
| NCL 175 | 2,2'-Bis(4-chloropyridin-3-ylmethylene)Carbonimidic dihydrazide hydrochloride | 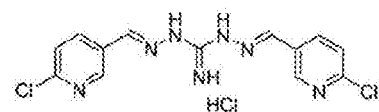 |
| NCL 176 | 2,2'-Bis(2-aminopyridin-3-ylmethylene) Carbonimidic dihydrazide hydrochloride | 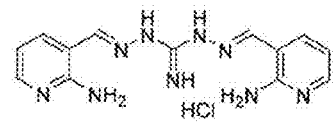 |
| NCL 177 | 2,2'-bis[1-(4-chlorophenyl)-2-hydroxyethylidene] carbonimidic dihydrazide hydrochloride | 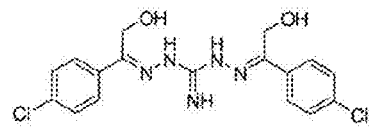 |
| NCL 178 | 4,6-bis(2-((E)-1-(4-chlorophenyl)ethylidene)hydrazinyl)pyrimidine | 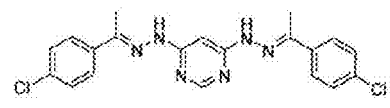 |
| NCL 179 | 4,6-bis(2-((E)-4-chlorobenzylidene)hydrazinyl)pyrimidin-2-amine | 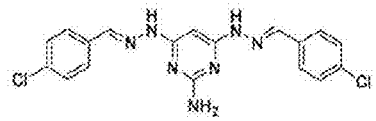 |
| NCL 180 | (2Z,2'Z)-2,2'-(pyrimidine-4,6-diylbis(hydrazin-2-yl-1-ylidene))bis(2-(4-chlorophenyl)ethan-1-ol) | 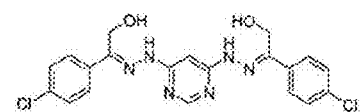 |
| NCL 181 | 4,6-bis(2-((E)-4-chlorobenzylidene)hydrazinyl)pyrimidine | 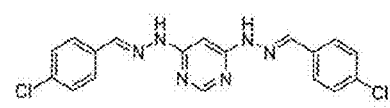 |

Figure 1 Continued...

| | | |
|---|---|---|
| NCL 182 | 6-chloro-N⁴-(1-phenylethyl)pyrimidine-2,4-diamine | 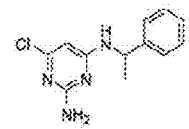 |
| NCL 183 | N⁴,N⁶-bis(1-phenylethyl)pyrimidine-4,6-diamine | 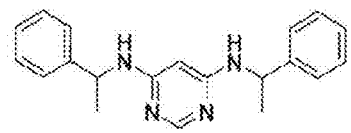 |
| NCL 184 | N⁴,N⁶-bis(1-phenylethyl)pyrimidine-2,4,6-triamine | 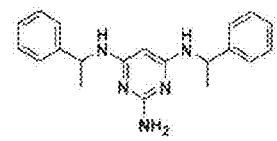 |
| NCL 185 | 4,6-bis(2-((E)-1-(4-chlorophenyl)ethylidene)hydrazinyl)pyrimidine hydrochloride | 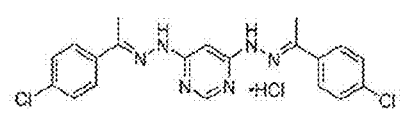 |
| NCL 186 | N²,N⁶-bis(1-(4-chlorophenyl)ethyl)pyrazine-2,5-diamine | 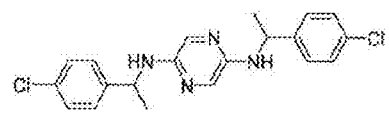 |
| NCL 187 | 4,6-bis(2-((E)-4-chlorobenzylidene)hydrazinyl)pyrimidine hydrochloride | 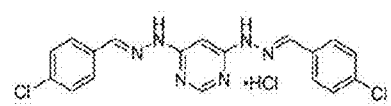 |
| NCL 188 | (E)-2-(1-(4-chlorophenyl)pentylidene)hydrazine-1-carboximidamide hydrochloride | 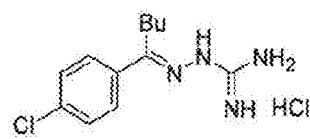 |
| NCL 189 | (2Z,2'Z)-2,2'-(pyrimidine-4,6-diylbis(hydrazin-2-yl-1-ylidene))bis(2-(4-chlorophenyl)ethan-1-ol) hydrochloride | 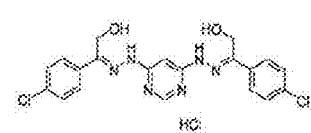 |
| NCL 190 | (Z)-2-(1-(4-chlorophenyl)-2-hydrazinylethylidene)hydrazine-1-carboximidamide hydrochloride | 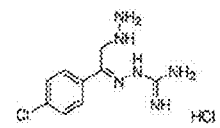 |

Figure 1 Continued...

| | | |
|---|---|---|
| NCL210 | 4,6-bis(2-((E)-4-(trifluoromethyl)benzylidene)hydrazinyl)-1,3,5-triazin-2-amine | |
| NCL211 | 4,4'-((1E,1'E)-((6-amino-1,3,5-triazine-2,4-diyl)bis(hydrazin-2-yl-1-ylidene))bis(methanylylidene))diphenol | |
| NCL212 | 4,6-bis(2-((E)-4-bromobenzylidene)hydrazinyl)-1,3,5-triazin-2-amine | |
| NCL213 | 4,6-bis(2-((E)-cyclohexylmethylene)hydrazinyl)-1,3,5-triazin-2-amine | |
| NCL214 | 4,6-bis(2-((E)-benzylidene)hydrazinyl)-1,3,5-triazin-2-amine | |
| NCL215 | (E)-N'-((E)-1-(4-chloro-2-fluorophenyl)ethylidene)-2-(1-(4-chloro-2-fluorophenyl)ethylidene)hydrazine-1-carboximidhydrazide hydrochloride | |
| NCL216 | N',2-bis((E)-4-chloro-2-fluorobenzylidene)hydrazine-1-carboximidhydrazide hydrochloride | |
| NCL217 | N',2-bis((E)-1-(p-tolyl)ethylidene)hydrazine-1-carboximidhydrazide hydrochloride | |

Figure 1 Continued...

| | | |
|---|---|---|
| NCL218 | 4-((E)-(2-(2-amino-6-(2-((E)-4-((diethoxyphosphoryl)oxy)benzylidene)hydrazinyl)pyrimidin-4-yl)hydrazono)methyl)phenyl diethyl phosphate | |
| NCL219 | (E)-N'-((E)-1-(4-(tert-butyl)phenyl)ethylidene)-2-(1-(4-(tert-butyl)phenyl)ethylidene)hydrazine-1-carboximidhydrazide hydrochloride | |
| NCL220 | 4,6-bis(2-((E)-4-fluorobenzylidene)hydrazinyl)pyrimidin-2-amine | |
| NCL221 | 4,6-bis(2-((E)-4-(trifluoromethyl)benzylidene)hydrazinyl)pyrimidin-2-amine | |
| NCL222 | 4,6-bis(2-((E)-3,4-difluorobenzylidene)hydrazinyl)pyrimidin-2-amine | |
| NCL223 | N,N'-(((1E,1'E)-((2-aminopyrimidine-4,6-diyl)bis(hydrazin-2-yl-1-ylidene))bis(methanylylidene))bis(4,1-phenylene))diacetamide | |
| NCL224 | ethyl 2-((E)-4-chlorobenzylidene)-1-((E)-N'-((E)-4-chlorobenzylidene)carbamohydrazonoyl)hydrazine-1-carboxylate | |
| NCL225 | isobutyl 2-((E)-4-chlorobenzylidene)-1-((E)-N'-((E)-4-chlorobenzylidene)carbamohydrazonoyl)hydrazine-1-carboxylate | |
| NCL226 | 2-((E)-4-chlorobenzylidene)-1-((E)-N'-((E)-4-chlorobenzylidene)carbamohydrazonoyl)-N-ethylhydrazine-1-carboxamide | |

Figure 1 Continued...

| NCL227 | N-benzyl-2-((E)-4-chlorobenzylidene)-1-((E)-N'-((E)-4-chlorobenzylidene)carbamohydrazonoyl)hydrazine-1-carboxamide |
| NCL228 | 2-((E)-4-chlorobenzylidene)-1-((E)-N'-((E)-4-chlorobenzylidene)carbamohydrazonoyl)-N-hexylhydrazine-1-carboxamide |
| NCL229 | 2-((E)-4-chlorobenzylidene)-1-((E)-N'-((E)-4-chlorobenzylidene)carbamohydrazonoyl)-N-(furan-2-ylmethyl)hydrazine-1-carboxamide |
| NCL230 | 4,6-bis(2-((E)-4-methoxybenzylidene)hydrazinyl)pyrimidin-2-amine |

Figure 1 Continued...

COMPOUNDS AND METHODS OF TREATING INFECTIONS

CROSS REFERENCE TO RELATED APPLICATIONS

This application is U.S. National Stage application of PCT/AU2014/000483, filed 1 May 2014, which claims priority to Australia application No. 2013901516, filed 1 May 2013, the contents of all of which are hereby incorporated by reference in their entirety.

SEQUENCE LISTING

The instant application contains a Sequence Listing which has been submitted electronically in ASCII format and is hereby incorporated by reference in its entirety. Said ASCII copy, created on 26 Nov. 2018, is named 273445_US_Seq_Listing_ST25 and is 1 kilobyte in size.

TECHNICAL FIELD

This invention relates to compounds of Formula I, methods of treating or preventing a bacterial infection in a subject using a compound of Formula I, the use of a compound of Formula I in the manufacture of a medicament for the treatment of a bacterial infection in a subject, and medical devices when used in a method of treating or preventing a bacterial infection in a subject.

BACKGROUND ART

A marked increase in prevalence of multi-drug resistance in disease-causing Gram-positive (G+ve) (*Staphylococcus aureus, Enterococcus* spp. and *Streptococcus pneumoniae*) and Gram negative (G−ve) pathogens (*Escherichia coli, Enterobacter* spp., *Salmonella* spp., *Acinetobacter baumannii, Klebsiela pneumoniae* and *Pseudomonas aeruginosa*) has coincided with an unprecedented global decline in investment in new anti-infective drugs. There are few currently registered alternatives for multidrug resistant (MDR) bacterial infections, forcing clinicians to consider older generation drugs such as colistin with narrow spectrum and considerable potential for toxic side-effects. In addition, there are fewer novel classes of antiinfective therapeutics moving through the drug development pipeline.

Since the year 2000, a period of almost 15 years, only 5 novel mode of action (MOA) antibacterial agents have been approved by the US FDA—linezolid (an oxazolidinone) in 2000, daptomycin (a lipopeptide) in 2003, retapamulin (a pleuromutiln) in 2007, fidaxomicin (a macrolide tiacumicin) in 2011, and bedaquiline (a diarylquinoine) in 2012. Notably, none of these agents has significant activity against gram negative bacteria. No novel MOA antibacterial agents were approved in 2013 and to date in 2014 only tedizolid and dalbavancin, both analogs of existing classes, have been recommended for approval in the US. While there are more than 300 anti-infective medicines in various stages of development, the large majority of these medicines are previously approved antibacterial compounds or their derivatives that are undergoing studies for new indications.

Furthermore, the prevalence of multidrug-resistance in animal-specific pathogens together with greater regulation of the registration and usage of antimicrobials in animals, has caused veterinarians to become increasingly reliant on the traditional classes of antimicrobial agents. The risk of transfer of MDR zoonotic organisms from animals to humans has also led to calls for further restrictions on the usage of some recently registered antibacterial drugs such as the fluoroquinolones and the third and fourth generation cephalosporins.

Epidemiology of Antibacterial Resistance Development in Pathogens of Humans and Animals Much of the evolution in resistance development is driven by changes in the epidemiology of key MDR organisms. Once only restricted to human hospitals and aged care facilities, methicillin resistant *Staphylococcus aureus* (MRSA) strains are now being isolated from the community in alarming proportions. Furthermore, community-acquired MRSA strains are more likely to carry the Panton-Valentine leukocidin (PVL) toxin, a virulence factor linked to skin and soft tissue lesions as well as a rapid, fulminating, necrotizing pneumonia with significant associated mortality. Recently MRSA strains have become host-adapted in several key animal species including livestock, horses and companion animals and regular cases of human-to-animal and animal-to-human transfer are being documented. This has important consequences for strain transmission and public health. A recent survey of 751 Australian veterinarians for MRSA nasal carriage found that a remarkable 21.4% of equine veterinarians were MRSA-positive compared to 4.9% of small animal veterinarians and 0.9% of veterinarians with little animal contact. These ecological shifts of MRSA together with the emergence of resistance to new drugs developed specifically for MRSA such as linezolid, confirm that new MRSA anti-infectives are urgently needed. Furthermore, hospitals that use vancomycin for treating MRSA then have to contend with outbreaks of vancomycin-resistant enterococci (VRE) infections in their patients, once again with limited alternative antimicrobial choices.

The global emergence and spread within the community of highly virulent MDR Gram-negative (G−ve) bacteria such as *E. coli* O25b:ST131 confirms that bacterial pathogens can simultaneously evolve both virulence and resistance determinants. Echoing recent MRSA epidemiology, *E. coli* O25b:ST131, a major cause of urinary tract and bloodstream infections in humans, has now been isolated from extraintestinal infections in companion animals, and poultry. The increasing significance of *E. coli* O25b:ST131 and other MDR Enterobacteriaceae with combined resistance to fluoroquinolones and extended spectrum β-lactams and carbapenems is another worrying trend, especially considering there have been few recent breakthroughs in the development of G−ve spectrum anti-infectives apart from incremental advances in the carbapenem family.

The World Health Organisation has identified antibiotic resistance as one of the three major future threats to global health. A recent report from the US Centers for Disease Control and Prevention (CDC) estimated that "in the United States, more than two million people are sickened every year with antibiotic-resistant infections, with at least 23,000 dying as a result." The extra medical costs, in the USA alone, associated with treating and managing a single case of antibiotic-resistant infection are estimated to be between US$18,588 and US$29,069 per year resulting in an overall direct cost to the US health system of over US$20 billion annually. In addition, the cost to US households in terms of lost productivity is estimated at over US$35 billion per annum. Twenty five thousand patients in the European Union (EU) still die annually from infection with MDR bacteria despite many EU countries having world's best practice hospital surveillance and infection control strategies. The EU costs from health care expenses and lost productivity associated with MDR infections are estimated to be at least €1.5 billion per year.

There is an unmet clinical need for antibacterial agents with novel mechanisms of action to supplement and replace currently available antibacterial agents, the efficacy of which is increasingly undermined by antibacterial resistance mechanisms. There additionally remains a need for alternative antibacterials in the treatment of infection by multi-resistant bacteria. However, as reported by the Infectious Diseases Society of America and the European Centre for Disease Control and Prevention, few new drugs are being developed that offer promising results over existing treatments (Infectious Diseases Society of America 2010, *Clinical Infectious Diseases*, 50(8):1081-1083).

It is an object of the present invention to overcome at least one of the failings of the prior art.

The discussion of the background art set out above is intended to facilitate an understanding of the present invention only. The discussion is not an acknowledgement or admission that any of the material referred to is or was part of the common general knowledge as at the priority date of the application.

SUMMARY OF INVENTION

According to one aspect of the invention, there is provided a compound of Formula I, or a stereoisomer, tautomer, pharmaceutically acceptable salt, or prodrug thereof:

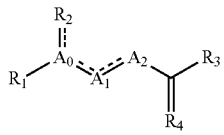

Formula I

In one preferred embodiment, $R_1$ is H, cycloalkyl, Formula II, or Formula III;

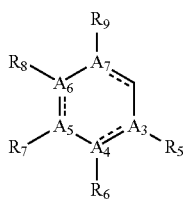

Formula II

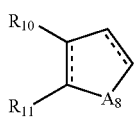

Formula III wherein $R_3$ is H, $NH_2$, $NHNH_2$, $O-CH_2-CH_3$, $NH-C(O)$-phenyl, NH-chlorophenyl, $NH-CH_2$-chlorophenyl, $NH-N=CH$-cycloalkyl, Formula IV, Formula V or Formula VI;

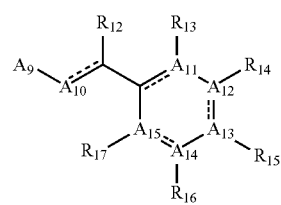

Formula IV

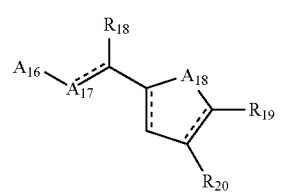

Formula V

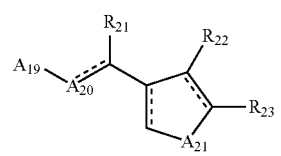

Formula VI wherein $A_0$ is N, C, CH, or $A_0$ is C and $A_0$ is bonded to $R_4$, via $R_2$, to form a triazole ring;
wherein $A_1$ is N, C, NH, $=CH-CH=N-$, $=(C_6H_5)C-CH=N-$, or Formula VII;

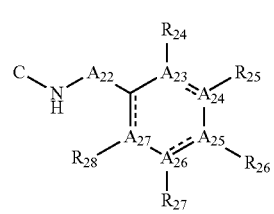

Formula VII $A_2$ is N, C, NH, N—C(O)-phenyl, or Formula VII;
wherein $A_3$, $A_4$, $A_5$, $A_6$, $A_7$, $A_8$, $A_{11}$, $A_{12}$, $A_{13}$, $A_{14}$, $A_{15}$, $A_{16}$, $A_{17}$, $A_{18}$, $A_{19}$, $A_{20}$, $A_{21}$, $A_{23}$, $A_{24}$, $A_{25}$, $A_{26}$ and $A_{27}$ are independently C, O, N, NH, S;
wherein $A_9$ is C, O, N, NH, $N-C(O)-O-CH_2-CH_3$, $N-C(O)-O-CH(CH_3)_2$, $N-C(O)-NH-CH_2-CH_3$, $N-C(O)-NH-CH_2$-phenyl, $N-C(O)-CH-CH_2-CH_2-CH_2-CH_2-CH_3$, $N-C(O)-CH_2$-furan-2-yl;
wherein $A_{10}$ is C, NH, $-N=CH-CH-$, $-N=CH-C(C_6H_5)=$;
wherein $A_{22}$ is $-CH(CH_3)-$, $-N-CH-$, $-N-C(CH_3)-$, $N-C(CH_2OH)-$;
$R_2$ is H, COOH, $CH_2NH_2$, $CH_2OH$, $CH_2NHNH_2$, methyl, ethyl, propyl, butyl, cyclopentyl, or Formula VII and $R_2$ are $R_4$ are bonded together to form a pyrimidine, pyrazine or triazine ring, or $R_2$ and $R_9$ are bonded together to form a pyrrolidinyl oxindole ring;
wherein $R_4$ is N, NH, O, S, or $R_4$ and $A_0$ are bonded, via $R_2$, to form a triazole ring, or $R_4$ is N and $R_4$ and $R_2$ are bonded together to form a pyrimidine ring;
wherein $R_7$ is H, Cl, Br, F, OH, $CH_3$, $OCH_3$, $SCH_3$, CN, CCH, CF, $OCF_3$, $SCF_3$, $NO_2$, butyl, t-butyl, dimethylamino, phenyl, n-propyl, i-propyl, $-NH-C(O)-CH$, $-CH=CH-COOH$, piperazin-1-yl, or $R_7$ and $R_8$ are bonded together to form a substituted or unsubstituted, saturated or unsaturated aliphatic ring, heterocyclic ring or benzene ring;

wherein $R_6$, $R_8$, $R_{14}$, $R_{16}$, $R_{25}$ and $R_{27}$ are independently H, OH, Cl, F, Br, $CH_3$, CN, $OCH_3$, COOH, $NO_2$, $CF_3$, $R_6$ and $R_7$ bond together to form a substituted or unsubstituted, saturated or unsaturated aliphatic ring, heterocyclic ring, or benzene ring, $R_{14}$ and $R_{15}$ are bonded together to form a substituted or unsubstituted, saturated or unsaturated aliphatic ring, heterocyclic ring or benzene ring, $R_8$ and $R_9$ are bonded together to form a substituted or unsubstituted, saturated or unsaturated aliphatic ring, heterocyclic ring or benzene ring, or $R_{14}$ and $R_{15}$ are bonded together to form a substituted or unsubstituted saturated or unsaturated aliphatic ring, heterocyclic ring or benzene ring;

wherein $R_5$, $R_9$, $R_{17}$, $R_{24}$ and $R_{26}$ are independently H, O, OH, Cl, F, Br, $NH_2$, $CH_3$, $CF_3$, $OCH_3$, CN, $NO_2$, phenyl, $-NH-CH(OH)-CH_3$, $-NH-C(O)-CH_3$, or $R_9$ and $R_8$ are bonded together to form a substituted or unsubstituted, saturated or unsaturated aliphatic ring, heterocyclic ring or benzene ring, or $R_{13}$ and $R_{14}$ are bonded together to form a substituted or unsubstituted saturated or unsaturated aliphatic ring, heterocyclic ring or benzene ring;

wherein $R_{10}$, $R_{11}$, $R_{19}$, $R_{20}$, $R_{22}$ and $R_{23}$ are independently H, Cl, or Br, or $R_{10}$ and $R_{11}$ are bonded together to form a substituted or unsubstituted, saturated or unsaturated aliphatic ring, heterocyclic ring or benzene ring, or $R_{19}$ and $R_{20}$ are bonded together to form a substituted or unsubstituted, saturated or unsaturated aliphatic ring, heterocyclic ring or benzene ring, or $R_{22}$ and $R_{23}$ are bonded together to form a substituted or unsubstituted, saturated or unsaturated aliphatic ring, heterocyclic ring or benzene ring;

wherein $R_{12}$, $R_{16}$ and $R_{21}$ are independently H, COOH, $CH_2NH_2$, $CH_2OH$, methyl, ethyl, propyl, butyl, cyclopentyl, or $R_{12}$ and $R_{13}$ are bonded together to form a pyrrolidinyl oxindole ring;

wherein $R_{15}$ and $R_{26}$ are independently H, Cl, Br, F, OH, $CH_3$, $OCH_3$, $SCH_3$, CN, $CF_3$, $OCF_3$, $SCF_3$, $NO_2$, CCH, n-butyl, t-butyl, dimethylamino, phenyl, n-propyl, i-propyl, $-NH-C(O)-CH_3$, $-CH=CH-COOH$, piperazin-1-yl, or $R_{15}$ and $R_{14}$ are bonded together to form a substituted or unsubstituted, saturated or unsaturated aliphatic ring, heterocyclic ring or benzene ring; and wherein "----" is a double bond or a single bond.

The compound of Formula I is preferably a chloride salt.

In another aspect of the invention, there is provided a compound, or a stereoisomer, tautomer, pharmaceutically acceptable salt, or prodrug thereof, selected from the list of compounds presented in FIG. 1. Where a salt is presented in FIG. 1, the invention covers both the salt as presented and the freebase of that salt, and stereoisomers, tautomers, other pharmaceutically acceptable salts, and also other prodrugs of the freebase.

Preferably, the compound is a compound of Formula I, or a stereoisomer, tautomer, pharmaceutically acceptable salt, or prodrug thereof,
wherein $A_0$ is C;
wherein $A_1$ is N; or Formula VII;
wherein $A_2$ is N; or NH;
wherein $A_3$, $A_4$, $A_6$, $A_7$, $A_{11}$, $A_{12}$, $A_{14}$, $A_{15}$, are N; or C;
wherein $A_5$, $A_{13}$, $A_{23}$, $A_{24}$, $A_{25}$, $A_{26}$ and $A_{27}$ are C;
wherein $A_8$ and $A_{21}$ are S;
wherein $A_9$ is NH;
wherein $A_{10}$ is N;
wherein $A_{22}$ is $-N-CH-$; $-N-C(CH_3)-$; or $-N-C(CH_2OH)-$;

wherein $R_1$ is H; Formula II; Formula III; cycloalkyl;
wherein $R_2$ is H; methyl; ethyl; $CH_2NHNH_2$; $CH_2OH$; butyl; cyclopentyl; or Formula VII and $R_2$ is bonded to $R_4$, to form a pyrimidine ring;
wherein $R_3$ is $NH_2$; Formula IV; Formula V; Formula VI; $NH_2$, $NH-N=CH-$ cycloalkyl; or $O-CH_2-CH_3$;
wherein $R_4$ is NH; O; S; or $R_4$ is N and $R_4$ and $R_2$ are bonded together to form a pyrimidine ring;
wherein $R_7$ is H; F; Cl; $CF_3$; methyl; $R_7$ and $R_8$ are bonded together to form an unsubstituted, benzene ring; OH; t-butyl; phenyl; dimethylamino; i-propyl; n-propyl; CN; CCH; n-butyl; $SCH_3$; $R_7$ and $R_8$ are bonded together to form an unsubstituted, unsaturated heterocyclic ring; $OCH_3$; Br, $OCF_3$; piperazin-1-yl; or $SCF_3$;
wherein $R_6$, $R_8$, $R_{14}$, and $R_{16}$ are independently H; OH; F; $OCH_3$; $CF_3$; methyl; Cl; CN; Br; $R_8$ and $R_7$ are bonded together to form an unsubstituted, benzene ring;
$R_8$ and $R_7$ are bonded together to form an unsubstituted, unsaturated heterocyclic ring; $R_{14}$ and $R_{15}$ are bonded together to form an unsubstituted, benzene ring; or $R_{14}$ and $R_{15}$ are bonded together to form an unsubstituted, unsaturated heterocyclic ring;
wherein $R_5$, $R_9$, $R_{13}$, and $R_{17}$ are independently H; OH; $NH_2$; Cl; F; $OCH_3$; OH; $-NH-CH(OH)-CH_3$;
wherein $R_{12}$ is H; methyl; ethyl; $CH_2OH$; or cyclopentyl;
wherein $R_{15}$ is H; F; Cl; $CF_3$; methyl; $R_7$ and $R_8$ are bonded together to form an unsubstituted, benzene ring; OH; t-butyl; phenyl; dimethylamino; i-propyl; n-propyl; CN; CCH; n-butyl; $SCH_3$; $R_{15}$ and $R_{14}$ are bonded together to form an unsubstituted, unsaturated heterocyclic ring; $OCH_3$; Br; $OCF_3$; piperazin-1-yl; or $SCF_3$;
wherein $R_{24}$ and $R_{28}$ are independently H; OH; or Cl;
wherein $R_{25}$ and $R_{27}$ are independently H; or OH;
wherein $R_{26}$ is H; $CH_3$; Br; Cl; OH; dimethylamino; $-O-P(O)(OEt)_2$; $CF_3$; or F; and
wherein "----" is independently a single or a double bond.

More preferably, the compound is a compound of Formula I, or a stereoisomer, tautomer, pharmaceutically acceptable salt, or prodrug thereof, selected from the group comprising: NCL008; NCL009; NCL023; NCL025; NCL026; NCL029; NCL036; NCL037; NCL039; NCL040; NCL050; NCL061; NCL064; NCL065; NCL068; NCL075; NCL076; NCL078; NCL079; NCL080; NCL081; NCL084; NCL085; NCL086; NCL088; NCL089; NCL090; NCL092; NCL094; NCL095; NCL097; NCL098; NCL099; NCL101; NCL104; NCL105; NCL106; NCL108; NCL111; NCL112; NCL114; NCL115; NCL116; NCL118; NCL119; NCL121; NCL122; NCL123; NCL124; NCL125; NCL126; NCL130; NCL131; NCL132; NCL133; NCL135; NCL136; NCL137; NCL138; NCL139; NCL140; NCL141; NCL144; NCL145; NCL146; NCL147; NCL148; NCL150; NCL152; NCL153; NCL154; NCL156; NCL157; NCL158; NCL159; NCL161; NCL162; NCL164; NCL165; NCL166; NCL167; NCL168; NCL169; NCL170; NCL171; NCL172; NCL173; NCL174; NCL176; NCL177; NCL178; NCL179; NCL180; NCL181; NCL183; NCL184; NCL185; NCL186; NCL187; NCL188; NCL189; NCL190; NCL193; NCL194; NCL195; NCL196; NCL197; NCL198; NCL199; NCL200; NCL201; NCL202; NCL203; NCL204; NCL205; NCL206; NCL207; NCL208; NCL209; NCL210; NCL211; NCL212; NCL213; NCL215; NCL216; NCL217; NCL218; NCL219; NCL220; NCL221; NCL222; NCL223; NCL224; NCL225; NCL226; NCL227; NCL228; NCL229; and NCL230.

Even more preferably, the compound is a compound of Formula I, or a stereoisomer, tautomer, pharmaceutically acceptable salt, or prodrug thereof, selected from the group comprising: NCL040; NCL078; NCL079; NCL080; NCL081; NCL084; NCL088; NCL089; NCL097; NCL099; NCL123; NCL146; NCL157; NCL158; NCL177; NCL179; NCL188; NCL193; NCL195; NCL196; NCL197; NCL199; NCL202; NCL204; NCL205; NCL215; NCL216; NCL217; NCL219; and NCL221.

Even more preferably, the compound is a compound of Formula I, or a stereoisomer, tautomer, pharmaceutically acceptable salt, or prodrug thereof, selected from the group comprising: NCL078; NCL079; NCL080; NCL081; NCL084; NCL089; NCL097; NCL157; NCL158; NCL179; NCL188; NCL193; NCL195; NCL196; NCL199; NCL204; NCL216; NCL217; NCL219; and NCL221.

Even more preferably, the compound is a compound of Formula I, or a stereoisomer, tautomer, pharmaceutically acceptable salt, or prodrug thereof, selected from the group comprising: NCL089; NCL097; NCL157; NCL179; NCL188; NCL193; NCL195; NCL196; NCL216; NCL219; and NCL221.

Most preferably, the compound is a compound of Formula I, or a stereoisomer, tautomer, pharmaceutically acceptable salt, or prodrug thereof, selected from the group comprising: NCL097; NCL157; NCL179; NCL188; NCL195; and NCL196.

In one preferred embodiment of the invention, the compound is a compound of Formula I, or a stereoisomer, tautomer, pharmaceutically acceptable salt, or prodrug thereof, wherein the compound is not a compound selected from the group consisting of: NCL812, NCL001, NCL002, NCL003, NCL004, NCL005, NCL006, NCL007, NCL010, NCL011, NCL012, NCL013, NCL014, NCL015, NCL016, NCL017, NCL018, NCL019, NCL020, NCL021, NCL022, NCL024, NCL027, NCL028, NCL030, NCL031. NCL032, NCL033, NCL034, NCL035, NCL038, NCL041, NCL042, NCL043, NCL044, NCL045, NCL046 NCL047, NCL048, NCL049, NCL051, NCL052, NCL053, NCL054, NCL055, NCL056, NCL057, NCL058, NCL059, NCL060, NCL062, NCL063, NCL066, NCL067, NCL069, NCL070, NCL071, NCL072, NCL073, NCL074, NCL077, NCL082, NCL083, NCL087, NCL091, NCL093, NCL096, NCL100, NCL102, NCL103, NCL107, NCL109, NCL110, NCL113, NCL117, NCL120, NCL127, NCL128, NCL129, NCL134, NCL142, NCL143, NCL149, NCL151, NCL155, NCL160, NCL163, NCL175, NCL182, NCL191, NCL192, and NCL214.

In a preferred aspect of the invention, the compound of Formula I is not robenidine (also referenced in this specification as NCL812 and also known as 1,3-bis[(E)-(4-chlorophenyl)methyleneamino]guanidine), which has a structure as follows:

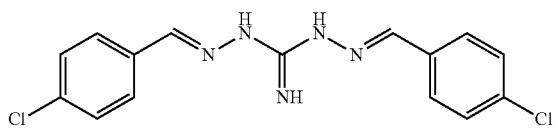 [SMILES: N=C(N/N=C/c1ccc(Cl)cc1)N/N=C/c1ccc(Cl)cc1]

In one preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0, A_3, A_4, A_5, A_6, A_7, A_{11}, A_{12}, A_{13}, A_{14}$ and $A_{15}$, are C; $R_2, R_5, R_6, R_7, R_9, R_{12}, R_{13}, R_{15}, R_{16}, R_{17}$ are H; $R_4$ is O; $R_8$ and $R_{14}$ are $CF_3$; and "----" in Formula I between $A_0$ and $A_1$, all Formula II and all Formula IV "----" are double bonds. An example of a compound of this embodiment of the invention includes:

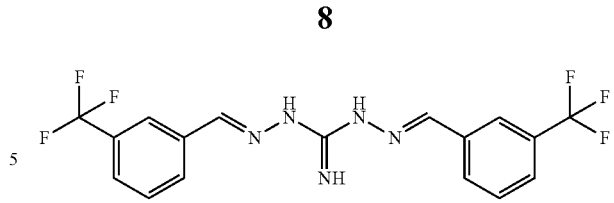

In another preferred embodiment of the invention, the compound is a compound of Formula I, or a stereoisomer, tautomer, pharmaceutically acceptable salt, or prodrug thereof, wherein $R_1$ is Formula II; R is $NH_2$; $A_1$ is N and $A_2$ is NH; $A_0, A_3, A_4, A_5, A_6,$ and $A_7$ are C; $R_2, R_5, R_6, R_7,$ and $R_8$ are H; $R_4$ is NH; $R_9$ is Cl; and "----" in Formula I between $A_0$ and $A_1$ and all Formula II "----" are double bonds. An example of a compound of this embodiment of the invention includes:

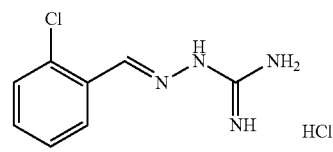 [SMILES: N=C(N)N/N=C/c1ccccc1Cl ; Cl]

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0, A_3, A_4, A_5, A_6, A_7, A_{11}, A_{12}, A_{13}, A_{14}$ and $A_{15}$, are C; $R_2, R_5, R_6, R_8, R_9, R_{12}, R_{13}, R_{14}, R_{16}, R_{17}$ are H; $R_4$ is NH; $R_7$ and $R_{15}$ are F; and "----" in Formula I between $A_0$ and $A_1$, all Formula II and all Formula IV "----" are double bonds. An example of a compound of this embodiment of the invention includes:

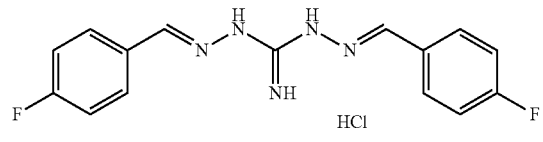 [SMILES: N=C(N/N=C/c1ccc(F)cc1)N/N=C/c1ccc(F)cc1 ; Cl]

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0, A_3, A_4, A_5, A_6, A_7, A_{11}, A_{12}, A_{13}, A_{14}$ and $A_{15}$, are C; $R_2, R_5, R_6, R_7, R_9, R_{12}, R_{14}, R_{15}, R_{16}, R_{17}$ are H; $R_4$ is NH; $R_8$ and $R_{14}$ are F; and "----" in Formula I between $A_0$ and $A_1$, all Formula II and all Formula IV "----" are double bonds. An example of a compound of this embodiment of the invention includes:

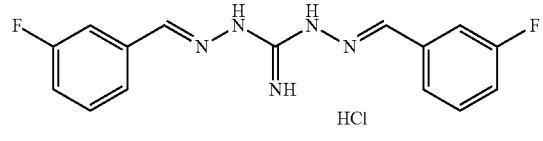 [SMILES: N=C(N/N=C/c1cccc(F)c1)N/N=C/c1cccc(F)c1 ; Cl]

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV $A_1$ and $A_{10}$ are N; $A_2$ and $A_9$ are NH; $A_0, A_3, A_4, A_5, A_6, A_7, A_{11},$ $A_{12}$, $A_{13}$, $A_{14}$ and $A_{15}$, are C; $R_2$, $R_5$, $R_6$, $R_7$, $R_9$, $R_{12}$, $R_{14}$, $R_{15}$, $R_{16}$, $R_{17}$ are H; $R_4$ is NH; $R_9$ and $R_{13}$ are $OCH_3$; and "----" in Formula I between $A_0$ and $A_1$, all Formula II and all Formula IV "----" are double bonds. An example of a compound of this embodiment of the invention includes:

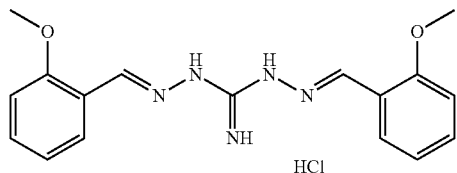 [SMILES: COc1ccccc1/C=N/NC(=N)N/N=C/c1ccccc1OC ; Cl]

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_6$, $R_7$, $R_9$, $R_{12}$, $R_{13}$, $R_{15}$, $R_{16}$, $R_{17}$ are H; $R_4$ is NH; $R_8$ and $R_{14}$ are $OCH_3$; and "----" in Formula I between $A_0$ and $A_1$, all Formula II and all Formula IV "----" are double bonds. An example of a compound of this embodiment of the invention includes:

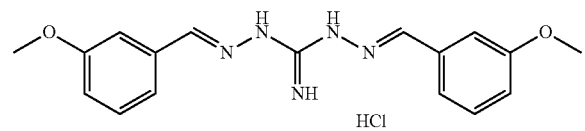

In another preferred embodiment of the invention, the compound is a compound of Formula I, or a stereoisomer, tautomer, pharmaceutically acceptable salt, or prodrug thereof, wherein $R_1$ is Formula II; $R_3$ is $NH_2$; $A_1$ is N; $A_2$ is NH; $A_0$, $A_3$, $A_4$, $A_5$, $A_6$, and $A_7$ are C; $R_2$, $R_5$, $R_6$, $R_8$ and $R_9$ are H; $R_4$ is NH; $R_7$ is Cl; and "----" in Formula I between $A_0$ and $A_1$, and all Formula II "----" are double bonds. An example of a compound of this embodiment of the invention includes:

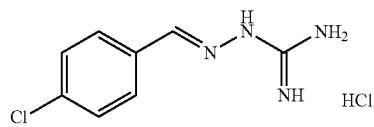 [SMILES: N=C(N)N/N=C/c1ccc(Cl)cc1 ; Cl]

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_6$, $R_8$, $R_9$, $R_{12}$, $R_{13}$, $R_{14}$, $R_{16}$, $R_{17}$ are H; $R_4$ is NH; $R_7$ and $R_{15}$ are $CF_3$; and "----" in Formula I between $A_0$ and $A_1$, all Formula II and Formula IV "----" are double bonds. An example of a compound of this embodiment of the invention includes:

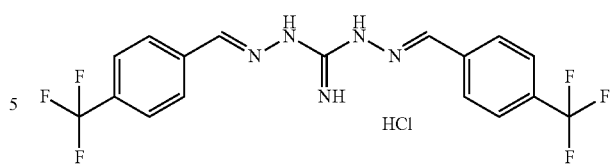

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_6$, $R_8$, $R_9$, $R_{12}$, $R_{13}$, $R_{14}$, $R_{16}$, $R_{17}$ are H; $R_4$ is NH; $R_7$ and $R_{15}$ are methyl; and "----" in Formula I between $A_0$ and $A_1$, all Formula II and Formula IV "----" are double bonds. An example of a compound of this embodiment of the invention includes:

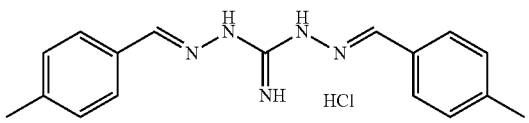

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_6$, $R_7$, $R_9$, $R_{12}$, $R_{14}$, $R_{15}$, $R_{16}$, $R_{17}$ are H; $R_4$ is NH; $R_9$ and $R_{13}$ are methyl; and "----" in Formula I between $A_0$ and $A_1$, all Formula II and Formula IV "----" are double bonds. An example of a compound of this embodiment of the invention includes:

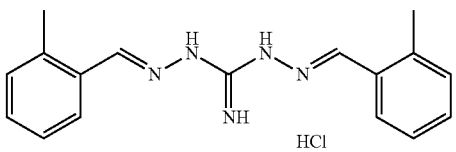 [SMILES: Cc1ccccc1/C=N/NC(=N)N/N=C/c1ccccc1C ; Cl]

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_6$, $R_7$, $R_9$, $R_{12}$, $R_{13}$, $R_{15}$, $R_{16}$ and $R_{17}$ are H; $R_4$ is NH; $R_8$ and $R_{14}$ are methyl; and "----" in Formula I between $A_0$ and $A_1$, all Formula II and Formula IV "----" are double bonds. An example of a compound of this embodiment of the invention includes:

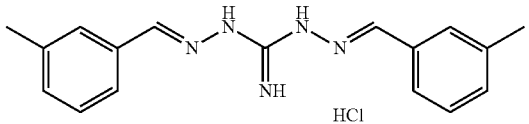

In another preferred embodiment of the invention, the compound is a compound of Formula I, or a stereoisomer, tautomer, pharmaceutically acceptable salt, or prodrug thereof, wherein $R_1$ is Formula II; $R_3$ is $NH_2$; $A_1$ is N; $A_2$ is NH; $A_0$, $A_3$, $A_4$, $A_5$, $A_6$, and $A_7$ are C; $R_2$, $R_5$, $R_6$, $R_8$, and $R_9$ are H; $R_4$ is NH; $R_7$ is $CF_3$; and "----" in Formula I between $A_0$ and $A_1$, and all Formula II "----" are double bonds. An example of a compound of this embodiment of the invention includes:

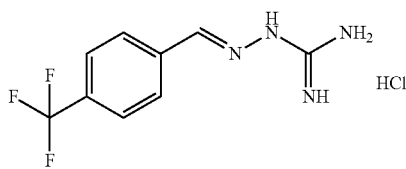 [SMILES: N=C(N)N/N=C/c1ccc(C(F)(F)F)cc1 ; Cl]

In another preferred embodiment of the invention, the compound is a compound of Formula I, or a stereoisomer, tautomer, pharmaceutically acceptable salt, or prodrug thereof, wherein $R_1$ is Formula II; $R_3$ is $NH_2$; $A_1$ is N; $A_2$ is NH; $A_0$, $A_3$, $A_4$, $A_5$, $A_6$, and $A_7$ are C; $R_2$, $R_5$, $R_6$, $R_7$, and $R_9$ are H; $R_4$ is NH; $R_8$ is $CF_3$; and "----" in Formula I between $A_0$ and $A_1$, and all Formula II "----" are double bonds. An example of a compound of this embodiment of the invention includes:

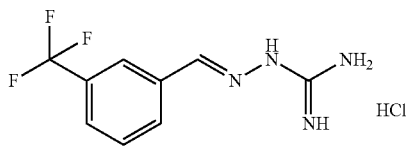 [SMILES: N=C(N)N/N=C/c1cccc(C(F)(F)F)c1 ; Cl]

In another preferred embodiment of the invention, the compound is a compound of Formula I, or a stereoisomer, tautomer, pharmaceutically acceptable salt, or prodrug thereof, wherein $R_1$ is Formula II; $R_3$ is $NH_2$; $A_1$ is N; $A_2$ is NH; $A_0$, $A_3$, $A_4$, $A_5$, $A_6$, and $A_7$ are C; $R_2$, $R_5$, $R_6$, $R_8$, and $R_9$ are H; $R_4$ is NH; $R_7$ is methyl; and "----" in Formula I between $A_0$ and $A_1$, and all Formula II "----" are double bonds. An example of a compound of this embodiment of the invention includes:

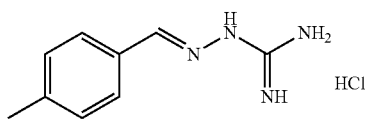

In another preferred embodiment of the invention, the compound is a compound of Formula I, or a stereoisomer, tautomer, pharmaceutically acceptable salt, or prodrug thereof, wherein $R_1$ is Formula II; $R_3$ is $NH_2$; $A_1$ is N; $A_2$ is NH; $A_0$, $A_3$, $A_4$, $A_5$, $A_6$, and $A_7$ are C; $R_2$, $R_5$, $R_6$, $R_7$, and $R_9$ are H; $R_4$ is NH; $R_8$ is Cl; and "----" in Formula I between $A_0$ and $A_1$, and all Formula II "----" are double bonds. An example of a compound of this embodiment of the invention includes:

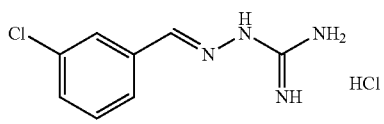 [SMILES: N=C(N)N/N=C/c1cccc(Cl)c1 ; Cl]

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_6$, $R_7$, $R_9$, $R_{12}$, $R_{13}$, $R_{15}$, $R_{16}$, $R_{17}$ are H; $R_4$ is NH; $R_8$ and $R_{14}$ are Cl; and "----" in Formula I between $A_0$ and $A_1$, all Formula II and Formula IV "----" are double bonds. An example of a compound of this embodiment of the invention includes:

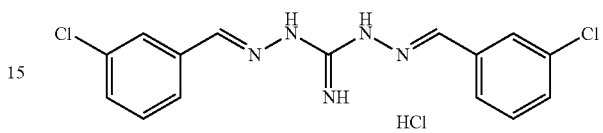

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$ and $R_{12}$ are methyl; $R_5$, $R_6$, $R_8$, $R_9$, $R_{13}$, $R_{14}$, $R_{16}$, $R_{17}$ are H; $R_4$ is NH; $R_7$ and $R_{15}$ are $CF_3$; and "----" in Formula I between $A_0$ and $A_1$, all Formula II and Formula IV "----" are double bonds. An example of a compound of this embodiment of the invention includes:

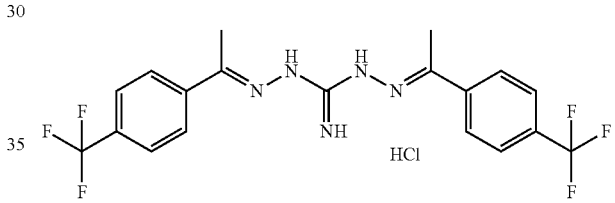

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$ and $R_{12}$ are methyl; $R_5$, $R_6$, $R_8$, $R_9$, $R_{13}$, $R_{14}$, $R_{16}$ and $R_{17}$ are H; $R_4$ is NH; $R_7$ and $R_{15}$ are Cl; and "----" in Formula I between $A_0$ and $A_1$, all Formula II and Formula IV "----" are double bonds. An example of a compound of this embodiment of the invention includes:

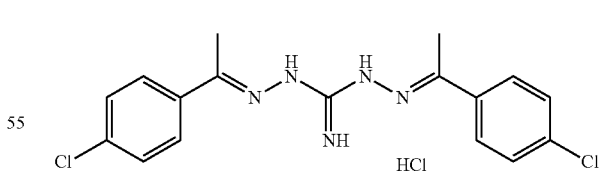

In another preferred embodiment of the invention, the compound is a compound of Formula I, or a stereoisomer, tautomer, pharmaceutically acceptable salt, or prodrug thereof, wherein $R_1$ is Formula II; $R_3$ is $NHNH_2$; $A_1$ is N; $A_2$ is NH; $A_0$, $A_3$, $A_4$, $A_5$, $A_6$, and $A_7$ are C; $R_2$ is methyl, $R_5$, $R_6$, $R_8$ and $R_9$ are H; $R_4$ is NH; $R_7$ is Cl; and "----" in Formula I between $A_0$ and $A_1$, and all Formula II "----" are double bonds. An example of a compound of this embodiment of the invention includes:

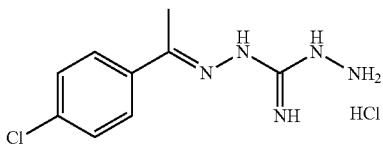

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_6$, $R_7$, $R_9$, $R_{12}$, $R_{13}$, $R_{15}$, $R_{16}$, and $R_{17}$ are H; $R_4$ is S; $R_8$ and $R_{14}$ are Cl; and "----" in Formula I between $A_0$ and $A_1$, all Formula II and Formula IV "----" are double bonds. An example of a compound of this embodiment of the invention includes:

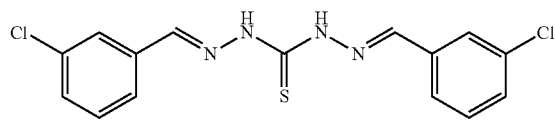 [SMILES: S=C(N/N=C/c1cccc(Cl)c1)N/N=C/c1cccc(Cl)c1]

In another preferred embodiment of the invention, the compound is a compound of Formula I, or a stereoisomer, tautomer, pharmaceutically acceptable salt, or prodrug thereof, wherein $R_1$ is Formula II; $R_3$ is $NH_2$; $A_1$ is N; $A_2$ is NH; $A_0$, $A_3$, $A_4$, $A_5$, $A_6$, and $A_7$ are C; $R_2$, $R_5$, $R_6$, $R_8$, and $R_9$ are H; $R_4$ is NH; $R_7$ is Cl; and "----" in Formula I between $A_0$ and $A_1$, and all Formula II "----" are double bonds. An example of a compound of this embodiment of the invention includes:

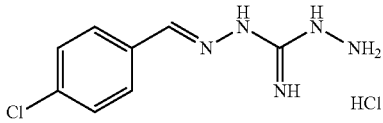 [SMILES: N=C(NN)N/N=C/c1ccc(Cl)cc1 ; Cl]

In another preferred embodiment of the invention, the compound is a compound of Formula I, or a stereoisomer, tautomer, pharmaceutically acceptable salt, or prodrug thereof, wherein $R_1$ is Formula II; $R_3$ is $NHNH_2$; $A_1$ is N; $A_2$ is NH; $A_0$, $A_3$, $A_4$, $A_5$, $A_6$, and $A_7$ are C; $R_2$ is methyl; $R_5$, $R_6$, $R_8$, and $R_9$ are H; $R_4$ is NH; $R_7$ is $CF_3$; and "----" in Formula I between $A_0$ and $A_1$, and all Formula II "----" are double bonds. An example of a compound of this embodiment of the invention includes:

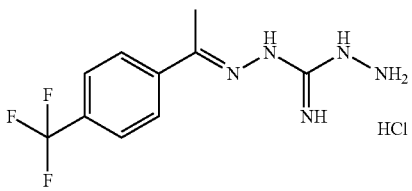 [SMILES: C/C(=N\NC(=N)NN)c1ccc(C(F)(F)F)cc1 ; Cl]

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_6$, $R_8$, $R_9$, $R_{12}$, $R_{13}$, $R_{14}$, and $R_{16}$ are H; $R_4$ is NH; $R_7$, $R_{15}$ and $R_{17}$ are Cl; and "----" in Formula I between $A_0$ and $A_1$, all Formula II and Formula IV "----" are double bonds. An example of a compound of this embodiment of the invention includes:

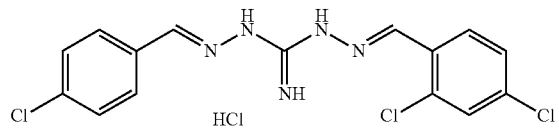 [SMILES: N=C(N/N=C/c1ccc(Cl)cc1)N/N=C/c1ccc(Cl)cc1Cl ; Cl]

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_6$, $R_8$, $R_9$, $R_{12}$, $R_{13}$, $R_{14}$, and $R_{16}$ are H; $R_4$ is NH; $R_7$ is Cl; $R_{15}$ is $CF_3$; $R_{17}$ is F; and "----" in Formula I between $A_0$ and $A_1$, all Formula II and Formula IV "----" are double bonds. An example of a compound of this embodiment of the invention includes (NCL078):

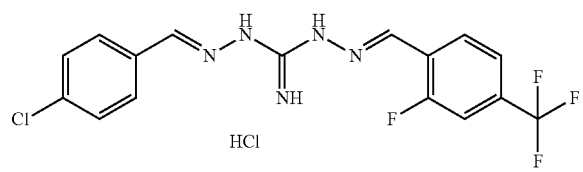 [SMILES: N=C(N/N=C/c1ccc(Cl)cc1)N/N=C/c1ccc(C(F)(F)F)cc1F ; Cl]

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_6$, $R_8$, $R_9$, $R_{12}$, $R_{13}$, $R_{14}$, $R_{16}$ and $R_{17}$ are H; $R_4$ is NH; $R_7$ is Cl; $R_{15}$ is F; and "----" in Formula I between $A_0$ and $A_1$, all Formula II and Formula IV "----" are double bonds. An example of a compound of this embodiment of the invention includes (NCL079):

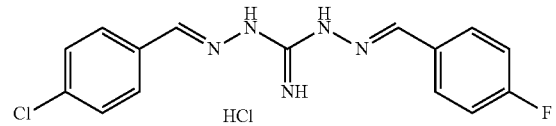 [SMILES: N=C(N/N=C/c1ccc(F)cc1)N/N=C/c1ccc(Cl)cc1 ; Cl]

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_6$, $R_8$, $R_9$, $R_{13}$, $R_{14}$, $R_{16}$ and $R_{17}$ are H; $R_4$ is NH; $R_7$ is Cl; $R_{12}$ is methyl; $R_{15}$ is $CF_3$; and "----" in Formula I between $A_0$ and $A_1$, all Formula II and Formula IV "----" are double bonds. An example of a compound of this embodiment of the invention includes (NCL080):

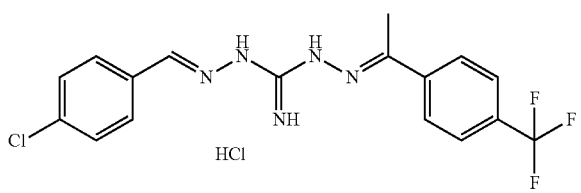 [SMILES: C/C(=N\NC(=N)N/N=C/c1ccc(Cl)cc1)c1ccc(C(F)(F)F)cc1 ; Cl]

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_6$, $R_8$, $R_9$, $R_{13}$, $R_{14}$, $R_{16}$ and $R_{17}$ are H; $R_4$ is NH; $R_7$ and $R_{15}$ are Cl; $R_{12}$ is methyl; and "----" in Formula I $A_0$ and $A_1$, all Formula II and Formula IV "----" are double bonds. An example of a compound of this embodiment of the invention includes:

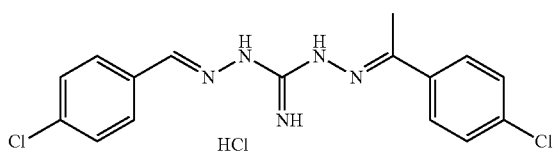 [SMILES: C/C(=N\NC(=N)N/N=C/c1ccc(Cl)cc1)c1ccc(Cl)cc1 ; Cl]

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_6$, $R_8$, $R_9$, $R_{12}$, $R_{13}$, $R_{14}$, $R_{15}$, and $R_{16}$ are H; $R_4$ is NH; $R_7$ and $R_{17}$ are Cl; and "----" in Formula I between $A_0$ and $A_1$, all Formula II and Formula IV "----" are double bonds. An example of a compound of this embodiment of the invention includes:

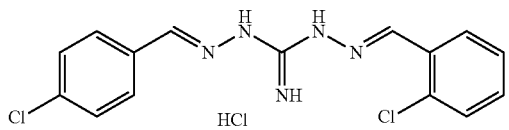 [SMILES: N=C(N/N=C/c1ccc(Cl)cc1)N/N=C/c1ccccc1Cl ; Cl]

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_6$, $R_8$, $R_9$, $R_{12}$, $R_{13}$, $R_{14}$, and $R_{16}$ are H; $R_4$ is NH; $R_7$ and $R_{15}$ are Cl; $R_{17}$ is F; and "----" in Formula I between $A_0$ and $A_1$, all Formula II and Formula IV "----" are double bonds. An example of a compound of this embodiment of the invention includes (NCL084):

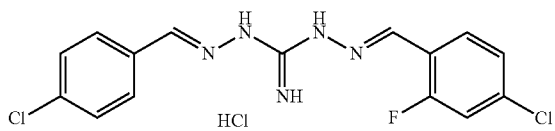 [SMILES: N=C(N/N=C/c1ccc(Cl)cc1)N/N=C/c1ccc(Cl)cc1F ; Cl]

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_6$, $R_8$, $R_9$, $R_{12}$, $R_{13}$, $R_{15}$, $R_{16}$, and $R_{17}$ are H; $R_4$ is NH; $R_7$ is Cl; $R_{14}$ is CN; and "----" in Formula I between $A_0$ and $A_1$, all Formula II and Formula IV "----" are double bonds. An example of a compound of this embodiment of the invention includes:

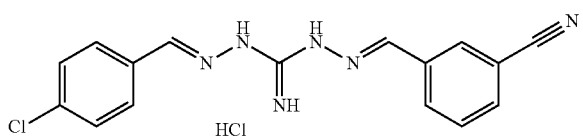 [SMILES: N#Cc1cccc(/C=N/NC(=N)N/N=C/c2ccc(Cl)cc2)c1 ; Cl]

In another preferred embodiment of the invention, the compound is a compound of Formula I, or a stereoisomer, tautomer, pharmaceutically acceptable salt, or prodrug thereof, wherein $R_1$ is Formula $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_6$, $R_8$, $R_9$, $R_{12}$, $R_{13}$, $R_{14}$, $R_{15}$, and $R_{16}$ are H; $R_4$ is NH; $R_7$ is Cl; $R_{17}$ is F; and "----" in Formula I between $A_0$ and $A_1$, all Formula II and Formula IV "----" are double bonds. An example of a compound of this embodiment of the invention includes:

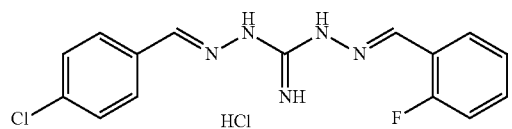 [SMILES: N=C(N/N=C/c1ccc(Cl)cc1)N/N=C/c1ccccc1F ; Cl]

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$ and $R_{12}$ are methyl; $R_5$, $R_6$, $R_8$, $R_9$, $R_{13}$, $R_{14}$, $R_{16}$, and $R_{17}$ are H; $R_4$ is NH; $R_7$ is Cl; $R_{15}$ is $CF_3$; and "----" in Formula I between $A_0$ and $A_1$, all Formula II and Formula IV "----" are double bonds. An example of a compound of this embodiment of the invention includes (NCL089):

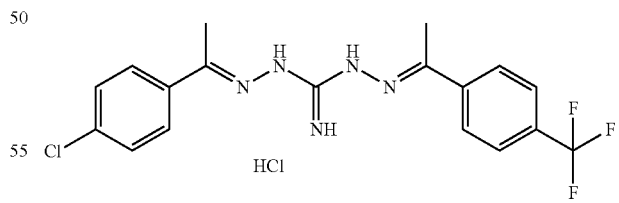

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_6$, $R_9$, $R_{12}$, $R_{13}$, $R_{16}$, and $R_{17}$ are H; $R_4$ is NH; $R_7$ and $R_8$ are bonded together to form an unsubstituted, benzene ring; $R_{14}$ and $R_{15}$ are bonded together to form an unsubstituted, benzene ring; and "----"

in Formula I between $A_0$ and $A_1$, all Formula II and Formula IV "----" are double bonds. An example of a compound of this embodiment of the invention includes:

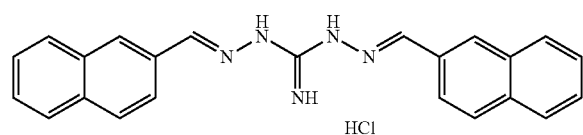 [SMILES: N=C(N/N=C/c1ccc2ccccc2c1)N/N=C/c1ccc2ccccc2c1 ; Cl]

In another preferred embodiment of the invention, the compound is a compound of Formula I, or a stereoisomer, tautomer, pharmaceutically acceptable salt, or prodrug thereof, wherein $A_0$ is C; $A_1$ is N; $A_2$ is NH; $R_1$ is cyclohexyl; $R_3$ is NH—N=CH-cyclohexyl; $R_4$ is NH; $R_2$ is H; and "----" in Formula I between $A_0$ and $A_1$ is a double bond. An example of a compound of this embodiment of the invention includes:

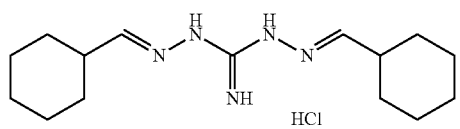 [SMILES: N=C(N/N=C/C1CCCCC1)N/N=C/C1CCCCC1 ; Cl]

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{12}$, $A_{13}$, $A_{14}$ and $A_{15}$, are C; $R_2$, $R_5$, $R_9$, $R_{12}$, $R_{13}$ and $R_{17}$ are H; $R_4$ is NH; $R_6$, $R_7$, $R_8$, $R_{14}$, $R_{15}$, and $R_{16}$ are OH; and "----" in Formula I between $A_0$ and $A_1$, all Formula II and Formula IV "----" are double bonds. An example of a compound of this embodiment of the invention includes (NCL097):

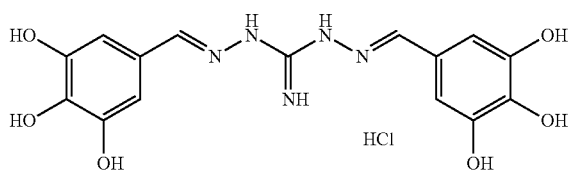 [SMILES: N=C(N/N=C/c1cc(O)c(O)c(O)c1)N/N=C/c1cc(O)c(O)c(O)c1 ; Cl]

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_6$, $R_8$, $R_9$, $R_{12}$, $R_{13}$, $R_{14}$, $R_{16}$ and $R_{17}$ are H; $R_4$ is NH; $R_7$ and $R_{15}$ are t-butyl; and "----" in Formula I between $A_0$ and $A_1$, all Formula II and Formula IV "----" are double bonds. An example of a compound of this embodiment of the invention includes:

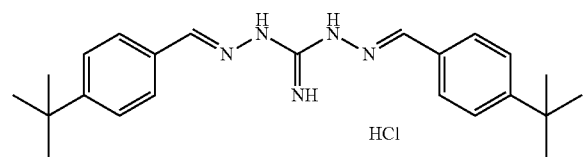 [SMILES: CC(C)(C)c1ccc(/C=N/NC(=N)N/N=C/c2ccc(C(C)(C)C)cc2)cc1 ; Cl]

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_7$, $R_8$, $R_9$, $R_{12}$, $R_{13}$, $R_{14}$, and $R_{15}$ are H; $R_4$ is NH; $R_5$, $R_6$, $R_{16}$, and $R_{17}$ are OH; and "----" in Formula I between $A_0$ and $A_1$, all Formula II and Formula IV "----" are double bonds. An example of a compound of this embodiment of the invention includes:

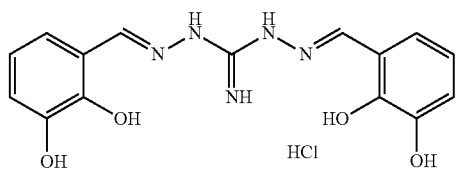 [SMILES: N=C(N/N=C/c1cccc(O)c1O)N/N=C/c1cccc(O)c1O ; Cl]

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_8$, $R_{12}$, $R_{14}$, and $R_{17}$ are H; $R_4$ is NH; $R_6$, $R_7$, $R_9$, $R_{13}$, $R_{15}$, and $R_{16}$ are OH; and "----" in Formula I between $A_0$ and $A_1$, all Formula II and Formula IV "----" are double bonds. An example of a compound of this embodiment of the invention includes:

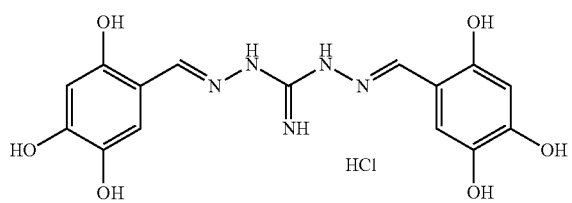 [SMILES: N=C(N/N=C/c1cc(O)c(O)cc1O)N/N=C/c1cc(O)c(O)cc1O ; Cl]

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_6$, $R_{12}$, $R_{16}$, and $R_{17}$ are H; $R_4$ is NH; $R_7$, $R_8$, $R_9$, $R_{13}$, $R_{14}$, and $R_{15}$ are OH; and "----" in Formula I between $A_0$ and $A_1$, all Formula II and Formula IV "----" are double bonds. An example of a compound of this embodiment of the invention includes (NCL097):

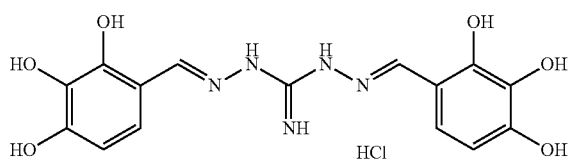 [SMILES: N=C(N/N=C/c1ccc(O)c(O)c1O)N/N=C/c1ccc(O)c(O)c1O ; Cl]

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_6$, $R_7$, $R_8$, $R_9$, $R_{12}$, $R_{13}$, $R_{14}$, $R_{15}$, and $R_{16}$ are H; $R_4$ is NH; $R_5$ and $R_{17}$ are OH; and "----" in Formula I between $A_0$ and $A_1$, all Formula II and Formula IV "----" are double bonds. An example of a compound of this embodiment of the invention includes:

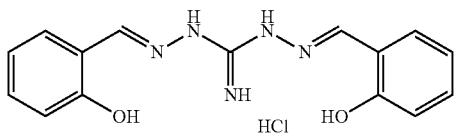 [SMILES: N=C(N/N=C/c1ccccc1O)N/N=C/c1ccccc1O ; Cl]

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_7$, $R_8$, $R_9$, $R_{12}$, $R_{13}$, $R_{14}$, $R_{15}$, and $R_{17}$ are H; $R_4$ is NH; $R_8$ and $R_{16}$ are OH; and "----" in Formula I between $A_0$ and $A_1$, all Formula II and Formula IV "----" are double bonds. An example of a compound of this embodiment of the invention includes:

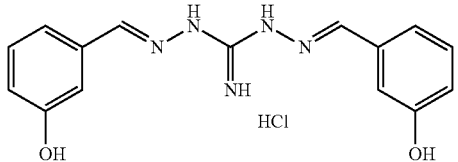 [SMILES: N=C(N/N=C/c1cccc(O)c1)N/N=C/c1cccc(O)c1 ; Cl]

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_8$, $R_9$, $R_{12}$, $R_{13}$, $R_{14}$, and $R_{17}$ are H; $R_4$ is NH; $R_6$, $R_7$, $R_{15}$, and $R_{18}$ are OH; and "----" in Formula I between $A_0$ and $A_1$, all Formula II and Formula IV "----" are double bonds. An example of a compound of this embodiment of the invention includes:

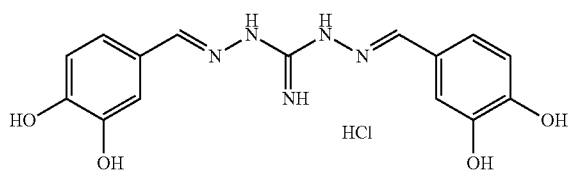 [SMILES: N=C(N/N=C/c1ccc(O)c(O)c1)N/N=C/c1ccc(O)c(O)c1 ; Cl]

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_6$, $R_8$, $R_9$, $R_{12}$, $R_{13}$, $R_{14}$, $R_{16}$, and $R_{17}$ are H; $R_4$ is NH; $R_7$ and $R_{15}$ are phenyl; and "----" in Formula I between $A_0$ and $A_1$, all Formula II and Formula IV "----" are double bonds. An example of a compound of this embodiment of the invention includes:

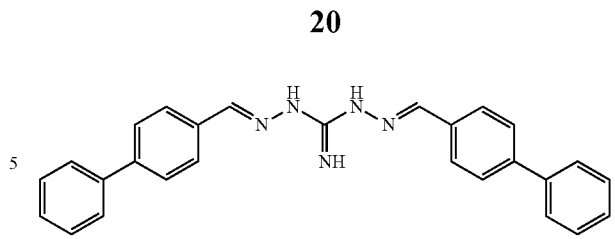

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_6$, $R_8$, $R_9$, $R_{12}$, $R_{13}$, $R_{14}$, $R_{16}$, and $R_{17}$ are H; $R_4$ is NH; $R_7$ and $R_{15}$ are dimethylamino; and "----" in Formula I between $A_0$ and $A_1$, all Formula II and Formula IV "----" are double bonds. An example of a compound of this embodiment of the invention includes:

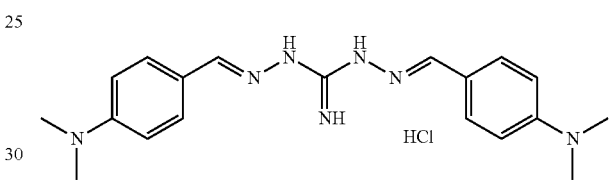

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_8$, $R_9$, $R_{12}$, $R_{13}$, $R_{14}$, and $R_{17}$ are H; $R_4$ is NH; $R_6$ and $R_{18}$ are OCH$_3$; $R_7$ and $R_{15}$ are OH; and "----" in Formula I between $A_0$ and $A_1$, all Formula II and Formula IV "----" are double bonds. An example of a compound of this embodiment of the invention includes:

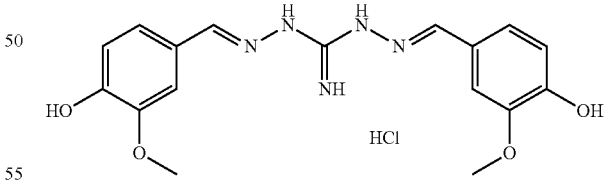

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_6$, $R_8$, $R_9$, $R_{12}$, $R_{13}$, $R_{14}$, $R_{16}$, and $R_{17}$ are H; $R_4$ is NH; $R_7$ and $R_{15}$ are i-propyl; and "----" in Formula I between $A_0$ and $A_1$, all Formula II and Formula IV "----" are double bonds. An example of a compound of this embodiment of the invention includes:

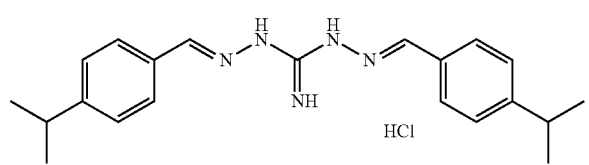 [SMILES: CC(C)c1ccc(/C=N/NC(=N)N/N=C/c2ccc(C(C)C)cc2)cc1 ; Cl]

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_6$, $R_8$, $R_9$, $R_{12}$, $R_{13}$, $R_{14}$, $R_{16}$, and $R_{17}$ are H; $R_4$ is NH; $R_7$ and $R_{15}$ are n-propyl; and "----" in Formula I between $A_0$ and $A_1$, all Formula II and Formula IV "----" are double bonds. An example of a compound of this embodiment of the invention includes:

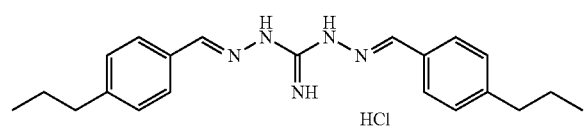 [SMILES: CCCc1ccc(/C=N/NC(=N)N/N=C/c2ccc(CCC)cc2)cc1 ; Cl]

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_0$, $A_7$, $A_{11}$, $A_{12}$, $A_{13}$, $A_{14}$ and $A_{15}$, are C; $R_2$, $R_5$, $R_8$, $R_9$, $R_{12}$, $R_{13}$, $R_{14}$, and $R_{17}$ are H; $R_4$ is NH; $R_6$, $R_7$, $R_{15}$, and $R_{16}$ are F; and "----" in Formula I between $A_0$ and $A_1$, all Formula II and Formula IV "----" are double bonds. An example of a compound of this embodiment of the invention includes:

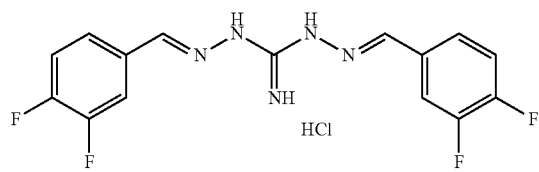 [SMILES: N=C(N/N=C/c1ccc(F)c(F)c1)N/N=C/c1ccc(F)c(F)c1 ; Cl]

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_6$, $R_8$, $R_9$, $R_{12}$, $R_{13}$, $R_{14}$, $R_{16}$, and $R_{17}$ are H; $R_4$ is NH; $R_7$ and $R_{15}$ are CCH; and "----" in Formula I between $A_0$ and $A_1$, all Formula II and Formula IV "----" are double bonds. An example of a compound of this embodiment of the invention includes:

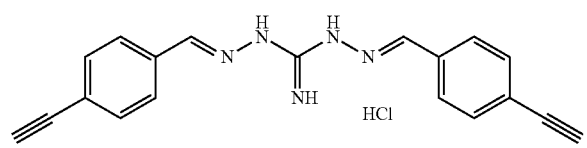 [SMILES: C#Cc1ccc(/C=N/NC(=N)N/N=C/c2ccc(C#C)cc2)cc1 ; Cl]

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_7$, $R_8$, $R_9$, $R_{12}$, $R_{13}$, $R_{14}$, $R_{15}$, and $R_{17}$ are H; $R_4$ is NH; $R_6$ and $R_{18}$ are Br; and "----" in Formula I between $A_0$ and $A_1$, all Formula II and Formula IV "----" are double bonds. An example of a compound of this embodiment of the invention includes:

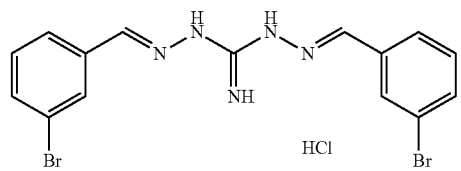 [SMILES: N=C(N/N=C/c1cccc(Br)c1)N/N=C/c1cccc(Br)c1 ; Cl]

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_6$, $R_8$, $R_9$, $R_{12}$, $R_{13}$, $R_{14}$, $R_{16}$, and $R_{17}$ are H; $R_4$ is NH; $R_7$ and $R_{15}$ are butyl; and "----" in Formula I between $A_0$ and $A_1$, all Formula II and Formula IV "----" are double bonds. An example of a compound of this embodiment of the invention includes:

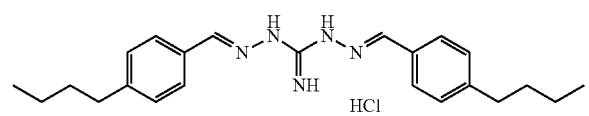 [SMILES: CCCCc1ccc(/C=N/NC(=N)N/N=C/c2ccc(CCCC)cc2)cc1 ; Cl]

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ is —C($C_6H_5$)—CH—N— and $A_{10}$ is —N=CH—C($C_6H_5$)=; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_6$, $R_7$, $R_8$, $R_9$, $R_{12}$, $R_{13}$, $R_{14}$, $R_{15}$, $R_{16}$, and $R_{17}$ are H; $R_4$ is NH; and "----" in Formula I between $A_0$ and $A_1$, all Formula II and Formula IV "----" are double bonds. An example of a compound of this embodiment of the invention includes:

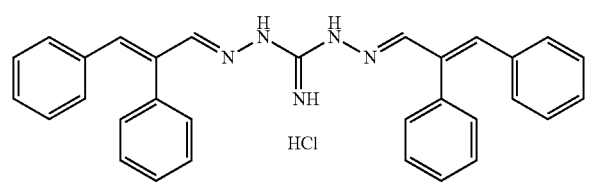 [SMILES: N=C(N/N=C/C(=C/c1ccccc1)c1ccccc1)N/N=C/C(=C/c1ccccc1)c1ccccc1 ; Cl]

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_6$, $R_8$, $R_9$, $R_{12}$, $R_{13}$, $R_{14}$, $R_{16}$, and $R_{17}$ are H; $R_4$ is NH; $R_7$ and $R_{15}$ are $CH_3S$; and "----" in Formula I between $A_0$ and $A_1$, all Formula II and Formula IV "----" are double bonds. An example of a compound of this embodiment of the invention includes:

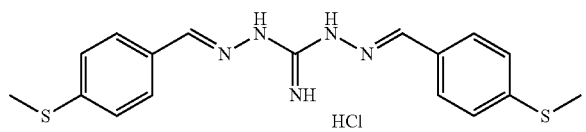

In another preferred embodiment of the invention, the compound is a compound of Formula I, or a stereoisomer, tautomer, pharmaceutically acceptable salt, or prodrug thereof, wherein $R_1$ is Formula III; $R_3$ is Formula VI; $A_0$ is C; $R_2$ and $R_{21}$, are H; $A_1$ and $A_{20}$ are N; $A_2$ and $A_{19}$ are NH; $A_8$ and $A_{21}$ are S; $R_4$ is NH; $R_{10}$ and $R_{11}$ are bonded together to form a substituted benzene ring; $R_{22}$ and $R_{23}$ are bonded together to form a substituted benzene ring; and "----" in Formula I between $A_0$ and $A_1$, and all Formula III and Formula VI "----" are double bonds. An example of a compound of this embodiment of the invention includes:

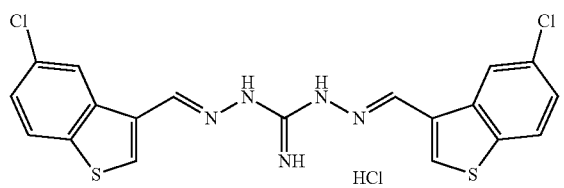 [SMILES: N=C(N/N=C/c1csc2ccc(Cl)cc12)N/N=C/c1csc2ccc(Cl)cc12 ; Cl]

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$ and $R_{12}$ are methyl; $R_5$, $R_6$, $R_7$, $R_8$, $R_9$, $R_{13}$, $R_{14}$, $R_{15}$, $R_{16}$, and $R_{17}$ are H; $R_4$ is NH; and "----" in Formula I between $A_0$ and $A_1$, all Formula II and Formula IV "----" are double bonds. An example of a compound of this embodiment of the invention includes:

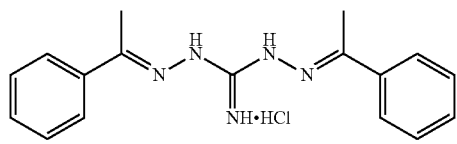

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_6$, $R_9$, $R_{12}$, $R_{13}$, $R_{16}$, and $R_{17}$ are H; $R_4$ is NH; $R_7$ and $R_8$ are bonded together to form an unsubstituted, heterocyclic ring; $R_{14}$ and $R_{15}$ are bonded together to form an unsubstituted, unsaturated heterocyclic ring; and "----" in Formula I between $A_0$ and $A_1$, all Formula II and Formula IV "----" are double bonds. An example of a compound of this embodiment of the invention includes:

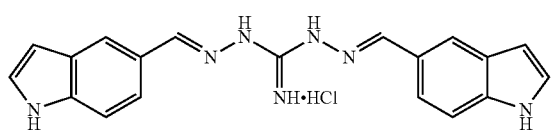

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ is =CH—CH=N— and $A_{10}$ is —N—(CH)$_2$—; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_6$, $R_8$, $R_9$, $R_{12}$, $R_{13}$, $R_{14}$, $R_{16}$, and $R_{17}$ are H; $R_4$ is NH; $R_7$ and $R_{15}$ are OCH$_3$; and "----" in Formula I between $A_0$ and $A_1$, all Formula II and Formula IV "----" are double bonds. An example of a compound of this embodiment of the invention includes:

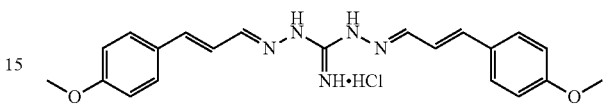

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_6$, $R_8$, $R_9$, $R_{12}$, $R_{13}$, $R_{14}$, $R_{16}$, and $R_{17}$ are H; $R_4$ is NH; $R_7$ and $R_{15}$ are OH; and "----" in Formula I between $A_0$ and $A_1$, all Formula II and Formula IV "----" are double bonds. An example of a compound of this embodiment of the invention includes:

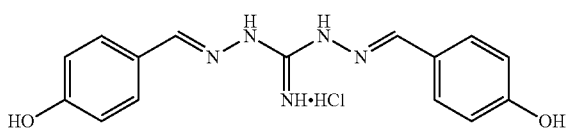

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$ and $R_{12}$ are ethyl; $R_5$, $R_6$, $R_8$, $R_9$, $R_{13}$, $R_{14}$, $R_{16}$, and $R_{17}$ are H; $R_4$ is NH; $R_7$ and $R_{15}$ are Cl; and "----" in Formula I between $A_0$ and $A_1$, all Formula II and Formula IV "----" are double bonds. An example of a compound of this embodiment of the invention includes:

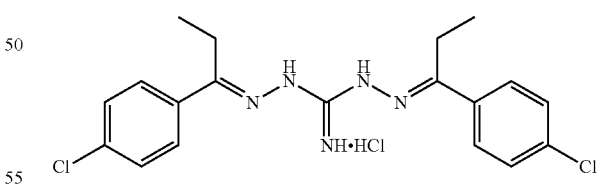

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$ and $R_{12}$ are methyl; $R_5$, $R_6$, $R_8$, $R_9$, $R_{13}$, $R_{14}$, $R_{16}$, and $R_{17}$ are H; $R_4$ is NH; $R_7$ and $R_{15}$ are Br; and "----" in Formula I between $A_0$ and $A_1$, all Formula II and Formula IV "----" are double bonds. An example of a compound of this embodiment of the invention includes:

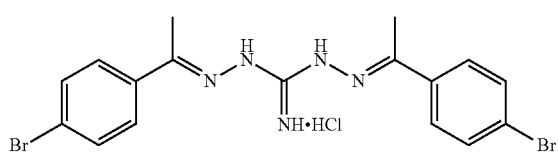

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_6$, $R_8$, $R_{12}$, $R_{14}$, $R_{16}$, and $R_{17}$ are H; $R_4$ is NH; $R_7$ and $R_{15}$ are Cl; $R_9$ and $R_{13}$ are $NH_2$; and "----" in Formula I between $A_0$ and $A_1$, all Formula II and Formula IV "----" are double bonds. An example of a compound of this embodiment of the invention includes (NCL157):

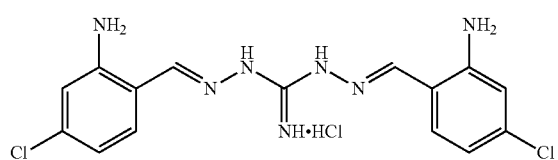

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$ and $R_{12}$ are ethyl; $R_5$ and $R_{17}$ are OH; $R_6$, $R_8$, $R_9$, $R_{13}$, $R_{14}$, and $R_{18}$ are H; $R_4$ is NH; $R_7$ and $R_{15}$ are Cl; and "----" in Formula I between $A_0$ and $A_1$, all Formula II and Formula IV "----" are double bonds. An example of a compound of this embodiment of the invention includes (NCL158):

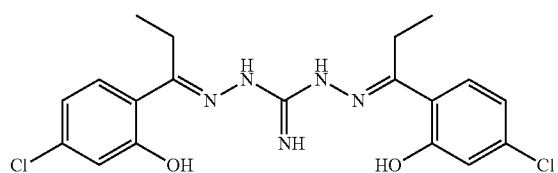 [SMILES: CC/C(=N\NC(=N)N/N=C(\CC)c1ccc(Cl)cc1O)c1ccc(Cl)cc1O]

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{12}$, $A_{13}$, $A_{14}$ and $A_{15}$, are C; $R_2$ and $R_{12}$ are cyclopentyl; $R_5$ and $R_{17}$ are OH; $R_6$, $R_8$, $R_9$, $R_{13}$, $R_{14}$, and $R_{16}$ are H; $R_4$ is NH; $R_7$ and $R_{15}$ are Cl; and "----" in Formula I between $A_0$ and $A_1$, all Formula II and Formula IV "----" are double bonds. An example of a compound of this embodiment of the invention includes:

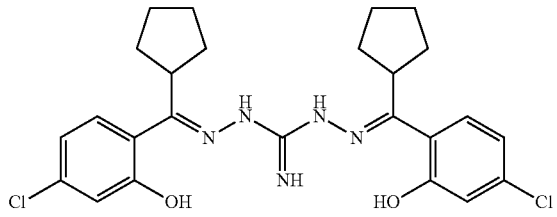 [SMILES: N=C(N/N=C(/c1ccc(Cl)cc1O)C1CCCC1)N/N=C(/c1ccc(Cl)cc1O)C1CCCC1]

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_6$, $R_8$, $R_9$, $R_{12}$, $R_{13}$, $R_{14}$, $R_{16}$ and $R_{17}$ are H; $R_4$ is NH; $R_7$ and $R_{15}$ are $OCF_3$; and "----" in Formula I between $A_0$ and $A_1$, all Formula II and Formula IV "----" are double bonds. An example of a compound of this embodiment of the invention includes:

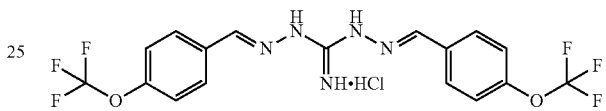

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$ and $R_{12}$ are methyl; $R_5$, $R_6$, $R_8$, $R_9$, $R_{13}$, $R_{14}$, $R_{16}$ and $R_{17}$ are H; $R_4$ is NH; $R_7$ and $R_{15}$ are piperazin-1-yl; and "----" in Formula I between $A_0$ and $A_1$, all Formula II and Formula IV "----" are double bonds. An example of a compound of this embodiment of the invention includes:

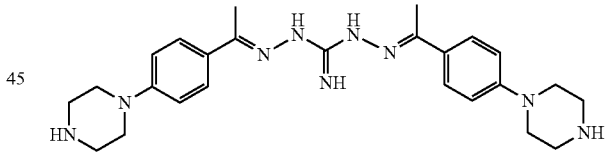

In another preferred embodiment of the invention, the compound is a compound of Formula I, or a stereoisomer, tautomer, pharmaceutically acceptable salt, or prodrug thereof, wherein $R_1$ is Formula II; $R_3$ is $O—CH_2—CH_3$; $A_1$ is N; $A_2$ is NH; $A_0$, $A_3$, $A_4$, $A_5$, $A_8$ and $A_7$ are C; $R_2$ is methyl; $R_5$, $R_6$, $R_8$, and $R_9$ are H; $R_4$ is NH; $R_7$ is Cl; and "----" in Formula I between $A_0$ and $A_1$, and all Formula II "----" are double bonds. An example of a compound of this embodiment of the invention includes:

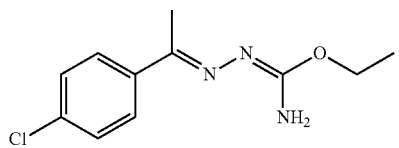 [SMILES: CCO/C(N)=N/N=C(\C)c1ccc(Cl)cc1]

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_6$, $R_8$, $R_9$, $R_{12}$, $R_{13}$, $R_{14}$, $R_{16}$ and $R_{17}$ are H; $R_4$ is NH; $R_7$ and $R_{15}$ are $SCF_3$; and "----" in Formula I between $A_0$ and $A_1$, all Formula II and Formula IV "----" are double bonds. An example of a compound of this embodiment of the invention includes:

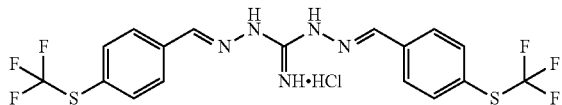

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_6$, $R_8$, $R_9$, $R_{12}$, $R_{13}$, $R_{14}$, and $R_{16}$ are H; $R_4$ is NH; $R_7$ and $R_{15}$ are Cl; $R_5$ and $R_{17}$ are —NH—CH(OH)—$CH_3$; and "----" in Formula I between $A_0$ and $A_1$, all Formula II and Formula IV "----" are double bonds. An example of a compound of this embodiment of the invention includes:

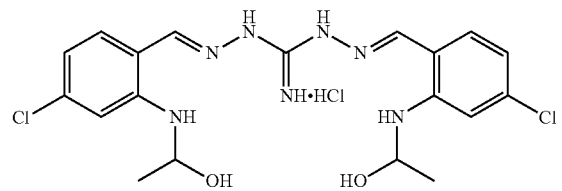

In another preferred embodiment of the invention, the compound is a compound of Formula I, or a stereoisomer, tautomer, pharmaceutically acceptable salt, or prodrug thereof, wherein $A_0$ is C; $R_1$ is H; $A_2$ and $R_4$ are N; $R_3$ is $NH_2$; $A_1$ is Formula VII; $R_2$ is Formula VII and $R_2$ is bonded to $R_4$, forming a pyrimidine ring; "----" in Formula I between $R_2$ and $A_0$, and between $A_1$ and $A_2$ are double bonds; $A_{22}$ is —N—CH—; $R_{24}$, $R_{25}$, $R_{27}$ and $R_{26}$ are H; $A_{23}$, $A_{24}$, $A_{25}$, $A_{26}$ and $A_{27}$ are C; and $R_{26}$ is Cl. An example of a compound of this embodiment of the invention includes (NCL179):

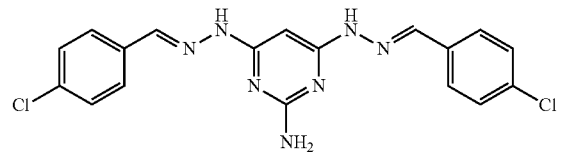 [SMILES: Nc1nc(N/N=C/c2ccc(Cl)cc2)cc(N/N=C/c2ccc(Cl)cc2)n1]

In another preferred embodiment of the invention, the compound is a compound of Formula I, or a stereoisomer, tautomer, pharmaceutically acceptable salt, or prodrug thereof, wherein $R_1$ is Formula II; $R_3$ is $NH_2$; $A_1$ is N; $A_2$ and $R_4$ are NH; $A_0$, $A_3$, $A_4$, $A_5$, $A_6$, and $A_7$ are C; $R_5$, $R_6$, $R_8$, and $R_9$ are H; $R_2$ is butyl; $R_7$ is Cl; and "----" in Formula I between $A_0$ and $A_1$, and all Formula II "----" are double bonds. An example of a compound of this embodiment of the invention includes (NCL188):

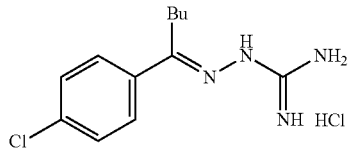

In another preferred embodiment of the invention, the compound is a compound of Formula I, or a stereoisomer, tautomer, pharmaceutically acceptable salt, or prodrug thereof, wherein $A_0$ is C; $R_1$ is H; $A_2$ and $R_4$ are N; $R_3$ is $NH_2$; $A_1$ is Formula VII; $R_2$ is Formula VII and $R_2$ is bonded to $R_4$, forming a pyrimidine ring; "----" in Formula I between $R_2$ and $A_0$, and between $A_1$ and $A_2$ are double bonds; $A_{22}$ is —N—CH—; $R_{24}$, $R_{25}$, $R_{27}$ and $R_{28}$ are H; $A_{23}$, $A_{24}$, $A_{25}$, $A_{26}$ and $A_{27}$ are C; and $R_{26}$ is $CH_3$. An example of a compound of this embodiment of the invention includes (NCL195):

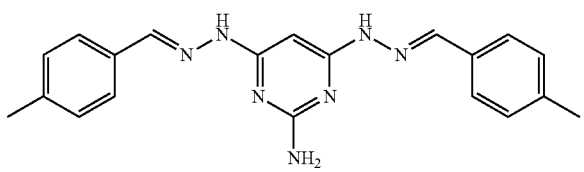

In another preferred embodiment of the invention, the compound is a compound of Formula I, or a stereoisomer, tautomer, pharmaceutically acceptable salt, or prodrug thereof, wherein $A_0$ is C; $R_1$ is H; $A_2$ and $R_4$ are N; $R_3$ is $NH_2$; $A_1$ is Formula VII; $R_2$ is Formula VII and $R_2$ is bonded to $R_4$, forming a pyrimidine ring; "----" in Formula I between $R_2$ and $A_0$, and between $A_1$ and $A_2$ are double bonds; $A_{22}$ is —N—CH—; $R_{24}$, $R_{25}$, $R_{27}$ and $R_{28}$ are H; $A_{23}$, $A_{24}$, $A_{25}$, $A_{26}$ and $A_{27}$ are C; and $R_{26}$ is OH. An example of a compound of this embodiment of the invention includes (NCL196):

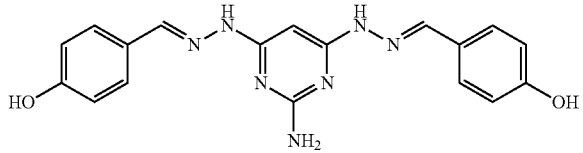 [SMILES: Nc1nc(N/N=C/c2ccc(O)cc2)cc(N/N=C/c2ccc(O)cc2)n1]

In another preferred embodiment of the invention, the compound is a compound of Formula I, or a stereoisomer, tautomer, pharmaceutically acceptable salt, or prodrug thereof, wherein $A_0$ is C; $R_1$ is H; $A_2$ and $R_4$ are N; $R_3$ is $NH_2$; $A_1$ is Formula VII; $R_2$ is Formula VII and $R_2$ is bonded to $R_4$, forming a pyrimidine ring; "----" in Formula I between $R_2$ and $A_0$, and between $A_1$ and $A_2$ are double bonds; $A_{22}$ is —N—CH—; $R_{24}$, $R_{25}$, $R_{27}$ and $R_{28}$ are H; $A_{23}$, $A_{24}$, $A_{25}$, $A_{26}$ and $A_{27}$ are C; and $R_{26}$ is Br. An example of a compound of this embodiment of the invention includes (NCL193):

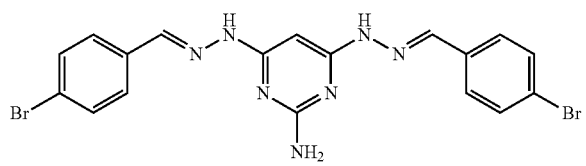 [SMILES: Nc1nc(N/N=C/c2ccc(Br)cc2)cc(N/N=C/c2ccc(Br)cc2)n1]

In another preferred embodiment of the invention, the compound is a compound of Formula I, or a stereoisomer, tautomer, pharmaceutically acceptable salt, or prodrug thereof, wherein $A_0$ is C; $R_1$ is H; $A_2$ and $R_4$ are N; $R_3$ is $NH_2$; $A_1$ is Formula VII; $R_2$ is Formula VII and $R_2$ is bonded to $R_4$, forming a pyrimidine ring; "----" in Formula I between $R_2$ and $A_0$, and between $A_1$ and $A_2$ are double bonds; $A_{22}$ is —N—CH—; $R_{24}$, $R_{25}$, $R_{26}$, $R_{27}$ and $R_{28}$ are H; and $A_{23}$, $A_{24}$, $A_{25}$, $A_{26}$ and $A_{27}$ are C. An example of a compound of this embodiment of the invention includes (NCL199):

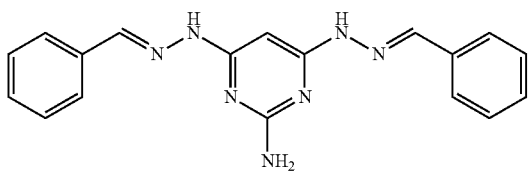 [SMILES: Nc1nc(N/N=C/c2ccccc2)cc(N/N=C/c2ccccc2)n1]

In another preferred embodiment of the invention, the compound is a compound of Formula I, or a stereoisomer, tautomer, pharmaceutically acceptable salt, or prodrug thereof, wherein $A_0$ is C; $R_1$ is H; $A_2$ and $R_4$ are N; $R_3$ is $NH_2$; $A_1$ is Formula VII; $R_2$ is Formula VII and $R_2$ is bonded to $R_4$, forming a pyrimidine ring; "----" in Formula I between $R_2$ and $A_0$, and between $A_1$ and $A_2$ are double bonds; $A_{22}$ is —N—C(CH$_3$)—; $R_{24}$, $R_{25}$, $R_{27}$ and $R_{28}$ are H; $A_{23}$, $A_{24}$, $A_{25}$, $A_{26}$ and $A_{27}$ are C; and $R_{26}$ is Cl. An example of a compound of this embodiment of the invention includes (NCL204):

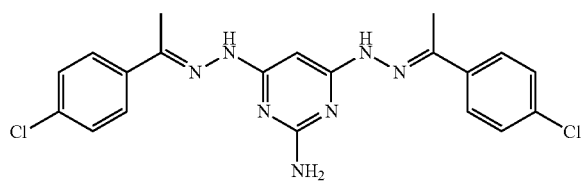 [SMILES: C/C(=N\Nc1cc(N/N=C(\C)c2ccc(Cl)cc2)nc(N)n1)c1ccc(Cl)cc1]

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_6$, $R_8$, $R_9$, $R_{12}$, $R_{13}$, $R_{14}$, and $R_{16}$ are H; $R_4$ is NH; $R_7$ and $R_{15}$ are Cl; $R_5$ and $R_{17}$ are F; and "----" in Formula I between $A_0$ and $A_1$, all Formula II and Formula IV "----" are double bonds. An example of a compound of this embodiment of the invention includes (NCL216):

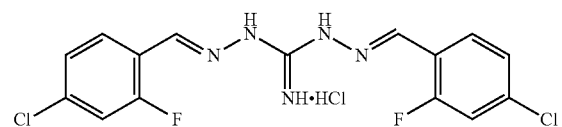

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$ and $R_{12}$ are methyl; $R_5$, $R_6$, $R_8$, $R_9$, $R_{13}$, $R_{14}$, $R_{16}$ and $R_{17}$ are H; $R_4$ is NH; $R_7$ and $R_{15}$ are CH$_3$; and "----" in Formula I between $A_0$ and $A_1$, all Formula II and Formula IV "----" are double bonds. An example of a compound of this embodiment of the invention includes (NCL217):

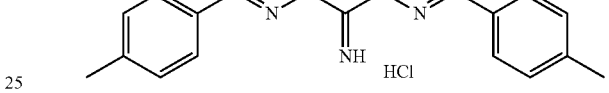

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$ and $R_{12}$ are methyl; $R_5$, $R_6$, $R_8$, $R_9$, $R_{13}$, $R_{14}$, $R_{16}$ and $R_{17}$ are H; $R_4$ is NH; $R_7$ and $R_{15}$ are t-butyl; and "----" in Formula I between $A_0$ and $A_1$, all Formula II and Formula IV "----" are double bonds. An example of a compound of this embodiment of the invention includes (NCL219):

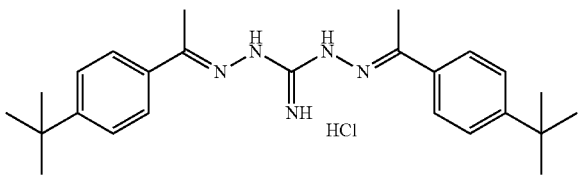 [SMILES: C/C(=N\NC(=N)N/N=C(\C)c1ccc(C(C)(C)C)cc1)c1ccc(C(C)(C)C)cc1 ; Cl]

In another preferred embodiment of the invention, the compound is a compound of Formula I, or a stereoisomer, tautomer, pharmaceutically acceptable salt, or prodrug thereof, wherein $A_0$ is C; $R_1$ is H; $A_2$ and $R_4$ are N; $R_3$ is $NH_2$; $A_1$ is Formula VII; $R_2$ is Formula VII and $R_2$ is bonded to $R_4$, forming a pyrimidine ring; "----" in Formula I between $R_2$ and $A_0$, and between $A_1$ and $A_2$ are double bonds; $A_{22}$ is —N—CH—; $R_{24}$, $R_{25}$, $R_{27}$ and $R_{28}$ are H; $A_{23}$, $A_{24}$, $A_{25}$, $A_{26}$ and $A_{27}$ are C; and $R_{26}$ is CF$_3$. An example of a compound of this embodiment of the invention includes (NCL221):

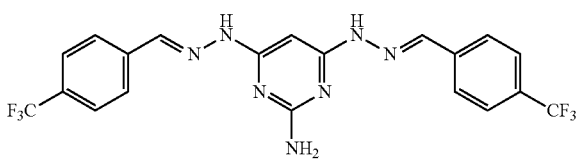 [SMILES: Nc1nc(N/N=C/c2ccc(C(F)(F)F)cc2)cc(N/N=C/c2ccc(C(F)(F)F)cc2)n1]

According to another aspect of the invention, there is provided a method of treating or preventing a bacterial colonisation or infection in a subject, the method comprising the step of administering a therapeutically effective amount of a compound of Formula I, or a therapeutically acceptable salt thereof, to the subject. In this aspect, the bacterial infection is caused by a bacterial agent. The method of treating or preventing a bacterial infection or colonisation in a subject, may also comprise the administration of the pharmaceutical or veterinary compositions of the invention.

According to a further aspect of the invention, there is provided the use of a compound of Formula I, or a therapeutically acceptable sal thereof, in the manufacture of medicament the treatment of a bacterial colonisation or infection in a subject. In this aspect, the bacterial infection is caused by a bacterial agent.

The subject may be any subject capable of colonisation and infection by bacteria. The subject may be mammalian, or may be piscine or avian. Preferably, the subject is selected from the group comprising, but not limited to, human, canine, feline, bovine, ovine, caprine, other ruminant species, porcine, equine, avian, or piscine.

The compound of Formula I may be administered to the subject in a dose selected from the group comprising 0.1 mg/kg to 250 mg/kg body weight, preferably 1 mg/kg to 100 mg/kg body weight, and more preferably 5 mg/kg to 50 mg/kg body weight. The compound of Formula I may be administered to the subject using a dosing schedule selected from the group consisting of: hourly, 3 times daily; twice daily; daily; every second day; twice weekly; once weekly; once fortnightly; once monthly; once every two months or by constant rate or variable rate infusion. Preferably, the compound of Formula I is administered until colonisation or the signs and symptoms of infection or colonisation have at least been partially treated or alleviated.

In one embodiment, the concentration of compound of Formula I (or a metabolite) in the subject's blood after treatment is within a range selected from the group comprising, but not limited to: between 0.1 and 10 ug/mL at 2 hours, 1 and 200 ug/mL after 12 hours; between 0.1 and 5 ug/mL after 24 h; between 0.01 and 2 ug/mL after 48 hours; between 0.0001 and 1 ug/mL after 72 h. Preferably, the concentration is selected from the group comprising, but not limited to: less than 200 ug/mL after 12 hours; less than 5 ug/mL after 24 hours; less than 1 ug/L after 48 hours and less than 0.5 ug/mL after 72 hours.

The agent causing the bacterial infection is a bacterial agent. In one preferred embodiment, the agent is not a protozoan species. In one preferred embodiment, the agent is not a coccidian protozoan. More preferably, the agent is not *Clostridium perfringens* nor a heterotrophic bacterial species present in soil samples collected by Hansen et al from Jyndevad Denmark as discussed in the following papers: Hansen at al. 2012, *Chemosphere*, 86:212-215; and Hansen et al. 2009, *Environmental Pollution* 157:474-480.

In another embodiment, the bacterial agent is gram negative. In another embodiment, the bacterial agent is gram positive. In another embodiment, the bacterial agent has no cell wall. In another embodiment, the bacterial infection is caused by a mixture of at least two agents selected from the group consisting of: gram negative, gram positive and bacterial agents with no cell wall.

The bacterial agent causing the bacterial infection may be a gram positive bacterial agent selected from the group comprising, but not limited to, *Staphylococcus* spp, *Streptococci*, *Enterococcus* spp, *Leuconostoc* spp, *Corynebacterium* spp, *Arcanobacteria* spp, *Trueperella* spp, *Rhodococcus* spp, *Bacillus* spp, Anaerobic Cocci, Anaerobic Gram-Positive Nonsporulating Bacilli, *Actinomyces* spp, *Clostridium* spp, *Nocardia* spp, *Erysipelothrix* spp, *Listeria* spp, *Kytococcus* spp, *Mycoplasma* spp, *Ureaplasma* spp, and *Mycobacterium* spp.

In one embodiment, the bacterial agent is gram positive and is selected from the group comprising, but not limited to, *Staphylococcus* spp. Examples of *Staphylococcus* spp include *Staphylococcus epidermidis*, *Staphylococcus haemolyticus*, *Staphylococcus lugdunensis*, *Staphylococcus saprophyticus*, *Staphylococcus auricularis*, *Staphylococcus capitis*, *Staphylococcus caprae*, *Staphylococcus carnosus*, *Staphylococcus cohnil*, *Staphylococcus hominis*, *Staphylococcus pasteur*, *Staphylococcus pettenkoflei*, *Staphylococcus pulverer*, *Staphylococcus saccharolyticus*, *Staphylococcus simulans*, *Staphylococcus schleiferi*, *Staphylococcus warneri*, *Staphylococcus xylosus*, *Staphylococcus arlettee*, *Staphylococcus caseolyticus*, *Staphylococcus chromogenes*, *Staphylococcus condiment*, *Staphylococcus delphini*, *Staphylococcus equorum*, *Staphylococcus felis*, *Staphylococcus fleurettii*, *Staphylococcus gallinarum*, *Staphylococcus hyicus*, *Staphylococcus intermedius*, *Staphylococcus kloosii*, *Staphylococcus lentus*, *Staphylococcus lutrae*, *Staphylococcus muscae*, *Staphylococcus nepalensis*, *Staphylococcus piscifermentans*, *Staphylococcus pseudintermedius*, *Staphylococcus sciuri*, *Staphylococcus simiae*, *Staphylococcus succinus*, and *Staphylococcus vitulinus*.

In another embodiment, the bacterial agent is gram positive and is selected from the group comprising, but not limited to, *Streptococcus* spp. Examples of *Streptococcus* spp include *Streptococcus agalactiae*, *Streptococcus alactolyticus*, *Streptococcus anginosus*, *Streptococcus canis*, *Streptococcus constellatus*, *Streptococcus cricetus*, *Streptococcus cristatus*, *Streptococcus downei*, *Streptococcus dysgalactiae* subsp. *dysgalactiae*, *Streptococcus dysgalactiae* subsp. *equisimilis*, *Streptococcus equi* subsp. *equi*, *Streptococcus equi* subsp. *zooepidemicus*, *Streptococcus ferus*, *Streptococcus gallolyticus* subsp. *gallolyticus* (formerly *Streptococcus bovis* biotype i), *Streptococcus gallolyticus* subsp. *pasteurianus* (formerly *Streptococcus bovis* biotype ii/2), *Streptococcus gordonii*, *Streptococcus hyointestinalis*, *Streptococcus hyovaginalis*, *Streptococcus infantarius*, *Streptococcus infantarius* subsp *infantarius*, *Streptococcus infantis*, *Streptococcus iniae*, *Streptococcus intermedius*, *Streptococcus lutetiensis* (formerly *Streptococcus bovis* biotype ii.1), *Streptococcus macaccae*, *Streptococcus mitis*, *Streptococcus mutans*, *Streptococcus oralis*, *Streptococcus orisratti*, *Streptococcus parasanguinis*, *Streptococcus peroris*, *Streptococcus pneumoniae*, *Streptococcus porcinus*, *Streptococcus pseudintermedius*, *Streptococcus pyogenes*, *Streptococcus ratti*, *Streptococcus salivarius*, *Streptococcus sanguinis*, *Streptococcus sobrinus*, *Streptococcus suis*, *Streptococcus thermophilus*, *Streptococcus vestibularis*, and Nutritionally Variant (Deficient) Streptococci (*Abiotrophia defectiva*, *Granulicatella adiacens*, *Granulicatella elegans*, and *Granulicatella para-adiacens*) and related species such as *Rothia mucilaginosa* (formerly *Stomatococcus mucilaginosus*) and *Pediococcus*.

In another embodiment, the bacterial agent is gram positive and selected from the group comprising, but not limited to, *Enterococcus* spp. Examples of *Enterococcus* spp include *Enterococcus faecalis*, *Enterococcus faecium*, *Enterococcus gallinarum*, *Enterococcus durans*, *Enterococcus avium*, *Enterococcus raffinosus*, *Enterococcus peens*, *Enterococcus gilvus*, *Enterococcus cecorum*, *Enterococcus malodoratus*, *Enterococcus italicus*, *Enterococcus sanguinicola*, *Enterococcus mundtii*, *Enterococcus casseliflavus/flavescens*,

*Enterococcus dispar, Enterococcus hirae, Enterococcus pseudoavium,* and *Enterococcus bovis.*

In another embodiment, the bacterial agent is gram positive and selected from the group comprising, but not limited to, *Leuconostoc* spp. Examples of *Leuconostoc* spp include *Leuconostoc mesenteroides, Leuconostoc pseudomesenteroides, Leuconostoc paramesenteroides, Leuconostoc citreum,* and *Leuconostoc lactis.*

In another embodiment, the bacterial agent is gram positive and selected from the group comprising, but not limited to, *Corynebacterium* spp. Examples of *Corynebacterium* spp include nonlipophilic, fermentative *Corynebacterium* spp such as *Corynebacterium ulcerans, Corynebacterium pseudotuberculosis, Corynebacterium xerosis, Corynebacterium striatum, Corynebacterium minutissimum, Corynebacterium amycolatum, Corynebacterium glucuronolyticum, Corynebacterium argentoratense, Corynebacterium matruchotii, Corynebacterium riegelii, Corynebacterium confusum, Corynebacterium cystidis, Corynebacterium diphtheria, Corynebacterium simulans, Corynebacterium sundvallense, Corynebacterium thomssensii, Corynebacterium freneyi,* and *Corynebacterium aurimucosum,* nonlipophilic, nonfermentative *Corynebacterium* spp such as *Corynebacterium afermentans afermentans, Corynebacterium auris, Corynebacterium pseudodiphtheriticum,* and *Corynebacterium propinquum* and lipophilic *Corynebacterium* spp such as *Corynebacterium jeikeium, Corynebacterium urealyticum, Corynebacterium afermentans lipophilum, Corynebacterium accolens, Corynebacterium macginleyi, Corynebacterium tuberculostearum, Corynebacterium kroppenstedtii, Corynebacterium kutscheri, Corynebacterium pilosum, Corynebacterium bovis,* CDC coryneform groups F-1 and G, and *Corynebacterium lipophiloflavum,* and other *Corynebacterium* spp such as *Turicella, Arthrobacter, Brevibacterium, Dermabacter, Rothia, Oerskovia, Microbacterium,* and *Leifsonia aquatica.*

In another embodiment, the bacterial agent is gram positive and selected from the group comprising, but not limited to, Arcanobacteria spp. Examples of Arcanobacteria spp include *A. haemolyticum, A. pyogenes* (now known as *Trueperella pyogenes,* originally known as *Actinomyces pyogenes*), and *A. bernardiae.*

In another embodiment, the bacterial agent is gram positive and selected from the group comprising, but not limited to, *Rhodococcus* spp. Examples of *Rhodococcus* spp include *Rhodococcus equi, Rhodococcus erythropolis, Rhodococcus fasciens,* and *Rhodococcus rhodochrous.*

In another embodiment, the bacterial agent is gram positive and selected from the group comprising, but not limited to, *Gordonia* spp.

In another embodiment, the bacterial agent is gram positive and selected from the group comprising, but not limited to, *Tsukamurella* spp.

In another embodiment, the bacterial agent is gram positive and selected from the group comprising, but not limited to, *Acholeplasma* spp.

In another embodiment, the bacterial agent is gram positive and selected from the group comprising, but not limited to, Actinobacteria such as *Crossiella equi.*

In another embodiment, the bacterial agent is gram positive and selected from the group comprising, but not limited to, *Bacillus* spp. Examples of *Bacillus* spp include *Bacillus anthracis, Bacillus cereus, Bacillus circulans, Bacillus licheniformis, Bacillus megaterium, Bacillus pumilus, Bacillus sphaericus, Bacillus subtilis, Brevibacillus brevis, Brevibacillus laterosporus,* and *Paenibacillus alvei.*

In another embodiment, the bacterial agent is gram positive and selected from the group comprising, but not limited to, Anaerobic Cocci. Examples of Anaerobic Cocci include *Anaerococcus murdochii, Anaerococcus prevotii, Anaerococcus tetradius, Anaerococcus octavius, Anaerococcus hydrogenalis, Anaerococcus lactolyticus, Anaerococcus vaginalis, Atopobium parvulum, Finegoldia magna, Gallicola barnesae, Gemella asaccharolytica, Gemella bergeri, Gemella cuniculi, Gemella haemolysans, Gemella morbillorum, Gemella palaticanis, Gemella sanguinis, Parvimonas micra, Peptococcus niger, Peptoniphilus asaccharolyticus, Peptoniphilus gorbachii, Peptoniphilus indolicus, Peptoniphilus harei, Peptoniphilus ivorii, Peptoniphilus lacrimalis, Peptoniphilus olsenii, Peptostreptococcus stomatis, Peptostreptococcus anaerobius, Ruminococcus productus, Slackia heliotrinireducens,* and *Staphylococcus saccharolyticus.*

In another embodiment, the bacterial agent is gram positive and selected from the group comprising, but not limited to, Anaerobic Gram-Positive Nonsporulating Bacilli. Examples of Anaerobic Gram-Positive Nonsporulating Bacilli include *Alloscardovia omnicolens, Atopobium* species (such as *Atopobium minutum, Atopobium rimae, Atopobium parvulum,* and *Atopobium vaginae*), *Bifidobacteria* (such as *Bifidobacteria adolescentis, Bifidobacteria dentium, Bifidobacteria scardovfi*), *Catabacter hongkongensis, Collinsella aerofaciens, Eggerthella* (such as *Eggerthella lenta, Eggerthella hongkongensis* and *Eggerthella sinensis*), *Eubacterium* and related species (such as *Eubacterium nodatum, Eubacterium tenue, Eubacterium brachy, Eubacterium infirmum, Eubacterium minutum, Eubacterium nodatum, Eubacterium saphenum, Eubacterium sulci, Filifactor alocis, Mogibacterium timidum, Mogibacterium vescum, Pseudoramibacter alactolyticus, Bulleidia extructa,* and *Solobacterium moorei*), *Lactobacillus* species (such as *Lactobacillus rhamnosus, Lactobacillus casei, Lactobacillus fermentum, Lactobacillus gassefi, Lactobacillus plantarum, Lactobacillus acidophilus, Lactobacillus iners* and *Lactobacillus ultunensis*), *Mobiluncus* species (such as *Mobiluncus curtisii, Mobiluncus mulieris*), *Moryella indoligenes, Olsenella* oral species (such as *Olsenella uli* and *Olsenella profuse*), *Oribacterium sinus, Propionibacterium* (such as *Propionibacterium acnes* and *Propionibacterium propionicum*), *Slackia exigua,* and *Turicibacter sanguine.*

In another embodiment, the bacterial agent is gram positive and selected from the group comprising, but not limited to, *Actinomyces* spp. Examples of *Actinomyces* spp include *Actinomyces israelii, Actinomyces naeslundii, Actinomyces viscosus, Actinomyces odontolyticus, Actinomyces meyeri,* and *Actinomyces gerencseriae* (formerly *Actinomyces israelii* serotype II), *Actinomyces europaeus, Actinomyces neuii, Actinomyces radingae, Actinomyces graevenitzii, Actinomyces hordeovulneris, Actinomyces turicensis, Actinomyces georgiae, Arcanobacterium (Actinomyces) pyogenes, Arcanobacterium (Actinomyces) bernardiae, Actinomyces funkei, Actinomyces lingnae, Actinomyces houstonensis,* and *Actinomyces cardiffensis.*

In another embodiment, the bacterial agent is gram positive and selected from the group comprising, but not limited to, *Clostridium* spp. Examples of *Clostridium* spp include *Clostridium baratii, Clostridium bifermentans, Clostridium botulinum, Clostridium botulinum* (types A, B, C, D, E, F, G), *Clostridium butyricum, Clostridium difficile, Clostridium histolyticum, Clostridium novyi* (type A), *Clostridium novyi* (type 8), *Clostridium perfringens, Clostridium perfringens* (types A-E), *Clostridium ramosum,*

*Clostridium septicum, Clostridium sordelli, Clostridium sphenoides, Clostridium tertium*, and *Clostridium tetani*.

In another embodiment, the bacterial agent is gram positive and selected from the group comprising, but not limited to, *Nocardia* spp. Examples of *Nocardia* spp include *Nocardia asteroides, Nocardia brasiliensis, Nocardia farcinica, Nocardia nova, Nocardia otitidiscaviarum*, and *Nocardia transvalensis*.

In another embodiment, the bacterial agent is gram positive and selected from the group comprising, but not limited to, *Erysipelothrix* spp, such as *Erysipelothrix rhusiopathiae*.

In another embodiment, the bacterial agent is gram positive and selected from the group comprising, but not limited to, *Listeria* spp, such as *Listeria monocytogenes*.

In another embodiment, the bacterial agent is gram positive and selected from the group comprising, but not limited to, *Kytococcus* spp, such as *Kytococcus schroeteri*.

In another embodiment, the bacterial agent is gram positive and selected from the group comprising, but not limited to, *Mycobacterium* spp. Examples of *Mycobacterium* spp include *Mycobacterium abscessus, Mycobacterium arupense, Mycobacterium asiaticum, Mycobacterium aubagnense, Mycobacterium avium* complex, *Mycobacterium bolletii, Mycobacterium bolletii, Mycobacterium branderi, Mycobacterium canettii, Mycobacterium caprae, Mycobacterium celatum, Mycobacterium chelonae, Mycobacterium chimaera, Mycobacterium colombiense, Mycobacterium conceptionense, Mycobacterium conspicuum, Mycobacterium elephantis, Mycobacterium farcinogenes, Mycobacterium florentinum, Mycobacterium fortuitum* group, *Mycobacterium genavense, Mycobacterium goodii, Mycobacterium haemophilum, Mycobacterium heckeshornense, Mycobacterium heidelbergense, Mycobacterium houstonense, Mycobacterium immunogenum, Mycobacterium interjectum, Mycobacterium intracellulare, Mycobacterium senegalense, Mycobacterium africanum, Mycobacterium avium* subsp *paratuberculosis, Mycobacterium kansasii, Mycobacterium lacus, Mycobacterium lentiflavum, Mycobacterium leprae, Mycobacterium lepraemurium, Mycobacterium mageritense, Mycobacterium malmoense, Mycobacterium marinum, Mycobacterium massiliense, Mycobacterium microti, Mycobacterium montefiorense* (eels), *Mycobacterium moracense, Mycobacterium mucogenicum, Mycobacterium nebraskense, Mycobacterium neoaurum, Mycobacterium novocastrense, Mycobacterium palustre, Mycobacterium parmense, Mycobacterium phlei, Mycobacterium phocaicum, Mycobacterium pinnipedii, Mycobacterium porcinum, Mycobacterium pseudoshottsii* (fish), *Mycobacterium pseudotuberculosis, Mycobacterium saskatchewanense, Mycobacterium scrofulaceum, Mycobacterium senuense, Mycobacterium septicum, Mycobacterium simiae, Mycobacterium smegmatis, Mycobacterium szulgai, Mycobacterium terrae/chromogenicum* complex, *Mycobacterium triplex, Mycobacterium tuberculosis, Mycobacterium tusciae, Mycobacterium ulcerans, Mycobacterium wolinskyi*, and *Mycobacterium xenopi*.

In another embodiment, the bacterial agent is gram positive and selected from the group comprising, but not limited to, *Trueperella* spp. Examples of *Trueperella* spp include *Trueperella abortisuis, Trueperella bernardiae, Trueperella bialowiezensis, Trueperella bonasi, Trueperella pyogenes (Arcanobacterium pyogenes)*.

In another embodiment, the bacterial agent is gram positive, gram negative or does not have a cell wall and selected from the group comprising, but not limited to, livestock pathogens. Examples of livestock pathogens include *Actinobaculum suis, Actinomyces bovis, Arcanobacterium pyogenes, Bacillus anthracis, cereus, licheniformis, pumilus, melaninogenicus*, *subtilis*, *Clostridium botulinum*, *chauvoei*, *haemolyticum*, *novyi*, *perfringens*, *septicum*, *sordellii*, *tetani*, *colinum*, *Corynebacterium pseudotuberculosis*, *renale*, *Dermatophilus congolensis*, *Enterococcus* spp (such as *E. faecalis*, *E. faecium*, *E. durans*, *E. avium*, *E. hirae*), *Erysipelothrix rhusiopathiae*, *Listeria ivanovii*, *grayi*, *innocua*, *seeligeri*, *welshimeri*, *monocytogenes*, *Mycobacterium avium*, *bovis*, *paratuberculosis* (Johne's Disease), *Mycoplasma* (such as *capricolum* subsp. *capripneumoniae*, subsp. *capricolum*, *M. mycoides* subsp *mycoides*, *M. agalactiae*, *M. ovipneumoniae*, *M. conjunctivae*, *M. arginini*, *M. bovis*, and *M. putrefaciens*) *Mycoplasma bovis*, *dispar*, *mycoides* subsp. *mycoides* (such as Contagious bovine pleuropneumonia CBPP) *Mycoplasma gallisepticum* (MG), *iowae meleagridis* (MM), *synoviae* (MS) *Mycoplasma haemosuis* (formerly *Eperythrozoon suis*), *alkalescens*, *bovigenitalum*, *bovirhinis*, *bovoculi*, *californicum*, *canadense*, *cynos*, *equigenitalium*, *gateae*, *haemocanis*, *haemofelis*, *hyopneumoniae*, *hyorhinis*, *hyosynoviae*, *iowae*, *leachii*, *meleagridis*, *mycoides* subsp *capri*, *wenyonii*, *suis*, *Rhodococcus equi*, *Staphylococcus epidermidis*, *Staphylococcus simulans*, *Staphylococcus fells*, *Staphylococcus xylosus*, *Staphylococcus chromogenes*, *Staphylococcus warneri*, *Staphylococcus haemolyticus*, *Staphylococcus sciuri*, *Staphylococcus saprophyticus*, *Staphylococcus hominis*, *Staphylococcus caprae*, *Staphylococcus cohnii* subsp. *cohnii*, *Staphylococcus cohnii* subsp. *urealyticus*, *Staphylococcus capitis* subsp. *capitis*, *Staphylococcus capitis* subsp. *urealyticus*, *Staphylococcus hyicus*, *Staphylococcus aureus*, *Staphylococcus pseudintermedius*, *Staphylococcus delphini*, *Staphylococcus schleiferi* subsp. *coagulans*, *Staphylococcus aureus* subsp. *anaerobius*, *Streptococcus uberis*, *Streptococcus canis*, *Streptococcus agalactiae*, *Streptococcus dysgalactiae*, *Streptococcus pyogenes*, *Streptococcus bovis*, *Streptococcus equi* subsp. *Zooepidemicus*, *Streptococcus equinus*, *Streptococcus equi* (*Streptococcus equi* subsp *equi*), *Streptococcus equisimilis* (*Streptococcus dysgalactiae* subsp *equisimilis*), *porcinus*, *suis*, *zooepidemicus*, *Streptococcus zooepidemicus* (*Streptococcus equi* subsp *zooepidemicus*), *Streptococcus dysgalactiae* subsp. *equisimilis*, *Propionibacterium acnes*, *Propionibacterium granulosum*, *Eubacterium*, *Peptococcus indolicus*, and *Peptostreptococcus anaerobius*; and various species of the following Gram negative genera: *Actinobacillus*, *Aeromonas*, *Anaplasma*, *Arcobacter*, *Avibacterium*, *Bacteroides*, *Bartonella*, *Bordetella*, *Borrelia*, *Brachyspira*, *Brucella*, *Campylobacter*, *Capnocytophaga*, *Chlamydia*, *Chlamydophila*, *Chryseobacterium*, *Coxiella*, *Cytophaga*, *Dichelobacter*, *Edwardsiella*, *Ehrlichia*, *Escherichia*, *Flavobacterium*, *Francisella*, *Fusobacterium*, *Gallibacterium*, *Haemophilus*, *Histophilus*, *Klebsiella*, *Lawsonia*, *Leptospira*, *Mannheimia*, *Megasphaera*, *Moraxella*, *Neorickettsia*, *Nicoletella*, *Ornithobacterium*, *Pasteurella*, *Photobacterium*, *Piscichlamydia*, *Piscirickettsia*, *Porphyromonas*, *Prevotella*, *Proteus*, *Pseudomonas*, *Rickettsia*, *Riemerella*, *Salmonella*, *Streptobacillus*, *Tenacibaculum*, *Vibrio*, and *Yersinia*.

In another embodiment, the bacterial agent is selected from the group comprising, but not limited to, pathogens of companion animal species such as cats, dogs and horses. Examples of such pathogens include equine pathogens such as *Streptococcus equi*, *Streptococcus zooepidemicus*, *Rhodococcus equi*, *Clostridium difficile*, *Clostridium perfringens*, *Corynebacterium pseudotuberculosis*, *Clostridium piliforme*, *Actinomyces bovis*, *Staphylococcus aureus*, β-haemolytic *Steptococcus* spp, *Dermatophilus congolense*, *Clostridiium tetani*, and *Clostridium botulinum*. Further examples include pathogens of dogs and cats such as *Staphylococcus* spp, *Streptococcus* spp, *Clostridium* spp, *Actinomyces* spp, *Enterococcus* spp, *Nocardia* spp, *Mycoplasma* spp, and *Mycobacterium* spp.

In another embodiment, the bacterial agent is gram negative and selected from the group consisting of the following representative families and species: Acetobacteraceae: —*Roseomonas cervicalis; Roseomonas fauriae; Roseomonas gilardii.* —Aeromonadaceae: —*Aeromonas allosacharophila; Aeromonas aquariorum; Aeromonas caviae; Aeromonas hydrophila* (and subspecies); *Aeromonas salmonicida; Aeromonas shubertii; Aeromonas veronii biovar sobria (Aeromonas sobria).* —Alcaligenaceae: —*Achromobacter xylosoxidans; Alcaligenes faecalis; Bordetella ansorpii; Bordetella avium; Bordetella bronchiseptica; Bordetella hinzii; Bordetella holmesii; Bordetella parapertussis; Bordetella pertussis; Bordetella petrii; Bordetella trematum; Oligella ureolytica; Oligella urethralis.* —Anaplasmataceae: —*Anaplasma phagocytophilum; Anaplasma platys; Anaplasma bovis; Anaplasma centrale; Anaplasma marginale; Anaplasma odocoilei; Anaplasma ovis; Ehrlichia canis; Ehrlichia chaffeensis; Ehrlichia ewingii; Ehrlichia muris; Ehrlichia ovina; Ehrlichia ruminantium; Neoehrlichia lotoris; Neoehrlichia mikurensis; Neorickettsia helminthoeca; Neorickettsia Neorickettsia sennetsu; Wolbachia pipientis.* —Armatimonadaceae: —*Armatimonas rosea.* —Bacteroidaceae: —*Bacteroides forsythus; Bacteroides fragilis; Bacteroides melaninogenicus; Bacteroides ruber; Bacteroides urealtyicus.* —Bartonellaceae: —*Bartonella alsatica; Bartonella australis; Bartonella bacilliformis; Bartonella birtlesii; Bartonella bovis; Bartonella capreoli; Bartonella chomelii; Bartonella clarridgeiae; Bartonella doshiae; Bartonella elizabethae; Bartonella grahamii; Bartonella henselae; Bartonella koehlerae; Bartonella peromysci; Bartonella phoceensis; Bartonella quintana; Bartonella rattimassiliensis; Bartonella rochalimae; Bartonella schoenbuchensis; Bartonella talpae; Bartonella tamiae; Bartonella taylorii; Bartonella tribocorum; Bartonella vinsonii* subsp. *berkhoffii; Bartonella vinsonii* subsp. *arupensis; Bartonella vinsonii* subsp. *vinsonii.* —Bdellovibrionaceae: —*Bdellovibrio* spp. —Brachyspiraceae: —*Brachyspira* spp including *Brachyspira hampsonii, Brachyspira hyodysenteriae, Brachyspira murdochii, Brachyspira pilosicoli.* —Brucellaceae: —*Brucella abortus; Brucella canis; Brucella ceti; Brucella melitensis; Brucella ovis; Brucella pinnipedialis; Brucella suis; Ochrobactrum anthropi; Ochrobactrum intermedium.* —Burkholderiaceae: —*Burkholderia aboris; Burkholderia ambifaria* (genomovar VII); *Burkholderia anthina* (genomovar VIII); *Burkholderia cenocepacia* (genomovar III); *Burkholderia cepacia* (genomovar I); *Burkholderia diffusa; Burkholderia dolosa* (genomovar VI); *Burkholderia latens; Burkholderia mallei; Burkholderia metallica; Burkholderia multivorans* (genomovar II); *Burkholderia pseudomallei; Burkholderia pyrrocinia* (genomovar IX); *Burkholderia seminalis; Burkholderia stabilis* (genomovar IV); *Burkholderia ubonensis* (genomovar X); *Burkholderia vietnamiensis* (genomovar V); *Cupriavidus pauculus; Cupriavidus gilardii; Ralstonia pickettii; Ralstonia mannitolilytica; Sphaerotilus hippei; Sphaerotilus montanus; Sphaerotilus natans.* —Campylobacteraceae: —*Arcobacter* spp including *Arcobacter skirrowii; Campylobacter coli; Campylobacter concisus; Campylobacter curvus; Campylobacter fetus; Campylobacter gracilis; Campylobacter helveticus; Campylobacter hominis; Campylobacter hyointestinalis; Campylobacter insulaenigrae; Campylobacter jejuni; Campylobacter lanienae; Campylobacter lari; Campylobacter laridis; Campylobacter mucosalis; Campylobacter rectus; Campylobacter showae; Campylobacter sputorum; Campylobacter upsaliensis.* —Candidatus: —*Piscichlamydia salmonis.* —Cardiobacteriaceae: —*Cardiobacterium hominis; Cardiobacterium valvarum; Dichelobacter nodosus.* —Chlamydiaceae: —*Chlamydia* spp including *Chlamydia avium, Chlamydia gaffinacea, Chlamydia muridarum, Chlamydia suis, Chlamydia trachomatis; Chlamydophila* spp including *Chlamydophila pneumoniae, Chlamydophila pecorum, Chlamydophila psittaci, Chlamydophila abortus, Chlamydophila caviae,* and *Chlamydophila felis.* —Chthonomonadaceae: —*Chthonomonas calidirosea.* —Comamonadaceae: —*Comamonas testosteroni; Verminephrobacter* spp. —Coxiellaceae: —*Coxiella burnetii.* —Cytophagaceae: —*Cytophaga columnaris; Cytophaga hutchinsonii; Flexibacter echinicida; Flexibacter elegans; Flexibacter flexilis; Flexibacter litoralis; Flexibacter polymorphus; Flexibacter roseolus; Flexibacter ruber.* —Desulfovibrionaceae: —*Bilophila wadsworthia; Lawsonia intracellularis.* —Enterobacteriaceae: —*Cedecea davisae; Cedecea lapagei; Cedecea neteri; amalonaticus; Citrobacter diversus; Citrobacter freundii; Citrobacter koseri; Cronobacter condimenti; Cronobacter dublinensis; Cronobacter helveticus; Cronobacter malonaticus; Cronobacter muytjensii; Cronobacter pulveris; Cronobacter sakazakii; Cronobacter turicensis; Cronobacter universalis; Cronobacter zurichensis; Edwardsiella ictaluri; Edwardsiella tarda; Enterobacter aerogenes; Enterobacter agglomerans; Enterobacter cloacae; Enterobacter cowanii; Escherichia albertii; Escherichia coli,* including AIEC=adherent invasive *E. coli,* EaggEC=enteroaggregative *E. coli;* EHEC=enterohemorrhagic *E. coli;* EIEC=enteroinvasive *E. coli;* EPEC=enteropathogenic *E. coli;* ETEC=enterotoxigenic *E. coli;* ExPEC=extraintestinal pathogenic *E. coli,* NMEC=neonatal meningitis *E. coli,* NTEC=necrotoxigenic *E. coli,* UPEC=uropathogenic *E. coli; Escherichia fergusonii; Ewingella americana; Hafnia alvei; Hafnia paralvei; Klebsiella granulomatis; Klebsiella oxytoca; Klebsiella pneumoniae; Kluyvera ascorbata; Kluyvera cryocrescens; Morganella morganii; Pantoea* (formerly *Enterobacter) agglomerans; Photorhabdus asymbiotica; Plesiomonas shigelloides; Proteus mirabilis; Proteus penneri; Proteus vulgaris; Providencia alcalifaciens; Providencia rettgeri; Providencia stuartii; Raoultella electrica; Raoultella omithinolytica; Raoultella planticola; Raoultella terrigena; Salmonella bongori, Salmonella enterica* subspecies *enterica* (many serotypes); *Serratia liquifaciens; Serratia marcesans; Shigella boydii; Shigella dysenteriae; Shigella flexneri; Shigella sonnei; Yersinia enterocolitica; Yersinia pestis; Yersinia pseudotuberculosis; Yersinia ruckeri.* —Fimbriimonadaceae: —*Fimbriimonas ginsengisofi.* —Flavobacteriaceae: —*Bergeyella zoohelcum; Capnocytophaga canimorsus; Capnocytophaga cynodegmi; Capnocytophaga gingivalis; Capnocytophaga granulosa; Capnocytophaga haemolytica; Capnocytophaga leadbetteri; Capnocytophaga ochracea; Capnocytophaga sputigena; Chryseobacterium indologenes; Chryseobacterium piscicola; Elizabethkingia meningoseptica; Flavobacterium branchiophilum; Flavobacterium columnare; Flavobacterium oncorhynchi; Flavobacterium piscicida; Flavobacterium psychrophilum; Myroides odoratus; Myroides odoratimimus; Omithobacterium rhinotracheale; Riemerella anatipestifer; Riemerella columbina; Riemerella columbipharyngis; Tenacibaculum dicentrarchi; Tenacibaculum discolour; Tenacibaculum gallaicum; Tenacibaculum maritimum; Tenacibaculum soleae; Weeksella virosa.* —Francisellaceae: —*Francisella tularensis* subsp. *tularensis; Fran-*

*cisella tularensis* subsp. *holarctica; Francisella tularensis* subsp. *novicida; Francisella philomiragia; Francisella noatunensis; Francisella noatunensis* subsp. *orientalis* (also termed *Francisella asiatica*). —Fusobacteriaceae: —*Fusobacterium* spp. including *Fusobacterium necrophorum, Fusobacterium nucleatum, Fuso-bacterium polymorphum*. —Helicobacteraceae: —*Helicobacter cinaedi; Helicobacter fennelliae; Helicobacter pylori*. —Legionellaceae: —*Legionella pneumophila* and other species including; *Legionella anisa; Legionella birminghamensis; Legionella bozemannii; Legionella cincinnatiensis; Legionella dumoffii; Legionella feeleii; Legionella gormanii; Legionella hackeliae; Legionella jordanis; Legionella lansingensis; Legionella longbeachae; Legionella maceachemii; Legionella micdadei; Legionella oakridgensis; Legionella parisiensis; Legionella sainthelens; Legionella tusconensis; Legionella wadsworthii; Legionella waltersii*. —Leptospiraceae: —*Leptospira alexanderi* (including *Leptospira alexanderi* serovar *Hebdomadis, Leptospira alexanderi* serovar *Manhao* 3); *Leptospira alstoni* (including *Leptospira alstoni* serovar *Pingchang, Leptospira alstoni* serovar *Sichuan*); *Leptospira biflexa* (including *Leptospira biflexa* serovar *Ancona, Leptospira biflexa* serovar *Canela*); *Leptospira borgpetersenii* (including *Leptospira borgpetersenii* serovar *Hardjo, Leptospira borgpetersenii* serovar *Hardjo-bovis, Leptospira borgpetersenii* serovar *Pomona, Leptospira borgpetersenii* serovar *Tarassovi*); *Leptospira broomii* (including *Leptospira broomii* serovar *Hurstbridge*); *Leptospira fainei* (including *Leptospira fainei* serovar *Hurstbridge*); *Leptospira Leptospira inadai* (including *Leptospira inadai* serovar *Lyme, Leptospira inadai* serovar *Malaya*); *Leptospira interrogans* (including *Leptospira interrogans* serovar *Australis, Leptospira interrogans* serovar *Autumnalis, Leptospira interrogans* serovar *Bratislava, Leptospira interrogans* serovar *Canicola, Leptospira interrogans* serovar *Grippotyphosa, Leptospira interrogans* serovar *Hardjo, Leptospira interrogans* serovar *Hardjo-bovis, Leptospira interrogans* serovar *Icterohaemorrhagiae, Leptospira interrogans* serovar *Pomona, Leptospira interrogans* serovar *Pyrogenes, Leptospira interrogans* serovar *Tarassovi*); *Leptospira kirschneri* (including *Leptospira kirschneri* serovar *Bulgarica, Leptospira kirschneri* serovar *Cynopteri, Leptospira kirschneri* serovar *Grippotyphosa*); *Leptospira kmetyi; Leptospira licerasiae; Leptospira meyeri* (including *Leptospira meyeri* serovar *Sofia*); *Leptospira noguchii* (including *Leptospira noguchii* serovar *Panama, Leptospira noguchii* serovar *Pomona*); *Leptospira santarosai; Leptospira terpstrae; Leptospira vanthielii; Leptospira weilii* (including *Leptospira weilii* serovar *Celledoni, Leptospira weilii* serovar *Sarmin*); *Leptospira wolbachii; Leptospira wolffii; Leptospira yanagawae*. —Leptotrichiaceae: —*Leptotrichia buccalis; Streptobacillus moniliformis*. —Methylobacteriaceae: —*Methylobacterium extorquens* group; *Methylobacterium fujisawaense; Methylobacterium mesophilicum; Methylobacterium zatmanii*. —Moraxellaceae: —*Acinetobacter baumannfi* (genomic species 2); *Acinetobacter baylyi; Acinetobacter bouvetii; Acinetobacter calcoaceticus* (genomic species 1); *Acinetobacter gerneri; Acinetobacter grimontii; Acinetobacter haemolyticus* (genomic species 4); *Acinetobacter johnsonii* (genomic species 7); *Acinetobacter junii* (genomic species 5); *Acinetobacter Iwoffi* (genomic species 8/9); *Acinetobacter parvus; Acinetobacter radioresistens* (genomic species 12); *Acinetobacter schindleri; Acinetobacter tandoii; Acinetobacter tjernbergiae; Acinetobacter towneri; Acinetobacter ursingii; Acinetobacter venetianus; Moraxella atlantae; Moraxella boevrei; Moraxella bovis; Moraxella bovoculi; Moraxella canis; Moraxella caprae; Moraxella catarrhalis; Moraxella caviae; Moraxella cuniculi; Moraxella equi; Moraxella lacunata; Moraxella lincolnii; Moraxella macacae; Moraxella nonliquefaciens; Moraxella oblonga; Moraxella osloensis; Moraxella ovis; Moraxella phenylpyruvica; Moraxella pluranimalium; Moraxella pond*. —Moritellaceae: —*Moritella abyssi; Moritella dasanensis; Moritella japonica; Moritella marina; Moritella pro-funda; Moritella viscosa; Moritella yayanosii*. —Neisseriaceae: —*Chromobacterium violaceum; Eikenella corrodens; Kingella denitrificans, Kingella kingae, Kingella oralis, Kingella potus; Neisseria cinerea; Neisseria elongata; Neisseria flavescens; Neisseria gonorrhoeae; Neisseria lactamica; Neisseria meningitidis; Neisseria mucosa; Neisseria polysaccharea; Neisseria sicca; Neisseria subflava; Neisseria weaver; Vitreoscilla* spp. —Nitrosomonadaceae: —*Nitrosomonas eutropha; Nitrosomonas halophile; Nitrosomonas oligotropha*. —Pasteurellaceae: —*Actinobacillus actinomycetemcomitans; Actinobacillus equuli; Actinobacillus lignieresii; Actinobacillus pleuropneumoniae; Actinobacillus seminis; Actinobacillus succinogenes; Actinobacillus ureae; Aggregatibacter actinomycetemcomitans, Aggregatibacter segnis, Aggregatibacter aphrophilus; Avibacterium avium; Avibacterium endocarditidis; Avibacterium gaffinarum; Avibacterium paragaffinarum; Avibacterium volantium; Bibersteinia trehalose; Gallibacterium anatis; Gallibacterium genomospecies* 1; *Gallibacterium genomospecies* 2; *Gallibacterium genomospecies* 3; *Gallibacterium* group V; *Gallibacterium melopsittaci; Gallibacterium salpingitidis; Gallibacterium trehalosifermentans; Haemophilus aegyptius; Haemophilus avium; Haemophilus ducreyi; Haemophilus haemolyticus; Haemophilus influenzae; Haemophilus parahaemolyticus; Haemophilus parainfluenzae; Haemophilus parasuis; Histophilus somni; Mannheimia caviae; Mannheimia glucosida; Mannheimia granulomatis; Mannheimia haemolytica; Mannheimia ruminalis; Mannheimia varigena; Nicoletella semolina; Pasteurella aerogenes; Pasteurella bettyae; Pasteurella cabaffi; Pasteurella canis; Pasteurella dagmatis; Pasteurella multocida* (subspecies *multocida, septicum, gallicida*); *Pasteurella pneumotropica; Pasteurella stomatic; Pasteurella trehalosi*. —Piscirickettsiaceae: —*Piscirickettsia salmonis*. —Plesiomonadaceae: —*Plesiomonas shigelloides*. —Polyangiaceae: —*Sorangium cellulosum*. —Porphyromonadaceae: —*Dysgonomonas capnocytophagoides; Dysgonomonas gadei; Dysgonomonas hofstadii; Dysgonomonas mossii; Dysgonomonas oryzarvi; Dysgonomonas wimpennyi; Porphyromonas gingivalis*. —Prevotellaceae: —*Prevotella* spp. including *Prevotella intermedia, Prevotella melaninogenica*. —Pseudomonadaceae: —*Chryseomonas luteola; Pseudomonas aeruginosa; Pseudomonas luteola; Pseudomonas fluorescens; Pseudomonas putida; Pseudomonas stutzeri; Pseudomonas oryzihabitans*. —Rhizobiaceae: —*Agrobacterium tumefaciens; Rhizobium radiobacter*. —Rickettsiaceae: —*Orientia chuto; Orientia tsutsugamushi; Rickettsia aeschlimannii; Rickettsia africae; Rickettsia akari; Rickettsia argasii; Rickettsia asiatica; Rickettsia australis; Rickettsia bellii; Rickettsia canadensis; Rickettsia conorii; Rickettsia cooleyi; Rickettsia fells; Rickettsia heilongjiangensis; Rickettsia helvetica; Rickettsia honei; Rickettsia hoogstraalii; Rickettsia hulinensis; Rickettsia hulinii; Rickettsia japonica; Rickettsia marmionii; Rickettsia martinet; Rickettsia massiliae; Rickettsia monacensis; Rickettsia montanensis; Rickettsia monteiroi; Rickettsia moreli; Rickettsia parkeri; Rickettsia peacockii; Rickettsia philipii; Rickettsia prowazekii; Rickettsia raoultii; Rickettsia rhipicephali; Rickettsia rickettsii; Rick-*

*ettsia sibirica* subgroup; *Rickettsia slovaca*; *Rickettsia tamurae*; *Rickettsia typhi*. —Shewanellaceae: —*Shewanella putrefaciens*. —Sphingomonadaceae: —*Sphingobacterium multivorum*; *Sphingobacterium spiritivorum*; *Sphingomonas paucimobilis*. —Spirillaceae: —*Spirillum minus*; *Spirillum volutans*; *Spirillum winogradskyi*. —Spirochaetaceae: —*Borrelia afzelii*; *Borrelia anserina*; *Borrelia bissettii*; *Borrelia burgdorferi*; *Borrelia coriaceae*; *Borrelia duttonii*; *Borrelia garinii*; *Borrelia hermsii*; *Borrelia hispanica*; *Borrelia japonica*; *Borrelia lonestari*; *Borrelia lusitaniae*; *Borrelia miyamotoi*; *Borrelia parkeri*; *Borrelia persica*; *Borrelia recurrentis*; *Borrelia spielmanii*; *Borrelia turicatae*; *Borrelia turicatae*; *Borrelia valaisiana*; *Treponema carateum*; *Treponema pallidum* ssp. *endemicum*; *Treponema pallidum* ssp. *pallidum*; *Treponema pallidum* ssp. *pertenue*. —Succinivibrionaceae: —*Anaerobiospirillum* spp. —Sutterellaceae: —*Sutterella* spp including *Sutterella wadsworthia*. —Thermaceae: —*Meiothermus* spp. —Thermotogaceae: —*Thermotoga neapolitana*. —Veillonellaceae: —*Dialister* spp; *Megamonas* spp; *Megasphaera* spp; *Pectinatus* spp; *Pelosinus* spp; *Propionispora* spp; *Sporomusa* spp; *Veillonella* spp.; *Zymophilus* spp. —Vibrionaceae: —*Photobacterium damselae*; *Vibrio adaptatus*; *Vibrio alginolyticus*; *Vibrio azasii*; *Vibrio campbeffii*; *Vibrio cholera*; *Vibrio damsel*; *Vibrio fluvialis*; *Vibrio furnisii*; *Vibrio hoffisae*; *Vibrio metchnikovii*; *Vibrio mimicus*; *Vibrio parahaemolyticus*; *Vibrio vulnificus*. —Wolbachieae: —*Wolbachia* spp. —Xanthomonadaceae: —*Luteimonas aestuarii*; *Luteimonas aquatica*; *Luteimonas coirposti*; *Luteimonas lutimaris*; *Luteimonas marina*; *Luteimonas mephitis*; *Luteimonas vadosa*; *Pseudoxanthomonas broegbernensis*; *Pseudoxanthomonas japonensis*; *Stenotrophomonas maltophilia*; *Stenotrophomonas nitritireducens*.

Most preferably, the bacterial agent causing the bacterial infection is gram negative and is selected from the group comprising: *Acinetobacter* species, *Aeromonas hydrophila*, *Citrobacter* species, *Enterobacter* species, *Escherichia coli*, *Klebsiella pneumoniae*, *Morganella morganii*, *Pseudomonas aeruginosa*, and *Stenotrophomonas maltophilia*.

In another preferred embodiment, the bacteria agent causing the bacterial colonisation or infection is resistant to a conventional antibiotic used to treat the colonisation or infection. In one preferred embodiment, the bacterial agent is resistant to a compound selected from the group comprising: one or more of aminoglycosides (for example gentamicin, tobramycin, amikacin, or netilmicin); anti-MRSA cephalosporins (for example ceftaroline); antipseudomonal penicillins+β-lactamase inhibitors (for example ticarcillin-clavulanic acid or piperacillin-tazobactam); carbapenems (for example ertapenem, imipenem, meropenem or doripenem); non-extended spectrum cephalosporins; 1st and 2nd generation cephalosporins (for example cefazolin or cefuroxime); extended-spectrum cephalosporins; 3rd and 4th generation cephalosporins (for example cefotaxime or ceftriaxone); cephamycins (for example cefoxitin or cefotetan); fluoroquinolones (for example ciprofloxacin); folate pathway inhibitors (for example trimethoprim-sulphamethoxazole); glycylcyclines (for example tigecycline); monobactams (for example aztreonam); penicillins (for example ampicillin); penicillins+β-lactamase inhibitors (for example amoxicillin-clavulanic acid or ampicillin-sulbactam); phenicols (for example chloramphenicol); phosphonic acids (for example fosfomycin); polymyxins (for example colistin); and tetracyclines (for example tetracycline, doxycycline or minocycline. Preferably, the bacterial agent resistant to these compounds is gram negative.

Preferably, the bacterial agent is resistant to a compound selected from the group comprising: penicillins, cephalosporins, carbapenems, monobactams and other β-lactam antibiotics, fusidanes, aminoglycosides, fluoroquinolones, streptogramins, tetracyclines, glycylcyclines, chloramphenicol and other phenicols, macrolides and ketolides, lincosamides, oxazolidinones, aminocyclitols, polymyxins, glycopeptides, lipopeptides, bacitracin, mupiricin, pleuromutilins, rifamycins, sulphonamides and trimethoprim. Preferably, the compound is selected from the group comprising: beta lactams, glycopeptides, lipopeptides, macrolides, oxazolidinones and tetracyclines. Preferably, the bacterial agent is resistant to the compound when the compound is at a concentration range selected from the following: 0.001 μg/mL-10,000 μg/mL; 0.01 μg/mL-1000 μg/mL; 0.10 μg/mL-100 μg/mL; and 1 μg/mL-50 μg/mL.

In another preferred embodiment, the bacterial agent causing the bacterial infection is selected from the group comprising, but not limited to, gram positive bacteria. The microbe is preferably a gram positive bacterial agent selected from the group comprising *Staphylococcus aureus*, *Staphylococcus pseudintermedius*, *Streptococcus pneumoniae*, *Streptococcus pyogenes*, *Streptococcus agalactiae*, *Streptococcus uberis*, *Enterococcus faecium*, *Enterococcus faecalis*, and *Clostridium difficile*.

In one preferred embodiment, the bacterial agent has no cell wall. Preferably, the bacterial agent is selected from the group comprising: *Mycoplasma* spp, *Mycoplasma agalactiae*, *Mycoplasma alkalescens*, *Mycoplasma amphoriforme*, *Mycoplasma arginini*, *Mycoplasma bovigenitalum*, *Mycoplasma bovirhinis*, *Mycoplasma bovis*, *Mycoplasma bovoculi*, *Mycoplasma buccale*, *Mycoplasma californicum*, *Mycoplasma canadense*, *Mycoplasma capricolum* subsp. *capricolum*, *Mycoplasma capricolum* subsp. *capripneumoniae*, *Mycoplasma conjunctivae*, *Mycoplasma cynos*, *Mycoplasma dispar*, *Mycoplasma equigenitalium*, *Mycoplasma faucium*, *Mycoplasma fells*, *Mycoplasma fermentans* (incognitus str.), *Mycoplasma gallisepticum* (MG), *Mycoplasma gateae*, *Mycoplasma genitalium*, *Mycoplasma haemocanis*, *Mycoplasma haemofelis*, *Mycoplasma haemosuis* (formerly *Eperythrozoon suis*), *Mycoplasma hominis*, *Mycoplasma hyopneumoniae*, *Mycoplasma hyorhinis*, *Mycoplasma hyosynoviae*, *Mycoplasma iowae meleagridis* (MM), *Mycoplasma iowae*, *Mycoplasma leachii*, *Mycoplasma lipophilum*, *Mycoplasma meleagridis*, *Mycoplasma mycoides* subsp *capri*, *Mycoplasma mycoides* subsp *mycoides*, *Mycoplasma mycoides* subsp. *mycoides* (such as Contagious bovine pleuropneumonia CBPP), *Mycoplasma orale*, *Mycoplasma ovipneumoniae*, *Mycoplasma ovis*, *Mycoplasma penetrans*, *Mycoplasma pirum*, *Mycoplasma pneumoniae*, *Mycoplasma primatum*, *Mycoplasma putrefaciens*, *Mycoplasma salivarium*, *Mycoplasma spermatophilum*, *Mycoplasma suis*, *Mycoplasma synoviae* (MS), *Mycoplasma wenyonii*, *Mycoplasma*, *Ureaplasma* spp, *Ureaplasma parvum*, *Ureaplasma urealyticum*, *Ureaplasma*, and *Ureoplasma diversum*.

In another most preferred embodiment, the bacterial agent is *Staphylococcus aureus*.

In another preferred embodiment, the bacterial agent is resistant to a compound selected from the group comprising: one or more of aminoglycosides (for example gentamicin); ansamycins (for example rifampicin); anti-MRSA cephalosporins (for example ceftaroline); anti-staphylococcal β-lactams (or cephamycins) (for example oxacillin or cefoxitin); carbapenems (for example ertapenem, imipenem, meropenem or doripenem); non-extended spectrum cephalosporins; 1st and 2nd generation cephalosporins (for example cefazolin or cefuroxime); extended-spectrum cephalosporins; 3rd and 4th generation cephalosporins (for example cefotaxime or ceftriaxone); cephamycins (for example cefoxitin or cefotetan); fluoroquinolones (for example ciprofloxacin or moxifloxacin); folate pathway inhibitors (for example trimethoprim-sulphamethoxazole); fucidanes (for example fusidic acid); glycopeptides (for example vancomycin, teicoplanin or telavancin); glycylcyclines (for example tigecycline); lincosamides (for example clindamycin); lipopeptides (for example daptomycin); macrolides (for example erythromycin); oxazolidinones (for example linezolid or tedizolid); phenicols (for example chloramphenicol); phosphonic acids (for example fosfomycin); streptogramins (for example quinupristin-dalfopristin); and tetracyclines (for example tetracycline, doxycycline or minocycline). Preferably, the bacterial agent resistant to these compounds is gram positive.

In another most preferred embodiment, the bacterial agent is *Streptococcus pneumoniae*. The *Streptococcus pneumoniae* may be a strain that is resistant to one or more of β-lactams and macrolides.

In another most preferred embodiment, the bacterial agent is *Streptococcus pyogenes*.

In another most preferred embodiment, the bacterial agent is *Streptococcus agalactiae*.

In another most preferred embodiment, the bacterial agent is either *Enterococcus faecium* or *Enterococcus faecalis*. The *Enterococcus faecium* or *Enterococcus faecalis* may be a strain that is resistant to aminoglycosides (for example gentamicin (high level) or streptomycin (for example streptomycin (high level)); carbapenems (for example imipenem, meropenem or doripenem); fluoroquinolones (for example ciprofloxacin, levofloxacin or moxifloxacin); glycopeptides (for example vancomycin or teicoplanin); glycylcyclines (for example tigecycline); lipopeptides (for example daptomycin); oxazolidinones (for example linezolid); penicillins (for example ampicillin); streptogramins (for example quinupristin-dalfopristin); tetracycline (for example doxycycline or minocycline).

In another most preferred embodiment, the bacterial agent is *Clostridium difficile*.

The bacterial infection in the subject may cause a disease selected from the group comprising, but not limited to, nosocomial pneumonia caused by *Staphylococcus aureus* (MDR, XDR, PDR or methicillin-susceptible or -resistant strains), or invasive pneumococcal diseases such as pneumonia, bronchitis, acute sinusitis, otitis media, conjunctivitis, meningitis, bacteremia, sepsis, osteomyelitis, septic arthritis, endocarditis, peritonitis, pericarditis, cellulitis, and brain abscess caused by *Streptococcus pneumoniae* (including multi-drug resistant strains [MDRSP] such as those resistant to β-lactams and macrolides), complicated skin and skin structure infections, including diabetic foot infections, with or without concomitant osteomyelitis, caused by *Staphylococcus aureus* (methicillin-susceptible and -resistant strains), *Streptococcus pyogenes*, or *Streptococcus agalactiae*, uncomplicated skin and skin structure infections caused by *Staphylococcus aureus* (methicillin-susceptible and -resistant strains) or *Streptococcus pyogenes*, community-acquired pneumonia caused by *Streptococcus pneumoniae* (including multi-drug resistant strains [MDRSP], including cases with concurrent bacteraemia, or *Staphylococcus aureus* (methicillin-susceptible and -resistant strains) and *Staphylococcus aureus* bloodstream infections (bacteraemia), including those with right-sided infective endocarditis, caused by methicillin-susceptible and methicillin-resistant isolates, vancomycin-resistant *enterococcus* infections, including cases with concurrent bacteraemia, and treatment of *Clostridium difficile*-associated diarrhea (CDAD).

Gram negative organisms are important causes of many infectious diseases in humans and other animal species. Bone and joint infections (Gram-negative organisms or mixed bacteria, are an important cause of vertebral osteomyelitis and septic arthritis), cardiovascular system infections (including endocarditis caused by the HACEK group—*Haemophilus parainfluenzae, Haemophilus aphrophilus, Aggregatibacter actinomycetemcomitans, Cardiobacterium hominis, Eikenella corrodens, Kingella kingae*), central nervous system infections (the commonest causes of bacterial meningitis are *Neisseria meningitidis, Streptococcus pneumoniae* and, in nonvaccinated young children, *Haemophilus influenzae* type b (Hib), in neonates and infants less than 3 months of age, *Streptococcus agalactiae* (group B *streptococcus*), *Escherichia coli* and other aerobic Gram-negative rods are important pathogens, brain abscess or subdural empyema, the infecting organism(s) vary with the underlying predisposing cause but where the likely site of origin is the ear, enteric Gram-negative bacilli are commonly involved), eye infections (common pathogens include *Haemophilus influenza, Neisseria gonorrhoeae* or *Chlamydia trachomatis*), gastrointestinal tract infections (a wide range of pathogens are implicated including enterotoxigenic *Escherichia coli* (ETEC), *Salmonella, Campylobacter, Shigella, Vibrio cholera* and *Yersinia enterocolitica*), genital infections (bacterial vaginosis is a polymicrobial clinical syndrome with high concentrations of anaerobic (eg *Mobiluncus* species) and other fastidious bacteria (including *Gardnerella vaginalis* and *Atopobium vaginae*), and *Mycoplasma hominis*; non-sexually acquired pelvic inflammatory disease (PID) is usually caused by mixed vaginal flora, including anaerobes, facultative Gram-negative bacteria and *Mycoplasma hominis*, while sexually acquired PID is usually initiated by *C. trachomatis* or *N. gonorrhoeae* with growing evidence that *M. genitalium* infection is involved in a significant minority of cases), intra-abdominal infections (peritonitis due to perforated viscus is usually a polymicrobial infection with aerobic and anaerobic bowel flora while spontaneous bacterial peritonitis (SBP) is usually caused by enteric Gram-negative bacilli, such as *Escherichia coli* and *Klebsiella* species, *Klebsiella pneumoniae* is an increasingly identified cause of liver abscess), community-acquired pneumonia (*Mycoplasma pneumoniae, Chlamydophila (Chlamydia) pneumoniae, Chlamydophila (Chlamydia) psittaci, Haemophilus* influenza, aerobic Gram-negative bacilli including *Klebsiella pneumonia, Pseudomonas aeruginosa, Acinetobacter baumannii, Burkholderia pseudomallei*), otitis externa (including acute diffuse) (bacterial cultures commonly yield *Pseudomonas aeruginosa, Staphylococcus aureus,* and *Proteus* and *Klebsiella* species), otitis media (including acute) (common bacterial pathogens include *Streptococcus pneumoniae, Haemophilus influenzae* and *Moraxella catarrhalis*), sepsis (including severe) (including *Acinetobacter baumannii*, disseminated gonococcal sepsis, Gram-negative enteric bacteria, *Neisseria meningitidis* (meningococcal sepsis) and *Pseudomonas aeruginosa*), Systemic infections (Spotted fevers (*Rickettsia*) and scrub typhus (Orientia), Brucellosis, Cat-scratch disease and other *Bartonella* infections, Leptospirosis, Lyme disease, Melioidosis, Q fever, Typhoid and paratyphoid fevers (enteric fevers), urinary tract infections (acute cystitis, acute pyelonephritis, recurrent urinary tract infections and atheter-associated bacteriuria and urinary tract infections).

In humans gram negative bacteria are common causes of intra-abdominal infections (IAIs), urinary tract infections (UTIs), hospital acquired pneumonia, and bacteraemia. *Escherichia coli* (*E. coli*), *Klebsiella pneumoniae* (*K. pneumoniae*), and *Pseudomonas aeruginosa* (*P. aeruginosa*) are important pathogens in the hospital setting, accounting for 27% of all pathogens and 70% of all Gram-negative pathogens causing healthcare-associated infections [Sievert D M, Ricks P, Edwards J R, et al. Antimicrobial-resistant pathogens associated with healthcare-associated infections: summary of data reported to the National Healthcare Safety Network at the Centers for Disease Control and Prevention, 2009-2010. Infect Control Hosp Epidemiol. 2013; 34:1-14.].

Gram negative bacteria are showing rising rates of resistance to current therapies. The production of extended-spectrum β-lactamase (ESBL) enzymes is a common mechanism of resistance. Rates of ESBL-producing *E. coli* and *K. pneumoniae* have risen substantially, with the result that these bacteria are increasingly resistant to widely used antimicrobials.

*P. aeruginosa* is the most common Gram-negative cause of nosocomial pneumonia and the second most common cause of catheter-related UTIs in the U.S.

*E. coli* is the most common cause of UTIs. Cases of UTI caused by ESBL-producing *E. coli* and *K. pneumoniae* as well as *P. aeruginosa*, including MDR strains, are increasing. ESBL-producing *E. coli* and *K. pneumoniae* are also frequently isolated in patients with complicated IAI (cIAI).

*P. aeruginosa* is a clinically challenging and virulent pathogen that can be a cause of common infections in humans such as nosocomial pneumonia, UTI, IAI, and bloodstream infections. *P. aeruginosa* is the most common Gram-negative organism causing ventilator associated pneumonia and the second most common cause of catheter-associated UTIs.

The increase in the number of infections caused by Gram-negative bacteria is being accompanied by rising rates of resistance. Treatment options to meet this challenge are increasingly limited. There is a critical need for new antibiotics to meet the needs of patients now and in the future.

In one preferred aspect, more than one compound of the invention is administered to the subject.

In another preferred embodiment, a compound of the invention, or a therapeutically acceptable salt thereof, is administered together with a compound or agent that removes or substantially removes or reduces the integrity of the cell wall of the bacterial agent. As an example, the compound is selected from the group consisting of: β lactams, fosfomycin, lysozyme, polymyxins and chelating agents such as ethylenediaminetetraacetic acid (EDTA). As an example, the agent is an immunological agent (such as an antibody or vaccine) that reduces the integrity of the cell wall. In one preferred embodiment, the compound, or a therapeutically acceptable salt thereof, is administered together with a compound that removes or substantially removes or weakens the integrity of the outer cell wall of a gram negative bacterial agent.

According to another aspect of the invention, there is provided an antibacterial pharmaceutical composition comprising a therapeutically effective amount of a compound of Formula I, or a therapeutically acceptable salt thereof. Preferably, the composition is an anti-bacterial pharmaceutical composition.

According to another aspect of the invention, there is provided an antibacterial veterinary composition comprising a therapeutically effective amount of a compound of Formula I, or a therapeutically acceptable salt thereof. Preferably, the composition is an anti-bacterial veterinary composition.

The pharmaceutical composition may optionally include a pharmaceutically acceptable excipient or carrier. The veterinary composition may optionally include a veterinary acceptable excipient or carrier.

The pharmaceutical or veterinary composition of the invention preferably contains a compound of Formula I, or a pharmaceutically acceptable salt, at a concentration of selected from the group consisting of: 1 mg/g to 500 mg/g; 5 mg to 400 mg/g; 10 mg/g to 200 mg/g; 20 mg/g to 100 mg/g; 30 mg/g to 70 mg/g; and 40 mg/g to 60 mg/g.

In another embodiment, the pharmaceutical or veterinary composition comprises impurities, wherein the quantity of impurities as a percentage of the total weight of the composition is selected from the group consisting of: less than 20% impurities (by total weight of the composition); less than 15% impurities; less than 10% impurities; less than 8% impurities; less than 5% impurities; less than 4% impurities; less than 3% impurities; less than 2% impurities; less than 1% impurities; less than 0.5% impurities; less than 0.1% impurities. In one embodiment, the pharmaceutical or veterinary composition comprises microbial impurities or secondary metabolites, wherein the quantity of microbial impurities as a percentage of the total weight of the composition is selected from the group consisting of: less than 5%; less than 4%; less than 3%; less than 2%; less than 1%; less than 0.5%; less than 0.1%; less than 0.01%; less than 0.001%. In one embodiment, the pharmaceutical or veterinary composition is sterile and stored in a sealed and sterile container. In one embodiment, the pharmaceutical or veterinary composition contains no detectable level of microbial contamination.

The pharmaceutical or veterinary composition of the invention may comprise a further antimicrobial agent. The further antimicrobial agent may be an antifungal agent or antibacterial agent. The method of treating or preventing a bacterial infection or colonisation in a subject, may also comprise the administration of a compound of the invention with a further antimicrobial agent.

The pharmaceutical or veterinary composition of the invention may comprise more than one compound of the invention. For example, a combination of compounds. The method of treating or preventing a bacterial infection or colonisation in a subject, may also comprise the administration of more than one compound of the invention.

In one embodiment, the antifungal agent is selected from the group comprising, but not limited to naturally occurring agents including Echinocandins (Anidulafungin, Caspofungin, Micafungin), Polyenes (Amphotericin B, Candicidin, Filipin, Fungichromin (Pentamycin), Hachimycin, Hamycin, Lucensomycin, Mepartricin, Natamycin, Nystatin, Pecilocin, Perimycin), and other naturally occurring antifungal agents including Griseofulvin, Oligomycins, Pyrrolnitrin, Siccanin, and Viridin. The antifungal agent may be a synthetic compound selected from the group comprising, but not limited to Allylamines (Butenafine, Naftifine, Terbinafine) Imidazoles (Bifonazole, Butoconazole, Chlormidazole, Climbazole, Croconazole (Cloconazole), Clotrimazole, Eberconazole, Econazole, Enilconazole, Fenticonazole, Flutrimazole, Fosfluconazole, Isoconazole, Ketoconazole, Lanoconazole, Luliconazole, Miconazole, Neticonazole, Omoconazole, Oxiconazole Nitrate, Parconazole, Sertaconazole, Sulconazole, Tioconazole), Thiocarbamates (Liranaftate, Tolciclate, Tolindate, Tolnaftate), Triazoles (Fluconazole, Isavuconazole, Itraconazole, Posaconazole, Ravuconazole, Saperconazole, Terconazole, Voriconazole), and other synthetic agents such as Acrisorcin, Amorolfine, Bromosalicylchloranilide (Bromochlorosalicylanilide), Buclosamide, Calcium Propionate, Chlorphenesin, Ciclopirox, Cloxyquin (Cloxiquine), Coparaffinate, Exalamide, Flucytosine, Haloprogin, Hexetidine, Loflucarban, Nifuratel, Nifuroxime, Piroctone, Potassium Iodide, Propionic Acid, Pyrithione, Salicylanilide, Sodium Parachlorobenzoate, Sodium Propionate, Sulbentine, Tenonitrozole, Triacetin, Trimetrexate, Undecylenic Acid (Undecenoic Acid), and Zinc Propionate.

The composition of the invention may comprise an antibiotic adjunct selected from the group comprising, but not limited to, β-Lactamase Inhibitors (Avibactam, Clavulanic Acid, Sulbactam, Sultamicillin, Tazobactam), Renal Dipeptidase Inhibitors (Cilastatin), and Renal Protectant (Betamipron).

In one embodiment, the composition of the invention comprises a further antibiotic selected from the group comprising, but not limited to, 2,4-DIAMINOPYRIMIDINES, including Baquiloprim, Brodimoprim, Iclaprim, Ormetoprim, Pyrimethamine, Tetroxoprim, Trimethoprim; AMINOCOUMARINS, including Novobiocin; AMINOCYCLITOLS, including Spectinomycin; AMINOGLYCOSIDES, including Amikacin, Apramycin, Arbekacin, Bekanamycin, Butirosin, Dibekacin, Dihydrostreptomycin, Etimicin, Fortimicins (Astromicin), Framycetin, Gentamicin, Hygromycin B, Isepamicin, Kanamycin, Micronomicin, Neomycin, Netilmicin, Paromomycin, Plazomicin, Ribostamycin, Sisomicin, Streptomycin, Tobramycin, Verdamicin; AMINOMETHYLCYCLINES, including Omadacycline; AMPHENICOLS, including Azidamfenicol, Chloramphenicol, Florfenicol, Thiamphenicol; ANSAMYCINS, including Rifabutin, Rifamide, Rifampin (Rifampicin), Rifamycin, Rifapentine, Rifaximin; ANTISEPTIC AGENTS, including Acridine derivatives (including acriflavine, aminoacridine, ethacridine, proflavine), Bispyridines (including octenidine dihydrochloride), Brominated salicylanilides (including bromsalans), Chlorhexidine, Phenol derivatives (including thymol and triclosan), Quarternary ammonium compounds (including Alkyldimethylethylbenzyl Ammonium Chloride, benzalkonium chloride, cetylpyridinium chloride, benzethonium chloride, cetrimonium); ANTITUBERCULAR AGENTS, including Cycloserine, Delamanid, Ethambutol, Ethionamide, Isoniazid (Ftivazide), Morinamide, p-Aminosalicylic Acid (PAS), Protionamide, Pyrazinamide, Terizidone, Thioacetazone, Tiocarlide; ARSENICALS, including Arsanilic Acid, Roxarsone; BACTERIOCINS, including Nisin, Brilacidin (PMX-30063); β-LACTAM CARBACEPHEMS, including Loracarbef; β-LACTAM CARBAPENEMS, including Biapenem, Doripenem, Ertapenem, Faropenem, Imipenem, Meropenem, Panipenem, Razupenem, Ritipenem, Sulopenem, Tebipenem, Tomopenem; β-LACTAM CEPHALOSPORINS, including Cefacetrile, Cefaclor, Cefadroxil, Cefalexin, Cefaloglycin, Cefalonium, Cefaloridine, Cefalothin, Cefamandole, Cefapirin, Cefatrizine, Cefazaflur, Cefazedone, Cefazolin, Cefcapene, Cefdinir, Cefditoren, Cefepime, Cefetamet, Cefixime, Cefmenoxime, Cefodizime, Cefonicid, Cefoperazone, Ceforanide, Cefoselis, Cefotaxime, Cefotiam, Cefovecin, Cefozopran, Cefpimizole, Cefpiramide, Cefpirome, Cefpodoxime, Cefprozil, Cefquinome, Cefradine, Cefroxadine, Cefsulodin, Ceftaroline, Ceftazidime, Cefteram, Ceftezole, Ceftibuten, Ceftiofur, Ceftizoxime, Ceftobiprole, Ceftolozane, Ceftradine, Ceftrezole, Ceftriaxone, Ceftroxadine, Cefuroxime, Cefuzonam, Pivcefalexin; β-LACTAM CEPHAMYCINS, including Cefbuperazone, Cefmetazole, Cefminox, Cefotetan, Cefoxitin; β-LACTAM MONOBACTAMS, including Aztreonam, Carumonam, Tigemonam; β-LACTAM OXACEPHEMS, including Flomoxef, Latamoxef, Moxalactam; β-LACTAM PENICILLINS, including Amdinocillin (Mecillinam), Amoxicillin, Ampicillin, Apalcillin, Aspoxicillin, Azidocillin, Azlocillin, Bacampicillin, Carbenicillin, Carindacillin, Ciclacillin, Clemizole Penicillin, Clometocillin, Cloxacillin, Cyclacillin, Dicloxacillin, Epicillin, Fenbenicillin, Floxacillin (Flucloxacillin), Hetacillin, Lenampicillin, Mecillinam, Metampicillin, Methicillin Sodium, Mezlocillin, Nafcillin, Oxacillin, Penamecillin, Penethamate Hydriodide, Penicillin G, Penicillin G Benzathine, Penicillin G Procaine, Penicillin N, Penicillin O, Penicillin V, Phenethicillin Potassium, Piperacillin, Pivampicillin, Pivmecillinam, Propicillin, Quinacillin, Sulbenicillin, Sultamicillin, Talampicillin, Temocillin, Ticarcillin; BICYCLOMYCINS, including Bicozamycin; BORON CONTAINING ANTIBACTERIAL AGENTS, including AN3365 (aminomethylbenzoxaboroles), GSK2251052 (leucyl-tRNA synthetase inhibitors); CYCLIC ESTERS, including Fosfomycin; FATTY ACID SYNTHESIS INHIBITORS (FabI), AFN-1252, MUT056399, FAB-001; FLUOROQUINOLONES, including Avarofloxacin, Balofloxacin, Besifloxacin, Chinfloxacin, Cinoxacin, Ciprofloxacin, Clinafloxacin, Danofloxacin, Delafloxacin, Difloxacin, Enoxacin, Enrofloxacin, Finafloxacin, Fleroxacin, Flumequine, Garenoxacin, Gatifloxacin, Gemifloxacin, Grepafloxacin, Ibafloxacin, Levofloxacin, Lomefloxacin, Marbofloxacin, Miloxacin, Moxifloxacin, Nadifloxacin, Norfloxacin, Ofloxacin, Orbifloxacin, Pazufloxacin, Pefloxacin, Pradofloxacin, Prulifloxacin, Rosoxacin, Rufloxacin, Sarafloxacin, Sitafloxacin, Sparfloxacin, Temafloxacin, Tosufloxacin, Trovafloxacin, Zabofloxacin; FUSIDANES, including Fusidic Acid; GLYCOLIPODEPSIPEPTIDE, including Ramoplanin; GLYCOPEPTIDES, including Avoparcin, Dalbavancin, Norvancomycin, Oritavancin, Teicoplanin, Telavancin, Vancomycin; GLYCOPHOSPHOLIPIDS, including Bambermycins (bambermycin, moenomycins, flavophospholipol); GLYCYLCYCLINES, including Tigecycline; HYBRIDS, Cadazolid (Oxazolidinone-quinolone), TD-1792 (glycopeptide-cephalosporin); LINCOSAMIDES, including Clindamycin, Lincomycin, Pirlimycin; LIPOPEPTIDES, including Daptomycin, Surotomycin; MACROLIDES, including Azithromycin, Carbomycin, Cethromycin, Clarithromycin, Dirithromycin, Erythromycin, Fidaxomicin, Flurithromycin, Gamithromycin, Josamycin, Kitasamycin, Leucomycin, Meleumycin, Midecamycins, Miokamycin, Mirosamycin, Oleandomycin, Primycin, Rokitamycin, Rosaramicin, Roxithromycin, Sedecamycin, Solithromycin, Spiramycin, Telithromycin, Terdecamycin, Tildipirosin, Tilmicosin, Troleandomycin, Tulathromycin, Tylosin, Tylvalosin; NITROFURANS, including Furaltadone, Furazidin, Furazolidone, Furazolium Chloride, Nifuratel, Nifurfoline, Nifuroxazide, Nifurpirinol, Nifurtoinol, Nifurzide, Nitrofural, Nitrofurantoin, Nitrofurazone; NITROIMIDAZOLES, including Dimetridazole, Metronidazole, Ornidazole, Ronidazole, Secnidazole, Tinidazole; OLIGOSACCHARIDES, including Avilamycin, Everninomicin; OTHER ANTIBACTERIAL AGENTS, including Auriclosene, Chloroxine, Chlorquinaldol, Clioquinol, Clofoctol, Halquinol, Lotilibcin, Mandelic Acid, Methenamine (hexamine), Nitazole, Nitroxoline, Perchlozone, Taurolidine, Thenoic Acid, Xibornol; OXAZOLIDINONES, including Eperezolid, Linezolid, Posizolid, Radezolid, Sutezolid, Tedizolid (Torezolid); PEPTIDE DEFORMYLASE INHIBITORS, including GSK1322322; PEPTIDES, including Omiganan, Pexiganan; PLEUROMUTILINS, including Retapamulin, Tiamulin, Valnemulin; POLYETHER IONOPHORES, including Laidlomycin, Lasalocid, Maduramicin, Monensin, Narasin, Salinomycin, Semduramicin; POLYMYXINS, including Colistin, Polymyxin B; POLYPEPTIDES, including Amphomycin, Bacitracin, Capreomycin, Enduracidin, Enramycin, Enviomycin, Fusafungine, Gramicidin(s), Iseganan, Magainins, Nosiheptide, Ristocetin, Thiostrepton, Tuberactinomycin, Tyrocidine, Tyrothricin, Viomycin; PSEUDOMONIC ACIDS, including Mupirocin; QUINOLONES, including Nalidixic Acid, Nemonoxacin, Oxolinic Acid, Ozenoxacin, Pipemidic Acid, Piromidic Acid; QUINOXALINES, including Carbadox, Olaquindox; RIMINOFENAZINES, including Clofazimine; STATINS, including Atorvastatin, Fluvastatin, Lovastatin, Mevastatin, Pitavastatin, Pravastatin, Rosuvastatin, Simvastatin; STREPTOGRAMINS, including Dalfopristin, Flopristin, Linopristin, Pristinamycin, Quinupristin, Virginiamycin; STREPTOTHRICINS, including Nourseothricin; SULFONAMIDES, including Acetyl Sulfamethoxypyrazine, Chloramine-B, Chloramine-T, Dichloramine T, Formosulfathiazole, Mafenide, N4-Sulfanilylsulfanilamide, Noprylsulfamide, N-Sulfanilyl-3,4-xylamide, Ormaosulfathiazole, Phthalylsulfacetamide, Phthalylsulfathiazole, Salazosulfadimidine, Succinylsulfathiazole, Sulfabenzamide, Sulfacarbamide, Sulfacetamide, Sulfachlorpyridazine, Sulfachrysoidine, Sulfaclozine, Sulfacytine, Sulfadiazine, Sulfadicramide, Sulfadimethoxine, Sulfadimidine, Sulfadoxine, Sulfaethidole, Sulfaguanidine, Sulfaguanole, Sulfalene, Sulfaloxic Acid, Sulfamerazine, Sulfameter, Sulfamethazine, Sulfamethizole, Sulfamethomidine, Sulfamethoxazole, Sulfamethoxypyridazine, Sulfamethylthiazole, Sulfametopyrazine, Sulfametrole, Sulfamidochrysoidine, Sulfamonomethoxine, Sulfamoxole, Sulfanilamide, Sulfanilylurea, Sulfaperine, Sulfaphenazole, Sulfaproxyline, Sulfapyrazine, Sulfapyridine, Sulfaquinoxaline, Sulfathiazole, Sulfathiourea, Sulfatroxazole, Sulfisomidine, Sulfisoxazole (Sulfafurazole); SULFONES, including Acediasulfone, Dapsone, Glucosulfone Sodium, p-Sulfanilylbenzylamine, Succisulfone, Sulfanilic Acid, Sulfoxone Sodium, Thiazolsulfone; TETRACYCLINES, including Chlortetracycline, Clomocycline, Demeclocycline, Doxycycline, Eravacycline, Guamecycline, Lymecycline, Meclocycline, Methacycline, Minocycline, Oxytetracycline, Penimepicycline, Pipacycline, Rolitetracycline, Sarecycline, and Tetracycline.

The composition of the invention may further comprise an excipient selected from the group comprising, but not limited to, binders and compression aids, coatings and films, colouring agents diluents and vehicles disintegrants, emulsifying and solubilising agents, flavours and sweeteners, repellents, glidants and lubricants, plasticisers, preservatives, propellants, solvents, stabilisers, suspending agents and viscosity enhancers.

According to a further aspect of the invention, there is provided a medical device when used in a method of treating or preventing a bacterial infection in the subject.

According to further aspect of the invention, there is provided a medical device comprising the composition of the invention. The composition of the invention may be any slow release form, and/or in the form of a coating of the medical device.

The medical device may be in a form selected from the group comprising: an implant, a plaster, a bandage, and other dressing applied to a bacterial infection in a subject.

According to further aspect of the invention, there is provided a method of killing bacteria, the method including the step of contacting the bacteria with a compound of the invention, or a therapeutically acceptable salt thereof.

According to further aspect of the invention, there is provided the use of a compound of the invention, or a therapeutically acceptable salt thereof, to kill bacteria, said use comprising the step of contacting the bacteria with a compound of the invention, or a therapeutically acceptable salt thereof.

Terms used herein will have their customary meanings in the art unless specified. As used herein, the term robenidine, NCL812 (also known as 1,3-bis[(E)-(4-chlorophenyl)methyleneamino]guanidine) refers to a compound having the following chemical structure:

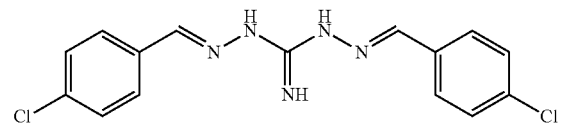 [SMILES: N=C(N/N=C/c1ccc(Cl)cc1)N/N=C/c1ccc(Cl)cc1]

BRIEF DESCRIPTION OF THE DRAWINGS

Further features of the present invention are more fully described in the following description of several non-limiting embodiments thereof. This description is included solely for the purposes of exemplifying the present invention. It should not be understood as a restriction on the broad summary, disclosure or description of the invention as set out above. The description will be made with reference to the accompanying drawings in which.

DESCRIPTION OF EMBODIMENTS

General

Figure 1:
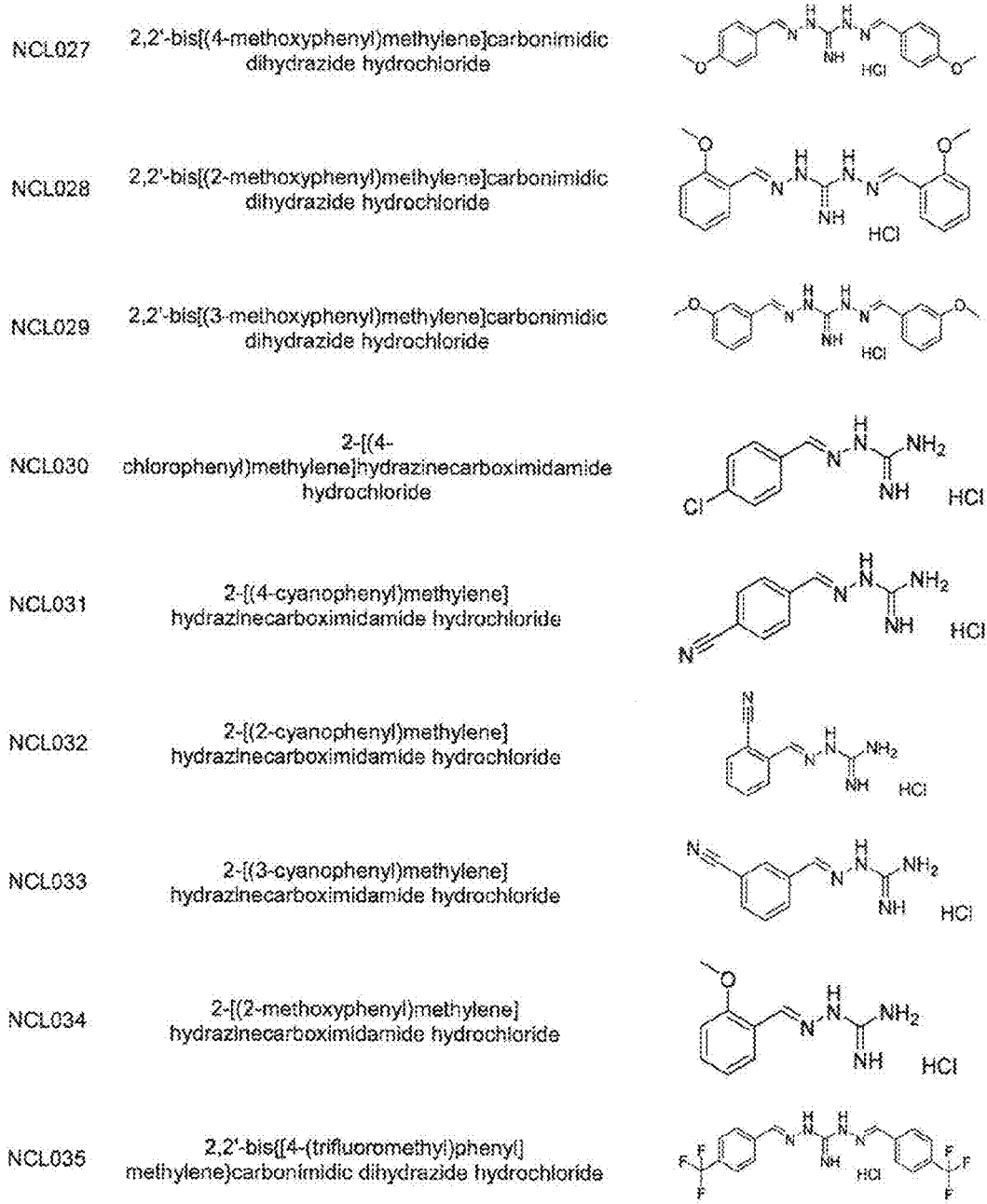
FIG. 1 presents the chemical name and chemical structure of the compounds NCL001 to NCL230.
Figure 1:
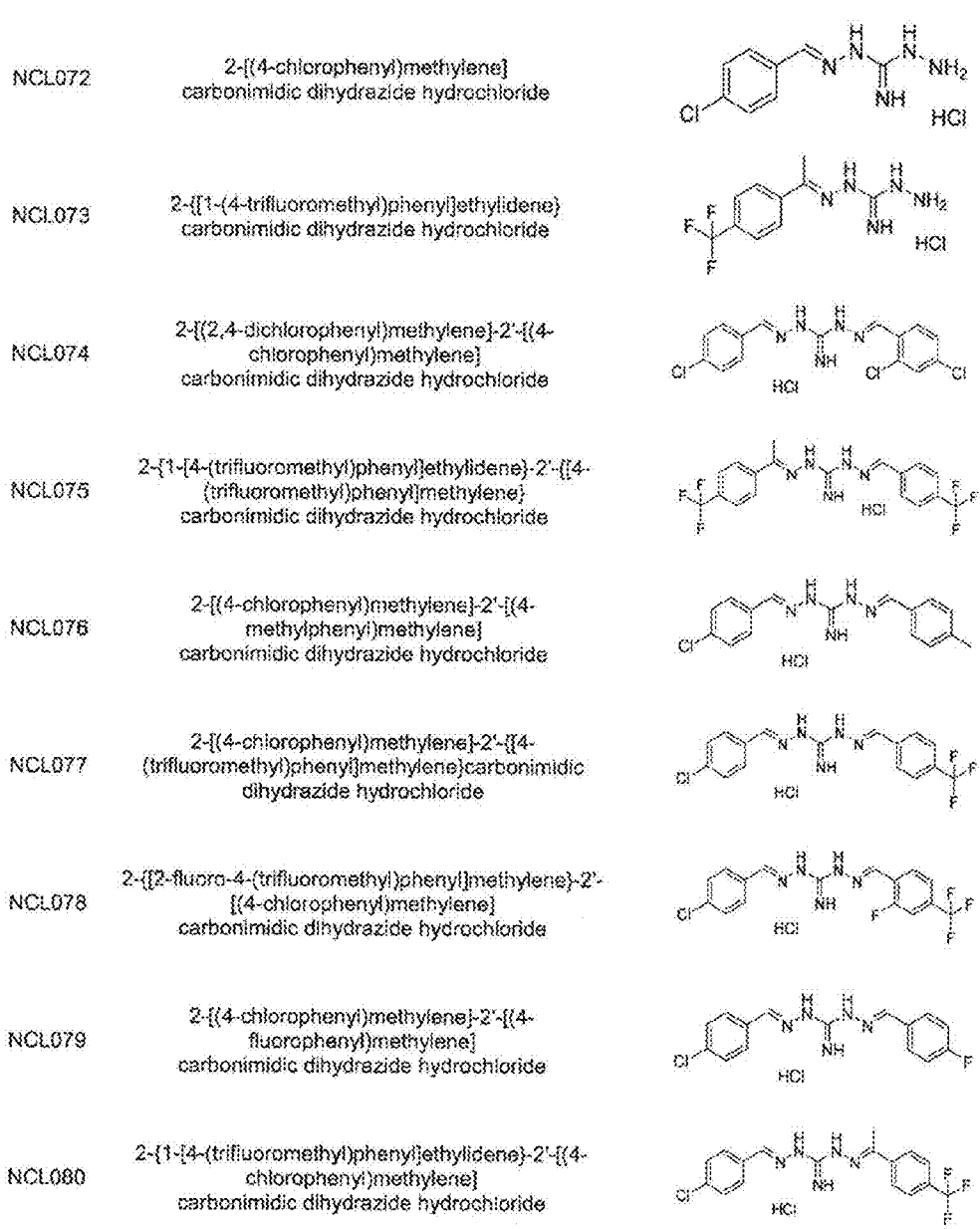
Figure 1:
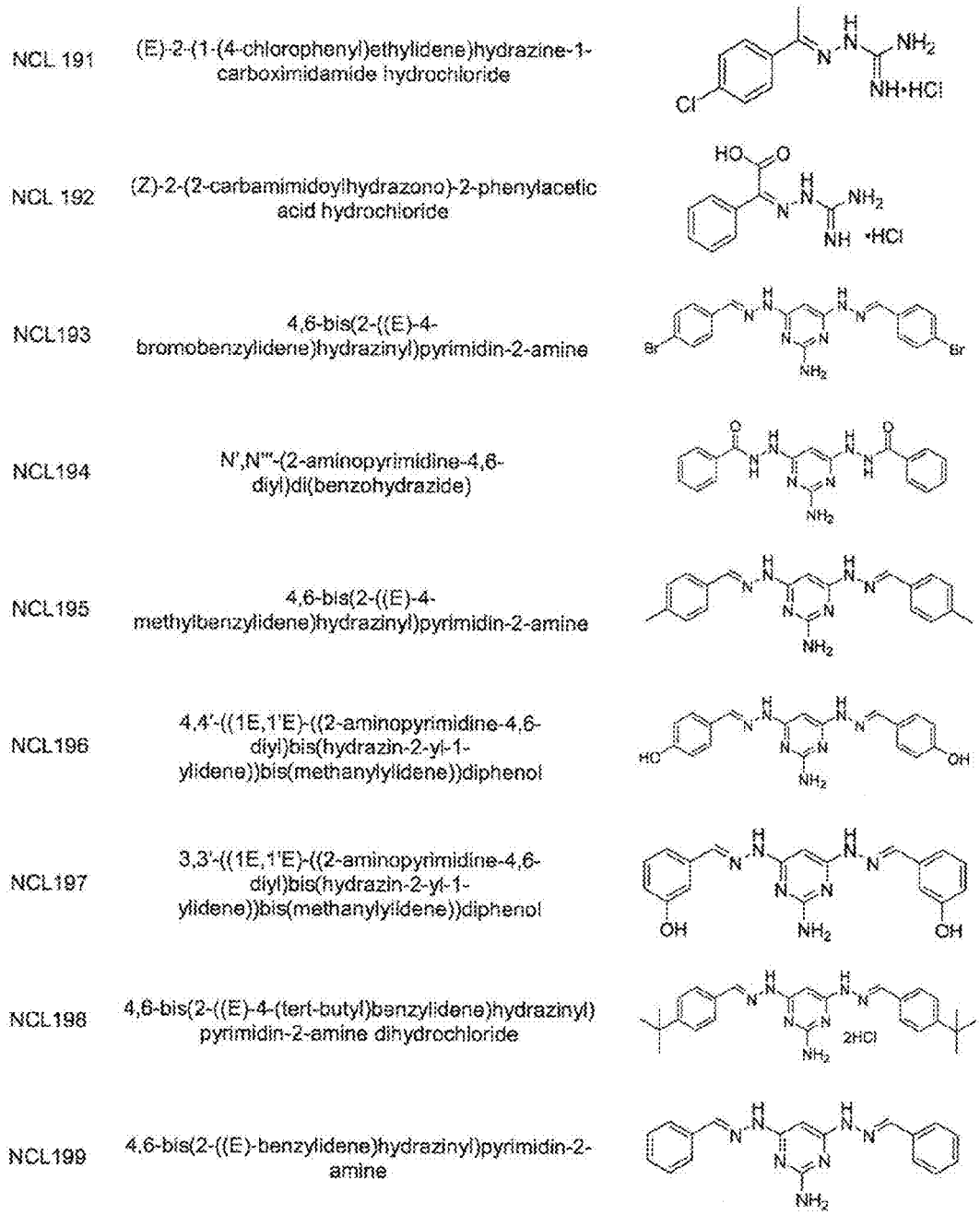
Figure 1:
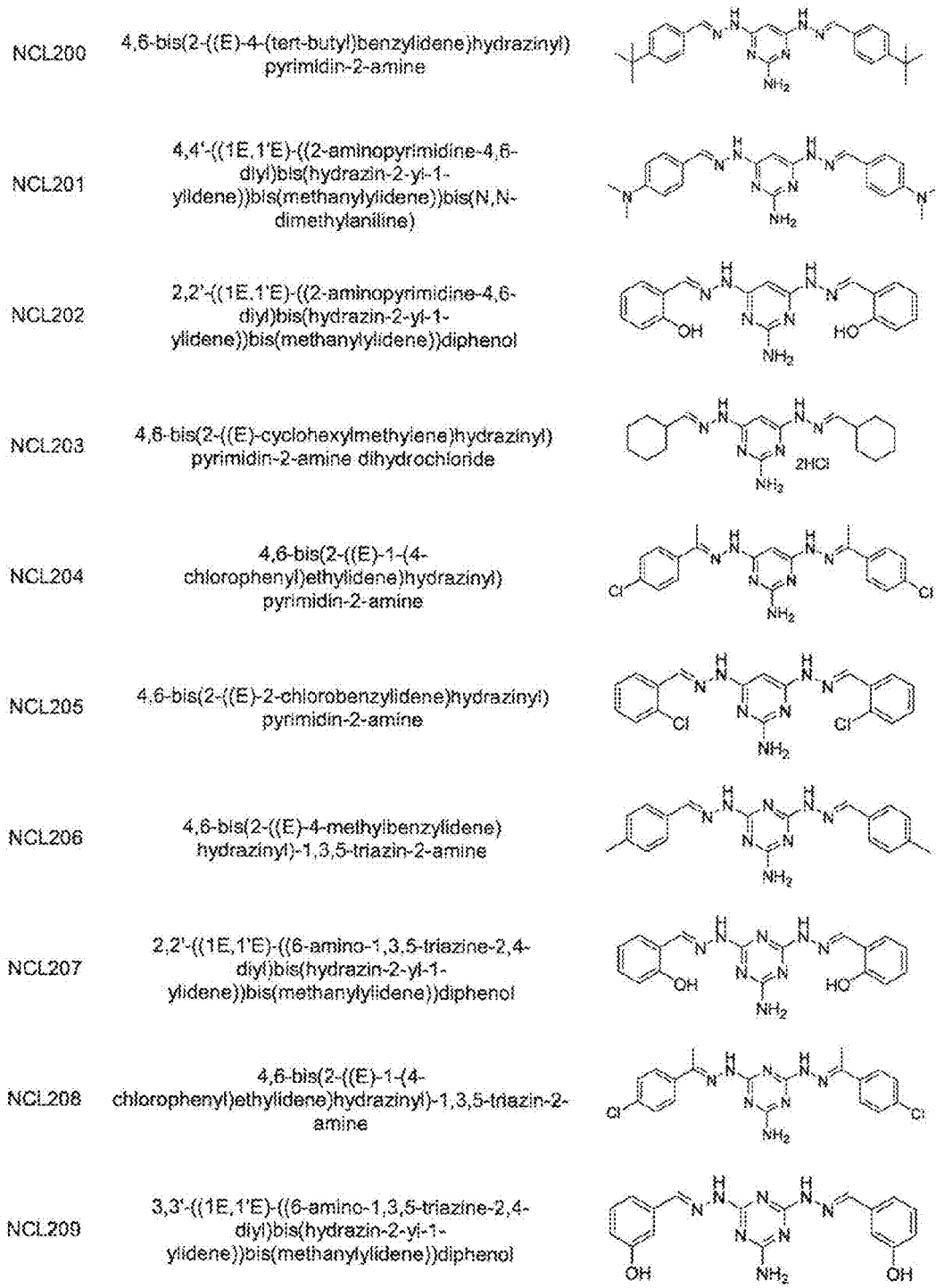

Before describing the present invention in detail, it is to be understood that the invention is not limited to particular exemplified methods or compositions disclosed herein. It is also to be understood that the terminology used herein is for the purpose of describing particular embodiments of the invention only, and is not intended to be limiting.

All publications referred to herein, including patents or patent applications, are incorporated by reference in their entirety. However, applications that are mentioned herein are referred to simply for the purpose of describing and disclosing the procedures, protocols, and reagents referred to in the publication which may have been used in connection with the invention. The citation of any publications referred to herein is not to be construed as an admission that the invention is not entitled to antedate such disclosure by virtue of prior invention.

In addition, the carrying out of the present invention makes use of, unless otherwise indicated, conventional microbiological techniques within the skill of the art. Such conventional techniques are known to the skilled worker.

As used herein, and in the appended claims, the singular forms "a", "an", and "the" include the plural unless the context clearly indicates otherwise.

Unless otherwise indicated, all technical and scientific terms used herein have the same meanings as commonly understood by one of ordinary skill in the art to which this invention belongs. Although any materials and methods similar to, or equivalent to, those described herein may be used to carry out the present invention, the preferred materials and methods are herein described.

The invention described herein may include one or more ranges of values (e.g. size, concentration, dose etc). A range of values will be understood to include all values within the range, including the values defining the range, and values adjacent to the range that lead to the same or substantially the same outcome as the values immediately adjacent to that value which define the boundary of the range.

The pharmaceutical or veterinary compositions of the invention may be administered in a variety of unit dosages depending on the method of administration, target site, physiological state of the patient, and other medicaments administered. For example, unit dosage form suitable for oral administration include solid dosage forms such as powder, tablets, pills, and capsules, and liquid dosage forms, such as elixirs, syrups, solutions and suspensions. The active ingredients may also be administered parenterally in sterile liquid dosage forms. Gelatin capsules may contain the active ingredient and inactive ingredients such as powder carriers, glucose, lactose, sucrose, mannitol, starch, cellulose or cellulose derivatives, magnesium stearate, stearic acid, sodium saccharin, talcum, magnesium carbonate, and the like.

The phrase "therapeutically effective amount" as used herein refers to an amount sufficient to inhibit bacterial growth associated with a bacterial infection or colonisation. That is, reference to the administration of the therapeutically effective amount of a compound of Formula I according to the methods or compositions of the invention refers to a therapeutic effect in which substantial bacteriocidal or bacteriostatic activity causes a substantial inhibition of bacterial infection. The term "therapeutically effective amount" as used herein, refers to a sufficient amount of the composition to provide the desired biological, therapeutic, and/or prophylactic result. The desired results include elimination of bacterial infection or colonisation or reduction and/or alleviation of the signs, symptoms, or causes of a disease, or any other desired alteration of a biological system. An effective amount in any individual case may be determined by one of ordinary skill in the art using routine experimentation. In relation to a pharmaceutical or veterinary composition, effective amounts can be dosages that are recommended in the modulation of a diseased state or signs or symptoms thereof. Effective amounts differ depending on the composition used and the route of administration employed. Effective amounts are routinely optimized taking into consideration pharmacokinetic and pharmacodynamic characteristics as well as various factors of a particular patient, such as age, weight, gender, etc and the area affected by disease or disease causing microbes.

As referred to herein, the terms "treatment" or "treating" refers to the full or partial removal of the symptoms and signs of the condition. For example, in the treatment of a bacterial infection or colonisation, the treatment completely or partially removes the signs of the infection. Preferably in the treatment of infection, the treatment reduces or eliminates the infecting bacterial pathogen leading to microbial cure.

As referred to herein, the term "bacteria" refers to members of a large domain of prokaryotic microorganisms. Typically a few micrometers in length, bacteria have a number of shapes, ranging from spheres to rods and spirals and can be present as individual cells or present in linear chains or clusters of variable numbers and shape. Preferably the terms "bacteria" and its adjective "bacterial" refer to bacteria such as the Gram positive *Staphylococcus* spp, *Streptocccus* spp, *Bacillus* spp, *Enterococcus* spp, *Listeria* spp, and anaerobic bacteria; Gram negative *Escherichia coli*, *Enterobacter* spp, *Klebsiella* spp and *Pseudomonas* spp; and the cell wall free bacteria such as *Mycoplasma* spp and *Ureaplasma* spp. The terms may refer to an antibiotic-sensitive strain or an antibiotic-resistant strain. In a preferred embodiment, the terms refer to MRSA or MRSP. In another preferred embodiment, the terms refer to MDR *Staphylococcus* spp, *Streptococcus* spp, *Enterococcus* spp, *Clostridium Escherichia coli*, *Enterobacter* spp, *Klebsiella* spp and *Pseudomonas* spp.

Referred to herein, the term "methicillin-resistant bacteria" (such as methicillin-resistant *Staphylococcus*) refers a bacteria isolate that demonstrates resistance at any dose to all β-lactams including penicillins, carbapenems and first to fourth generation cephalosporins, but not to the fifth generation anti-MRSA cephalosporins (for example ceftaroline). Multidrug-resistant (MDR) is defined as acquired non-susceptibility to at least one agent in three or more antimicrobial categories, extensively drug-resistant (XDR) is defined as non-susceptibility to at least one agent in all but two or fewer antimicrobial categories (i.e. bacterial isolates remain susceptible to only one or two categories) and pandrug-resistant (PDR) is defined as non-susceptibility to all agents in all antimicrobial categories currently available.

An example of susceptible, MDR, XDR and PDR bacteria includes the following. Wild type, antibacterial unexposed isolates of *Staphylococcus aureus* that are likely to be susceptible to all of the following antibacterial categories (and agents): aminoglycosides (for example gentamicin); ansamycins (for example rifampicin); anti-MRSA cephalosporins (for example ceftaroline); anti-staphylococcal β-lactams (for example oxacillin or cefoxitin); carbapenems (for example ertapenem, imipenem, meropenem or doripenem); non-extended spectrum cephalosporins; 1st and 2nd generation cephalosporins (for example cefazolin or cefuroxime); extended-spectrum cephalosporins; 3rd and 4th generation cephalosporins (for example cefotaxime or ceftriaxone); cephamycins (for example cefoxitin or cefotetan); fluoroquinolones (for example ciprofloxacin or moxifloxacin); folate pathway inhibitors (for example trimethoprim-sulphamethoxazole); fucidanes (for example fusidic acid); glycopeptides (for example vancomycin, teicoplanin or telavancin); glycylcyclines (for example tigecycline); lincosamides (for example clindamycin); lipopeptides (for example daptomycin); macrolides (for example erythromycin); oxazolidinones (for example linezolid or tedizolid); phenicols (for example chloramphenicol); phosphonic acids (for example fosfomycin); streptogramins (for example quinupristin-dalfopristin); and tetracyclines (for example tetracycline, doxycycline or minocycline). Isolates that are non-susceptible to more than one agent in more than three antimicrobial categories are classified as MDR (all MRSA, for example, meet the definition of MDR). Isolates that are non-susceptible to more than one agent in all but one or two antimicrobial categories are classified as XDR. Isolates that are non-susceptible to all listed antibacterial agents are PDR.

Pharmaceutically and veterinary acceptable salts include salts which retain the biological effectiveness and properties of the compounds of the present disclosure and which are not biologically or otherwise undesirable. In many cases, the compounds disclosed herein are capable of forming acid and/or base salts by virtue of the presence of amino and/or carboxyl groups or groups similar thereto. Acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as by way of example only, alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amines, trisubstituted cycloalkyl amines, cycloalkenyl amines, di(cycloalkenyl) amines, tri(cycloalkenyl) amines, substituted cycloalkenyl amines, disubstituted cycloalkenyl amines, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Pharmaceutically and veterinary acceptable acid addition salts may be prepared from inorganic and organic acids. The inorganic acids that can be used include, by way of example only, hydrochloric acid, hydrobromic acid, sulfuric acid, nitric acid, phosphoric acid, and the like. The organic acids that can be used include, by way of example only, acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

The pharmaceutically or veterinary acceptable salts of the compounds useful in the present disclosure can be synthesized from the parent compound, which contains a basic or acidic moiety, by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences. 17th ed., Mack Publishing Company, Easton, Pa. (1985), p. 1418, the disclosure of which is hereby incorporated by reference. Examples of such acceptable salts are the iodide, acetate, phenyl acetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, γ-hydroxybutyrate, β-hydroxybutyrate, butyne-1,4-dioate, hexyne-1,4-dioate, hexyne-1,6-dioate, caproate, caprylate, chloride, cinnamate, citrate, decanoate, formate, fumarate, glycollate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, propanesulfonate, ethanesulfonate, 2-hydroxyethanesulfonate, merhanesulfonate, naphthalene-1-sulfonate, naphthalene-2-sulfonate, p-toluenesulfonate, xylenesulfonate, tartarate, and the like.

The pharmaceutical or veterinary compositions of the invention may be formulated in conventional manner, together with other pharmaceutically acceptable excipients if desired, into forms suitable for oral, parenteral, or topical administration. The modes of administration may include parenteral, for example, intramuscular, subcutaneous and intravenous administration, oral administration, topical administration and direct administration to sites of infection such as intraocular, intraaural, intrauterine, intranasal, intramammary, intraperitoneal, intralesional, etc.

The pharmaceutical or veterinary compositions of the invention may be formulated for oral administration. Traditional inactive ingredients may be added to provide desirable colour, taste, stability, buffering capacity, dispersion, or other known desirable features. Examples include red iron oxide, silica gel, sodium laurel sulphate, titanium dioxide, edible white ink, and the like. Conventional diluents may be used to make compressed tablets. Both tablets and capsules may be manufactured as sustained-release compositions for the continual release of medication over a period of time. Compressed tablets may be in the form of sugar coated or film coated tablets, or enteric-coated tablets for selective disintegration in the gastrointestinal tract. Liquid dosage forms for oral administration may contain colouring and/or flavouring to increase patient compliance. As an example, the oral formulation comprising compounds of the invention may be a tablet comprising any one, or a combination of, the following excipients: calcium hydrogen phosphate dehydrate, microcrystalline cellulose, lactose, hydroxypropyl methyl cellulose, and talc.

The compositions described herein may be in the form of a liquid formulation. Examples of preferred liquid compositions include solutions, emulsions, injection solutions, solutions contained in capsules. The liquid formulation may comprise a solution that includes a therapeutic agent dissolved in a solvent. Generally, any solvent that has the desired effect may be used in which the therapeutic agent dissolves and which can be administered to a subject. Generally, any concentration of therapeutic agent that has the desired effect can be used. The formulation in some variations is a solution which is unsaturated, a saturated or a supersaturated solution. The solvent may be a pure solvent or may be a mixture of liquid solvent components. In some variations the solution formed is an in situ gelling formulation. Solvents and types of solutions that may be used are well known to those versed in such drug delivery technologies.

The composition described herein may be in the form of a liquid suspension. The liquid suspensions may be prepared according to standard procedures known in the art. Examples of liquid suspensions include micro-emulsions, the formation of complexing compounds, and stabilising suspensions. The liquid suspension may be in undiluted or concentrated form. Liquid suspensions for oral use may contain suitable preservatives, antioxidants, and other excipients known in the art functioning as one or more of dispersion agents, suspending agents, thickening agents, emulsifying agents, wetting agents, solubilising agents, stabilising agents, flavouring and sweetening agents, colouring agents, and the like. The liquid suspension may contain glycerol and water.

The composition described herein may be in the form of an oral paste. The oral paste may be prepared according to standard procedures known in the art.

The composition is described herein may be in the form of a liquid formulation for injection, such as intra-muscular injection, and prepared using methods known in the art. For example, the liquid formulation may contain polyvinylpyrrolidone K30 and water.

The composition is described herein may be in the form of topical preparations. The topical preparation may be in the form of a lotion or a cream, prepared using methods known in the art. For example, a lotion may be formulated with an aqueous or oily base and may include one or more excipients known in the art, functioning as viscosity enhancers, emulsifying agents, fragrances or perfumes, preservative agents, chelating agents, pH modifiers, antioxidants, and the like. For example, the topical formulation comprising one or more compounds of the invention may be a gel comprising anyone, or a combination of, the following excipients: PEG 8000, PEG 4000, PEG 200, glycerol, propylene glycol. The NCL812 compound may further be formulated into a solid dispersion using SoluPlus (BASF, www.soluplus.com) and formulated with anyone, or a combination of, the following excipients: PEG 8000, PEG 4000, PEG 200, glycerol, and propylene glycol.

For aerosol administration, the composition of the invention is provided in a finely divided form together with a non-toxic surfactant and a propellant. The surfactant is preferably soluble in the propellant. Such surfactants may include esters or partial esters of fatty acids.

The compositions of the invention may alternatively be formulated for delivery by injection. As an example, the compound is delivered by injection by any one of the following routes: intravenous, intramuscular, intradermal, intraperitoneal, and subcutaneous.

The compositions of the invention may alternatively be formulated using nanotechnology drug delivery techniques such as those known in the art. Nanotechnology-based drug delivery systems have the advantage of improving bioavailability, patient compliance and reducing side effects.

The formulation of the composition of the invention includes the preparation of nanoparticles in the form of nanosuspensions or nanoemulsions, based on compound solubility. Nanosuspensions are dispersions of nanosized drug particles prepared by bottom-up or top-down technology and stabilised with suitable excipients. This approach may be applied to the compounds of the invention which can have poor aqueous and lipid solubility, in order to enhance saturation solubility and improve dissolution characteristics. An example of this technique is set out in Sharma and Garg (2010) (Pure drug and polymer-based nanotechnologies for the improved solubility, stability, bioavailability, and targeting of anti-HIV drugs. *Advanced Drug Delivery Reviews*, 62: p. 491-502). Saturation solubility will be understood to be a compound-specific constant that depends on temperature, properties of the dissolution medium, and particle size (<1-2 µm).

The composition of the invention may be provided in the form of a nansuspension. For nanosuspensions, the increase in the surface area may lead to an increase in saturation solubility. Nanosuspensions are colloidal drug delivery systems, consisting of particles below 1 µm. Compositions of the invention may be in the form of nanosuspensions including nanocrystalline suspensions, solid lipid nanoparticles (SLNs), polymeric nanoparticles, nanocapsules, polymeric micelles and dendrimers. Nanosuspensions may be prepared using a top-down approach where larger particles may be reduced to nanometer dimensions by a variety of techniques known in the art including wet-milling and high-pressure homogenisation. Alternatively, nanosuspensions may be prepared using a bottom-up technique where controlled precipitation of particles may be carried out from solution.

The composition of the invention may be provided in the form of a nanoemulsion. Nanoemulsions are typically clear oil-in-water or water-in-oil biphasic systems, with a droplet size in the range of 100-500 nm, and with compounds of interest present in the hydrophobic phase. The preparation of nanoemulsions may improve the solubility of the compounds of the invention described herein, leading to better bioavailability. Nanosized suspensions may include agents for electrostatic or steric stabilisation such as polymers and surfactants. Compositions in the form of SLNs may comprise biodegradable lipids such as triglycerides, steroids, waxes and emulsifiers such as soybean lecithin, egg lecithin, and poloxamers. The preparation of a SLN preparation may involve dissolving/dispersing drug in melted lipid followed by hot or cold homogenisation. If hot homogenisation is used, the melted lipidic phase may be dispersed in an aqueous phase and an emulsion prepared. This may be solidified by cooling to achieve SLNs. If cold homogenisation is used, the lipidic phase may be solidified in liquid nitrogen and ground to micron size. The resulting powder may be subjected to high-pressure homogenisation in an aqueous surfactant solution.

The Compounds of Formula I as described herein may be dissolved in oils/liquid lipids and stabilised into an emulsion formulation. Nanoemulsions may be prepared using high- and low-energy droplet reduction techniques. High-energy methods may include high-pressure homogenisation, ultrasonication and microfluidisation. If the low-energy method is used, solvent diffusion and phase inversion will generate a spontaneous nanoemulsion. Lipids used in nanoemulsions may be selected from the group comprising triglycerides, soybean oil, safflower oil, and sesame oil. Other components such as emulsifiers, antioxidants, pH modifiers and preservatives may also be added.

The composition may be in the form of a controlled-release formulation and may include a degradable or non-degradable polymer, hydrogel, organogel, or other physical construct that modifies the release of the compound. It is understood that such formulations may include additional inactive ingredients that are added to provide desirable colour, stability, buffering capacity, dispersion, or other known desirable features. Such formulations may further include liposomes, such as emulsions, foams, micelles, insoluble monolayers, liquid crystals, phospholipid dispersions, lamellar layers and the like. Liposomes for use in the invention may be formed from standard vesicle-forming lipids, generally including neutral and negatively charged phospholipids and a sterol, such as cholesterol.

The formulations of the invention may have the advantage of increased solubility and/or stability of the compounds, particularly for those formulations prepared using nanotechnology techniques. Such increased stability and/or stability of the compounds of Formula I may improve bioavailability and enhance drug exposure for oral and/or parenteral dosage forms.

Throughout this specification, unless the context requires otherwise, the word "comprise" or variations such as "comprises" or "comprising", will be understood to imply the

EXAMPLES

Example 1: The Minimum Inhibitory Concentrations (MIC) for NCL812 in Methicillin-Resistant *Staphylococcus aureus* (MRSA), Vancomycin-Resistant *Enterococcus* Spp. (VRE) and *Streptococcus pneumoniae*

Specific

As is apparent from the preceding summary of the invention, the invention relates to compounds of Formula I, methods of treatment of a bacterial infection, uses and medical devices.

This study was undertaken to determine minimum inhibitory concentrations (MIC) for antibacterial agent NCL812. The antibacterial agent represents a potentially new class of drug with a perceived narrow spectrum of activity against bacteria and a novel mechanism of action. This study focused on recent isolates of three major opportunistic pathogens of humans where the development of antibacterial resistance to existing antibacterial classes is problematic: methicillin-resistant *Staphylococcus aureus* (MRSA), vancomycin-resistant *Enterococcus* spp. (VRE) and *Streptococcus pneumoniae*.

In this example, NCL812 minimum inhibitory concentrations (MICs) were determined for 61 Australian clinical isolates (comprised of 21 MRSA, 20 putative VRE and 20 *S. pneumoniae* isolates). The MIC profiles for NCL812 were found to be remarkably consistent, with $MIC_{50}$ and $MIC_{90}$ values of 4 µg/mL recorded for each of the species tested.

Materials and Methods

Bacterial Isolate Collection and Identification

Sixty one test isolates were sourced from clinical diagnostic microbiology laboratories. The MRSA isolates were originally cultured on selective Brilliance MRSA Chromogenic Agar (Oxoid). Suspect colonies were selected on the basis of their colony appearance on this agar and identification as *Staphylococcus aureus* was determined using colony characteristics on non-selective Sheep Blood Agar (SBA) and phenotypic characteristics such as Gram stain, positive catalase test, positive coagulase test (tube coagulase test using rabbit plasma) and clumping factor (agglutination with the Oxoid Staphytect latex test), positive Voges Proskauer test, and the ability to produce acid from trehalose. A positive cefoxitin resistance screen confirmed the isolates as MRSA. All *Enterococcus* isolates underwent a standard biochemical identification. Biochemical profiling provisionally identified four of the VRE isolates as *Enterococcus faecalis* and the remainder as *Enterococcus faecium*. All *S. pneumoniae* isolates were identified on the basis of standard biochemical profiling.

Preparation of Antibacterials

Analytical grade NCL812 (batch 20081214) with a defined potency of 1000 mg/g (ie 100%) was obtained. The powder was stored at a temperature of −20° C. Aliquots (1 mL) of stock solution (25.6 mg/mL) were prepared in DMSO and stored at −80° C. and defrosted immediately before use.

Preparation of 96 Well Microtitre Plates for Broth Microdilution MIC Test Using NCL812

Cation adjusted Mueller Hinton Broth (CAMHB) was prepared using 100 mL sterile Mueller Hinton broth (pH adjusted). To each 100 mL volume, 125 µL of calcium stock solution (10 mg $Ca^{2+}$ per ml) and 43 µL magnesium stock solution (10 mg $Mg^{2+}$ per mL) was aseptically added. Sufficient broth is made up for daily use, with unused portions being stored at 4° C. overnight.

Microdilution trays with 4% lysed horse blood in CAMHB was prepared by lysing horse blood (Oxoid) by repeated freezing and thawing (3-4 times) and aseptically mixing the lysed horse blood (LHB) 50:50 with sterile distilled water. A cell free suspension was obtained by centrifuging 50% LHB at 16,000×g (7000 rpm) for 20 min. The supernatant was decanted, recentrifuged and stored frozen. 50% LHB was diluted with CAMHB to obtain a final concentration of 4% (7 mL LHB into 93 mL CAMHB). 4% LHB-CAMHB was used instead of CAMHB in all steps in the preparation of the microdilution trays and preparation of antimicrobial solutions for *Streptococcus* species.

A stock antibiotic working solution of NCL812 was prepared to a concentration of 25.60 mg/mL. Potency was described as 1000 mg/g or 100%. The powder was dissolved in 10 mL DMSO and 1 mL volumes were aliquoted into eppendorf tubes and stored at −80° C. When added to CAMHB, a fine cloudy precipitate formed, and was shaken well before and during aliquoting.

A stock solution of ampicillin was prepared to the concentration of 25.60 mg/mL. Ampicillin was used for internal quality control. The powdered ampicillin was dissolved in 4 mL of phosphate buffer pH 8.0, 0.1 mol/L, then diluted in 6 mL phosphate buffer pH 6.0, 0.1 mol/L. 1 mL volumes were aliquoted into eppendorf tubes and stored at −80° C.

For *Staphylococcus aureus*, a working solution of 256 µg/mL was prepared by diluting stock solutions as described above 1:100 in CAMHB (100 µL into 9.9 mL). When 90 µL was added to each well 12, there was a 1:2 dilution so that well 12 had 128 µg/mL of antibiotic. The range of antimicrobial was calculated as 0.25 µg/mL (well 3) to 128 µg/mL (well 12).

For *Enterococcus* species, a working solution of 64 µg/mL was prepared by diluting stock solutions as described above 1:400 in CAMHB (100 µL into 9.9 mL, then further dilute this 1:4). When 90 µL was added to well 12 there was a 1:2 dilution so that well 12 had 32 µg/mL of antibiotic.

For *Streptococcus pneumoniae*, a working solution of 64 µg/mL was prepared by diluting stock solutions as described above 1:400 in 4% LHB-CAMHB (100 µL into 9.9 mL, then further diluting this 1:4). When 90 µL Mars added to well 12 there was a 1:2 dilution so that well 12 had 32 µg/mL of antibiotic.

Serial dilutions were prepared in 96 well plates were set up in a safety cabinet according to methods standard in the art. Briefly: 90 µL of the working antibiotic solution was added to each well in Column 12 of the plate, and mixed well, before 90 µL was transferred to column 11. The solutions were mixed again, and then transferred to the next column as before, continuing the dilutions through to column 3. Mixing the well requires the pick up and expulsion of 90 µL in each well 3-4 times before picking up and transferring the 90 µL to the next well. Column 2 (bacterial positive control) and column 1 (negative control) did not form part of the serial dilution. The trays were set up as follows: 2 strains were tested in duplicate in one tray, such that strain 1 was located in rows A to D, strain 2 was located in rows E to H, etc. The MIC (µg/mL) Interpretive Standard for Ampicillin using Control strains is shown in Table 1 below. *Staphylococcus aureus* ATCC 29213 Acceptable MIC range for Ampicillin=0.5 to 2 µg/mL, *Enterococcus faecalis* ATCC 29212 Acceptable MIC range for Ampicillin=0.5 to 2 µg/mL, *Streptococcus pneumoniae* ATCC 49619 Acceptable MIC range for Ampicillin=0.06 to 0.25 µg/mL.

TABLE 1

MIC (μg/mL) Interpretive Standard for Ampicillin using
Control strains according to Example 1.

|  | Sensitive | Intermediate | Resistant |
|---|---|---|---|
| Staphylococcus aureus | ≤0.25 |  | ≥0.5 |
| Enterococcus species | ≤8 |  | ≥16 |
| Streptococcus pneumoniae | ≤2 | 4 | ≥8 |

Preparation of Bacterial Suspension for Broth Microdilution MIC Method

Fresh cultures of bacteria were prepared for testing on sheep blood agar (SBA), and overnight incubation at 37° C. as follows; 2-3 colonies of each strain in 7 mL sterile saline, and the $OD_{600}$ measured as an indication of the density (approx. 0.5×108 CFU/mL or 0.5 McFarland Standard). The bacterial suspension was adjusted to a final absorbance of 0.08 to 0.100, using saline to achieve correct density, and as the blank. Within 15 minutes of preparation, the adjusted bacterial suspension with sterile saline 1:20 (1 mL into 19 mL sterile saline) to achieve a final bacterial concentration of 4 to 5×10$^6$ CFU/mL. The bacterial solution was placed into a sterile trough and 10 μL of bacterial solution added into wells 2 through to 12 on each required row (dilution of 1:10, with final concentration of bacteria in wells=5×105 CFU/mL). The tray was sealed and incubated at 37° C. for 18-24 h. The purity of bacterial suspension was confirmed by streaking out 50 μL of the 1:20 dilution onto a SBA plate, which was incubated for 37° C. for 18 h and examined. Viable counts were carried out to ensure that the correct concentration of bacteria and been added to the wells. The diluted bacterial solution (4 to 5×10$^6$ CFU/mL) was diluted 1:10 downwards by adding 100 μL to 900 μL of sterile saline in sterile tubes, and the serial dilutions continued 1:10 for 5 tubes. 100 μL (4-5 drops) of the 4$^{th}$ and 5$^{th}$ dilutions (tube 4=105 and tube 5=106 CFU/ml) was plated around in duplicate on pre-dried PCA agar plates and incubated at 37° C. overnight. The following day the number of colonies on the plates was counted and the average count in 100 μL obtained. The study was multiplied by 10 to obtain a viable bacterial count per mL.

Description and Identification of Isolates

The MRSA isolates were originally cultured on selective Brilliance MRSA Chromogenic Agar (Oxoid). Suspect colonies were selected on the basis of their colony appearance on this agar and identification as Staphylococcus aureus was determined using colony characteristics on non-selective SBA and phenotypic characteristics such as Gram stain, positive catalase test, positive coagulase test (tube coagulase test using rabbit plasma) and clumping factor (agglutination with the Oxoid Staphytect latex test), positive Voges Proskauer test, and the ability to produce acid from trehalose. A positive cefoxitin resistance screen confirmed the isolates as MRSA.

MRSA clonal complexes were determined by rapid molecular typing. Two of the strains could not be typed using the rapid method, as shown in Table 2 below.

TABLE 2 a table showing the MRSA clonal complexes according to Example 1.

| Organism/Sample no. | Clonal complex |
|---|---|
| Staph. aureus ATCC 29213 | NA |
| MRSA 718 | CC8 |
| MRSA 741 | CC8 |
| MRSA 580 | CC8 |
| MRSA 622 | CC22 |
| MRSA 815 | CC88 |
| MRSA 844 | CC22 |
| MRSA 606 | CC22 |
| MRSA 786 | CC88 |
| MRSA 570 | CC8 |
| MRSA 773 | TBD |
| MRSA 698 | CC1 |
| MRSA 787 | CC8 |
| MRSA 728 | CC88 |
| MRSA 713 | CC8 |
| MRSA 747 | CC8 |
| MRSA 616 | CC5 |
| MRSA 734 | CC8 |
| MRSA 516 | TBD |
| MRSA 823 | CC8 |
| MRSA 778 | CC8 |
| MRSA 610 | CC22 |

NA: Not Applicable;
TBD: Isolates could not be typed using the rapid method and are currently being identified using traditional methodology.

All Enterococcus isolates underwent a simplified biochemical identification based on Quinn et al. (1994, Clinical Veterinary Microbiology, Mosby Ltd, New York). Biochemical profiling provisionally identified four of the VRE isolates as Enterococcus faecalis and the remainder as possibly Enterococcus faecium. All S. pneumoniae isolates were identified on the basis of standard biochemical profiling.

Test Product and Storage

Analytical grade NCL812 (batch 20081214) with a defined potency of 1000 mg/g (ie 100%) was obtained and the powder was stored at a temperature of −20° C. Aliquots (1 mL) of stock solution (25.6 mg/mL) were prepared in DMSO and stored at −80° C. and defrosted immediately before use.

Minimum Inhibitory Concentration Determination

Minimum inhibitory concentrations (μg/mL) were determined using the broth microdilution method recommended by the Clinical and Laboratory Standards Institute (CLSI) (Methods for Dilution Antimicrobial Susceptibility Tests for Bacteria That Grow Aerobically; Approved Standard—Seventh Edition. CLSI M7-A7, 2006; Performance Standards for Antimicrobial Disk and Dilution Susceptibility Tests for Bacteria Isolated from Animals; Approved Standard—Second Edition. CLSI M31-A2, 2002; Performance Standards for Antimicrobial Susceptibility Testing; CLSI M2-A9, 2006).

The MIC was regarded as the the lowest concentration of an antimicrobial agent that completely inhibited growth of the organism in the microdilution wells as detected by the unaided eye. MIC breakpoints were determined by visual assessment and then confirmed using an ELISA plate reader, measuring absorbance levels at 450 nm. Bacterial growth (turbidity) in the wells with antimicrobial was compared with the amount of growth (turbidity) in the growth-control well (containing no antimicrobial). All isolates were tested in duplicate, if there was a difference of greater than one two-fold dilution in the results, the test was repeated a third time. The purity of the isolates was closely monitored during testing by subculturing the prepared bacterial inoculum onto SBA. Control organisms (Enterococcus faecalis strain ATCC 29212, S. aureus strain ATCC 29213 and S. pneu-

*moniae* strain ATCC 49619) were used throughout the testing to monitor quality control. The MICs of the control strains for the antimicrobial ampicillin (range 1.0, 2.0 and 0.06 µg/mL, respectively) were determined for each testing run as an internal quality control. The $MIC_{50}$, $MIC_{90}$ and MIC range (minimum and maximum) were calculated for each of the bacterial groups.

Results

Ampicillin MIC values obtained for the ATCC control strains were within the normal range expected on the basis of CLSI recommendations. The NCL812 and ampicillin MIC values for each isolate are indicated in Table 3 (MRSA isolates), Table 4 (VRE isolates) and Table 5 (*S. pneumoniae* isolates) below. $MIC_{50}$, $MIC_{90}$, MIC mode and MIC range for each of the species of bacteria tested are shown in Table 6 below. The $MIC_{50}$ is considered to be the lowest concentration which inhibits visible growth for 50% of the isolates. The $MIC_{90}$ is considered to be the lowest concentration which inhibits visible growth for 90% of the isolates. The MIC mode is the most commonly occurring MIC value and MIC range the minimum and maximum MIC values obtained.

TABLE 3

The Minimum Inhibitory Concentrations for the individual *Staphylococcus aureus* isolates according to Example 1.

| MIC Testing-AMP/NCL812 Organism/Sample no. | Test 1 AMP | Test 2 AMP | Test 1 NCL812 | Test 2 NCL812 |
|---|---|---|---|---|
| *Staph. aureus* ATCC 29213 | 2 µg/ml | 2 µg/ml | 4 µg/ml | 4 µg/ml |
| MRSA 718 | >128 µg/ml | >128 µg/ml | 4 µg/ml | 8 µg/ml |
| MRSA 741 | 8 µg/ml | 8 µg/ml | 4 µg/ml | 4 µg/ml |
| MRSA 580 | >128 µg/ml | >128 µg/ml | 4 µg/ml | 4 µg/ml |
| MRSA 622 | 64 µg/ml | 64 µg/ml | 4 µg/ml | 4 µg/ml |
| MRSA 815 | 64 µg/ml | 64 µg/ml | 4 µg/ml | 4 µg/ml |
| MRSA 844 | 128 µg/ml | 128 µg/ml | 4 µg/ml | 4 µg/ml |
| MRSA 606 | 32 µg/ml | 32 µg/ml | 4 µg/ml | 4 µg/ml |
| MRSA 786 | 32 µg/ml | 64 µg/ml | 4 µg/ml | 4 µg/ml |
| MRSA 570 | >128 µg/ml | >128 µg/ml | 4 µg/ml | 4 µg/ml |
| MRSA 773 | 128 µg/ml | 64 µg/ml | 4 µg/ml | 4 µg/ml |
| MRSA 698 | 64 µg/ml | 64 µg/ml | 4 µg/ml | 4 µg/ml |
| MRSA 787 | >128 µg/ml | >128 µg/ml | 4 µg/ml | 4 µg/ml |
| MRSA 728 | 64 µg/ml | 64 µg/ml | 4 µg/ml | 4 µg/ml |
| MRSA 713 | >128 µg/ml | >128 µg/ml | 4 µg/ml | 4 µg/ml |
| MRSA 747 | >128 µg/ml | >128 µg/ml | 8 µg/ml | 4 µg/ml |
| MRSA 616 | 64 µg/ml | 64 µg/ml | 8 µg/ml | 4 µg/ml |
| MRSA 734 | >128 µg/ml | >128 µg/ml | 4 µg/ml | 4 µg/ml |
| MRSA 516 | 32 µg/ml | 32 µg/ml | 4 µg/ml | 4 µg/ml |
| MRSA 823 | >128 µg/ml | >128 µg/ml | 4 µg/ml | 4 µg/ml |
| MRSA 778 | >128 µg/ml | >128 µg/ml | 4 µg/ml | 4 µg/ml |
| MRSA 610 | 128 µg/ml | 128 µg/ml | 4 µg/ml | 4 µg/ml |
| AMP Ampicillin MIC90 | >128 µg/ml | >128 µg/ml | 4 µg/ml | 4 µg/ml |

TABLE 4

The Minimum Inhibitory Concentrations for the individual *Enterococcus* isolates according to Example 1.

| MIC Testing-AMP/NCL812 Organism/Sample no. | Test 1 AMP | Test 2 AMP | Test 1 NCL812 | Test 2 NCL812 |
|---|---|---|---|---|
| *Enterococcus* spp. ATCC 29212 | 1 µg/ml | 1 µg/ml | 4 µg/ml | 4 µg/ml |
| VRE 001 | 0.5 µg/ml | 0.5 µg/ml | 2 µg/ml | 2 µg/ml |
| VRE 002 | 1 µg/ml | 1 µg/ml | 4 µg/ml | 4 µg/ml |
| VRE 003 | 0.5 µg/ml | 0.5 µg/ml | 2 µg/ml | 2 µg/ml |
| VRE 004 | 1 µg/ml | 1 µg/ml | 4 µg/ml | 4 µg/ml |
| VRE 005 | 1 µg/ml | 1 µg/ml | 2 µg/ml | 2 µg/ml |
| VRE 006 | 1 µg/ml | 1 µg/ml | 2 µg/ml | 2 µg/ml |
| VRE 007 | 1 µg/ml | 1 µg/ml | 4 µg/ml | 4 µg/ml |
| *Enterococcus* 008 | 1 µg/ml | 1 µg/ml | 4 µg/ml | 4 µg/ml |
| Enterococcus 009 | 1 µg/ml | 1 µg/ml | 4 µg/ml | 4 µg/ml |
| *Enterococcus* 010 | 2 µg/ml | 2 µg/ml | 4 µg/ml | 4 µg/ml |
| *Enterococcus* 011 | 1 µg/ml | 1 µg/ml | 2 µg/ml | 4 µg/ml |
| *Enterococcus* 012 | 0.5 µg/ml | 0.5 µg/ml | 2 µg/ml | 2 µg/ml |
| *Enterococcus* 013 | 2 µg/ml | 2 µg/ml | 2 µg/ml | 2 µg/ml |
| *Enterococcus* 014 | 1 µg/ml | 1 µg/ml | 4 µg/ml | 4 µg/ml |
| B09/2192 | 1 µg/ml | 1 µg/ml | 4 µg/ml | 4 µg/ml |
| B09/2121 | 1 µg/ml | 1 µg/ml | 4 µg/ml | 4 µg/ml |
| B09/2088 | 1 µg/ml | 1 µg/ml | 2 µg/ml | 2 µg/ml |
| B09/2087 | 2 µg/ml | 1 µg/ml | 2 µg/ml | 4 µg/ml |
| B09/2032 | 2 µg/ml | 2 µg/ml | 4 µg/ml | 4 µg/ml |

TABLE 4-continued

The Minimum Inhibitory Concentrations for the individual
*Enterococcus* isolates according to Example 1.

| MIC Testing-AMP/NCL812 Organism/Sample no. | Test 1 AMP | Test 2 AMP | Test 1 NCL812 | Test 2 NCL812 |
|---|---|---|---|---|
| B09/2021 | 1 µg/ml | 1 µg/ml | 4 µg/ml | 4 µg/ml |
| AMP Ampicillin MIC90 | 2 µg/ml | 2 µg/ml | 4 µg/ml | 4 µg/ml |

TABLE 5

The Minimum Inhibitory Concentrations for the individual
*Streptococcus pneumoniae* isolates according to Example 1.

| MIC Testing-AMP/NCL812 Organism/Sample no. | Test 1 AMP | Test 2 AMP | Test 1 NCL812 | Test 2 NCL812 |
|---|---|---|---|---|
| Strep. pneumoniae ATCC 49619 | <0.25 µg/ml | <0.25 µg/ml | 4 µg/ml | 4 µg/ml |
| Strep. pneumoniae 1 | <0.25 µg/ml | <0.26 µg/ml | 4 µg/ml | 4 µg/ml |
| Strep. pneumoniae 2 | <0.26 µg/ml | <0.25 µg/ml | 4 µg/ml | 4 µg/ml |
| Strep. pneumoniae 3 | <0.25 µg/ml | <0.25 µg/ml | 4 µg/ml | 2 µg/ml |
| Strep. pneumoniae 4 | <0.25 µg/ml | <0.25 µg/ml | 4 µg/ml | 4 µg/ml |
| Strep. pneumoniae 5 | <0.25 µg/ml | <0.26 µg/ml | 4 µg/ml | 4 µg/ml |
| Strep. pneumoniae 6 | <0.26 µg/ml | <0.25 µg/ml | 4 µg/ml | 4 µg/ml |
| Strep. pneumoniae 7 | <0.25 µg/ml | <0.26 µg/ml | 4 µg/ml | 4 µg/ml |
| Strep. pneumoniae 8 | <0.25 µg/ml | <0.25 µg/ml | 4 µg/ml | 4 µg/ml |
| Strep. pneumoniae 9 | <0.26 µg/ml | <0.25 µg/ml | 4 µg/ml | 4 µg/ml |
| Strep. pneumoniae 10 | <0.06 µg/ml | <0.06 µg/ml | 4 µg/ml | 4 µg/ml |
| Strep. pneumoniae 12 | <0.06 µg/ml | <0.06 µg/ml | 4 µg/ml | 4 µg/ml |
| Strep. pneumoniae 13 | <0.06 µg/ml | <0.06 µg/ml | 4 µg/ml | 4 µg/ml |
| Strep. pneumoniae 14 | <0.06 µg/ml | <0.06 µg/ml | 8 µg/ml | 8 µg/ml |
| Strep. pneumoniae 15 | 0.25 µg/ml | 0.25 µg/ml | 4 µg/ml | 4 µg/ml |
| Strep. pneumoniae 16 | 2 µg/ml | 2 µg/ml | 0.5 µg/ml | 1 µg/ml |
| Strep. pneumoniae 18 | 0.25 µg/ml | 0.25 µg/ml | 4 µg/ml | 4 µg/ml |
| Strep. pneumoniae 19 | 0.25 µg/ml | 0.25 µg/ml | 4 µg/ml | 4 µg/ml |
| Strep. pneumoniae 20 | 2 µg/ml | 2 µg/ml | 4 µg/ml | 4 µg/ml |
| AMP Ampicillin MIC90 | 0.25 µg/ml | 0.25 µg/ml | 4 µg/ml | 4 µg/ml |

TABLE 6

The NCL812 $MIC_{50}$, $MIC_{90}$, MIC mode and MIC range for Australian isolates of MRSA, VRE and *S. pneumoniae*.

| Bacteria | No. Isolates | $MIC_{50}$ (µg/ml) | $MIC_{90}$ (µg/ml) | MIC mode (µg/ml)* | MIC range (µg/ml) |
|---|---|---|---|---|---|
| MRSA | 21 | 4 (64)§ | 4 (>128) | 4 (>128) | 4-8 (8->128) |
| VRE | 20 | 4 (1) | 4 (2) | 4 (1) | 2-4 (0.5-2) |
| E. faecium | 16 | 4 (1) | 4 (2) | 4 (1) | 2-4 (1) |
| E. faecalis | 4 | NA | NA | NA | 2-4 (1) |
| Str. pneumoniae | 20 | 4 (<0.25) | 4 (0.25) | 4 (<0.25) | 0.5-8 (<0.06-2) |

*Mode-the most commonly occurring MIC value.
§Comparative ampicillin MICs are shown in parenthesis.

NCL812 MIC values were consistent within and between each of the three species. $MIC_{50}$ and $MIC_{90}$ values were both equal (4 µg/ml) for MRSA, VRE and *S. pneumoniae* isolates, with less than 10% of isolates showing MIC values either 1-2 dilutions below or only one dilution above this figure.

On the basis of these results, NCL812 represents a new antibacterial.

Example 2: Effect of NCL812 on *Staphylococcus aureus* Macromolecular Synthesis

Materials and Methods
Test Compounds

Test compound NCL812 was transported to the experimental facility under conditions of ambient temperature and then stored at 2-8° C. until assayed. Stock solutions were made by dissolving NCL812 dry powder in 100% DMSO to a concentration of 6,400 µg/mL. Vancomycin (Cat. #1134335), Rifampicin (Cat. # R-7382) and Cerulenin (Cat. # C-2389) were all obtained from Sigma, Ciprofloxacin was obtained from USP (Cat. #1134335) and Linezolid was obtained from ChemPacific (Cat. #35710).

Minimal Inhibitory Concentration Testing

The MIC assay method followed the procedure described by the Clinical and Laboratory Standards Institute, or CLSI (Clinical and Laboratory Standards Institute. Methods for Dilution Antimicrobial Susceptibility Tests for Bacteria That Grow Aerobically; Approved Standard—Eighth Edition. CLSI document M07-A8 [ISBN 1-56238-689-1]. Clinical and Laboratory Standards Institute, 940 West Valley Road, Suite 1400, Wayne, Pa. 19087-19898 USA, 2009), and employed automated liquid handlers to conduct serial dilutions and liquid transfers. The medium employed for the MIC assay was Mueller Hinton II Broth (MHB II-Becton Dickinson, Sparks, Md.; Cat No 212322; Lot 9044411). *S. aureus* ATCC 29213 served as the quality control strain, and linezolid was utilized as the quality control antibiotic to validate the assay. NCL812 and linezolid were both dissolved in 100% DMSO before addition to the growth medium.

Macromolecular Synthesis Assays
Bacteria and Growth Conditions

The effect of NCL812 on whole cell DNA, RNA, cell wall, protein and lipid synthesis was investigated using *S. aureus* ATCC 29213. Cells were grown at 35° C. overnight on Trypticase Soy agar. A colony from the plate was used to inoculate 10 ml of Mueller Hinton broth II (MHBII), and the culture was grown to early exponential growth phase ($OD_{600}$=0.2 to 0.3) while incubating in a shaker at 35° C. and 200 rpm.

DNA, RNA, and Protein Synthesis

When cells reached early exponential phase, 100 µL of culture was added to triplicate wells containing various concentrations of test compound or control antibiotics (5 µL) at 20× the final concentration in 100% DMSO. A 5% DMSO treated culture served as the "no drug" control for all experiments. Cells were added in MHBII at 105% to account for the volume of drug added to each reaction or in M9 minimal medium for protein synthesis reactions. Following 15 min incubation at room temperature, either [$^3$H] thymidine (DNA synthesis), [$^3$H] uridine (RNA synthesis) or [$^3$H] leucine (protein synthesis) was added at 0.5-1.0 µCi per reaction, depending on the experiment. Reactions were allowed to proceed at room temperature for 15-30 min and then stopped by adding 12 µL of cold 5% trichloroacetic acid (TCA) or 5% TCA/2% casamino acids (protein synthesis only). Reactions were incubated on ice for 30 min and the TCA precipitated material was collected on a 25 mm GF/A filter. After washing three times with 5 ml of cold 5% TCA, the filters were rinsed two times with 5 mL 100% ethanol, allowed to dry, and then counted using a Beckman LS3801 liquid scintillation counter.

Cell Wall Synthesis

Bacterial cells in early exponential growth phase were transferred to M9 minimal medium and added to 1.5 mL eppendorf tubes (100 µL/tube) containing various concentrations of test compound or control antibiotics (5 µL) at 20× the final concentration in 100% DMSO as described above. Following a 5 min incubation at 37° C., [$^{14}$C]N-acetylglucosamine (0.4 µCi/reaction) was added to each tube and incubated for 45 min in a 37° C. heating block. Reactions were stopped through the addition of 100 µL of 8% SDS to each tube. Reactions were then heated at 95° C. for 30 min in a heating block, cooled, briefly centrifuged, and spotted onto pre-wet HA filters (0.45 µM). After washing three times with 5 mL of 0.1% SDS, the filters were rinsed two times with 5 ml of deionized water, allowed to dry, and then counted using a Beckman LS3801 liquid scintillation counter.

Lipid Synthesis

Bacterial cells were grown to early exponential growth phase in MHBII broth and added to 1.5 mL eppendorf tubes (in triplicate) containing various concentrations of test compound or control antibiotics as described above. Following a 5 min incubation at room temperature, [$^3$H] glycerol was added at 0.5 µCi per reaction.

Reactions were allowed to proceed at room temperature for 15 min and then stopped through the addition of 375 µL chloroform/methanol (1:2) followed by vortexing for 20 seconds after each addition. Chloroform (125 µL) was then added to each reaction, vortexed, followed by the addition of 125 µL dH$_2$O and vortexing. Reactions were centrifuged at 13,000 rpm for 10 min, and then 150 µL of the organic phase was transferred to a scintillation vial and allowed to dry in a fume hood for at least 1 hr. Samples were then counted via liquid scintillation counting.

Results

Susceptibility testing was conducted with NCL812 and *S. aureus* ATCC 29213 to determine the concentrations of drug needed in the macromolecular synthesis assays.

Table 7 shows that the MIC for NCL812 was 4 µg/mL, while the quality control agent linezolid was within the CLSI-established quality control range (Clinical and Laboratory Standards Institute. *Performance Standards for Antimicrobial Susceptibility Testing; Nineteenth Informational Supplement.* CLSI document M100-S20 [ISBN 1-56238-716-2]. Clinical and Laboratory Standards Institute, 940 West Valley Road, Suite 1400, Wayne, Pa. 19087-1898 USA, 2010). Precipitation of NCL812 was observed at ≥8 µg/mL in plates that were prepared in an identical fashion, but did not receive an inoculum of *S. aureus*. Macromolecular synthesis inhibition studies were performed using concentrations of NCL812 that were equivalent to 0, 0.25, 0.5, 1, 2, 4 or 8-fold the MIC value (4 µg/ml) for *S. aureus* ATCC 29213 (FIGS. 11-16).

TABLE 7

Minimum Inhibitory Concentrations values for NCL812 (robenidine) and linezolid against *Staphylococcus aureus* ATCC29213 according to Example 2.

| Compound | *Staphylococcus aureus* ATCC[1] 29213 |
|---|---|
| NCL812 | 4 |
| Linezolid | 4 |
| Quality control range for linezolid[2] | 1-4 |

Figure 2:
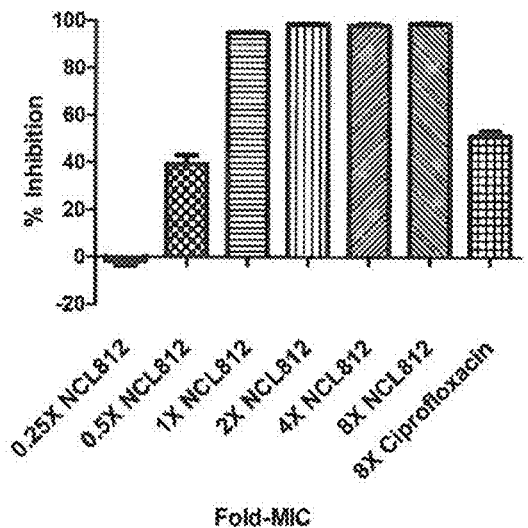
FIG. 2 shows a graph of the effect of NCL812 on DNA macromolecular synthesis in *Staphylococcus aureus* according to example 2.
Figure 3:
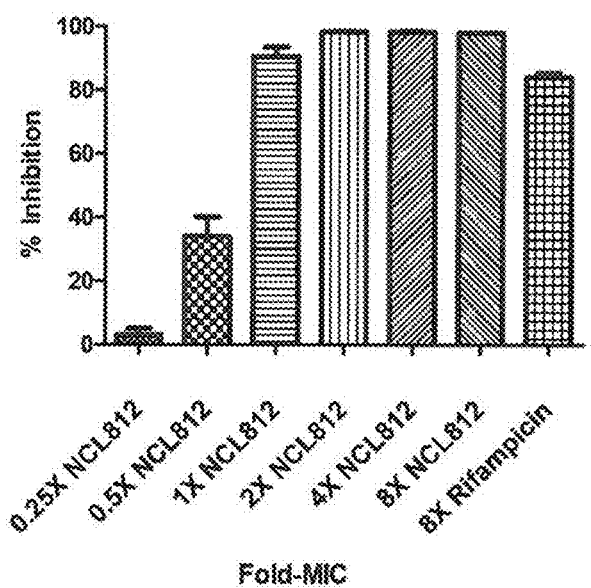
FIG. 3 shows a graph of the effect of NCL812 on RNA macromolecular synthesis in *Staphylococcus aureus* according to example 2.

FIG. 2 shows the effect of NCL812 on DNA synthesis. NCL812 demonstrated no inhibition at 0.25 fold the MIC, 40% inhibition at 0.5 fold, and approximately 95% inhibition at the MIC. This is compared to the control ciprofloxacin which showed approximately 51% at 8 fold the MIC (0.5 µg/mL). The results for NCL812 inhibition of RNA synthesis were very similar to the DNA synthesis study, with rifampicin serving as the positive control (FIG. 3. It should be noted that precipitation was observed at 4 to 8 fold the MIC in the Mueller Hinton broth II utilized in the DNA and RNA synthesis assays.

Figure 4:
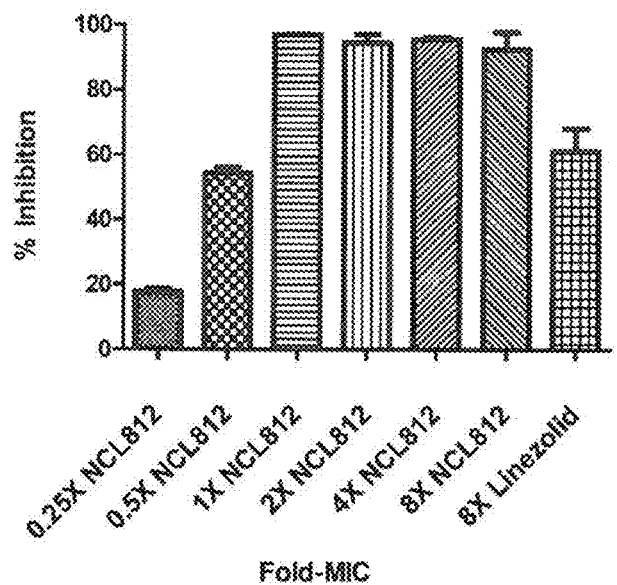
FIG. 4 shows a graph of the effect of NCL812 on protein macromolecular synthesis in *Staphylococcus aureus* (ATCC29213) according to example 2.

Protein synthesis was inhibited in a dose-dependent manner at 0.25, 0.5, and 1 fold the MIC value of NCL812 showing up to 97% inhibition at the MIC (FIG. 4. Linezolid demonstrated approximately 61% inhibition of protein synthesis at 8 fold the MIC (2 µg/mL). Precipitation of NCL812 occurred at 4 and 8 fold the MIC in the protein synthesis assay.

Figure 5:
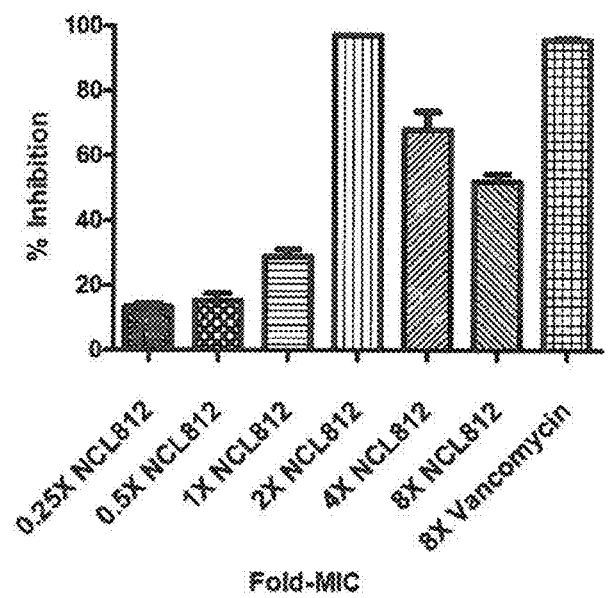
FIG. 5 shows a graph of the effect of NCL812 on cell wall macromolecular synthesis in *Staphylococcus aureus* (ATCC29213) according to example 2.
Figure 6:
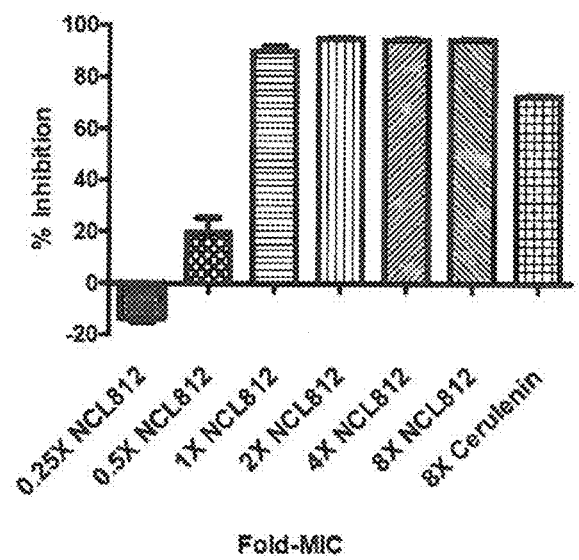
FIG. 6 shows a graph of the effect of NCL812 on lipid macromolecular synthesis in *Staphylococcus aureus* (ATCC29213) according to example 2.

In FIG. 5 NCL812 also showed a somewhat dose-dependent inhibition of cell wall synthesis, though there was a large increase in inhibition from 1 to 2 fold the MIC. However, inhibition dropped to approximately 68% and 52% at 4 fold and 8 fold the MIC, respectively. Precipitation of NCL812 occurred at 2, 4, and 8 fold the MIC in the M9 minimal medium used for the cell wall synthesis assay, and that is the likely cause of the decline in inhibition. In comparison, the positive control vancomycin showed 96% inhibition at 8 fold the MIC (2 µg/mL). NCL812 demonstrated a similar inhibition profile against lipid synthesis as that shown for DNA and RNA synthesis, reaching approximately 90% inhibition at the MIC (FIG. 6). The positive control inhibitor cerulenin demonstrated 72% inhibition at 8 fold the MIC (32 µg/mL).

Figure 7:
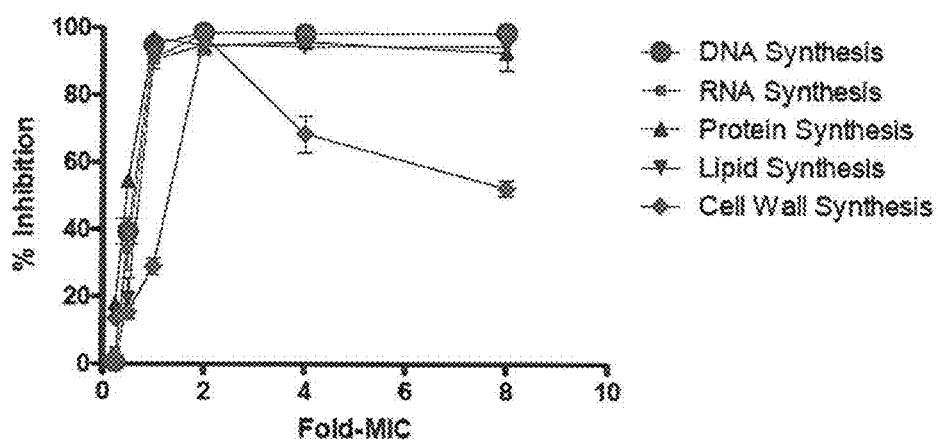
FIG. 7 shows a graph summarising the effect of NCL812 on macromolecular synthesis in *Staphylococcus aureus* (ATCC29213) according to example 2.

FIG. 7 represents a composite of all five macromolecular synthesis reactions. It can be observed that the inhibition curves were similar for each pathway, suggesting a global inhibition of several pathways simultaneously by NCL812. It is possible that NCL812 targets the cell membrane, causing leakage of essential ions and/or metabolites, thereby leading to a global shutdown of the cell synthesis pathways.

In summary, NCL812 inhibited DNA, RNA, protein, cell wall, and lipid pathways in a growing culture of *S. aureus*. Though some instances of dose-dependent inhibition of pathways was observed, all five macromolecular synthesis reactions were similarly sensitive to NCL812.

Example 3: Effect of NCL812 on ATP Release from *Staphylococcus aureus*

Materials and Methods
Test Compounds

The test compound NCL812 was shipped under conditions of ambient temperature and then stored at 2-8° C. until assayed. Stock solutions were made by dissolving NCL812 dry powder in 100% DMSO to a concentration of 1,600 µg/mL. Polymyxin B was obtained from Sigma (Cat. # P-4932).

Test Organism

S. aureus ATCC 29213 was originally acquired from the American Type Culture Collection (Manassas, Va.).

ATP Release Assay

The CellTiter-Glo Luminescent Cell Viability Assay (Promega) was utilized to measure the leakage of ATP from bacteria. Cultures were grown to early exponential phase (0.2-0.3 $OD_{600}$) in Mueller-Hinton Broth II and then treated with seven different concentrations of either NCL812 or polymyxin B (positive control) utilizing the MIC for each compound as a guide (0, 0.25, 0.5, 1, 2, 3, 4, or 8 fold the MIC). The negative control received 2% DMSO, which represented the final DMSO concentration in each assay. After a 30 min exposure to drug, cells were sedimented by centrifugation and the supernatant was analyzed for the presence of ATP. Results were expressed as ATP concentration released to the medium (µM).

Results

The MIC for NCL812 has been previously determined to be 4 µg/mL. The ATP release assay is conducted by growing S. aureus to exponential phase and then adding drug at multiples of the MIC in an effort to detect a dose-dependent response.

Figure 8:
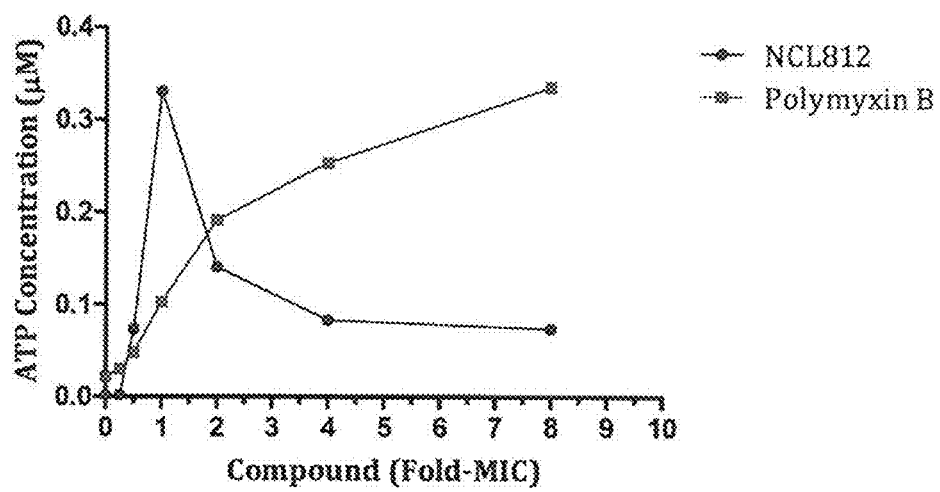
FIG. 8 shows a graph of the effect of NCL812 on ATP release from *Staphylococcus aureus* (ATCC29213) according to example 3.

As shown in FIG. 8 the positive control polymyxin B released ATP from S. aureus cells in a dose-dependent fashion with maximal release of approximately 0.34 µM ATP at 8 fold the MIC (256 µg/mL). ATP release in the presence of NCL812 was dose-dependent at 0.5-1 fold the MIC, resulting in maximal release (0.33 µM) observed at the MIC (4 µg/ml). ATP release actually decreased thereafter at 2 to 8 fold the MIC. It should be noted that in previous studies precipitation of NCL812 was observed at 4 to 8 fold the MIC in Mueller Hinton broth II.

In summary, NCL812 demonstrated dose-dependent release of ATP from actively growing S. aureus cells. ATP release from the cells into the growth medium reached maximum levels at the MIC value, and this was followed by a decrease in ATP release at higher doses. The data indicated that NCL812 may interact with the cell membrane of S. aureus, causing leakage of vital metabolites such as ATP.

Example 4: In Vitro Antibacterial Activity of NCL812 Against Methicillin-Resistant and Methicillin-Susceptible Staphylococcus aureus Materials and Methods Antimicrobial Agents Aliquots of stock solution of NCL812 (25.6 mg/ml) was prepared in DMSO, stored at −80° C. and defrosted immediately before use. Ampicillin stock was obtained from Sigma-Aldrich (Australia). Antimicrobial discs were obtained from Thermo Fisher Scientific (Australia).

Microorganisms

Clinical isolates of MRSA that represented the most common sequence types of both hospital-acquired (HA) and community-associated (CA) MRSA in Australia were obtained and are described in Table 8 below. The S. aureus control organism ATCC 49775 was used. Isolate identification was confirmed by conventional phenotypic methodologies, including the slide coagulase test, Vogues-Proskauer test, polymyxin B sensitivity (300 units), and Staphytect Plus Protein A latex slide agglutination (Thermo Fisher Scientific Australia). Bacteria were stored at −80° C. in 40% glycerol broth and routinely grown from stock on sheep blood agar (SBA) incubated at 37° C. In subsequent experiments, only fresh cultures <24 h were used.

TABLE 8

Staphylococcus aureus clone/isolate name, type, source, antibiogram, clindamycin resistance status, multi-locus sequence type (MLST), staphylococcal cassette chromosome (SCCmec) type, clonal complex, Panton-Valentine leukocidin status (PVL), and spa type for isolates used according to example 4

| Name/Clone | Type | Source | Epi Number | Antibiogram | Clindamycin | MLST | SCCmec | Clonal Complex | PVL | spa |
|---|---|---|---|---|---|---|---|---|---|---|
| MSSA CN-55 | Cat MSSA | M.B | — | — | — | — | — | — | — | — |
| MSSA DE-25 | Dog MSSA | M.B | — | — | — | — | — | — | — | — |
| MSSA DG-27 | Dog MSSA | M.B | — | — | — | — | — | — | — | — |
| MSSA COW-1 | Cow MSSA | G | — | — | — | — | — | — | — | — |
| MSSA COW-2 | Cow MSSA | J.P. | — | — | — | — | — | — | — | — |
| MSSA H-D | MSSA | VIMP | — | — | — | — | — | — | — | — |
| MSSA H-50 | MSSA | VIMP | — | — | — | — | — | — | — | — |
| MSSA ATCC 49775 | MSSA | S.P. | — | — | — | — | — | — | POS | — |
| MSSA H-46 | MSSA | VIMP | — | — | — | — | — | — | — | — |
| MSSA H-48 | MSSA | VIMP | — | — | — | — | — | — | — | — |
| MRSA H-79 | HA-MRSA | VIMP | — | — | — | — | — | — | — | — |
| MRSA H-32 | HA-MRSA | VIMP | — | — | — | — | — | — | — | — |
| UK EMRSA-15 | HA-MRSA | G.C. | 01-16337 | Em, Ci | Inducible | ST22 | IV | 22 | NEG | t022 |
| UK EMRSA-15 PVL pos | HA-MRSA | G.C. | 07-16386 | Gn, Tm | — | ST22 | IVb | 22 | POS | t891 |
| UK EMRSA-16 | HA-MRSA | G.C. | 02-17900 | Em, Ci | Constitutive resistance | ST36 | II | 30 | NEG | t018 |
| UK EMRSA-17 | HA-MRSA | G.C. | 03-15701 | Gn, Em, Ci, Te, FA, Rf | Constitutive resistance | ST247 | I | 8 | NEG | t051 |
| Irish EMRSA-1 | HA-MRSA | G.C. | 04-16780 | Gn, Em, Ci, Mp, Tm | Inducible | ST8 | II | 8 | NEG | t498 |
| CLASSIC MRSA | HA-MRSA | G.C. | 03-17590 | Em | Inducible | ST250 | I | 8 | NEG | t008 |
| NY/JAPAN | HA-MRSA | G.C. | 03-16981 | Em, Ci | Constitutive resistance | ST5 | II | 5 | NEG | t242 |
| Queensland clone (PVL pos) | CA-MRSA | G.C. | 03-16790 | Fully S | — | ST93 | IVa | Singleton | POS | t202 |
| Taiwan cMRSA | CA-MRSA | G.C. | 03-16672 | Em, Te | Constitutive resistance | ST59 | 5 (C2&5) | 59 | POS | t437 |

TABLE 8-continued

Staphylococcus aureus clone/isolate name, type, source, antibiogram, clindamycin resistance status, multi-locus sequence type (MLST), staphylococcal cassette chromosome (SCCmec) type, clonal complex, Panton-Valentine leukocidin status (PVL), and spa type for isolates used according to example 4

| Name/Clone | Type | Source | Epi Number | Antibiogram | Clindamycin | MLST | SCCmec | Clonal Complex | PVL | spa |
|---|---|---|---|---|---|---|---|---|---|---|
| WA MRSA-1 | CA-MRSA | G.C. | WBG 8287 | Em, FA | Inducible | ST1 | IVa | 1 | NEG | t127 |
| WA MRSA-2 | CA-MRSA | G.C. | 03-16926 | Em | Inducible | ST78 | IVa | 88 | NEG | t186 |
| WA MRSA-3 | CA-MRSA | G.C. | WBG 8378 | Em | Inducible | ST5 | IVa | 5 | NEG | t002 |
| USA 300 MRSA | CA-MRSA | G.C. | 04-15086 | Te | | ST8 | IVc | 8 | POS | t008 |
| Bengal Bay clone | CA-MRSA | G.C. | 07-17048 | Gn, Em, Ci, Tm | Non-inducible | ST772 | V | 1 | POS | t3387 |
| WSPP MRSA (PVL neg) | CA-MRSA | G.C. | 08-19231 | Mp, Tm | — | ST30 | IVa | 30 | NEG | t5074 |
| ST398-MRSA-V | CA-MRSA | G.C. | 09-16870 | Em, Te, Tm | Constitutive resistance | ST398 | V | 398 | NEG | t034 |
| WA MRSA-84 | CA-MRSA | G.C. | 07-16502 | Ci | — | ST45 | V | 45 | NEG | t1081 |

MSSA; methicillin-susceptible *S. aureus*.
HA-MRSA; hospital-acquired methicillin-resistant *S. aureus*.
CA-MRSA; community-associated methicillin-resistant *S. aureus*.
Em; Erythromycin.
Ci; Ciprofloxacin.
Gn; Gentamicin.
Tm; Trimethoprim.
Te; Tetracycline.
FA; Fusidic Acid.
Rf; Rifampicin.
Mp; Mupirocin Isolate Resistotyping Antibiotic-susceptibility profiling of the isolate collection was undertaken using Kirby-Bauer disc diffusion, as recommended by the Clinical and Laboratory Standards Institute (CLSI) on Mueller-Hinton agar. Isolates were grown overnight on SBA at 37° C. Colonies were suspended in physiological saline. Turbidity was adjusted to a 0.5 McFarland standard and suspensions were spread over the medium. Antibiotic discs according to Table 9 below were transferred onto the inoculated medium and analysed after 24 h incubation at 37° C. Isolates labelled as MRSA that were not β-lactam-resistant on the basis of the Kirby-Bauer test were grown from stock on plate count agar supplemented with 5 μg/ml ampicillin and subject to repeat testing, as PBP2a expression can be induced by exposure to β-lactam antimicrobials.

Molecular Detection of the Protein A and mecA Genes to Confirm MRSA Status

Isolate identities were confirmed genotypically using a duplex polymerase chain reaction (PCR) test targeting the spa (protein A) and mecA (methicillin resistance) genes. In addition, the isolates were tested in a mecA and spa Sybr green real-time PCR. Approximately ten colonies of each overnight bacterial subculture was suspended in 1× phosphate buffered saline (pH 7.4) and vortexed. Isolates were subject to DNA extraction using the QIAamp® DNA Mini Kit (Qiagen, Australia) following the manufacturers protocols. Template DNA was eluted in 50 μL of elution buffer and either used directly in PCR, or stored at −20° C. prior to DNA amplification using the spa forward (5'-TGATACAG-TAAATGACATTG-3') and reverse (5'-TTCTTAT-CAACAACAAGTTC-3') primers and mecA forward (5'-TTCGTGTCTTTTAATAAGTGAGG-3') and reverse (5'-

TABLE 9

Antibacterial agent zone diameter interpretive sizes for Kirby-Bauer disc diffusion, as used in Example 4.

| Antimicrobial Class | Agent | Disk content | Zone diameter interpretive sizes (mm) | | |
|---|---|---|---|---|---|
| | | | Resistant | Intermediate | Susceptible |
| Aminoglycoside | Gentamicin | 10 μg | ≤12 | 13-14 | ≥15 |
| Ansamycin | Rifampicin | 5 μg | ≤16 | 17-19 | ≥20 |
| Cephalosporin | Cephalexin | 30 μg | ≤14 | 15-17 | ≥18 |
| Cephamycin | Cefotetan | 30 μg | ≤12 | 13-15 | ≥16 |
| Folate pathway inhibitor | Trimethoprim-sulfamethoxazole | 1.25/23.75 μg | ≤10 | 11-15 | ≥16 |
| Glycopeptide | Vancomycin | 30 μg | — | — | ≥15 |
| Lincosamide | Clindamycin | 2 μg | ≤14 | 15-20 | ≥21 |
| Macrolide | Erythromycin | 15 μg | ≤13 | 14-22 | ≥23 |
| Fluoroquinolone | Ciprofloxacin | 5 μg | ≤15 | 16-20 | ≥21 |
| Tetracycline | Tetracycline | 30 μg | ≤14 | 15-18 | ≥19 |
| β-lactam/penicillin | Penicillin-G | 10 units | ≤28 | — | ≥29 |
| β-lactam/penicillin-stable penicillin | Oxacillin | 1 μg | ≤10 | 11-12 | ≥13 |
| β-lactam/β-lactamase inhibitor combination | Amoxicillin-clavulanic add | 20/10 μg | ≤19 | — | ≥20 |

ATGAAGTGGTAAATGGTAATATCG-3) primers (Invitrogen, Australia). Conventional PCR amplification was performed in a 20 µL volume containing 10 µL Hot-StarTaq Plus Master Mix (Qiagen, Australia), 0.5 µM of each spa primer, 0.2 µM of each mecA primer, and 3 µL of extracted DNA. An automated thermal cycler (T100 Thermal Cycler, Bio-Rad) was used for PCR amplification of the spa and mecA genes according to the following conditions: PCR Stage (Enzyme activation at 95° C. for 300 s, followed by 38 amplification rounds of 94° C. for 30 s (denaturation), 50° C. for 30 s (annealing) and 72° C. for 38 s (extension) and then a cooling stage of 20° C. until required); Real-time PCR Stage (Enzyme activation at 95° C. for 300 s, followed by 40 amplification rounds of 95° C. for 15 s (denaturation), 50° C. for 20 s (annealing) and 70° C. for 40 s (extension), a single round at 95° C. for 5 s, a single round at 55° C. for 20 s, continuous melting curve from 95° C. to 0° C. and a cooling period of 40° C. for 30 s. The mecA and spa amplified products of 325 and 120 bp, respectively, were detected by GelRed staining followed by electrophoresis in 2% agarose gels.

Minimum Inhibitory Concentration Testing

The in vitro activities of NCL812 and ampicillin as a positive control were determined by broth microdilution as recommended by the CLSI in cation-adjusted Mueller-Hinton II broth. Microtiter plates containing two-fold dilutions of each antimicrobial agent were inoculated with ~$10^5$ CFU/ml of each isolate in a 100 µL final volume. Plates were incubated for 24 h at 37° C. Turbidity (absorbance at $OD_{600}$) was measured using a Bio-Rad Benchmark Plus microplate spectrophotometer in Microplate Manager® version 5.2.1 (Bio-Rad). Minimum inhibitory concentration (MIC) endpoints were defined as the lowest antimicrobial concentration assessed by the spectrophotometer that inhibited bacterial growth. ATCC 49775 was included in the isolate collection as a control organism using breakpoints defined by the CLSI. The $MIC_{50}$, $MIC_{90}$ (concentrations that inhibited growth of the lower 50% and 90% of total organisms, respectively), and MIC range (minimum and maximum) were calculated to profile the antimicrobial susceptibility of the isolate collection.

Bactericidal Activity

The bactericidal activity of NCL812 was established by determination of the minimum bactericidal concentration (MBC) and time-kill analyses using CLSI guidelines. The MBC was defined as the lowest drug concentration at which 99.95% of the original inoculum was eliminated.

Time-kill assays for ATCC 49775 were performed in cation-adjusted Mueller-Hinton II broth in Microtiter plates and again in 10 ml volumes for macrodilution assays at antimicrobial concentrations equivalent to 1× and 4× the MIC. Bactericidal activity in macrodilution assays was identified as a 3 $\log_{10}$ decrease from the initial inoculum size. Bacteria were cultured overnight at 37° C. on SBA. Colonies were suspended in broth and the turbidity was adjusted to a 0.5 McFarland standard to obtain a bacterial suspension of ~$10^5$ CFU/ml. Bacterial suspensions were incubated at 37° C. with shaking. Aliquots were removed at 0, 1, 2, 4, 8, 12, and 24 h after antimicrobial addition, diluted, plated onto SBA and incubated for 48 h at 37° C. for viable count determination. Turbidimetric growth curves for S. aureus were obtained for Microtiter plate assays by monitoring optical density changes using a Bio-Rad Benchmark Plus microplate spectrophotometer at 600 nm. Optical densities were measured at 0, 1, 2, 4, 8, 12, and 24 h after antimicrobial addition.

Statistical Methodology

Microbiological data was interpreted using CLSI guidelines. Data was examined using the student's t-test, Fisher's exact test, analysis of variance, and a generalized linear model for tests of between-subjects effects where appropriate. Differences were considered significant at the 0.05 level in IBM SPSS® version 19.0.

Results

Confirmation of Staphylococcus aureus Identity and mecA Status

Latex agglutination tests confirmed that all 30 isolates were protein A positive. The isolates tested positive for coagulase activity using slide agglutination. Voges-Proskauer and polymyxin B resistance tests confirmed that all isolates were S. aureus except for a single methicillin-susceptible isolate; MSSA DE-25, as shown in Table 10 below. Based on spa gene PCR amplification, this isolate was not identified as a S. aureus isolate despite testing positive in the protein A latex agglutination and slide coagulase tests. This canine-origin Staphylococcus spp. was identified as Staphylococcus pseudintermedius based on biochemical characteristics. mecA conventional and real-time PCR results confirmed that 66.66% of the isolates were classified as methicillin-resistant on the basis of possession of the mecA gene. There were no significant differences between the ability of conventional and real-time PCR to detect the mecA gene ($P>0.05$).

TABLE 10

Percentage of presumptively identified S. aureus isolates reporting positive to selected phenotypic and genotypic tests according to Example 4.

| Organism | Biochemical tests | | | | PCR | | Real-time PCR | |
| --- | --- | --- | --- | --- | --- | --- | --- | --- |
| | Protein A | Slide coagulase | Voges-Proskauer | Polymyxin B | spa gene | mecA gene | spa gene | mecA gene |
| Methicillin-susceptible staphylococci (n = 10) | 100% | 100% | 90% | 90% | 90% | 0% | 90% | 0% |
| HA-MRSA (n = 10) | 100% | 100% | 100% | 100% | 100% | 100% | 100% | 100% |
| CA-MRSA (n = 10) | 100% | 100% | 100% | 100% | 100% | 90% | 100% | 100% |
| Total (n = 30) | 100% | 100% | 96.67% | 96.67% | 96.67% | 63.33% | 96.67% | 66.66% |

HA-MRSA; hospital-acquired S. aureus.

CA-MRSA; community-associated S. aureus.

S. aureus isolates were identified as testing positive to protein A latex agglutination (Protein A), slide coagulase, Voges-Proskauer and polymyxin B resistance tests, as well as testing positive for polymerase chain reaction (PCR) and real-time PCR amplification of the spa gene. Methicillin-resistant S. aureus isolates were identified as isolates testing positive to the criteria described above, as well as positive for PCR and real-time PCR of the mecA gene.

TABLE 11

Resistance of S. aureus isolates to antibacterial agents using the Kirby-Bauer disc diffusion method according to example 4

| Antimicrobial agent(s) | HA-MRSA (n = 10) | CA-MRSA (n = 10) | Methicillin-susceptible staphylococci (n = 10) | Total isolates resistant (n = 30) |
|---|---|---|---|---|
| Penicillin-G | 100.00% | 100.00% | 50.00% | 83.33% |
| Erythromycin | 80.00% | 100.00% | 40.00% | 73.33% |
| Amoxicillin-Clavulanic acid | 80.00% | 30.00% | 0.00% | 36.67% |
| Cefotetan | 80.00% | 20.00% | 0.00% | 33.33% |
| Cephalexin | 80.00% | 20.00% | 10.00% | 40.00% |
| Oxacillin | 80.00% | 10.00% | 0.00% | 30.00% |
| Ciprofloxacin | 60.00% | 20.00% | 20.00% | 33.33% |
| Clindamycin | 50.00% | 50.00% | 30.00% | 43.33% |
| Gentamicin | 20.00% | 0.00% | 0.00% | 20.00% |
| Tetracycline | 30.00% | 30.00% | 0.00% | 20.00% |
| Rifampicin | 10.00% | 0.00% | 0.00% | 3.33% |
| Trimethoprim-Sulfamethoxazole | 10.00% | 0.00% | 0.00% | 3.33% |
| Vancomycin | 0.00% | 0.00% | 0.00% | 0.00% |

HA-MRSA; hospital-acquired methicillin-resistant S. aureus.
CA-MRSA; community-associated methicillin-resistant S. aureus

Staphylococcus aureus Antimicrobial Susceptibility Profiles

Antimicrobial susceptibility assays revealed that HA-MRSA isolates had the highest mean prevalence of resistance to multiple antimicrobial classes ($P<0.000$). CA-MRSA isolates were next most resistant ($P<0.007$), followed by methicillin-susceptible staphylococci ($P<0.037$), as shown in Table 11 above. Oxacillin resistance was expressed in only 80.00% and 10.00% of HA-MRSA and CA-MRSA isolates, respectively. Cefotetan resistance was expressed in 80.00% and 20.00% of HA-MRSA and CA-MRSA isolates, respectively. Although oxacillin and cefotetan did not significantly differ in their ability to detect MRSA ($P>0.05$), detection was significantly improved when using the mecA PCR when compared to disc diffusion ($P<0.013$). The majority of HA-MRSA isolates expressed resistance to amoxicillin-clavulanic acid, cefotetan, cephalexin, clindamycin, erythromycin, oxacillin, and penicillin-G, whereas the majority of CA-MRSA isolates were resistant to only clindamycin, erythromycin, and penicillin-G. None of the isolates tested were vancomycin resistant. Overall, the most prevalent resistance phenotypes were penicillin-G (83.33%), erythromycin (73.33%), and clindamycin (43.33%), whilst only single isolates (3.33%) were resistant to trimethoprim-sulfamethoxazole and rifampicin.

Mec Gene Complex Interactions

All MRSA isolates belonging to mec gene complex A expressed resistance to both oxacillin and cefotetan, as shown in Table 12 below. However, only 20% of mec gene complex B MRSA isolates were phenotypically resistant to these antimicrobials. Of the MRSA isolates belonging to mec gene complex C2, only a single isolate expressed methicillin resistance to oxacillin and only two isolates expressed resistance to cefotetan. Unclassified MRSA isolates expressed full resistance to oxacillin and cefotetan.

TABLE 12

Number and percentage of identified mec gene complexes in 20 S. aureus strains classified as methicillin-resistant according to example 4

| mec gene complex (number of isolates) | SCCmec types | Oxacillin resistant isolates | Cefotetan resistant isolates |
|---|---|---|---|
| A (n = 4) | II | 3 (100%) | 3 (100%) |
|  | III | 1 (100%) | 1 (100%) |
|  | Overall | 4 (100%) | 4 (100%) |
| B (n = 10) | I | 1 (50%) | 1 (50%) |
|  | IV | 1 (12.5%) | 1 (12.5%) |
|  | Overall | 2 (20%) | 2 (20%) |
| C2 (n = 4) | V | 1 (25%) | 2 (50%) |
|  | Overall | 1 (25%) | 2 (50%) |
| Unclassified (n = 2) | Overall | 2 (100%) | 2 (100%) |

Figure 9:
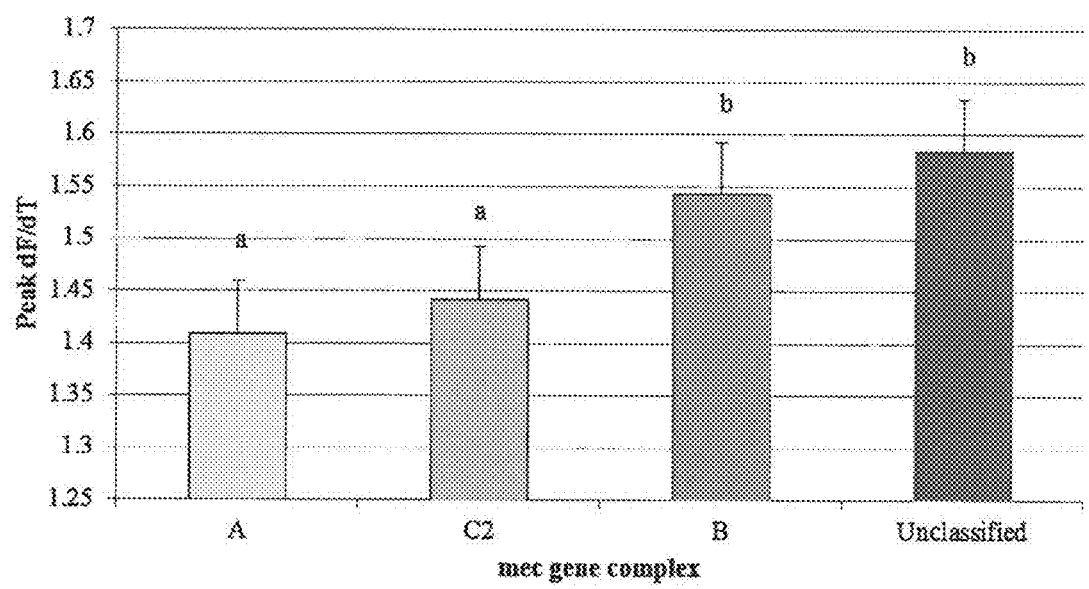
FIG. 9 shows a graph showing the average melting point peaks for the negative derivative dF/dT after real-time polymerase chain reaction of the mecA gene in methicillin-resistant *S. aureus* isolates grouped by mec gene complexes, A (n=4), B (n=10), C2 (n=4) and unclassified (n=2). Groups indicated with different superscripts are significantly different (P<0.05), according to example 4.

Respective staphylococcal cassette chromosome (SCCmec) complexes and types expressing phenotypic resistance to oxacillin and cefotetan are indicated as well as real-time mecA status, and the average negative dF/dT peak obtained from melting point analysis from real-time PCR of the mecA gene Melting point peaks for the mecA real-time PCR negative derivative plot −dF/dT differed between mec gene complex ($P<0.003$) (FIG. 9. On average, mec gene complex B and unclassified isolates demonstrated higher melting point peaks than other SCCmec types ($P<0.012$).

Physical Properties of Test Antimicrobials and Comparison of Minimum Inhibitory Concentration Results from Initial Analogue Testing Test antimicrobials were selected on the basis of solubility and antimicrobial activity from preliminary studies. Cloudy precipitates were observed when both NCL812 were dissolved in cation-adjusted Mueller-Hinton II broth, as shown in Table 13 below. Following initial structure-activity testing on each synthesized analogue, NCL812 was found to have consistent MIC values in this present study.

TABLE 13

Characteristics of antibacterial NCL812 and the β-lactam antibacterial ampicillin according to Example 4.

| Compound | Solubility | | Original MIC (µg/ml) at 24-h[1] | | Observed MIC (µg/ml) at 24-h | | |
|---|---|---|---|---|---|---|---|
|  | DMSO | CAMHB | MRSA580 | MRSA698 | MRSA580 | MRSA698 | ATCC 49775 |
| NCL812 | Good | Cloudy | 4 | 4 | 4 | 4 | 4 |
| Ampicillin | Good | Good | >128 | 16 | >128 | 16 | 0.25 |

Detailing antibacterial solubility in dimethyl sulfoxide (DMSO), solubility in cation-adjusted Mueller-Hinton II broth (CAMHB), and average minimum inhibitory concentrations (MIC) (µg/ml at 24 h) against methicillin-resistant S. aureus (MRSA) determined from preliminary studies and those determined during this present study.
ATCC 49775; methicillin-susceptible S. aureus isolate and ATCC control strain.
MRSA580; methicillin-resistant S. aureus isolate #580.
MRSA698; methicillin-resistant S. aureus isolate #698

In Vitro Antibacterial Activities: Minimum Inhibitory Concentrations $MIC_{50}$, and $MIC_{90}$ values for lead compound NCL812 (4- and 4-8 μg/mL) are shown in Table 14 below. MIC values differed by S. aureus classification (susceptible, HA- or CA-MRSA) (P<0.005). In many cases, NCL812 had significantly increased activity against CA-MRSA and methicillin-susceptible staphylococci by one dilution when compared to HA-MRSA (P<0.002 and P<0.020, respectively), however there were no significant differences between MIC values for methicillin-susceptible staphylococci and CA-MRSA (P>0.05). Ampicillin MIC values obtained for the ATCC control strain were within the normal range expected on the basis of CLSI guidelines activity of NCL812 was observed from 8-24 h. Although NCL812 was no longer bactericidal by 24 h, viable counts observed at 1× the MIC remained significantly lower than those obtained from unsupplemented broth (P<0.046).

In summary, the example set out above demonstrates bactericidal activity against both methicillin-susceptible staphylococci and MRSA. MIC and MBC values were consistently low across the selection of isolates ($MIC_{range}$ 2-8 μg/mL). NCL812 retained good in vitro antimicrobial activity against common, multidrug-resistant MRSA isolates, including the epidemic UK EMRSA-15, EMRSA-16, and EMRSA-17, Irish EMRSA-1, AUS EMRSA-3, NY/JAPAN HA-MRSA, and predominant CA-MRSA clones.

TABLE 14

In vitro activities of the novel antibacterial NCL812 and the β-lactam antibacterial ampicillin against S. aureus clinical isolates according to Example 4.

| Organism and antimicrobial agent (no. of isolates tested) | MIC (μg/ml) | | | MBC (μg/ml) | | |
|---|---|---|---|---|---|---|
| | $MIC_{range}$ | $MIC_{50}$ | $MIC_{90}$ | $MBC_{range}$ | $MBC_{50}$ | $MBC_{90}$ |
| Methicillin-susceptible staphylococci (n = 10) | | | | | | |
| NCL812 | 2-8 | 4 | 4 | 2-8 | 4 | 8 |
| Ampicillin[1] | 0.25-16 | 0.25 | 8 | — | — | — |
| HA-MRSA (n = 10) | | | | | | |
| NCL812 | 4-8 | 4 | 8 | 4-8 | 8 | 8 |
| Ampicillin[1] | 16->128 | 64 | >128 | — | — | — |
| CA-MRSA (n = 10) | | | | | | |
| NCL812 | 2-4 | 4 | 4 | 2-4 | 4 | 4 |
| Ampicillin[1] | 8-128 | 64 | 128 | — | — | — |
| Total bacterial isolates (n = 30) | | | | | | |
| NCL812 | 2-8 | 4 | 8 | 2-8 | 4 | 8 |
| Ampicillin[1] | 0.25->128 | 16 | 128 | — | — | — |

HA-MRSA; hospital-acquired methicillin-resistant S. aureus.
CA-MRSA; community-associated methicillin-resistant S. aureus.
MIC; minimum inhibitory concentration (μg/ml).
MBC; minimum bactericidal concentration (μg/ml).
MIC/MBCrange; minimum and maximum MIC/MBC for all isolates.
MIC/$MBC_{50}$; MIC/MBC at which 50% of isolates are inhibited.
MIC/$MBC_{90}$; MIC/MBC at which 90% of isolates are inhibited In Vitro Antibacterial Activities: Minimum Bactericidal Concentrations The MBCs determined from NCL812 were equivalent to the MIC for 93.33% and 83.33% of S. aureus isolates, respectively (Table 14). In all remaining cases, MBCs were one dilution higher. For NCL812, MBCs ranged from 2-8 μg/mL and 4-16 μg/mL, respectively.

Time-Kill Studies

Figure 10:
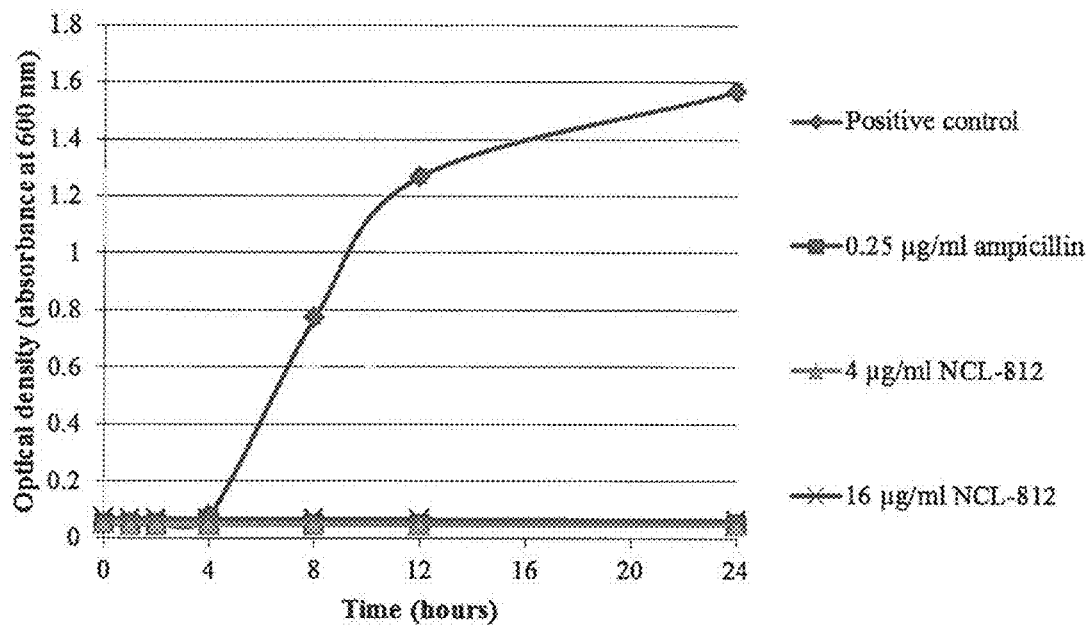
FIG. 10 shows a graph of the optical densities of the unsupplemented growth control, ampicillin and different concentrations of antibacterial agent NCL812 against methicillin-susceptible *S. aureus* ATCC 49775 using broth microdilution methodology according to example 4. The concentrations of NCL812 tested were at the MIC and four times the MIC determined under test conditions, up to 24 h incubation. Ampicillin was tested at the MIC. Bactericidal activity was tested at 0, 1, 2, 4, 8, 12, and 24 h for antibacterials.

In comparison to the turbidimetric growth curve of ATCC 49775, no visible bacterial growth was observed when ATCC 49775 was inoculated into cation-adjusted Mueller Hinton II broth supplemented with NCL812 at 1× and 4× the MIC in microdilution assays (P<0.033 and P<0.038, respectively) (FIG. 10).

Figure 11:
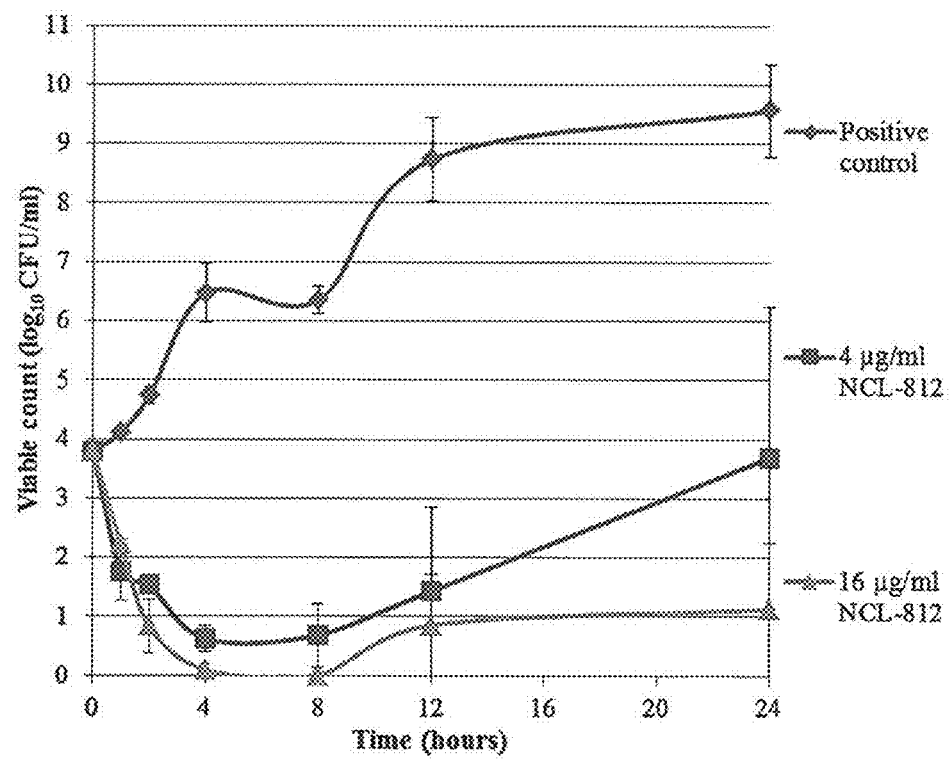
FIG. 11 shows a graph of kill kinetic curves for methicillin-susceptible *S. aureus* ATCC 49775 demonstrating bactericidal activity of NCL812 using the Clinical and Laboratory Standards Institute macrodilution methodology in a 10 ml vial according to example 4. The concentrations of antibacterials tested were at 1× and 4× the MIC determined under test conditions. Bactericidal activity was determined at 0, 1, 2, 4, 8, 12 and 24 h after antibacterial addition. Bactericidal activity was defined as a 3 $\log_{10}$ (99.9%) decrease in the number viable bacteria from the initial inoculum size.
Figure 12:
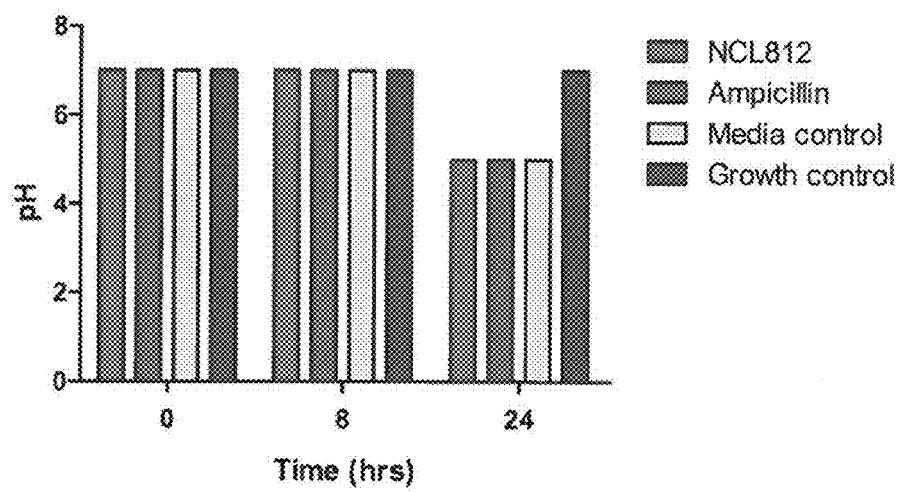
FIG. 12 shows a graph indicating the change of pH during macro-broth dilution assay for *S. pneumoniae* strain D39 exposed to 4 μg/mL in NCL812 and 0.0023 μg/mL ampicillin according to example 5.

When analysed in 10 mL macrodilution assays, broth supplemented with antimicrobials at 1× and 4× the MIC and inoculated with ATCC 49775 displayed significantly reduced viable counts for both NCL812 concentrations when compared to the growth control (0.000<P<0.008) (FIG. 11). Additionally, the time-kill profiles of each concentration of NCL812 did not significantly differ (P>0.05). Both concentrations remained bactericidal until approximately 8-12 h after antimicrobial addition, where bacterial regrowth was observed. Considerable variation in the killing NCL812 was also active against one S. pseudintermedius isolate that was originally identified as a S. aureus strain.

Preliminary testing suggests that NCL812 targets the S. aureus cell membrane, causing dose-dependent release of vital metabolites such as ATP. Disruption of the bacterial membrane bilayer or proteins that are integral to membrane function in bacteria is a target for numerous large antimicrobials which are ubiquitous in nature; including glycolipids, lipopeptides, lipoproteins, fatty acids, neutral lipids, phospholipids, and biosurfactants. Although NCL812 is a low molecular mass (≤500 Da) synthetic compound, it does appear to exert bactericidal activity in a similar manner to other antimicrobials which target the Gram-positive cell membrane, including the high molecular weight cyclic lipodepsipeptide antimicrobial agent daptomycin, or the low molecular mass quinolone-derived HT61, whose chemical structure is not currently available. Many of these lipophilic antibacterial agents are also not effective against Gram-negative microorganisms due to the presence of the outer lipid bilayer membrane, which contains narrow porin channels reducing the net penetration of some compounds into the cell.

The insolubility of NCL812 at even low concentrations in microbiological media may reflect the amphipathic and oligomeric nature of this antimicrobial and suggests that the real MIC may be much lower than observed, as it is likely that it is only NCL812 in solution that is biologically active. In time-kill studies, NCL812 exerted rapid in vitro bactericidal activity against ATCC 49775. Again, these findings are consistent with a time-kill profile of cell membrane function inhibitors such as daptomycin and HT61.

Importantly, the apparent short in vitro half-life of this antimicrobial resulted in bacterial regrowth observed at 12 h after antimicrobial addition. This suggests that if a viable bacterial population survives the initial exposure to NCL812 prior to antimicrobial inactivation, bacterial regrowth will occur. The development of resistance to NCL812 in these studies was ruled out as test bacteria remained susceptible to NCL812 following harvesting, washing and MIC testing. Whilst the apparent short in vitro half-life of NCL812 may be a desirable characteristic for future in vivo application, it does suggest that NCL812 should be administered every 8 h in future in vivo safety and efficacy experiments to maintain adequate systemic concentrations, though it would appear from the time-kill profile that the NCL compound series are concentration-dependent rather than time-dependent antimicrobials.

To overcome the methicillin-susceptible phenotype, extending disc diffusion incubation time from 24 to 48 h compensates for the slow derepression of the mecR gene. Although the effects of longer incubation were not examined, and the small sample size of MRSA isolates prevented further investigation into mec complex interactions; genetic techniques were of significantly improved sensitivity when compared to phenotypic methods for confirmation of the mecA status of the isolates in this study. Although genetic techniques are not always employed as a routine method for detecting MRSA, real-time PCR identification of the presence of the mecA gene in a *Staphylococcus* spp. isolate remains the diagnostic gold standard.

Example 5: In Vitro Pharmacodynamics of a New Antimicrobial Agent for *Streptococcus pneumoniae*

Materials and Methods
Pneumococcal Antimicrobial Susceptibility
Pneumococcal Strains and Growth Conditions Twenty pneumococcal isolates that comprised six characterised laboratory strains and 14 clinical isolates were the subject of this study (P9/6A, P21/3, WCH16/6A, WCH43/4, WCH46/4, WCH57/8, WCH77/5, WCH86/4, WCH89/7, WCH92/4, WCH137/6A, WCH158/19F, WCH184/19F and WCH211/11; strain/serotype, respectively). Other isolates used in this example were: A66.1/3 (Francis et al., 2001. *Infect Immun.* 69: 3350-2358); EF3030/19F (Briles et al., 2003 *J. Infec. Diseases.* 188:339-348); L82016/6B (Briles et al., 2000 *Infect Immun.* 68:796-800); TIGR4/4 (Tettlelin et al., 2001 *Science* 293:498-506); and WU2/3 (Briles et al., 1981 *J. Exp Med.* 153:694-705). See Table 15 below for the phenotypic characteristics of the isolates used in this study. The National Collection of Type Cultures (NCTC) control strain D39 (Avery et al., 2010 *Nature Reviews Microbiology* 8:260-271) was used as a growth control for all MIC and MBC assays. D39 was later designated for kill kinetics, point of resistance assays and transmission electron microscopy (TEM) studies as it is a well documented laboratory strain with a defined in vivo pathogenesis (Table 15) that displayed consistent NCL812 MICs and MBCs.

TABLE 15

*Pneumococcal* isolates and their phenotypic description according to Example 5.

| Strain | Phenotypic description | ID$_{50}$ |
|---|---|---|
| D39 (NCTC 7466) | Flat, round, 1 mm wide, dark green, α-haemolysis | $10^{2*}$ |
| A66.1 | Slightly raised, undulate, irregular in shape, 2 mm wide colonies, glossy, dark green, mucoid. α-haemolysis | $8 \times 10^3$ (10, 98) |
| EF3030 | Slightly raised, undulate, irregular in shape, 2 mm wide colonies, glossy, dark green, mucoid. α-haemolysis | $\geq 10^{5*}$ |
| L82016 | Flat, round, 1 mm wide, pale green, α-haemolysis | $\geq 10^{5*}$ |
| P9 | Flat, circular, 0.5 mm wide colonies, glossy, light green. α-haemolysis | $10^{4*}$ |
| P21 | Slightly raised, undulate, irregular in shape, 4 mm wide colonies, glossy, dark green, mucoid. α-haemolysis | $\leq 10^{1*}$ |
| TIGR4 | Flat, round, 1 mm wide, pale green, α-haemolysis | $10^{4*}$ |
| WU2 | Slightly raised, undulate, irregular in shape, 4 mm wide colonies, glossy, dark green, mucoid. α-haemolysis | $5 \times 10^{12*}$ |
| WCH16 | Flat, round, 1 mm wide, pale green, α-haemolysis | $5 \times 10^{4*}$ |
| WCH43 | Flat, round, 1 mm wide, pale green, α-haemolysis | $10^{2*}$ |
| WCH46 | Flat, round, 1 mm wide, pale green, α-haemolysis | $10^{4*}$ |
| WCH57 | Slightly raised, undulate, irregular in shape, 2 mm wide colonies, glossy, dark green, mucoid. α-haemolysis | $10^{4*}$ |
| WCH77 | Slightly raised, round in shape, <1 mm wide colonies, glossy, dark green, slight α-haemolysis. | $10^{4*}$ |
| WCH86 | Flat, round, 1 mm wide, pale green, α-haemolysis | $10^{4*}$ |
| WCH89 | Flat, round, >1 mm wide, pale green, α-haemolysis | $\geq 10^{5*}$ |
| WCH92 | Flat, round, 1 mm wide, dark green, α-haemolysis | $\leq 10^{4*}$ |
| WCH137 | Slightly raised, round in shape, <1 mm wide colonies, glossy, dark green, slight α-haemolysis. | ND |
| WCH158 | Round, sunken, 1 mm wide, dark green, α-haemolysis | $10^{5*}$ |
| WCH184 | Flat, round, 1 mm wide, dark green, α-haemolysis | $10^8$ (14) |
| WCH211 | Flat, round, >1 mm wide, dark green, α-haemolysis, irregular shape | $5 \times 10^{6*}$ |

ND = Not determined

For all in vitro assays, fresh pneumococcal isolates were grown overnight (O/N) on horse blood agar (HBA) plates (39 g/L Columbia blood agar base [Oxoid] 5% [v/v] defribinated horse blood [Oxoid] at 37° C. with 5% supplemented $CO_2$). Mueller-Hinton blood agar with 5% defibrinated sheep blood (MHSBA Roseworthy Media and Blood Service) was used for disk diffusion analysis as directed by Clinical Laboratory Standards Institute (CLSI) standards. Pneumococci were routinely grown in broth consisting of 4% lysed horse blood (LHB) with Cation Adjusted Mueller Hinton Broth (CAHMB, [Difco]) at 37° C. with 5% supplemented $CO_2$. Horse serum broth (HSB, 10% (v/v) donor horse serum in nutrient broth [10 g/L peptone, 10 g/L Lab Lemco (Oxoid) and 5 g/L NaCl]) was also used in some MIC assays. Isolates were stored in HSB at −80° C.

Antibiotic Stocks and Reagents

NCL812 was provided in dry powder form. A total of 256 mg was dispensed into 10 mL of 100% DMSO to make a stock of 25.6 mg/mL, which was then diluted 1:100 in CAHMB to make a final working stock of 256 μg/mL. Ampicillin dry powder was from Sigma A0166. The original 25.6 mg/mL stock was diluted in saline 1:100, 1:4, 1:20 and finally 1:16 in CAMHB to make a final working stock of 0.18 μg/mL. Erythromycin was purchased from Sigma Aldrich and choline chloride was from Roche Diagnostics.

Twenty micro liters of 0.05 µg/mL erythromycin was diluted 1:25 in 4.980 mL of CAMHB to give a final working stock of 0.2 µg/mL. Choline chloride (0.5%) was added to 4% LHB:CAMHB for specific kill kinetic assays.

Defining Antimicrobial Susceptibility of Pneumococcal Isolates

Isolate susceptibility to 12 different antimicrobials (Table 16) was determined by CLSI and European Committee on Antimicrobial Susceptibility Testing (EUCAST) methods. Antimicrobials were selected based upon the CLSI and EUCAST guidelines. Standardised bacterial suspensions were spread onto MHSBA using a sterile cotton swab. Bacterial suspensions from of *Streptococcus pneumoniae* were standardised to an $OD_600$ between 0.08 and 0.1 using a spectrophotometer and then diluted 1:20. Bacterial colonies were taken from an O/N horse blood agar plate. To ensure the purity of the 1:20 bacterial suspension, 50 µL was spread plated onto horse blood agar and incubated O/N at 37° C. with 5% $CO_2$. The CFU was calculated and compared to the initial plate counts. Antibiotic disks (Purchased from Sigma Aldrich) were placed using a disk dispenser (Purchased from Oxoid) according to CLSI standards. MHSBA plates were incubated for 16 h-24 h at 37° C. in 5% $CO_2$. Zones of complete inhibition were measured in triplicate to the nearest millimeter using a ruler on natural light-reflected growth, and the mode was represented as the diameter for each isolate. Pneumococcal isolates were categorised as sensitive, intermediate (I) or resistant (R) by CLSI standards and quality control (QC) ranges (Table 16).

account when planning the set up of a 96 well tray.] 10 µL of bacterial suspension was then added to the appropriate wells in the 96 well tray. Appropriate positive (no antimicrobial), negative (no antimicrobial or bacteria) and negative dilution (a serial dilution control of antimicrobial and broth) controls were included in each assay. MBC and plate counts for kill kinetic assays were determined by aliquotting 20 µL from each well of the 96 well microtitre tray onto HBA, and incubating at 37° C. with 5% $CO_2$. The MBC was determined by a 99.95% inhibition of *S. pneumoniae*, taking into account the dilution factor. MICs and MBCs were determined in quadruplicate and the mode was taken as the representative value. The $MIC_{50}$, $MIC_{90}$ and MIC range and $MBC_{50}$, $MBC_{90}$ and MBC range were determined according to CLSI standards. The $MIC_{50}$ and $MIC_{90}$, or $MBC_{50}$ and $MBC_{90}$, are defined by the lowest concentrations which, when all the MICs and MBCs of the isolates are arranged from lowest to highest, inhibited the 50th and 90th percentile of the total amount of isolates, respectively.

Micro-Broth Dilution Time Kill Studies with NCL812 Using Strain D39

Bacterial suspensions were added in triplicate to a 96 well microtitre tray containing NCL812 with a starting concentration of 128 µg/mL and serially diluted 1:2 sequentially to a concentration of 0.25 µg/mL. Negative dilution controls were subtracted from the median growth value to obtain a suitable indicator of overall bacterial production. The 96 well tray was incubated at 37° C. in 5% $CO_2$ and $OD_{600}$ read every 2 h for the first 12 h followed by final reads at 24 and

TABLE 16

Antibacterials used for disc diffusion analysis with interpretive standards of zone diameters (mm) according to Example 5.

| Antibiotic Class | Antimicrobial (µg) | Interpretive Standards for Zone Diameters (mm) (96) | | |
|---|---|---|---|---|
| | | Resistant (R) | Intermediate (I) | Sensitive |
| β-lactam | Oxacillin (1 µg)° | ≤20 | ≤20 | ≥20 |
| | Ampicillin (10 µg)° | ≤20 | ≤20 | ≥20 |
| | Amoxicillin-clavulanate (20/10 µg)° | ≤20 | ≤20 | ≥20 |
| Fluoroquinolone | Ciprofloxacin (5 µg)* | ≤20 | ≤20 | ≥20 |
| Folate pathway inhibitor | Trimethoprim-sulphamethoxazole (1.25/23.75 µg)° | ≤15 | 16-18 | ≥19 |
| Glycopeptide | Vancomycin (30 µg)° | — | — | ≤17 |
| Lincosamide | Clindamycin (2 µg)° | ≤15 | 16-18 | ≥19 |
| Marolide | Erythromycin (15 µg)° | ≤15 | 16-20 | ≥21 |
| | Clarithromycin (15 µg)° | ≤16 | 17-20 | ≥21 |
| Phenocol | Chloramphenicol (30 µg)° | ≤20 | — | ≥21 |
| Rifamycin | Rifampin (5 µg)° | ≤16 | 17-18 | ≥19 |
| Tetracycline | Tetracycline (30 µg)° | ≤18 | 19-22 | ≥23 |

°Zone diameters for antimicrobials other than Ciprofloxacin for *S. pneumoniae* were determined by CLSI standards.
*Zone diameters for Ciprofloxacin antimicrobial susceptibility to *S. pneumoniae* were determined by EUCAST.

Determination of NCL812 $MIC_{50}$, $MIC_{90}$, MIC Range and $MBC_{50}$, $MBC_{90}$, MBC Range MICs for NCL812 for all isolates listed in Table 15 were determined by measuring $OD_{600}$ (Spectramax spectrophotometer, Molecular Devices Corporation) as an indicator of bacterial growth using 96 well microtitre trays after incubation for 24 h at 37° C. in 5% $CO_2$. [Micro-broth dilutions and 96 well trays are prepared by the following method: 90 µL of 4% LHB:CAMHB is aliquotted into all wells using a multichannel pipette. 90 µL of working antimicrobial stocks were no serial diluted down the tray by a 1:2 dilution. Negative broth controls and dilution control were taken into 48 h. To further supplement this data, a separate experiment in which a 96 well tray was read automatically at half hourly intervals using a spectrophotometer (Spectramax spectrophotometer, Molecular Devices Corporation) for 14 h was performed to confirm the trends in growth curves observed from original micro-broth dilution studies.

MBC Time Kill Studies with NCL812 Using Strain D39

MBC kill kinetics assays involved the preparation of three 96 well microtitre trays. At specific time points, aliquots obtained from these trays provided viable counts following incubation at 37° C. in 5% $CO_2$ on HBA, and the MBC was determined after 24 h of growth.

Macro-Broth Dilution Time Kill Studies of D39 with NCL812

Bacterial suspensions and working antibiotic stocks were prepared as described above. [For preparing macro-broth dilutions, 20 mL tubes were filled each with 9 mL of 4% LHB:CAMHB. 9 mL of a working antimicrobial stock was diluted 1:2 when added to to one of the tubes, and then serial diluted down from a high to low concentration of antimicrobial. 1 mL of S. pneumoniae bacterial suspension was added to the appropriate tubes, including the positive control. Tubes were incubated at 37° C. with 5% $CO_2$ with gentle manual tilting of the tubes treated with NCL812 every 10 min for the first 12 h. At every 2-3 h during the first 12 h of growth and then at 24 h and 48 h, 50 μL of each bacterial suspension was spread plated onto HBA and incubated at 37° C. with 5% $CO_2$ for 16-24 h.]

Table 17 below indicates the concentrations used for each antimicrobial. Cultures were incubated at 37° C. in 5% $CO_2$ with gentle manual tilting every 10 min for the first 12 h. Viable counts from 50 μL aliquots of each concentration were read following incubation at 37° C. in 5% $CO_2$ for 24 h. The pH of each sample was measured at specific time points using pH indicator strips. Confluent growth was defined when more than 1000 colonies were counted per plate. A bactericidal effect was defined as a 1000 fold reduction (99.9%) of the original cell suspension determined at 24 h for each concentration.

TABLE 17

Antibacterial agent concentrations used in macro-broth dilution assays according to Example 5.

| Serial dilution | NCL812 (μg/ml) | NCL062 (μg/ml) | Ampicillin (μg/ml) |
|---|---|---|---|
| 1 | 128 | 128 | 0.09 |
| 2 | 64 | 64 | 0.045 |
| 3 | 32 | 32 | 0.023 |
| 4 | 16 | 16 | 0.011 |
| 5 | 8 | 8 | 0.0065 |
| 6 | 4 | | |
| 7 | 2 | | |

Point of Resistance Assay for NCL812

Macro-broth dilutions were prepared as above. Broth cultures of strain D39 (10 mL) were incubated in the presence of 2 μg/mL and 4 μg/mL of NCL812, and 0.022 μg/mL of Ampicillin for 6 h at 37° C. in 5% $CO_2$. Samples were centrifuged at a relative centrifugal force (RCF) of 101.45×g for 10 min and washed in 50 mL of phosphate buffered saline (PBS) twice to remove any residual antimicrobial, and/or bacterial end products and media. Washed bacteria were resuspended and MICs were performed.

Effect of NCL812 on D39 Cell Membrane Ultra-Structure Transmission Electron Microscopy Morphological appearance and morphometric analysis of the cell membrane was determined using transmission electron microscopy (TEM). Bacterial suspensions and 10 mL cultures of D39 were prepared as before. Samples were incubated at 37° C. in 5% $CO_2$ with gentle manual tilting of the cultures every 10 min. Cultures were exposed to either 1 μg/mL, 4 μg/mL or 16 μg/mL of NCL812 and harvested at 6 or 12 h by centrifugation at RCF of 101.45×g for 20 min and washed twice in 50 mL of PBS. Critical time points for TEM work were determined by analysing trends in the growth curves produced from the kill kinetics studies. Samples were resuspended in PBS containing 20% glycerol and stored at −80° C. until required. Before fixation, 20% glycerol was removed by centrifugation and washing on ice three times in 50 mL of PBS.

Samples were fixed using modified protocols defined by a previous study examining cell wall ultrastructure of S. pneumoniae (Hammerschmidt, S. et al. 2005. *Infect Immun* 73:4653-4667). A lysine acetate-based formaldehyde-glutaraldehyde ruthenium red-osmium fixation procedure involved fixing the bacterial pellets with a cacodylate buffer solution containing 2% formaldehyde, 2.5% glutaraldehyde, 0.075% ruthenium red and 0.075 M of lysine acetate for 1 h. After washing with cacodylate buffer containing 0.075% ruthenium red three times, a second fixation in cacodylate buffer solution containing 2% formaldehyde, 2.5% glutaraldehyde and 0.075% ruthenium red was undertaken for 1.5 h. Cells were subsequently washed three times with cacodylate buffer containing 0.075% ruthenium red and underwent a final fixation in 1% osmium tetroxide in cacodylate containing 0.075% ruthenium red for 1 h. The samples were then washed three times in cacodylate buffer containing 0.075% ruthenium red only.

Samples were washed and dehydrated using a graded series of ethanol (70, 90, 95 and 100%) for 10-20 min, two times for each step. Samples were infiltrated using 50:50 LR White resin in 100% ethanol for 1 h, and subsequently washed with 100% LR White resin for 1 h and left O/N in a third change of 100% LR white to ensure adequate infiltration of resin. The samples were then embedded in fresh LR White resin and incubated at 50° C. for 48 h. Sections were cut to 1 μm using a glass knife, stained with Toluidene Blue and viewed under a light microcrope at 400× to identify the presence of stained pneumococci. At least four ultra-thin sections were then cut to 90 nm using a diamond knife and placed on matrix grids, one section per grid. Ultra-thin sections were then stained with uranyl acetate and lead citrate alternatively at 5 min intervals, followed by three washes with distilled water in-between each exposure. Stained sections were then placed on grids and viewed between 25000× and 130000× on a Philips CM100 Transmission Electron Microscope. Images were obtained at 130000× magnification and analysed using analySIS [Olympus Soft Imaging Systems].

Statistical Analysis

Statistical analyses were conducted using statistics program GraphPad Prism (5th ed, GraphPad Software Inc.) for Windows. For growth curves, data presented were the mean and standard error of mean (SEM) (represented as error bars) for each data point except for macro-broth dilution studies where multiple replicates could not be obtained due to the high costs involved in this assay. Two tailed, unpaired t-tests were performed.

Results

Pharmacodynamics of NCL812 in S. pneumoniae

Quality Control Disk Diffusion Analysis for 20 S. pneumoniae Isolates

Although nine out of the twelve antimicrobials used for disk diffusion analysis had established QC ranges by EUCAST, QC ranges were not defined for amoxicillin-clavulanate, clarithromycin and clindamycin (Table 18 and Table 19). WCH16 and WCH184 were both resistant to at least two antimicrobials whereas EF3030 and WCH137 were intermediate and resistant to trimethoprim-sulphamethoxazole respectively (Table 19). The other remaining sixteen isolates were sensitive to all twelve antimicrobials. Sensitivity to ampicillin was confirmed for each isolate, enabling the use of ampicillin as a positive control in later micro-broth dilution assays (Table 18).

TABLE 18

Antibacterial susceptibility of 20 *S. pneumoniae* isolates for six different antibacterials according to Example 5.

| | Range of disk diffusion zone diameters (nearest whole mm) | | | | | |
|---|---|---|---|---|---|---|
| Antimicrobial | Ampicillin | Amoxicillin-clavulanate | Clarithromycin | Clindamycin | Chloramphenicol | Ciprofloxacin |
| Sensitivity standard | ≥20 mm | ≥20 mm | ≥21 mm | ≥19 mm | ≥21 mm | ≥22 mm |
| QC range | 25-31 mm | Not defined | Not defined | Not defined | 24-30 mm | 22-28 mm |
| A66.1 | 37 | 43 | 30 | 34 | 34 | 25 |
| D39 | 37 | 47 | 32 | 27 | 31 | 26 |
| EF3030 | 38 | 43 | 32 | 26 | 29 | 22 |
| L82016 | 41 | 39 | 34 | 32 | 26 | 26 |
| P9 | 33 | 42 | 40 | 31 | 31 | 27 |
| P21 | 40 | 47 | 38 | 25 | 35 | 23 |
| TIGR4 | 37 | 42 | 35 | 28 | 32 | 24 |
| WU2 | 38 | 42 | 31 | 27 | 30 | 28 |
| WCH16 | 41 | 46 | 33 | 28 | 11 (R) | 25 |
| WCH43 | 36 | 42 | 28 | 22 | 26 | 21 |
| WCH46 | 37 | 41 | 39 | 30 | 28 | 27 |
| WCH57 | 43 | 53 | 39 | 34 | 40 | 32 |
| WCH77 | 43 | 48 | 37 | 28 | 36 | 26 |
| WCH86 | 38 | 35 | 36 | 30 | 34 | 36 |
| WCH89 | 38 | 40 | 31 | 27 | 32 | 26 |
| WCH92 | 38 | 40 | 27 | 24 | 32 | 21 |
| WCH137 | 40 | 43 | 33 | 26 | 31 | 24 |
| WCH158 | 42 | 46 | 38 | 32 | 34 | 28 |
| WCH184 | 33 | 39 | 10 (R) | 10 (R) | 29 | 22 |
| WCH211 | 39 | 42 | 33 | 27 | 32 | 24 |

Blue cells represent sensitive isolates; orange cells represent intermediate (I) isolates; green cells represent resistant (R) isolates.

TABLE 19

Antibacterial susceptibility of 20 *S. pneumoniae* isolates for six different antibacterials according to example 5

| | Range of disk diffusion zone diameters (nearest whole mm) | | | | | |
|---|---|---|---|---|---|---|
| Antimicrobial | Erythromycin | Oxacillin | Rifampin (Rifampicin) | Tetracycline | Trimethoprim-sulphamethoxazole | Vancomycin |
| Sensitivity standard | ≥21 mm | ≥20 mm | ≥23 mm | ≥23 mm | ≥19 mm | ≥17 mm |
| QC range | 26-32 mm | 8-14 mm | 26-32 mm | 28-34 mm | 20-26 mm | 17-23 mm |
| A66.1 | 33 | 28 | 32 | 32 | 23 | 25 |
| D39 | 35 | 26 | 28 | 35 | 25 | 22 |
| EF3030 | 30 | 18 | 32 | 34 | 17 (I) | 22 |
| L82016 | 29 | 29 | 26 | 32 | 23 | 23 |
| P9 | 32 | 26 | 27 | 32 | 21 | 21 |
| P21 | 35 | 28 | 32 | 38 | 25 | 21 |
| TIGR4 | 34 | 26 | 30 | 35 | 24 | 22 |
| WU2 | 34 | 28 | 31 | 34 | 22 | 21 |
| WCH16 | 34 | 30 | 30 | 18 (R) | 21 | 23 |
| WCH43 | 29 | 26 | 27 | 31 | 22 | 20 |
| WCH46 | 27 | 27 | 29 | 30 | 24 | 21 |
| WCH57 | 41 | 32 | 38 | 48 | 32 | 28 |
| WCH77 | 37 | 28 | 33 | 39 | 29 | 24 |
| WCH86 | 30 | 34 | 31 | 31 | 27 | 22 |
| WCH89 | 35 | 29 | 32 | 35 | 25 | 25 |
| WCH92 | 28 | 25 | 22 | 29 | 23 | 22 |
| WCH137 | 34 | 29 | 30 | 37 | 10 (R) | 24 |
| WCH158 | 34 | 28 | 34 | 35 | 27 | 22 |
| WCH184 | 10 (R) | 11 | 32 | 11 (R) | 22 | 23 |
| WCH211 | 33 | 25 | 32 | 36-37 | 24 | 23 |

Blue cells represent sensitive isolates; orange cells represent intermediate (I) isolates; green cells represent resistant (R) isolates Solubility and Activity of NCL812 and NCL062 in Different Media NCL812 visually appeared to have higher solubility in 100% DMSO compared to NCL062 and only developed turbidity when it was further diluted into CAMHB or PBS (Table 20). Although a CAMHB diluent for NCL062 appeared to be transparent by visual inspection (Table 20), further studies on NCL062 with a CAMHB diluent resulted in complete confluence in microbroth dilution assays for six *S. pneumoniae* isolates in comparison to growth with the DMSO diluents (Table 21 and Table 22).

TABLE 20

Visual analysis of NCL812 and NCL062 and ampicillin solubility according to Example 5.

| Diluent | NCL812 | NCL062 | Ampicillin |
|---|---|---|---|
| CAMHB | Turbid | Transparent | Transparent |
| DMSO | Transparent | Precipitate | Transparent |
| PBS | Precipitate | Precipitate | Transparent |
| Media | | | |
| 4% LHB:CAMHB | Turbid | Transparent | Transparent |
| 10% horse serum-supplemented broth | Precipitate | Transparent | Transparent |

TABLE 21

Individual MICs of NCL062 for each pneumococcal isolate according to Example 5

| NCL062 | MIC ($\mu g \cdot mL^{-1}$) | MBC ($\mu g \cdot mL^{-1}$) |
|---|---|---|
| D39 | 2 | 4 |
| EF3030 | 16 | 16 |
| A66.1 | 8 | 32 |
| TIGR4 | 8 | 8 |
| WU2 | 16 | 64 |
| L82016 | 8 | 32 |
| P9 | 4 | 16 |
| P21 | 4 | 4 |
| WCH158 | 16 | 16 |
| WCH89 | 4 | 4 |
| WCH57 | 4 | 8 |
| WCH77 | 8 | 8 |
| WCH46 | 32 | 32 |
| WCH86 | 4 | 8 |
| WCH137 | 2 | 4 |
| WCH184 | 16 | 16 |
| WCH16 | 32 | 32 |
| WCH43 | 2 | 4 |
| WCH92 | 8 | 8 |
| WCH211 | 2 | 4 |

TABLE 22

Difference in activity of NCL812 and NCL062 in different media using micro-broth dilution to obtain an MIC as a predictor according to Example 5.

| Isolate | Resistance status to Ampicillin | NCL062 MIC ($\mu g/ml$) | NCL062 MBC ($\mu g/ml$) | Ampicillin MIC ($\mu g/ml$) | Ampicillin MBC ($\mu g/ml$) |
|---|---|---|---|---|---|
| D39 | Sensitive | Confluent | * | 0.0225 | * |
| A66.1 | Sensitive | Confluent | * | 0.045 | * |
| WU-2 | Sensitive | Confluent | * | 0.0225 | * |
| P21 | Sensitive | Confluent | * | 0.0225 | 0.045 |
| WCH158 | Sensitive | Confluent | 64 | 0.0225 | 0.022 |
| WCH57 | Sensitive | Confluent | * | 0.09 | 0.09 |

Growth of *S. pneumoniae* strain D39 in an MIC assay for NCL812 and NCL062 using 10% HSB (220 mL of horse serum is filtered to 10% in 180 mL of Lemco nutrient broth) resulted in a threefold increase in the MIC for D39 treated with NCL812 and NCL062 (Table 23) with a twofold increase for the positive ampicillin control. There was no notable change in MIC for D39 with differing storage conditions of pre-prepared 96 well microtitre trays (Table 24). During macro-broth dilutions, the pH of the media did not change compared to appropriate controls (FIG. 12.

TABLE 23

Growth of *S. pneumoniae* strain D39 in an MIC assay for NCL812 and NCL062 using horse serum supplemented broth

| | Relative MIC with media type for D39 ($\mu g \cdot mL^{-1}$) | | |
|---|---|---|---|
| Antimicrobial | 4% LHB:CAMHB | 10% horse serum-supplemented broth | Fold-increase |
| NCL812 | 4 | 32 | 3 |
| NCL062 | 4 | 32 | 3 |
| Ampicillin | 0.023 | 0.09 | 2 |

TABLE 24

Storage of prepared micro-titer trays for micro-broth dilution does not change MIC of D39 according to Example 5.

| | Storage condition | |
|---|---|---|
| Antimicrobial | −2° C. | 4° C. |
| NCL812 | 8 $\mu g \cdot mL^{-1}$ | 8 $\mu g \cdot mL^{-1}$ |
| NCL062 | 4 $\mu g \cdot mL^{-1}$ | 4 $\mu g \cdot mL^{-1}$ |
| Ampicillin | 0.023 $\mu g \cdot mL^{-1}$ | 0.023 $\mu g \cdot mL^{-1}$ |

Determination of *S. pneumoniae* in vitro susceptibility to NCL812 and NCL062

Determination of NCL812 and NCL062 $MIC_{50}$, $MIC_{90}$, MIC range

NCL812 exhibited a $MIC_{50}$ and $MIC_{90}$ $MIC_{90}$ of 8 μg/mL and MIC range of 4-8 μg/mL whereas for NCL062 these values were higher and more variable (Table 25 and Table 26). The MIC for ampicillin was comparable to recent published findings using micro-broth dilution as an endpoint for antimicrobial resistance in pneumococcal isolates, thus confirming the accuracy of MICs obtained for NCL812 and NCL062 (Tables 25 to 26 and FIG. 13).

TABLE 25

$MIC_{50}$, $MIC_{90}$, $MBC_{50}$, $MBC_{90}$ and MIC range for all isolates treated with NCL812, NCL062, and ampicillin according to Example 5.

| | NCL812 (μg/mL) | NCL062 (μg/mL) | Ampicillin (μg/mL) |
|---|---|---|---|
| $MIC_{50}$ | 8 | 8 | 0.023 |
| $MIC_{90}$ | 8 | 32 | 0.023 |
| MIC Range | 4-8 | 2-32 | 0.011-0.09 |
| $MBC_{50}$ | 8 | 16 | 0.023 |
| $MBC_{90}$ | 8 | 32 | 0.023 |
| MBC Range | 4-8 | 4-64 | 0.011-0.09 |

TABLE 26

MICs of NCL812 of each pneumococcal isolate according to Example 5.

| | NCL812 | | Ampicillin | |
|---|---|---|---|---|
| | MIC ($\mu g \cdot mL^{-1}$) | MBC ($\mu g \cdot mL^{-1}$) | MIC ($\mu g \cdot mL^{-1}$) | MBC ($\mu g \cdot mL^{-1}$) |
| D39 | 4 | 8 | 0.023 | 0.023 |
| EF3030 | 8 | 8 | 0.023 | 0.023 |
| A66.1 | 8 | 8 | 0.045 | 0.045 |
| TIGR4 | 4 | 8 | 0.023 | 0.023 |
| WU2 | 4 | 8 | 0.023 | 0.023 |
| L82016 | 8 | 8 | 0.023 | 0.023 |
| P9 | 8 | 8 | 0.023 | 0.023 |

TABLE 26-continued

MICs of NCL812 of each pneumococcal isolate according to Example 5.

|  | NCL812 | | Ampicillin | |
|---|---|---|---|---|
|  | MIC ($\mu g \cdot mL^{-1}$) | MBC ($\mu g \cdot mL^{-1}$) | MIC ($\mu g \cdot mL^{-1}$) | MBC ($\mu g \cdot mL^{-1}$) |
| P21 | 4 | 8 | 0.023 | 0.023 |
| WCH158 | 4 | 8 | 0.023 | 0.023 |
| WCH89 | 4 | 4 | 0.023 | 0.023 |
| WCH57 | 8 | 8 | 0.023 | 0.023 |
| WCH77 | 4 | 8 | 0.023 | 0.023 |
| WCH46 | 4 | 4 | 0.023 | 0.045 |
| WCH86 | 4 | 8 | 0.023 | 0.023 |
| WCH137 | 4 | 8 | 0.023 | 0.023 |
| WCH184 | 4 | 4 | 0.045 | 0.045 |
| WCH16 | 8 | autolysis | 0.023 | Autolysis |
| WCH43 | 4 | 8 | 0.023 | 0.023 |
| WCH92 | 8 | 8 | 0.09 | 0.09 |
| WCH211 | 4 | 8 | 0.023 | 0.023 |

Determination of NCL812 and NCL062 $MBC_{50}$, $MBC_{90}$, MBC Range

Minimum bactericidal concentrations ($MBC_{50}$, $MBC_{90}$ and MBC range respectively) were determined for NCL812 and ampicillin for all twenty isolates (Tables 25 to Table 26). The $MBC_{50}$, $MBC_{90}$, and MBC range was lower and more consistent for NCL812 compared with NCL062 (Table 25).

Figure 20:
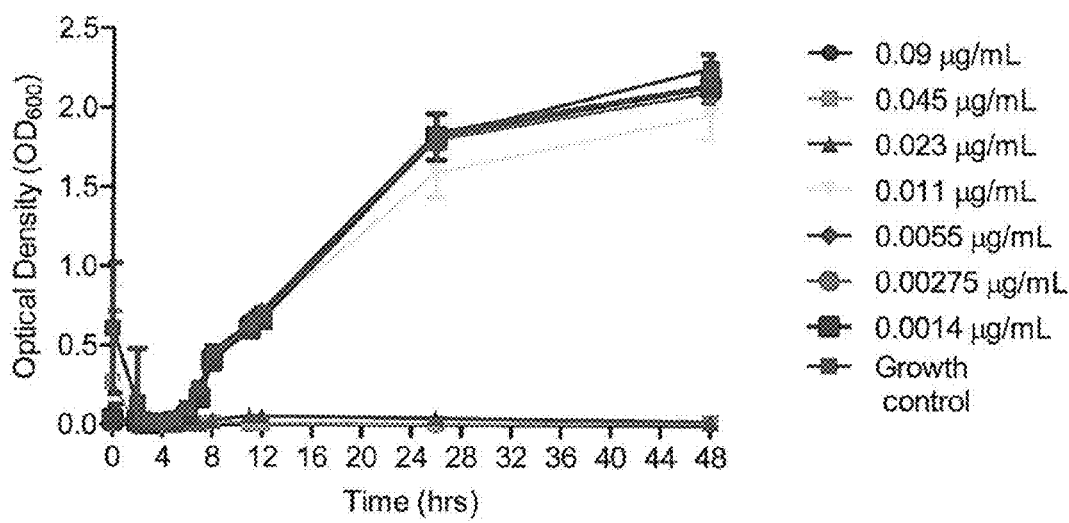
FIG. 20 shows a graph illustrating the 48-hour time-kill of *S. pneumoniae* strain D39 treated with ampicillin according to example 5.
Figure 21:
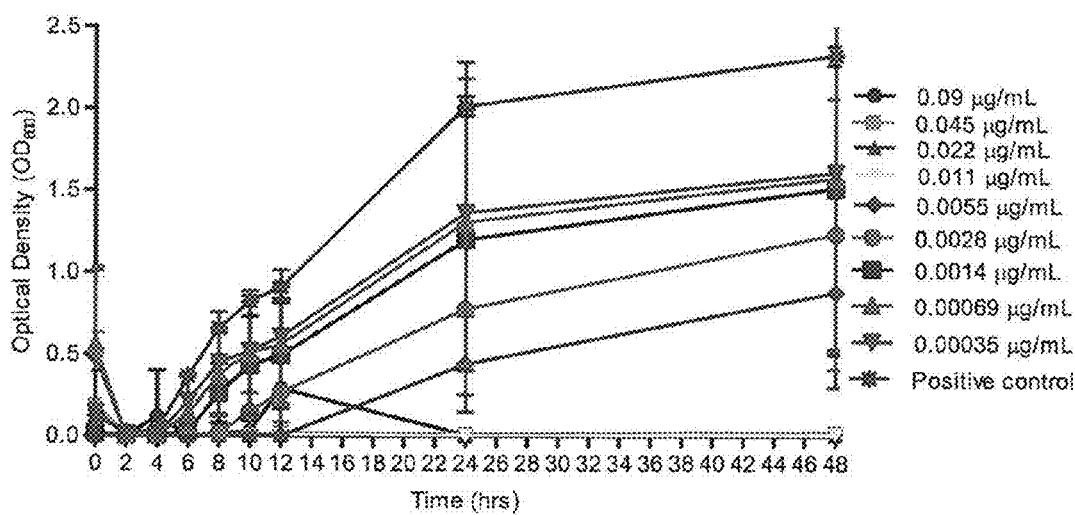
FIG. 21 shows a graph illustrating the 48-hour time-kill of *S. pneumoniae* strain D39 treated with erythromycin according to example 5.
Figure 22:
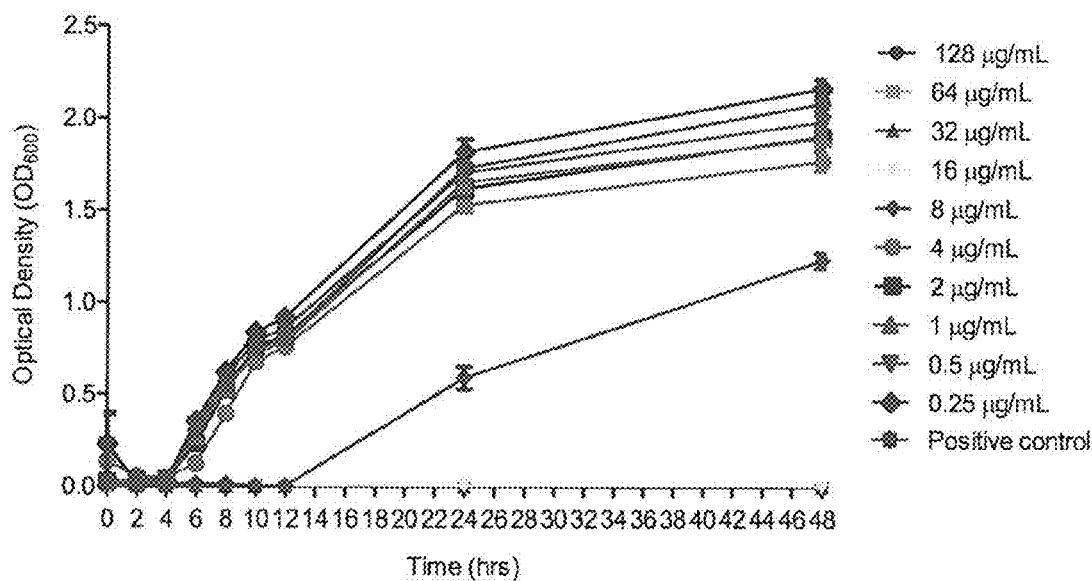
FIG. 22 shows a graph illustrating the 48-hour time-kill of *S. pneumoniae* strain D39 treated with NCL812 and 5% choline chloride.
Figure 23:
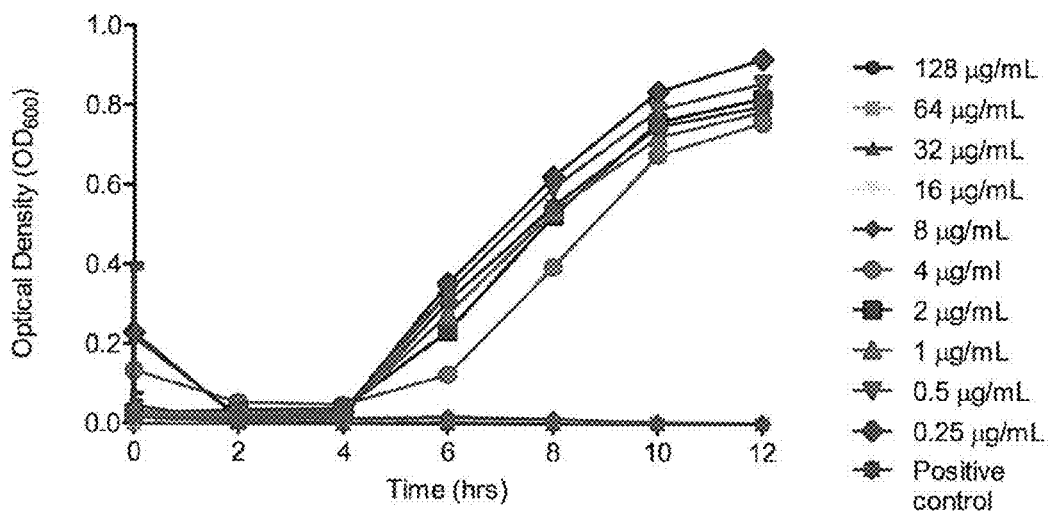
FIG. 23 shows a graph illustrating the 12-hour time-kill of *S. pneumoniae* strain D39 treated with NCL812 and 5% choline chloride according to example 5.
Figure 24:
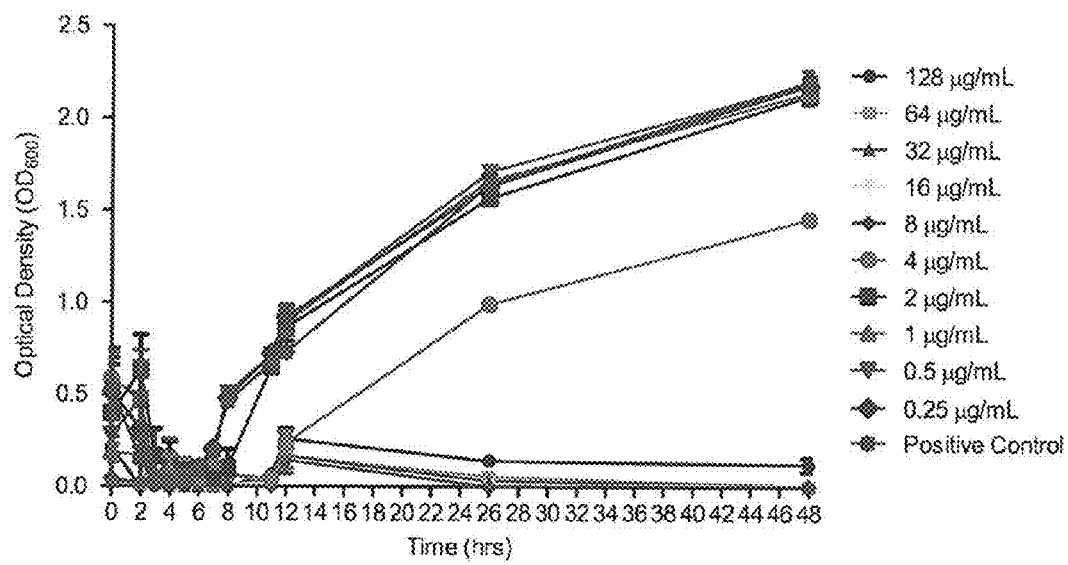
FIG. 24 shows a graph illustrating the 48-hour time-kill of *S. pneumoniae* strain D39 treated with NCL062 and 5% choline chloride according to example 5.
Figure 25:
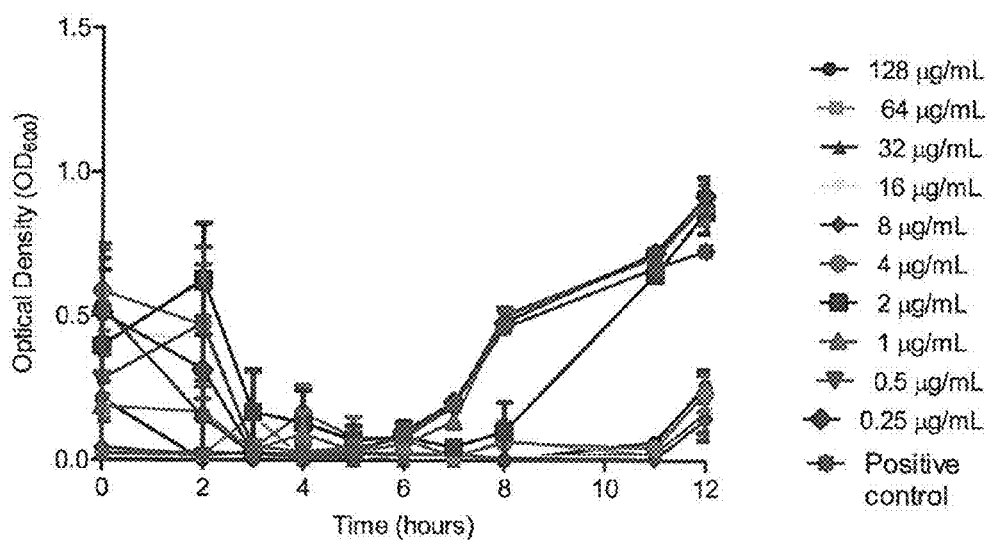
FIG. 25 shows a graph illustrating the 12-hour time-kill of *S. pneumoniae* strain D39 treated with NCL062 and 5% choline chloride according to example 5.
Figure 26:
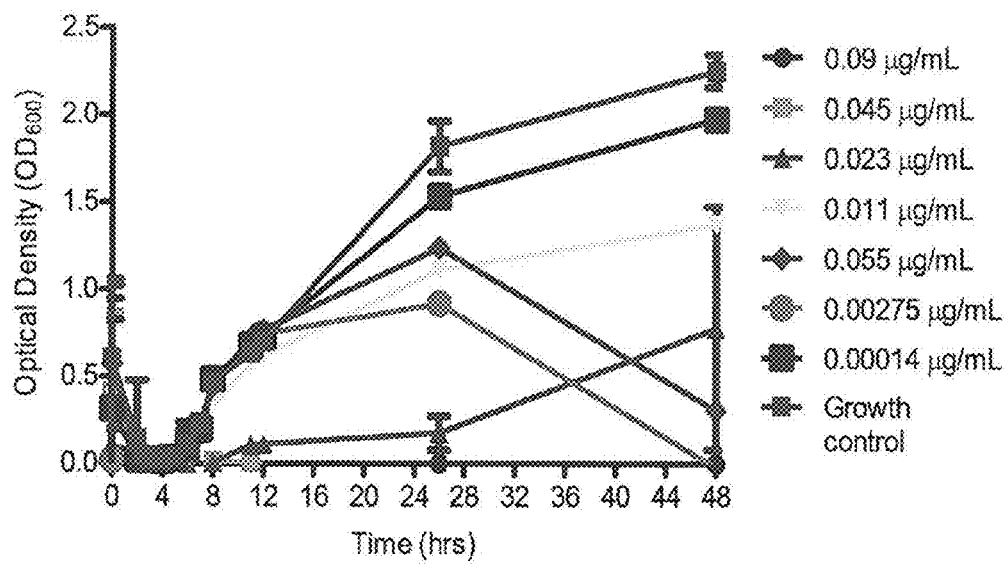
FIG. 26 shows a graph illustrating the 48-hour time-kill of *S. pneumoniae* strain D39 treated with ampicillin and choline chloride according to example 5.

The growth of D39 treated with NCL812 or NCL062 was compared to D39 treated with ampicillin or erythromycin over 48 h (FIGS. 20 and 21). D39 treated with ampicillin exhibited similar growth to D39 exposed to NCL812 or NCL062 over 48 h (FIG. 20). Erythromycin-treated D39 produced very different growth curves from NCL812 and NCL062 where a larger difference in growth between concentrations was observed (FIG. 21). The addition of 5% choline chloride to the media over a 48 h period resulted in no significant difference in growth for NCL812 and NCL062 compared to positive and growth controls (FIGS. 22 to 26).

Point of Resistance Testing

Figure 18:
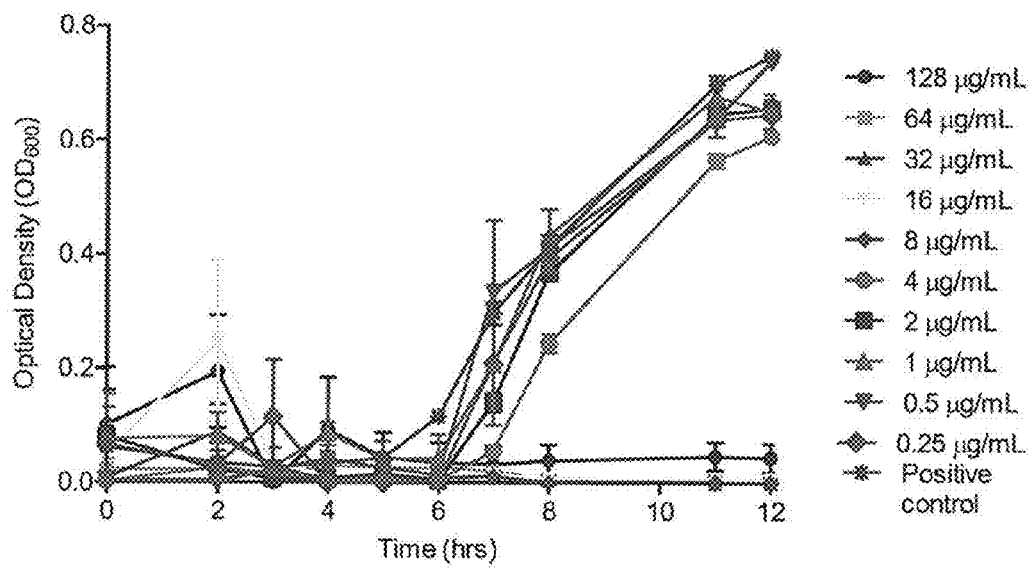
FIG. 18 shows a graph illustrating the 12-hour time-kill of *S. pneumoniae* strain D39 treated with NCL812, adopted from the FIG. 43, according to example 5.
Figure 19:
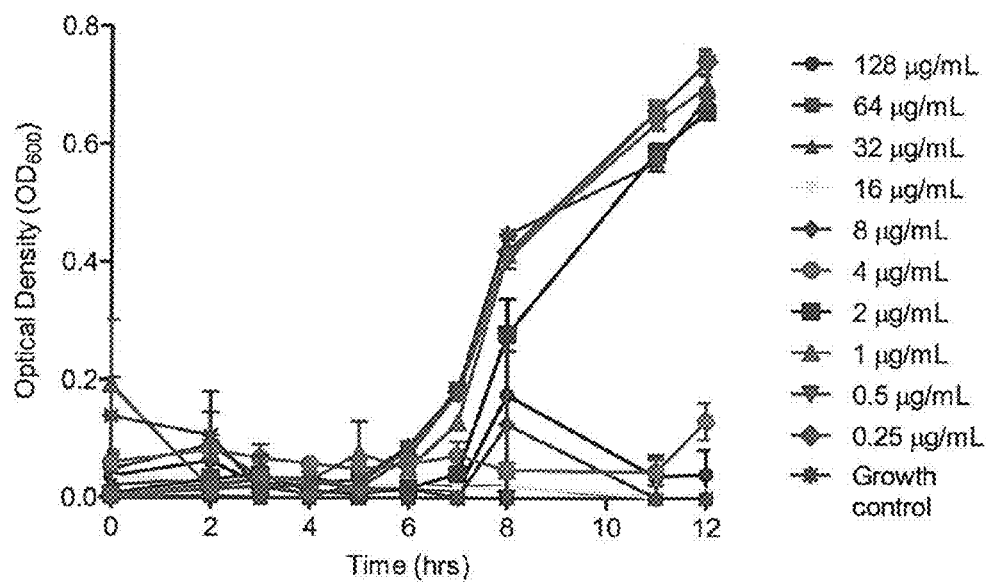
FIG. 19 shows a graph illustrating the 12-hour time-kill of *S. pneumoniae* strain D39 treated with NCL062, adopted from the FIG. 44, according to example 5.

D39 treated with 54 μg/mL NCL812 entered a log phase of growth at 6 h (FIGS. 13 and 18), as shown in four independent experiments. The possibility of antimicrobial resistance to NCL812 between 5 and 6 h was investigated by determining further MICs on D39 exposed to 2 μg/mL NCL812, 4 μg/mL NCL812 and 0.0225 μg/mL ampicillin for 6 h. Results showed no significant increase in MIC for all samples of D39 exposed to NCL812 compared to growth controls, and ampicillin (Table 27).

TABLE 27

MICs of D39 exposed to 2 μg/mL or 4 μg/mL of NCL812 for 6 h according to Example 5.

|  | Original MIC of D39 | MIC of D39 following exposure to NCL-812 for 6 hrs. | Original MBC of D39 | MBC of D39 following exposure to NCL-812 for 6 hrs |
|---|---|---|---|---|
| D39 exposed to 2 μg/ml NCL812 | 4 $\mu g \cdot mL^{-1}$ | 8 $\mu g \cdot mL^{-1}$ | 8 $\mu g \cdot mL^{-1}$ | 8 $\mu g \cdot mL^{-1}$ |
| D39 exposed to 4 μg/ml NCL812 | 4 $\mu g \cdot mL^{-1}$ | 8 $\mu g \cdot mL^{-1}$ | 8 $\mu g \cdot mL^{-1}$ | 8 $\mu g \cdot mL^{-1}$ |
| D39 exposed 0.023 μg/ml Ampicillin | 0.023 $\mu g \cdot mL^{-1}$ | 0.045 $\mu g \cdot mL^{-1}$ | 0.023 $\mu g \cdot mL^{-1}$ | 0.023 $\mu g \cdot mL^{-1}$ |
| D39 growth* | 8 $\mu g \cdot mL^{-1}$ | 8 $\mu g \cdot mL^{-1}$ | 8 $\mu g \cdot mL^{-1}$ | 8 $\mu g \cdot mL^{-1}$ |
| 039 growth2** | 8 $\mu g \cdot mL^{-1}$ | 8 $\mu g \cdot mL^{-1}$ | 8 $\mu g \cdot mL^{-1}$ | 8 $\mu g \cdot mL^{-1}$ |

*D39 growth control: S. pneumoniae strain D39 grown for 6 hrs in 4% LHB:CAMHB.
**D39 growth2 control: S. pneumoniae strain D39 on HBA O/N, resuspended in saline (0.1 $OD_{600}$) and diluted 1/20 in sterile saline.

Micro-Broth Dilution Time Kill Studies of D39 Treated with NCL812 and NCL062

Figure 13:
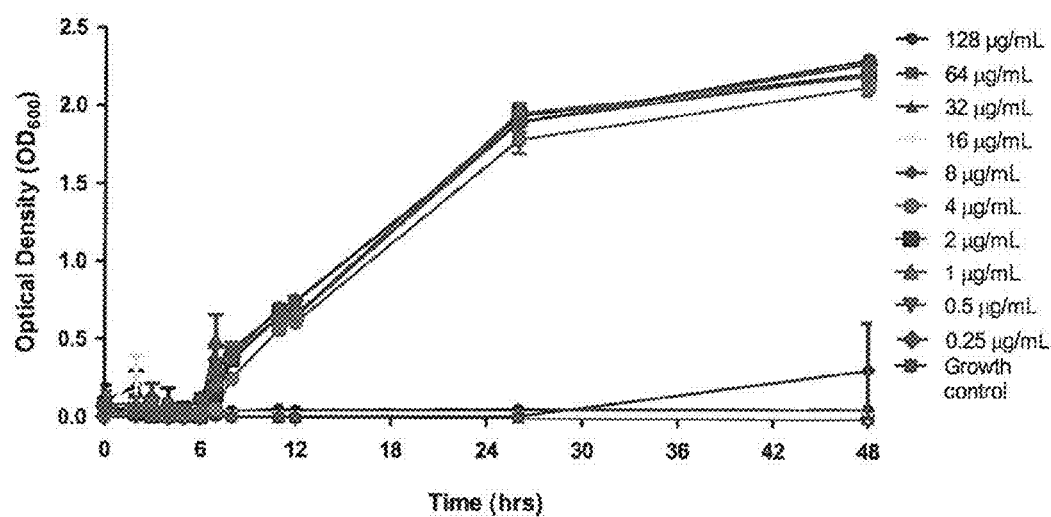
FIG. 13 shows a graph illustrating the 48-hour time-kill of *S. pneumoniae* strain D39 treated with NCL812 according to example 5.
Figure 14:
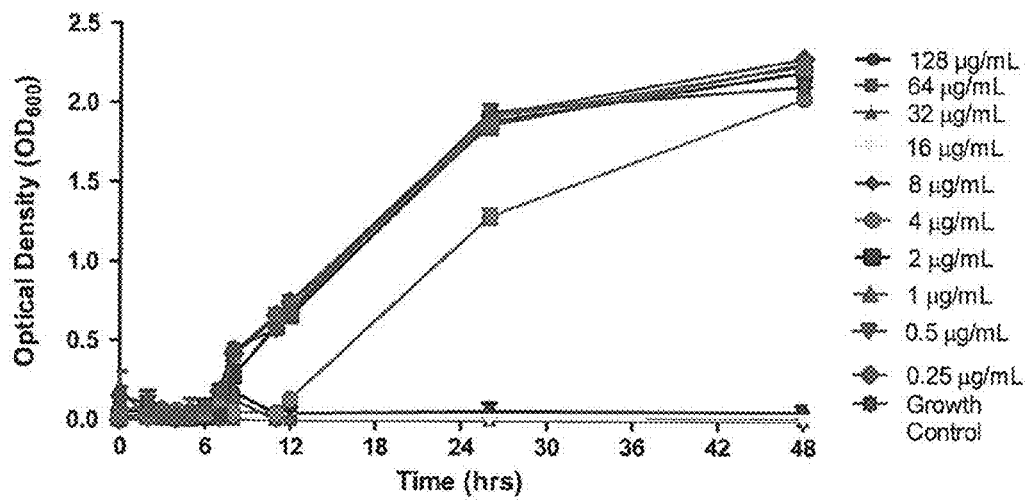
FIG. 14 shows a graph illustrating the 48-hour time-kill of *S. pneumoniae* strain D39 treated with NCL062 according to example 5.
Figure 15:
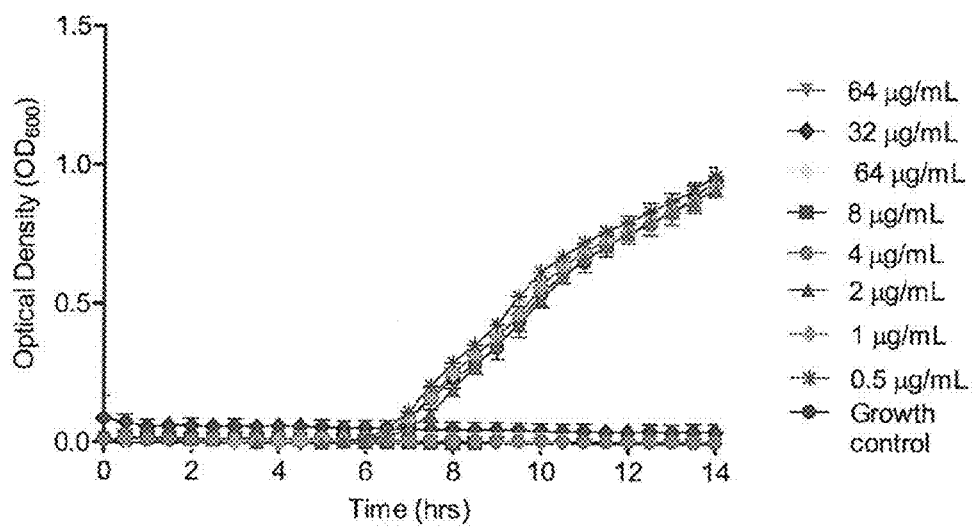
FIG. 15 shows a graph illustrating in the 14-hour time-kill of *S. pneumoniae* strain D39 treated with NCL812 according to example 5.
Figure 16:
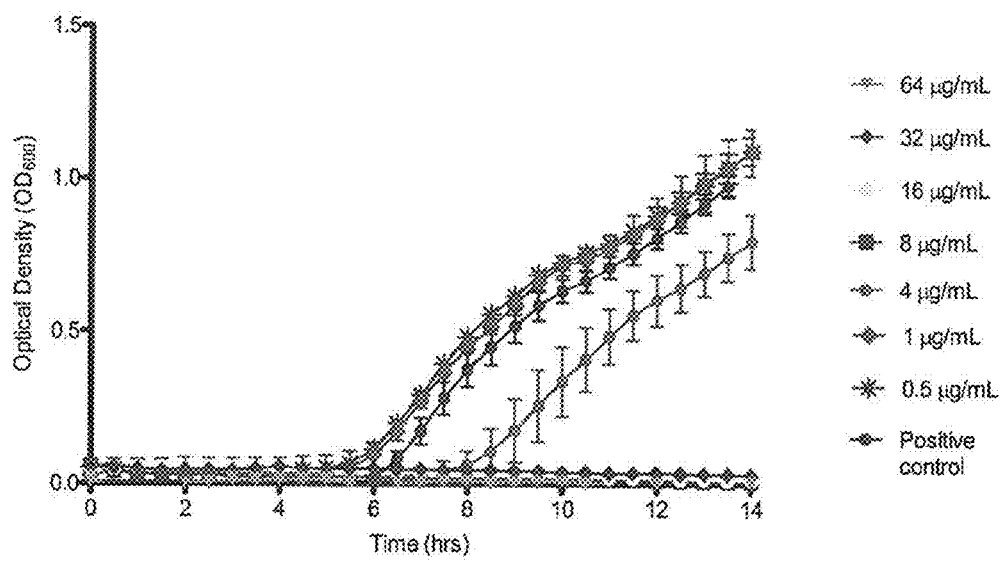
FIG. 16 shows a graph illustrating in the 14-hour time-kill of *S. pneumoniae* strain D39 treated with NCL062 according to example 5.
Figure 17:
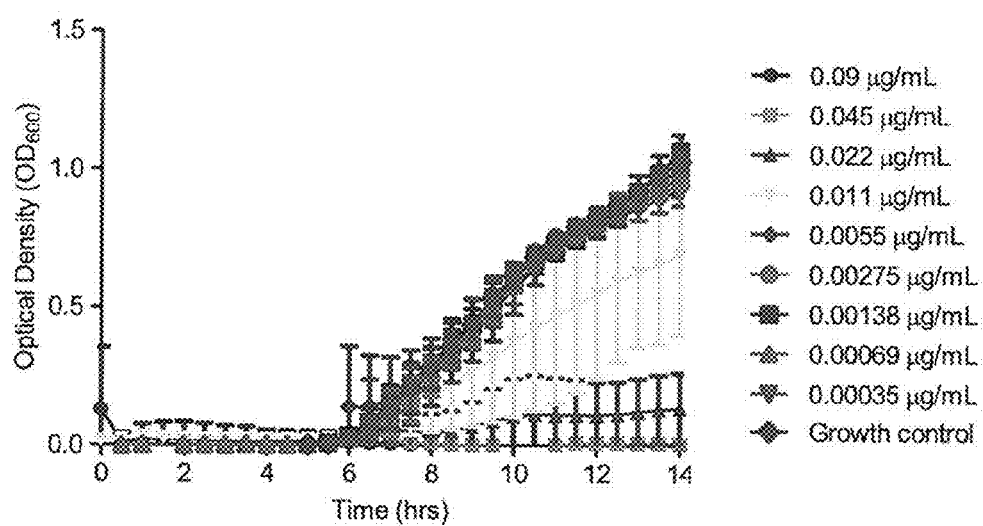
FIG. 17 shows a graph illustrating the 14-hour time-kill of *S. pneumoniae* strain D39 treated with ampicillin according to example 5.

D39 exposed to sub-inhibitory concentrations (≤2 μg/ml) of NCL812 or NCL062 grew similarly to unexposed controls over a 48 h period (FIGS. 13 and 14. Higher concentrations of NCL812 and NCL062 (≥16 μg/mL) resulted in no bacterial growth for 48 h (FIGS. 14 and 15. These growth characteristics were validated by a micro-broth kill kinetic study using a Spectramax spectrophotometer, which measured growth (represented as $OD_{600}$) at half-hourly intervals for 14 h for NCL812, NCL062 and ampicillin (FIGS. 15 to 17. There was an approximate six hour difference between the commencement of exponential growth for D39 treated with NCL812 and D39 treated with NCL062 (FIGS. 13, 14, 18 and 19).

Micro-Broth Dilutions by Measuring Relative MBC at Specific Time Points

Figure 27:
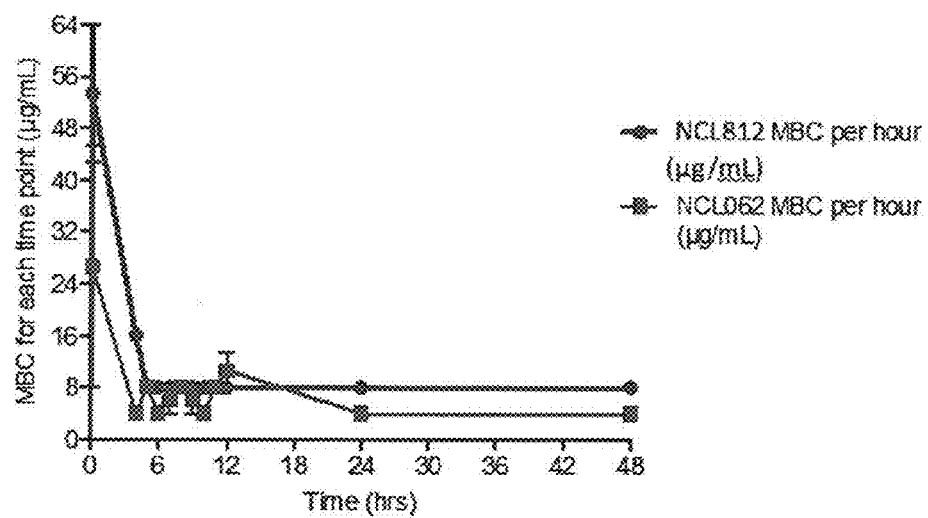
FIG. 27 shows a graph of the relative MBC of D39 treated with NCL812 or NCL062 for 48 hours according to example 5.
Figure 28:
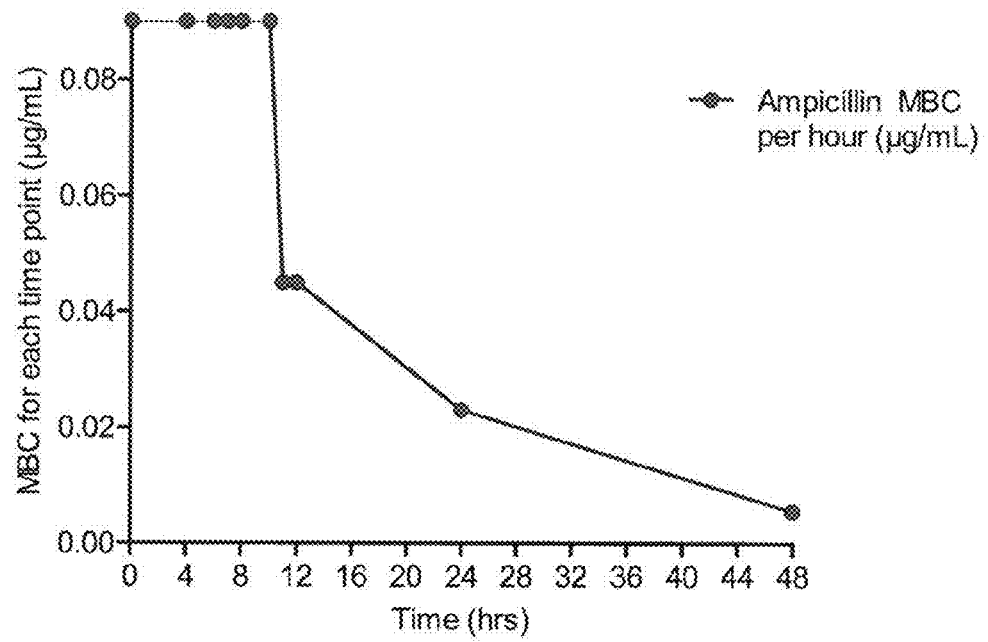
FIG. 28 shows a graph illustrating the relative minimal bactericidal concentration (MBC) of *S. pneumoniae* strain D39 treated with ampicillin over a 48 h time period according to example 5.
Figure 29:
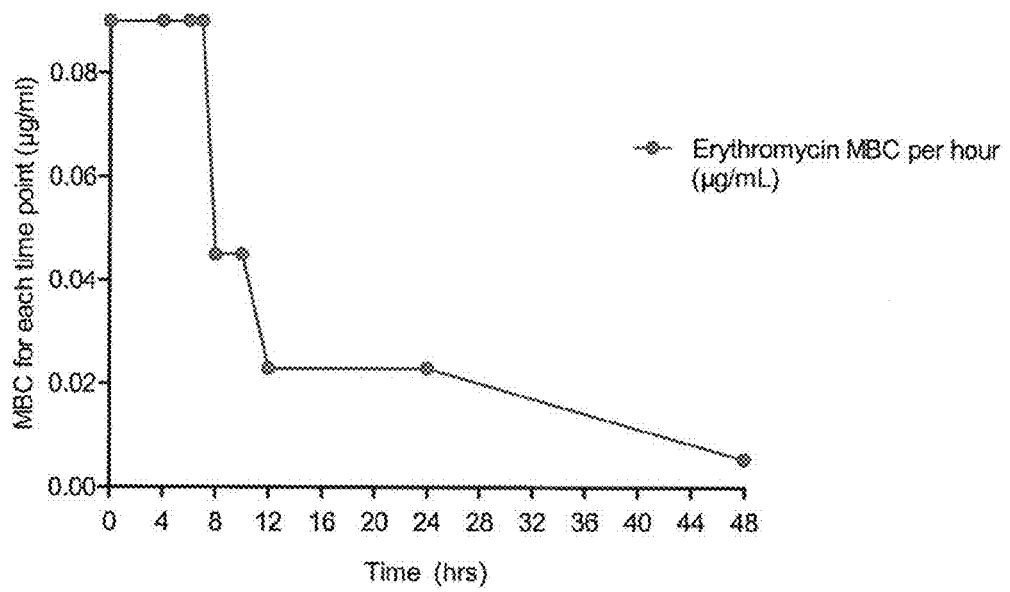
FIG. 29 shows a graph illustrating the relative MBC for *S. pneumoniae* strain D39 treated with erythromycin over a 48 h time period according to example 5.

Relative MBCs were determined at specific time intervals from using broth dilution assays incubated for 48 h for NCL812 and NCL062 (FIG. 27) and control antimicrobials ampicillin and erythromycin (FIGS. 20 and 21). MICs of ampicillin and erythromycin for D39 were determined (Tables 26 and 28). The comparative features of the growth of ampicillin, and erythromycin are described (FIGS. 28 and 29). Ampicillin and erythromycin demonstrated a time-dependent reduction in bacteria. NCL062 exhibited rapid bactericidal action, with an immediate (within the first 10 min of administration) MBC of 8 μg/mL (FIG. 27). Although there were inconsistencies in the MBCs for NCL062 between 5 and 12 h, NCL062 maintained a constant bactericidal concentration (4 μg/mL) between 24 and 48 h. NCL812 exhibited fast bactericidal action, evidenced by an approximate 3 fold decrease in MBC within 5 h (FIG. 27).

A consistent bactericidal concentration (8 μg/mL) was maintained for the full 48 h for NCL812.

TABLE 28

MIC and MBC for erythromycin with D39 according to Example 5.

| Isolate | Resistance status to Erythromycin | MIC (μg/ml) | MBC (μg/ml) |
|---|---|---|---|
| D39 | Sensitive | 0.00275 | 0.00275 |

Macro-Broth Dilution Time Kill Studies of D39 with NCL812 and NCL062

Figure 30:
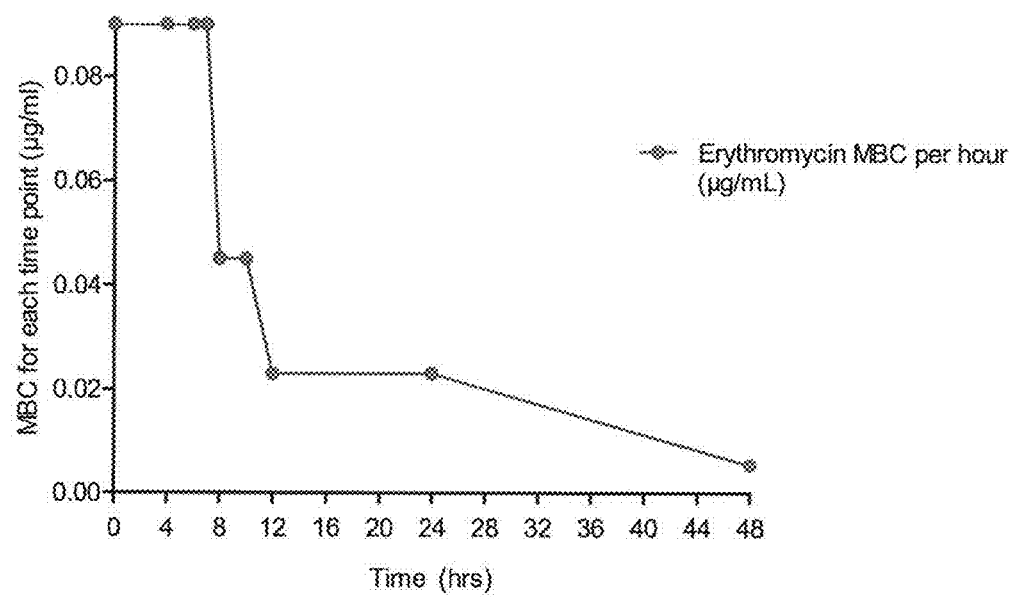
FIG. 30 shows a graph illustrating the viable count ($\log_{10}$ CFU/ml) of *S. pneumoniae* strain D39 treated with NCL812 from a macro-broth dilution of time-kill over 24 hours according to example 5.
Figure 31:
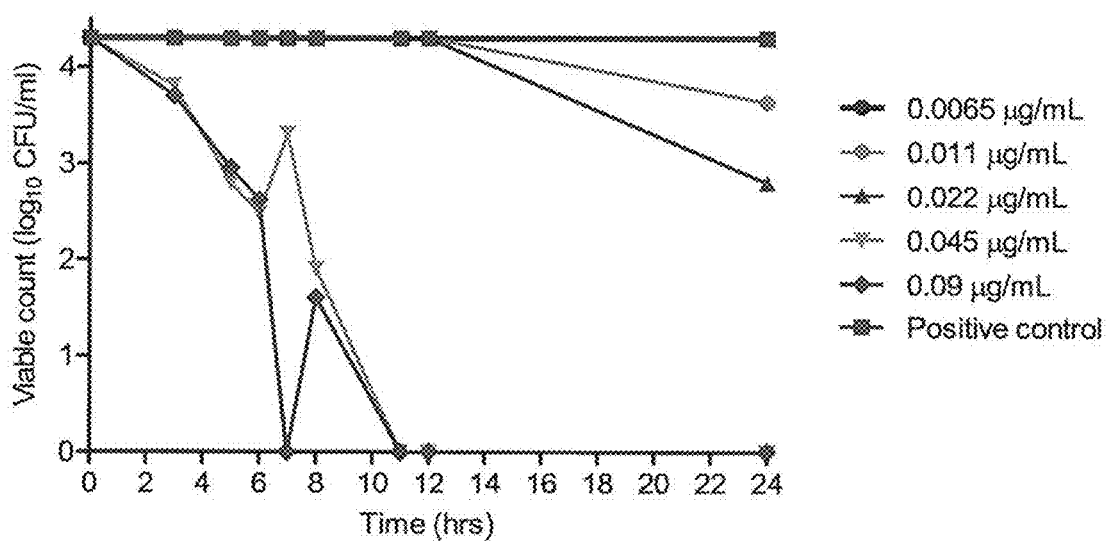
FIG. 31 shows a graph illustrating the viable count ($\log_{10}$ CFU/ml) of *S. pneumoniae* strain D39 treated with ampicillin from a macro-broth dilution of time-kill over 24 hours according to example 5.

Viable counts for each time point were represented as a $\log_{10}$ CFU/mL reduction for NCL812 (FIG. 30) and ampicillin (FIG. 31). Consistent confluent growth (determined by a limit of 2×10⁴ CFU) was observed for unexposed controls and 2 μg/mL NCL812. Complete bactericidal activity (defined by a 3 $\log_{10}$ reduction in CFU) for 128 μg/mL of NCL812 was observed by a 4 $\log_{10}$ reduction of CFU in 3 h and concentrations between 16 μg/mL and 64 μg/mL NCL812 were effective at eliminating bacterial growth within 8 h (FIG. 30). NCL812 at 4 μg/mL and 8 μg/mL appeared to be inactivated at 11 h post-exposure, as increased growth of strain D39 after this time point was observed (FIGS. 20 and 31). The viable counts of strain D39 treated with ampicillin demonstrated consistency for this particular assay by showing a constant diminished time-dependant killing over 48 h (FIG. 31).

Transmission Electron Microscopy

Figure 32:
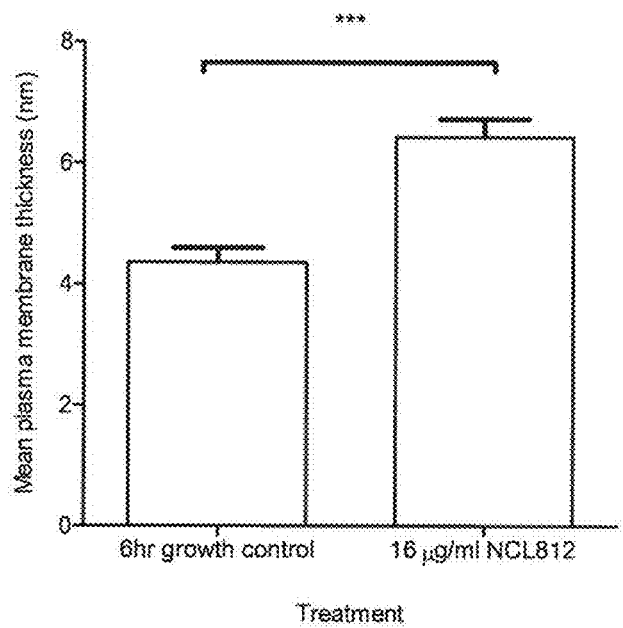
FIG. 32 is a bar graph illustrating the mean cell membrane thickness of treated and untreated D39 according to example 5.
Figure 33:
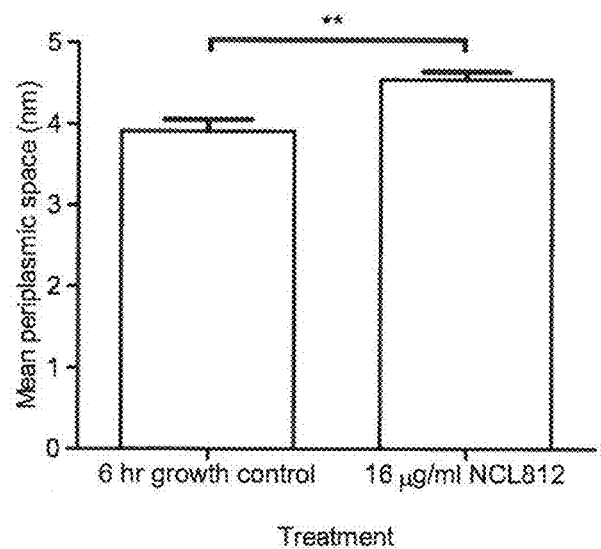
FIG. 33 is a bar graph illustrating the mean width of periplasmic space of treated (16 μg/mL NCL812) and untreated D39 samples according to example 5.

Morphometric analysis revealed significant changes to the cell membrane in strain D39 exposed to 16 μg/mL NCL812 for 6 h compared to growth controls. Samples treated with 4 μg/mL as well as 12 h cultures were not considered for morphometric analysis due to the lack of bacterial cells available in each section. Treated samples possessed significantly thicker cell membranes (6.43±0.29 nm) compared to untreated samples (4.35±0.24 nm) (p<0.0001) (FIGS. 32 and 29). The periplasmic space (intracellular space between the cell membrane and the cell wall) of D39 treated with 16 μg/mL NCL812 was significantly wider (4.54±0.096 nm) compared to untreated samples (3.91±0.14 nm) (p<0.001) (FIGS. 29 and 33).

TABLE 29

Morphometric studies on the ultra structures of D39 treated with NCL812 for 6 hours according to Example 5.

| Statistical test | Growth control Mean ± SEM | Treatment (16 μg/ml NCL812 for 6 h) Mean ± SEM | Unpaired t-test (P value) |
|---|---|---|---|
| Cell membrane | 4.35 ± 0.24 nm, n = 12 | 6.43 ± 0.29 nm, n = 13 | P < 0.0001 |
| Periplasmic space | 3.91 ± 0.14 nm, n = 11 | 4.54 ± 0.096 nm, n = 11 | P < 0.001 |

In summary, NCL812 produced highly consistent MICs and equivalent MBCs for the *S. pneumoniae* strain collection, confirming that it is bactericidal against this organism. In kill kinetics experiments, which measured the relative MBC over a 48 h period, a consistent bactericidal effect was elicited in D39 after 6 h from initial exposure to NCL812.

This demonstration of bactericidal activity is the first to be observed in *S. pneumoniae*. This demonstrates that NCL812 is effective against pneumococcal in vitro.

Competitive binding between components in blood, serum or broth decreased the antimicrobial activity of NCL. This was reflected in the increase of MIC observed between different broth types and diluents. Following the completion of these studies, recent independent research confirmed precipitation of NCL812 in PBS and reported complete solubility in water containing 4% DMSO, following initial dilution in 100% DMSO. A water-soluble NCL812 will greatly improve in vivo bioavailability and negative interaction between blood or serum proteins.

Based on the findings of this study, NCL812 exhibits a mechanism of action against *S. pneumoniae* that is different from β-lactam or macrolide classes, as it appears to exhibit concentration-dependent bactericidal activity as opposed to time-dependant qualities. Identifying the maximum pharmacokinetic serum concentration of NCL812 in vivo will assist confirmation of its concentration-dependant pharmacodynamic activity. Furthermore, the addition of choline chloride to the media confirmed that the mechanism of action for NCL is not associated with the affinity to cell wall choline binding proteins, and therefore may not be cell wall associated.

Morphometric analysis of the cell membrane and periplasmic space of D39 treated with 16 μg/mL NCL812 for 6 h showed that the cell membrane and periplasmic space was larger in treated samples, compared to control samples. The apparent increase in membrane size could be due to an accumulation of electron dense intracellular material beneath the cell membrane. The increase in the size of the periplasmic space may be have been due to disruption of the cell membrane, potentially by depolarisation or ATP inhibition. The mechanism of action of NCL812 may not be calcium-dependant as it appears that no competitive binding between NCL812 and ruthenium red, a calcium channel inhibitor of lipid bilayers, was observed in electron micrographs.

In conclusion, this in vitro study has demonstrated that NCL812 has many desirable characteristics as a fast-acting concentration-dependent bactericidal antimicrobial that appears to target the cell membrane of *S. pneumoniae*. These characteristics are desirable to treat acute pneumococcal infections. As NCL812 may possess a mechanism of action that targets the cell membrane, it will act much more quickly than time-dependent antimicrobials such as β-lactams and macrolides and potentially more effective than other bactericidal concentration-dependent antimicrobials such as fluoroquinolones which have intracellular targets.

Example 6: Characterization of Methicillin-Susceptible and Methicillin-Resistant Isolates of *Staphylococcus* Pseudintermedius from Australia and Preliminary In Vitro Efficacy of a New Anti-Staphylococcal Compound Materials and Methods Sample Collection and Identification of Methicillin Susceptible *Staphylococcus pseudintermedius* (MSSP) and Methicillin Resistant *Staphylococcus pseudintermedius* (MRSP)

A total of 23 *Staphylococcus* pseudintermedius isolates were obtained from dogs (Table 30).

TABLE 30

*Staphylococcus pseudintermedius isolates tested according to Example 6.*

| Adelaide # | GLY | BOX | SITE OF ISOLATION | Species | BREED | MRSP/ MSSP | mec gene Pert | mecA by RT-PCR Adl | Cefox-itin ZD (mm) | Cefox-itin ZD, Adl (mm) | oxa-cillin ZD (mm) | oxa-cillin ZD, Adl (mm) | oxa-cillin Etest MIC (mg/L) |
|---|---|---|---|---|---|---|---|---|---|---|---|---|---|
| S1P1 | 191 | 8 | AXILLA | S. pseudintermedius |  | MRSP | POS | POS | 0 | 0 | 0 | 0 | >256 |
| S2P2 | 193 | 8 | TISSUE | S. pseudintermedius | Shar pei X | MRSP | POS | POS | 21 | 21 | 0 | 0 | >256 |
| S3P3 | 194 | 8 | SKIN SWAB | S. pseudintermedius | Mastiff X | MRSP | POS | POS | 21 | 24 | 0 | 0 | >256 |
| S4P4 | 214 | 8 | SKIN SWAB | S. pseudintermedius | CKCS | MRSP | POS | POS | 29 | 20 | 0 | 0 | 2 |
| S5P5 | 215 | 8 | SKIN SWAB | S. pseudintermedius | Shar pei | MRSP | POS | POS | 26 | 30 | 0 | 0 | 4 |
| S6P6 | 218 | 8 | PAW SWAB | S. pseudintermedius | Dachshund | MRSP | POS | POS | 22 | 26 | 0 | 0 | >256 |
| S7P7 | 219 | 8 | SKIN SWAB | S. pseudintermedius | British Bulldog | MRSP | POS | POS | 21 | 19 | 0 | 0 | >256 |
| S8P8 | 220 | 8 | SKIN SWAB | S. pseudintermedius | British Bulldog | MRSP | POS | POS | 21 | 22 | 0 | 0 | >256 |
| S9P9 | 96 | 9 | SKIN SWAB | S. pseudintermedius | Akita | MRSP | POS | POS | 23 | 26 | 0 | 0 | 4 |
| S10P10 | 190 | 9 | SKIN SWAB | S. pseudintermedius | Akita | MRSP | POS | POS | 21 | 25 | 0 | 0 | >256 |
| S11P11 | 187 | 9 | TISSUE | S. pseudintermedius | Bull terrier | MSSP | POS | POS | 22 | 21 | 0 | 0 | >256 |
| S12P12 | 188 | 9 | SKIN SWAB | S. pseudintermedius | Great Dane | MRSP | POS | POS | 24 | 24 | 13 | 16 | 1.5 |
| S13P13 | 189 | 9 | R EAR SWAB | S. pseudintermedius | CKCS | MSSP | NEG | NEG | 36 | 40 | 26 | 36 | 0.125 |
| S14P14 | 185 | 9 | TISSUE | S. pseudintermedius | Labrador Retriever | MSSP | NEG | NEG | 34 | 32 | 22 | 29 | 0.25 |
| S15P15 | 191 | 9 | TISSUE | S. pseudintermedius | Maltese X | MSSP | NEG | NEG | 33 | 34 | 22 | 25 | 0.25 |
| S16P16 | 194 | 9 | SKIN SWAB | S. pseudintermedius | Maltese | MSSP | NEG | NEG | 38 | 42 | 26 | 34 | 0.19 |
| S17P17 | 195 | 9 | SKIN SWAB | S. pseudintermedius | Shar pei X | MSSP | NEG | NEG | 36 | 38 | 22 | 26 | 0.25 |
| S18P18 | 196 | 9 | TISSUE | S. pseudintermedius | JRT | MSSP | NEG | NEG | 25 | 40 | 22 | 30 | 0.25 |
| S19P19 | 197 | 9 | SKIN SWAB | S. pseudintermedius | Labrador Retriever | MSSP | NEG | NEG | 36 | 38 | 25 | 32 | 0.25 |
| S20P20 | 198 | 9 | SKIN SWAB | S. pseudintermedius | Fox Terrier | MSSP | NEG | NEG | 38 | 36 | 23 | 30 | 0.25 |
| S21P21 | 199 | 9 | R EAR SWAB | S. pseudintermedius | Labrador Retriever | MSSP | NEG | NEG | 36 | 40 | 27 | 37 | 0.125 |
| S22P22 | 200 | 9 | SKIN SWAB | S. pseudintermedius | Maltese | MSSP | NEG | NEG | 34 | 35 | 21 | 26 | 0.25 |
| S23P23 | 203 | 9 |  |  |  |  |  | POS | 29 | 26 | 13 | 14 | 1.5 |

Ten methicillin susceptible and 13 methicillin resistant *Staphylococcus* pseudintermedius were collected for the study. Isolates were phenotypically classified as methicillin resistant on the basis of in vitro resistance to oxacillin and genetically for the presence of mecA gene according to standard procedures.

Oxacillin and cefoxitin susceptibility testing using disk diffusion technique and Epsilometer testing were performed. Identification of mecA gene was performed using polymerase chain reaction (PCR)

CLSI disk diffusion susceptibility testing was performed on the 23 Sp. isolates for the following antimicrobials: penicillin, amoxicillin, erythromycin, gentamicin, clindamycin, ciprofloxacin, cephalexin, chloramphenicol, tetracycline, oxytetracycline, vancomycin, cefotetan, moxifloxacin and rifampin.

Minimum inhibitory concentration (MIC) and minimum bactericidal concentration (MBC) testing was undertaken using CLSI methodology for NCL812 and included ampicillin as a control. Anti-staphylococcal compounds were then tested against all 23 isolates and minimum inhibitory concentrations (MIC) were determined according to standard protocols. After the MICs were determined, the minimum bactericidal concentrations were performed to determine if these compounds are bacteriostatic or bacteriocidal.

Results

The mecA gene was present in 13 isolates of MRSP and negative in 10 MSSP (Tables 30 and 31). All MRSP isolates were resistant to oxacillin based on disc diffusion (≤17 mm) and E-test MIC (≥0.5 mg/L).

TABLE 31

*Staphylococcus pseudintermedius isolates tested according to Example 6.*

|  | mecA by RT-PCR | Penicillin | Ampicillin | Amoxicillin | Erythromicin | Gentamycin | Clindamycin | Ciprofloxacin | Cephalothin |
|---|---|---|---|---|---|---|---|---|---|
| S1P1 | POS | R | R | R | R | R | S | R | R |
| S2P2 | POS | R | R | R | R | R | I | R | S |
| S3P3 | POS | R | R | R | R | R | R | R | S |
| S4P4 | POS | R | R | R | R | R | R | R | I |
| S5P5 | POS | R | R | R | R | R | R | R | S |
| S6P6 | POS | R | R | R | R | R | R | R | S |
| S7P7 | POS | R | R | R | R | R | R | R | R |
| S8P8 | POS | R | R | R | R | R | R | R | I |
| S9P9 | POS | R | R | S | R | R | R | R | S |
| S10P10 | POS | R | R | R | R | R | R | R | S |
| S11P11 | POS | R | R | R | R | S | I | S | S |
| S12P12 | POS | R | R | S | S | R | S | R | S |
| S13P13 | NEG | R | R | S | S | S | S | S | S |
| S14P14 | NEG | R | R | S | S | S | S | S | S |

TABLE 31-continued

Staphylococcus pseudintermedius isolates tested according to Example 6.

| | | | | | | | | | |
|---|---|---|---|---|---|---|---|---|---|
| S15P15 | NEG | R | R | S | S | S | S | S | S |
| S16P16 | NEG | R | R | S | S | S | S | S | S |
| S17P17 | NEG | R | R | S | S | S | S | S | S |
| S18P18 | NEG | R | R | S | S | S | S | S | S |
| S19P19 | NEG | R | R | S | S | S | S | S | S |
| S20P20 | NEG | R | R | S | S | S | S | S | S |
| S21P21 | NEG | S | S | S | S | S | S | S | S |
| S22P22 | NEG | R | R | S | S | S | S | S | S |
| S23P23 | POS | R | R | S | R | S | I | S | S |

| | Chloramphenicol | Tetracyclin | Oxytetracycline | Vancomycin | Cefotetan | Maxifloxacin | Rifampin |
|---|---|---|---|---|---|---|---|
| S1P1 | S | R | R | R | S | S | S |
| S2P2 | R | S | S | R | S | I | S |
| S3P3 | R | I | R | S | R | S | S |
| S4P4 | R | R | R | S | S | S | S |
| S5P5 | R | R | R | S | S | S | S |
| S6P6 | R | I | R | S | S | S | S |
| S7P7 | R | R | R | R | S | S | S |
| S8P8 | R | R | R | S | S | S | S |
| S9P9 | R | R | I | S | S | S | S |
| S10P10 | R | I | R | S | S | S | S |
| S11P11 | S | S | S | S | S | S | S |
| S12P12 | S | R | R | S | S | S | S |
| S13P13 | S | S | S | S | S | S | S |
| S14P14 | S | S | S | S | S | S | S |
| S15P15 | S | I | I | S | S | S | S |
| S16P16 | S | S | S | S | S | S | S |
| S17P17 | S | S | S | S | S | S | S |
| S18P18 | S | S | S | S | S | S | S |
| S19P19 | S | S | S | S | S | S | S |
| S20P20 | S | R | I | S | S | S | S |
| S21P21 | S | S | S | S | S | S | S |
| S22P22 | S | S | S | S | S | S | S |
| S23P23 | S | S | S | S | S | S | S |

When cefoxitin resistance breakpoint was set at ≤24 mm, 3/13 (23%) and 5/13 (38%) of MRSP tested respectively were susceptible to cefoxitin. When cefoxitin resistance break point was set at ≤30 mm, only 1/13 (7.7%) of MRSP tested was susceptible (Tables 30 and 31).

The MRSP isolates were resistant to multiple antibiotic classes. Of the 13 MRSP isolates, all 13 were susceptible to rifampin. 3/13 (23%) were susceptible to chloramphenicol; 10/13 (77%) were susceptible to vancomycin (Tables 30 and 31).

Interestingly, 3/13 (23%) of the MRSP isolates were susceptible to amoxicillin; 8/13 (62%) were susceptible to cephalothin; 12/13 (92%) susceptible to cefotetan and 12/13 (92%) susceptible to moxifloxacin (Tables 30 and 31).

All 23 isolates were susceptible to NCL812 based on MICs. In addition, NCL812 has been shown to be bactericidal based on minimal bactericidal concentrations (MBC).

The MIC range of NCL812 against the Staphylococcus pseudintermedius isolates was found to be between 1 µg/mL and 4 µg/mL (Table 32). The $MIC_{50}$ and $MIC_{90}$ of NCL812 against the Staphylococcus pseudintermedius isolates was found to be 2 µg/mL and 4 µg/mL respectively (Table 33). The MIC mode and MIC range of NCL812 against the Staphylococcus pseudintermedius isolates was found to be 2 µg/mL and 1-4 µg/mL respectively (Table 33).

TABLE 32

MICs of NCL812 and ampicillin against Staphylococcus pseudintermedius isolates according to Example 6.

| Staphylococcus pseudintermedius isolate | Ampicillin MIC (µg · mL$^{-1}$) | NCL812 MIC (µg · mL$^{-1}$) |
|---|---|---|
| S1P1 | 128 | 4 |
| S2P2 | 128 | 2 |
| S3P3 | 128 | 2 |
| S4P4 | 128 | 1 |
| S5P5 | 16 | 2 |
| S6P6 | 64 | 2 |
| S7P7 | 128 | 2 |
| S8P8 | 128 | 2 |
| S9P9 | 32 | 2 |
| S10P10 | 64 | 2 |
| S11P11 | 128 | 4 |
| S12P12 | 32 | 2 |
| S13P13 | 0.25 | 2 |
| S14P14 | 1 | 2 |
| S15P15 | 4 | 4 |
| S16P16 | 0.25 | 2 |
| S17P17 | 1 | 2 |
| S18P18 | 4 | 4 |
| S19P19 | 0.5 | 4 |
| S20P20 | 4 | 4 |
| S21P21 | 0.1 | 2 |
| S22P22 | 8 | 4 |
| S23P23 | 32 | 2 |

TABLE 33

MIC50, MIC90, the MIC mode, an MIC range of NCL812 against *Staphylococcus pseudintermedius* isolates according to Example 6.

| Effectiveness against *Staphylococcus pseudintermedius* | Ampicillin | NCL812 |
|---|---|---|
| MIC50 (µg/ml) | 32 | 2 |
| MIC90 (µg/ml) | 128 | 4 |
| MIC mode (µg/ml) | 128 | 2 |
| MIC range (µg/ml) | 0.1-128 | 1-4 |

Methicillin resistant *Staphylococcus pseudintermedius* (MRSP) is an emerging problem in dogs, cats and horses. Two major clonal MRSP lineages have been reported from dogs in Europe (ST 71) and North America (ST 68). There were also reports of MRSP affecting dogs in Japan and a single case of MRSP in veterinary personnel in Hong Kong.

In this study, MRSP isolates were determined using a combination of presence of mecA gene and in vitro resistance to oxacillin. Cefoxitin susceptibility has been used as a substitute for oxacillin for methicillin resistant *Staphylococcus aureus*. However, cefoxitin disk diffusion tests using interpretive guidelines recommended for human isolates of methicillin resistant *Staphylococcus aureus* and coagulase negative staphylococci are unreliable in identifying MRSP. A cefoxitin breakpoint resistance of ≤30 mm=resistant and ≥31=susceptible has been proposed by Bemis et al, 2012 [Bemis, D. A., R. D. Jones, et al. (2012). "Evaluation of cefoxitin disk diffusion breakpoint for detection of methicillin resistance in *Staphylococcus pseudintermedius* isolates from dogs." Journal of Veterinary Diagnostic Investigation 24(5): 964-967]. This study is in agreement that this breakpoint may be more reliable in predicting methicillin resistant *Staphylococcus pseudintermedius*.

MRSP isolates are generally resistant to multiple antibiotic classes. Bacterial culture and antibiotic susceptibilities are therefore recommended for all suspect MRSP infections to allow appropriate selection of antibiotics. A limitation noted in this study is the apparent in vitro susceptibility of MRSP isolates to amoxicillin and cephalosporins (cephalothin and cefotetan).

NCL812 was effective against all 23 isolates of both MSSP and MRSP. A larger scale study is warranted to confirm the effectiveness of NCL812 against *Staphylococcus pseudintermedius* as it may provide a safe alternative antibiotic option for emerging MRSP infections in domestic animals.

Example 7: Preparation and Testing of NCL812 Analogues (Also Known as Compounds of the Invention)

Materials and Methods
NCL812

Analytical grade NCL812 with a defined potency of 960 mg/g (i.e. 96%) was obtained. The powder was stored in a sealed sample container out of direct sunlight and at room temperature at the study site. Aliquots (1 mL) of stock solution (containing 25.6 mg/mL of NCL812 in DMSO) were prepared and stored at −80° C. and defrosted immediately before use.

Synthesising and Testing of NCL812 Analogues

Analogues NCL001 to NCL230, as identified in FIG. 1, were synthesised using standard methods in the art. As an example, the methods used to manufacture compounds NCL097; NCL157; NCL179; NCL188; NCL195; and NCL196 are as follows:

NCL 097 (2,2'-bis[(3,4,5-trihydroxyphenyl)methylene]carbonimidic Dihydrazide Hydrochloride)

A suspension of 3,4,5-trihydroxybenzaldehyde (412.0 mg, 2.673 mmol, 2.21 eq.) and N,N'-diaminoguanidine hydrochloride (152.0 mg, 1.211 mmol) in EtOH (5 mL) was subjected to microwave irradiation (150 W) at 100° C. for 10 min. The reaction was then allowed to cool to ambient temperature. The resulting precipitate was collected and washed with chilled EtOH (5 mL) and $Et_2O$ (5 mL) to afford the carbonimidicdihydrazide (369.0 mg, 77%) as a pale brown solid. M.P. 292° C. (Decomp.). $^1$H NMR (300 MHz, DMSO-d6) δ 9.06 (br s, 6H), 8.25-8.01 (m, 4H), 6.83 (s, 4H). $^{13}$C NMR (75 MHz, DMSO-d6) δ 152.2, 149.7, 146.2, 136.5, 123.7, 107.4. LRMS(ESI$^+$): 361.95 [M+1]$^+$.

NCL157 (2,2'-bis[(2-amino-4-chlorophenyl)methylene]carbonimidic Dihydrazide Hydrochloride)

Synthesis of 2-amino-4-chloro-N-methoxy-N-methylbenzamide

To a solution of 2-amino-4-chlorobenzoic acid (5.6691 g, 33.041 mmol), N,O-dimethylhydroxylamine hydrochloride (5.7504 g, 58.954 mmol, 1.78 eq.), N-(3-dimethylaminopropyl)-N'-ethylcarbodiimide hydrochloride (7.7925 g, 40.649 mmol, 1.23 eq.) and N-hydroxybenzotriazole hydrate (5.2371 g, 38.793 mmol (anhydrous basis), 1.17 eq.) in DMF (100 mL) was added diisopropylethylamine (18.0 mL, 13.4 g, 104 mmol, 3.15 eq.) and the brown solution stirred at ambient temperature for 7 h. The reaction was then concentrated in vacuo before dilution with 1M NaOH (100 mL) and extracting with $CH_2Cl_2$ (3×100 mL) The combined organic extracts were washed with 1M HCl (100 mL) before drying over $MgSO_4$ and concentrating in vacuo to afford a brown syrup. This oil was then further dried at 60° C. under high vacuum to afford the crude Weinreb amide (7.021 g, 99%) as a brown syrup that crystallised on standing. The crude material was used without further purification. $^1$H NMR (400 MHz, CDCl$_3$) δ 7.24 (d, J=8.4 Hz, 1H), 6.62 (d, J=18 Hz, 1H), 6.54 (dd, J=8.4, 1.9 Hz, 1H), 4.75 (s, 2H), 3.48 (s, 3H), 3.24 (s, 3H). $^{13}$C NMR (101 MHz, CDCl$_3$) δ 169.2, 148.4, 137.1, 130.6, 116.6, 116.1, 115.0, 61.1, 34.0.

Synthesis of 2-amino-4-chlorobenzaldehyde

Crude 2-amino-4-chloro-N-methoxy-N-methylbenzamide (751.1 mg, 3.532 mmol) was broken up into ca. 120 mg batches and each dissolved in THF (10 mL) and cooled to 0° C. before LiAlH$_4$ (2M in THF, 0.5 mL) was added to each and the solutions stirred for 16 h, allowing the reactions to achieve room temperature. The reactions were quenched with saturated NH$_4$Cl (1 mL) before being combined, diluted with saturated NaHCO$_3$ (160 mL) and extracted with CHCl$_3$ (2×150 mL, 1×75 mL). The combined organics were dried over MgSO$_4$ and concentrated in vacuo to afford the crude benzaldehyde (463.3 mg, 85%) as yellow/orange crystals. The material was used without further purification. $^1$H (400 MHz, CD$_3$OD) 9.77 (d, J=0.7 Hz, 1H), 7.46 (d, J=8.3 Hz, 1H), 6.83-6.71 (m, 1H), 6.63 (dd, J=8.4, 1.9 Hz, 1H). $^{13}$C NMR (101 MHz, CD$_3$OD) δ 194.6, 153.0, 142.5, 138.4, 118.3, 116.8, 116.1.

Synthesis of 2,2'-bis[(2-amino-4-chlorophenyl)methylene]carbonimidic Dihydrazide Hydrochloride A suspension of 2-amino-4-chlorobenzaldehyde (128.0 mg, 0.823 mmol, 1.78 eq.) and N,N'-diaminoguanidine hydrochloride (58.0 mg, 0.462 mmol) in EtOH (2 mL) was subjected to microwave irradiation (100 W) at 60° C. for 5 minutes. Most solvent was then removed in vacuo, EtOH (1 mL) was added and the flask was transferred to the freezer to effect crystallisation. The resulting precipitate was collected and washed with EtOH (1 mL) to afford the carbonimidicdihydrazide (21.0 mg, 13%) as a pale yellow solid. $^1$H NMR (400 MHz, DMSO-$d_6$) δ 11.71 (br s, 2H), 8.40 (s, 2H), 8.37 (s, 2H), 7.29 (d, J=8.4 Hz, 2H), 6.87 (d, J=2.0 Hz, 2H), 6.73 (br s, 4H), 6.59 (dd, J=8.3, 2.0 Hz, 2H). $^{13}$C NMR (101 MHz, DMSO-$d_6$) δ 152.1, 151.5, 148.9, 136.0, 134.7, 115.1, 114.5, 112.8.

NCL179 (4,6-bis(2-((E)-4-chlorobenzylidene)hydrazinyl)pyrimidin-2-amine)

A suspension of 2-amino-4,6-dihydrazinylpyrimidine (67.3 mg, 0.434 mmol) and 4-chlorobenzaldehyde (198.8 mg, 1.414 mmol, 3.26 eq.) in EtOH (25 mL) was heated at reflux for 16 h. After this time, the condenser was removed and the solution concentrated to approx. 1 mL and the resulting precipitate filtered hot and washed with $Et_2O$ (10 mL) to afford the aminopyrimidine (42.8 mg, 25%) as an off-white amorphous powder. M.P. 275° C. (Decomp.). $^1$H NMR (400 MHz, DMSO) δ 10.70 (s, 2H), 8.02 (s, 2H), 7.67 (d, J=8.4 Hz, 4H), 7.52 (d, J=8.4 Hz, 4H), 6.28 (s, 1H), 5.85 (s, 2H). $^{13}$C NMR (101 MHz, DMSO) δ 162.8, 162.6, 138.8, 134.1, 133.1, 128.9, 127.6, 73.5.

NCL188 ((E)-2-(1-(4-chlorophenyl)pentylidene)hydrazine-1-carboximidamide Hydrochloride)

A suspension of 1-(4-chlorophenyl)pentanone (1.8319 g, 9.3146 mmol, 1.95 eq.) and aminoguanidine hydrochloride (527.6 mg, 4.773 mmol) in EtOH (15 mL) was heated at 65° C. for 16 h. The crude was cooled to ambient temperature before being diluted with $Et_2O$ (60 mL) and cooled to 0° C. to precipitate unreacted aminoguanidine hydrochloride (174.5 mg). The mother liquors were then concentrated in vacuo and the residue dissolved in $Et_2O$ (20 mL). The solution was then boiled and hexanes (10 mL) added to afford the carboximidamide as a cream solid. $^1$H NMR (400 MHz, DMSO) δ 11.54 (s, 1H), 7.99 (d, J=8.7 Hz, 2H), 7.90 (s, 3H), 7.47 (d, J=8.6 Hz, 2H), 2.91-2.82 (m, 2H), 1.48-1.32 (m, 4H), 0.89-0.84 (m, 3H). $^{13}$C NMR (101 MHz, DMSO) δ 156.2, 153.8, 134.8, 134.4, 128.7, 128.4, 28.1, 26.6, 22.0, 13.8

NCL195 (4,6-bis(2-((E)-4-methylbenzylidene)hydrazinyl)pyrimidin-2-amine)

A suspension of 2-amino-4,6-dihydrazinopyrimidine (58.9 mg, 0.380 mmol) and 4-methylbenzaldehyde (0.10 mL, 100 mg, 0.832 mmol, 2.19 eq.) in EtOH (4 mL) was heated at reflux for 16 h. The reaction mixture was cooled to ambient temperature before collecting the pellet-like precipitate, washing with $Et_2O$ (20 mL). The 'pellets' were then crushed and the solid further washed with $Et_2O$ (10 mL) to afford the pyrimidine (85.8 mg, 63%) as a white 'fluffy' powder. M.P. 274-276° C. $^1$H NMR (400 MHz, DMSO) δ 10.51 (s, 2H), 8.00 (s, 2H), 7.54 (d, J=8.0 Hz, 4H), 7.26 (d, J=7.9 Hz, 4H), 6.26 (s, 1H), 5.77 (s, 2H), 2.34 (s, 6H). $^{13}$C NMR (101 MHz, DMSO) δ 162.8, 162.6, 140.1, 138.4, 132.5, 129.4, 126.0, 73.3, 21.0.

NCL196 (4,4'-((1E,1'E)-((2-aminopyrimidine-4,6-diyl)bis(hydrazin-2-yl-1ylidene))bis(methanylylidene))diphenol)

A suspension of 2-amino-4,6-dihydrazinopyrimidine (70.4 mg, 0.454 mmol) and 4-hydroxybenzaldehyde (140.3 mg, 1.149 mmol, 2.53 eq.) in EtOH (3 mL) was heated at reflux for 16 h. The reaction mixture was cooled to ambient temperature before collecting the precipitate, washing with $Et_2O$ (25 mL), to afford the pyrimidine (91.4 mg, 55%) as an off-white powder. M.P. 298° C. (Decomp.). $^1$H NMR (400 MHz, DMSO) δ 10.31 (s, 2H), 9.74 (s, 2H), 7.94 (s, 2H), 7.48 (d, J=8.6 Hz, 4H), 6.83 (d, J=8.6 Hz, 4H), 6.20 (s, 1H), 5.70 (s, 2H). $^{13}$C (101 MHz, DMSO) δ 162.7, 162.5, 158.3, 140.5, 127.7, 126.3, 115.7, 73.0.

MIC Tests

Minimum inhibitory concentrations (μg/ml) were determined using the broth microdilution method recommended by the Clinical and Laboratory Standards Institute (CLSI). MIC breakpoints were determined by visual assessment and then confirmed using an ELISA plate reader, measuring absorbance levels at 600 nm. Bacterial growth (turbidity) in the wells with antimicrobial was compared with the amount of growth (turbidity) in the growth-control well (containing no antimicrobial). All isolates were tested in duplicate, if there was a difference of greater than one two-fold dilution in the results, the test was repeated a third time. The purity of the isolates was closely monitored during testing by subculturing the prepared bacterial inoculum onto SBA (sheep blood agar). The MICs of the control strains for the antimicrobial ampicillin were determined for each testing run as an internal quality control. The $MIC_{50}$, $MIC_{20}$ and MIC range (minimum and maximum) were calculated for each of the bacterial groups.

Activity of NCL812 and MIC Against Gram-Negative Bacteria

The activity of NCL812 against Gram-negative bacteria was assessed using the broth microdilution method recommended by the Clinical and Laboratory Standards Institute (CLSI), and the MICs (μg/mL) for NCL812 and ampicillin were determined.

Determination of Minimum Bactericidal Concentration (MBC)

CLSI Methodology

Briefly, 10 μL of the contents of each well starting at the MIC was inoculated on to a Columbia SBA plate and incubated at 37° C. for 48 h. Plates were examined at 24 and 48 h and the MBC was recorded as the lowest concentration of NCL812 at which no colonies of bacteria were observed on the plate (or significant inhibition of growth was observed compared to the control) (CLSI 2005).

Kill Kinetics Assays (MRSA & VRE)

MRSA/VRE were grown overnight on Columbia SBA at 37° C. A few colonies of bacteria were then suspended in CAMHB and adjusted to an optical density of 0.08 to 0.10. The bacterial suspension was diluted 1:10. One milliliter of the bacteria was added to 9 mL of CAMHB containing various concentrations (up to 4×MIC) of NCL812, to achieve a final bacterial concentration of 1 to $3×10^6$ CFU/ml. The tubes were incubated at 37° C. In order to determine the number of viable bacteria present at various time points, a 100 μL aliquot was removed from each tube and diluted in normal saline. Then, 100 μL of each dilution was spread onto colony count agar, in duplicate, and incubated for 48 h at 37°

C. After 24 h the numbers of colonies present on each plate were counted and therefore the number of viable bacteria present in the original suspension enumerated. Plates were re-checked after 48 hours.

Synergy Studies with Other Classes of Antimicrobial Agent.

The checkerboard method (Gunics et al., 2000 *Int. J. Antimicrob. Agents*. 14:239-42) was used to find interactions (synergy, antagonism, no effect) of NCL812 in combination with tetracycline, chloramphenicol, erythromycin (macrolide), ampicillin (β-lactam broad-spectrum), gentamicin (aminoglycoside), ciprofloxacin (fluoroquinolone), sulfamethoxazole (sulphonamide), or penicillin G (β-lactam narrow-spectrum). For initial experiments, a laboratory strain of *Staphylococcus aureus* T3-129 was used, however this strain gave inconsistent results for some of the antimicrobials and a new strain of *Staphylococcus* spp. designated MK1 (definitive species identification currently in progress) that was sensitive to all tested antimicrobials was used in subsequent tests.

Firstly, the MIC of each antibiotic alone was determined in accordance to CLSI standard guidelines. Secondly, the combination of NCL812 with each of above antibiotics was tested in duplicate. To evaluate the effect of the combination the fractional inhibitory concentration (FIC) was calculated for each antibiotic as follows:

FIC of tested antibiotic=MIC of tested antibiotic in combination/MIC of antibiotic alone.

FIC of NCL812=MIC of NCL812 in combination/MIC of NCL812 alone.

$FIC_I$=FIC index=FIC of NCL812+FIC of each tested antibiotic.

According to the checkerboard guidelines, Synergy (S) was defined as an $FIC_I$<0.5. No effect (NE) was defined as 0.5<$FIC_I$<4. Antagonism (A) was defined as a 4<$FIC_I$.

Testing of NCL812 Analogues

NCL812 analogues were stored at 4° C. until assayed. MICs were determined against two MRSA strains, two VRE strains and one strain each of *E. coli* and *Pseudomonas aeruginosa*.

Results

Determination of Minimum Inhibitory Concentration (MIC)

The comparative NCL812 and ampicillin MIC values (μg/mL) for 21 MRSA isolates were obtained. The results for the original experiments (phase I), and repeat testing (phase II) are shown in Table 34. Each MIC test was performed in duplicate.

TABLE 34

NCL812 and ampicillin MIC values (μg/ml) for 21 MRSA isolates obtained according to Example 7.

| | Phase I | | | | Phase II | | | |
| --- | --- | --- | --- | --- | --- | --- | --- | --- |
| Organism | NCL812 1st | NCL812 2nd | Ampicillin 1st | Ampicillin 2nd | NCL812 1st | NCL812 2nd | Ampicillin 1st | Ampicillin 2nd |
| MRSA 516 | 4 μg/ml | 4 μg/ml | 32 μg/ml | 32 μg/ml | 4 μg/ml | 4 μg/ml | 32 μg/ml | 16 μg/ml |
| MRSA 570 | 4 μg/ml | 4 μg/ml | >128 μg/ml | >128 μg/ml | 4 μg/ml | 4 μg/ml | >128 μg/ml | >128 μg/ml |
| MRSA 580 | 4 μg/ml | 4 μg/ml | >128 μg/ml | >128 μg/ml | 4 μg/ml | 4 μg/ml | >128 μg/ml | >128 μg/ml |
| MRSA 606 | 4 μg/ml | 4 μg/ml | 32 μg/ml | 32 μg/ml | 4 μg/ml | 4 μg/ml | 32 μg/ml | 32 μg/ml |
| MRSA 610 | 4 μg/ml | 4 μg/ml | 128 μg/ml | 128 μg/ml | 4 μg/ml | 4 μg/ml | 32 μg/ml | 32 μg/ml |
| MRSA 616 | 8 μg/ml | 4 μg/ml | 64 μg/ml | 64 μg/ml | 4 μg/ml | 4 μg/ml | 64 μg/ml | 64 μg/ml |
| MRSA 622 | 4 μg/ml | 4 μg/ml | 64 μg/ml | 64 μg/ml | 4 μg/ml | 4 μg/ml | 32 μg/ml | 32 μg/ml |
| MRSA 698 | 4 μg/ml | 4 μg/ml | 64 μg/ml | 64 μg/ml | 4 μg/ml | 4 μg/ml | 8 μg/ml | 8 μg/ml |
| MRSA 713 | 4 μg/ml | 4 μg/ml | >128 μg/ml | >128 μg/ml | 4 μg/ml | 4 μg/ml | 128 μg/ml | 128 μg/ml |
| MRSA 718 | 4 μg/ml | 8 μg/ml | >128 μg/ml | >128 μg/ml | 4 μg/ml | 4 μg/ml | 64 μg/ml | 64 μg/ml |
| MRSA 728 | 4 μg/ml | 4 μg/ml | 64 μg/ml | 64 μg/ml | 4 μg/ml | 4 μg/ml | 32 μg/ml | 32 μg/ml |
| MRSA 734 | 4 μg/ml | 4 μg/ml | >128 μg/ml | >128 μg/ml | 4 μg/ml | 4 μg/ml | 64 μg/ml | 64 μg/ml |
| MRSA 741 | 4 μg/ml | 4 μg/ml | 8 μg/ml | 8 μg/ml | 4 μg/ml | 4 μg/ml | 4 μg/ml | 4 μg/ml |
| MRSA 747 | 8 μg/ml | 4 μg/ml | >128 μg/ml | >128 μg/ml | 4 μg/ml | 4 μg/ml | 64 μg/ml | 64 μg/ml |
| MRSA 773 | 4 μg/ml | 4 μg/ml | 64 μg/ml | 64 μg/ml | 4 μg/ml | 4 μg/ml | 64 μg/ml | 64 μg/ml |
| MRSA 778 | 4 μg/ml | 4 μg/ml | >128 μg/ml | >128 μg/ml | 4 μg/ml | 4 μg/ml | 128 μg/ml | 128 μg/ml |
| MRSA 786 | 4 μg/ml | 4 μg/ml | 32 μg/ml | 32 μg/ml | 4 μg/ml | 4 μg/ml | 32 μg/ml | 32 μg/ml |
| MRSA 787 | 4 μg/ml | 4 μg/ml | >128 μg/ml | >128 μg/ml | 4 μg/ml | 4 μg/ml | 64 μg/ml | 64 μg/ml |
| MRSA 815 | 4 μg/ml | 4 μg/ml | 64 μg/ml | 64 μg/ml | 4 μg/ml | 4 μg/ml | 32 μg/ml | 32 μg/ml |
| MRSA 823 | 4 μg/ml | 4 μg/ml | >128 μg/ml | >128 μg/ml | 4 μg/ml | 4 μg/ml | 128 μg/ml | 128 μg/ml |
| MRSA 844 | 4 μg/ml | 4 μg/ml | 128 μg/ml | 128 μg/ml | 4 μg/ml | 4 μg/ml | 64 μg/ml | 32 μg/ml |

TABLE 35

Comparative NCL812 and ampicillin MIC values (μg/ml) for 13 VRE isolates obtained according to Example 7.

| | Phase I | | | | Phase II | | | |
| --- | --- | --- | --- | --- | --- | --- | --- | --- |
| Organism[1] | NCL812 1st | NCL812 2nd | Ampicillin 1st | Ampicillin 2nd | NCL812 1st | NCL812 2nd | Ampicillin 1st | Ampicillin 2nd |
| VRE 002 [H12c] | 4 μg/ml | 4 μg/ml | 1 μg/ml | 1 μg/ml | 2 μg/ml | 2 μg/ml | 0.25 μg/ml | 0.25 μg/ml |
| VRE 003 [H14t] | 2 μg/ml | 2 μg/ml | 0.5 μg/ml | 0.5 μg/ml | 2 μg/ml | 2 μg/ml | 0.25 μg/ml | 0.25 μg/ml |
| VRE 004 [H16c] | 4 μg/ml | 4 μg/ml | 1 μg/ml | 1 μg/ml | 2 μg/ml | 2 μg/ml | 0.25 μg/ml | 0.25 μg/ml |
| VRE 008 [H16c(dc)] | 4 μg/ml | 4 μg/ml | 1 μg/ml | 1 μg/ml | 2 μg/ml | 2 μg/ml | 1 μg/ml | 1 μg/ml |
| VRE 005 [H17c] | 2 μg/ml | 2 μg/ml | 1 μg/ml | 1 μg/ml | 2 μg/ml | 2 μg/ml | 0.25 μg/ml | 0.25 μg/ml |
| VRE 006 [H19t] | 2 μg/ml | 2 μg/ml | 1 μg/ml | 1 μg/ml | 2 μg/ml | 2 μg/ml | 0.25 μg/ml | 0.25 μg/ml |
| VRE 007 [H23c] | 4 μg/ml | 4 μg/ml | 1 μg/ml | 1 μg/ml | 2 μg/ml | 2 μg/ml | 0.25 μg/ml | 0.25 μg/ml |
| VRE 009 [H25c] | 4 μg/ml | 4 μg/ml | 1 μg/ml | 1 μg/ml | 2 μg/ml | 2 μg/ml | 1 μg/ml | 1 μg/ml |

TABLE 35-continued

Comparative NCL812 and ampicillin MIC values (μg/ml) for 13 VRE isolates obtained according to Example 7.

| Organism[1] | Phase I | | | | Phase II | | | |
|---|---|---|---|---|---|---|---|---|
| | NCL812 1st | NCL812 2nd | Ampicillin 1st | Ampicillin 2nd | NCL812 1st | NCL812 2nd | Ampicillin 1st | Ampicillin 2nd |
| VRE 011 [H26c(dc)] | 2 μg/ml | 4 μg/ml | 1 μg/ml | 1 μg/ml | 2 μg/ml | 2 μg/ml | 0.5 μg/ml | 0.5 μg/ml |
| VRE 010 [H26c(w)] | 4 μg/ml | 4 μg/ml | 2 μg/ml | 2 μg/ml | 2 μg/ml | 2 μg/ml | 1 μg/ml | 1 μg/ml |
| VRE 012 [H35t] | 2 μg/ml | 2 μg/ml | 0.5 μg/ml | 0.5 μg/ml | 2 μg/ml | 2 μg/ml | 0.25 μg/ml | 0.5 μg/ml |
| VRE 014 [H37c(g)] | 4 μg/ml | 4 μg/ml | 1 μg/ml | 1 μg/ml | 2 μg/ml | 2 μg/ml | 1 μg/ml | 1 μg/ml |
| VRE 013 [H37c(w)] | 2 μg/ml | 2 μg/ml | 2 μg/ml | 2 μg/ml | 2 μg/ml | 2 μg/ml | 1 μg/ml | 1 μg/ml |

The comparative NCL812 and ampicillin MIC values (μg/mL) for 13 VRE isolates were obtained. The results for the original experiments (phase I), and repeat testing (phase II) are shown in Table 35. Each MIC test was performed in duplicate.

NCL812 $MIC_{50}$, $MIC_{90}$, MIC mode and MIC range were obtained for Australian isolates of MRSA and VRE, as shown in Table 6 Comparative MIC values for ampicillin are shown in parentheses.

Activity of NCL812 and MIC Against Gram-Negative Bacteria

Comparative NCL812 and ampicillin MIC values (μg/mL) for *Escherichia coli*, *Pseudomonas aeruginosa* and *Salmonella arizonae* were obtained, as shown in Table 36. Each MIC test was performed in duplicate.

TABLE 36

Comparative NCL812 and ampicillin MIC values (μg/ml) for *Escherichia coli*, *Pseudomonas aeruginosa* and *Salmonella arizonae* obtained according to Example 7.

| Organism | NCL812 1st | NCL812 2nd | Ampicillin 1st | Ampicillin 2nd |
|---|---|---|---|---|
| E. coli | >128 μg/ml | >128 μg/ml | 4 μg/ml | 4 μg/ml |
| P. aeruginosa | >128 μg/ml | >128 μg/ml | >128 μg/ml | >128 μg/ml |
| S. arizonae | >128 μg/ml | >128 μg/ml | 1 μg/ml | 1 μg/ml |

The antimicrobial activity of NCL812 against the selected Gram-negative bacteria was >128 μg/ml.

Determination of Minimum Bactericidal Concentration (MBC)

MBC results for MRSA isolates are shown in Table 37 which shows NCL812 MBC values (μg/mL) for 20 MRSA isolates. Each MBC test was performed in duplicate starting from the NCL812 MIC concentration to 16 times the MIC. For all isolates, the MBC was equal to the MIC. However, inconsistent growth on agar plates was recorded for some concentrations.

TABLE 37

NCL812 MBC values (μg/ml) for 20 MRSA isolates according to Example 7.

| Organism/Sample No. | | NCL812 MBC | | | | |
|---|---|---|---|---|---|---|
| | | 4 μg/ml | 8 μg/ml | 16 μg/ml | 32 μg/ml | 64 μg/ml |
| MRSA 1 | $1^{st}$ | 0 | 0 | 0 | 0 | N** |
| | $2^{nd}$ | 0 | 0 | 0 | 0 | N |
| MRSA 2 | $1^{st}$ | 0 | 0 | 0 | 0 | N |
| | $2^{nd}$ | 0 | 0 | 0 | 0 | N |
| MRSA 3 | $1^{st}$ | 0 | GB* | 0 | 0 | N |
| | $2^{nd}$ | 0 | 0 | 0 | 0 | N |
| MRSA 4 | $1^{st}$ | 0 | 0 | 0 | 0 | N |
| | $2^{nd}$ | 0 | 0 | 0 | 0 | N |
| MRSA 5 | $1^{st}$ | 0 | 0 | 0 | 0 | N |
| | $2^{nd}$ | 0 | 0 | 0 | 0 | N |
| MRSA 6 | $1^{st}$ | 0 | 0 | 0 | 0 | N |
| | $2^{nd}$ | 0 | 0 | 0 | 0 | N |
| MRSA 7 | $1^{st}$ | 0 | 0 | 0 | 0 | N |
| | $2^{nd}$ | 0 | GB | 0 | 0 | N |
| MRSA 8 | $1^{st}$ | GB | 0 | 0 | 0 | N |
| | $2^{nd}$ | 0 | 0 | 0 | 0 | N |
| MRSA 9 | $1^{st}$ | 0 | 0 | 0 | 0 | N |
| | $2^{nd}$ | 0 | 0 | 0 | 0 | N |
| MRSA 10 | $1^{st}$ | 0 | 0 | 0 | 0 | N |
| | $2^{nd}$ | 0 | 0 | 0 | 0 | N |
| MRSA 11 | $1^{st}$ | 0 | 0 | 0 | 0 | N |
| | $2^{nd}$ | GB | 0 | 0 | 0 | N |
| MRSA 12 | $1^{st}$ | 0 | 0 | 0 | 0 | N |
| | $2^{nd}$ | 0 | GB | 0 | 0 | N |
| MRSA 13 | $1^{st}$ | 0 | 0 | 0 | 0 | N |
| | $2^{nd}$ | 0 | 0 | 0 | 0 | N |
| MRSA 14 | $1^{St}$ | 0 | 0 | 0 | 0 | N |
| | $2^{nd}$ | 0 | 0 | 0 | 0 | N |
| MRSA 516 | $1^{st}$ | 0 | 0 | 0 | 0 | 0 |
| | $2^{nd}$ | 0 | 0 | 0 | 0 | 0 |
| MRSA 570 | $1^{st}$ | 0 | 0 | 0 | 0 | 0 |
| | $2^{nd}$ | 0 | 0 | 0 | 0 | 0 |
| MRSA 580 | $1^{st}$ | 0 | 0 | 0 | 0 | 0 |
| | $2^{nd}$ | 0 | 0 | 0 | 0 | 0 |
| MRSA 606 | $1^{st}$ | 0 | 0 | 0 | 0 | GB |
| | $2^{nd}$ | 0 | 0 | 0 | 0 | 0 |
| MRSA 610 | $1^{st}$ | 0 | 0 | 0 | 0 | 0 |
| | $2^{nd}$ | 0 | GB | 0 | 0 | 0 |

GB = Bacterial Growth on Sheep Blood Agar
N** = Not cultured on Sheep Blood Agar The results for 10 VRE isolates are shown in Table 38. Each MBC test was performed in duplicate starting from NCL812 MIC concentration to 32 times the MIC. As with the MRSA isolates tested, the MBC appears to be equal to the MIC. However, with the VRE isolates, an anomaly was observed at higher NCL812 concentrations. There is significant inhibition of growth at concentrations near to the MIC, but as the NCL812 concentration increases, bacteria appear to be less subject to inhibition. High numbers of bacteria were observed on the plates at NCL812 concentrations ≥16 μg/mL.

TABLE 38

NCL812 MBC values (μg/ml) for 10 VRE isolates according to Example 7

| Organism/Sample No. | | NCL812 MBC | | | | | | |
|---|---|---|---|---|---|---|---|---|
| | | 2 μg/ml | 4 μg/ml | 8 μg/ml | 16 μg/ml | 32 μg/ml | 64 μg/ml | 128 μg/ml |
| VRE 26c(dc) | 1st | 90* | 20 | 4000 | M | M | M | M |
| | 2nd | 0 | 70 | 3500 | M | M | M | M |
| VRE 37c | 1st | 500 | 100 | 20 | 250 | M | M | M |
| | 2nd | M | 50 | 100 | 1100 | 1400 | M | M |
| VRE 35t | 1st | 0 | 0 | 0 | 720 | 0 | 0 | 0 |
| | 2nd | 0 | 0 | 0 | 0 | 10 | 20 | 10 |
| VRE 16c(dc) | 1st | 90 | 330 | 0 | M | M | M | M |
| | 2nd | 200 | 0 | 20 | M | M | M | M |
| VRE 23c | 1st | 0 | 120 | 20 | 10 | M | M | M |
| | 2nd | 0 | 0 | 0 | 0 | 570 | M | M |
| VRE 25c | 1st | 0 | 0 | M | M | M | M | M |
| | 2nd | 20 | 20 | M | M | M | M | M |
| VRE 16c | 1st | 10 | 820 | 980 | M | M | M | M |
| | 2nd | M | 790 | 890 | M | M | M | M |
| VRE 19t | 1st | 0 | 0 | 0 | 180 | 10 | 110 | M |
| | 2nd | 30 | 0 | 0 | 70 | 40 | M | M |
| VRE 14t | 1st | 10 | 0 | 10 | 0 | 180 | 970 | M |
| | 2nd | 0 | 0 | 0 | 40 | 780 | M | M |
| VRE 12c | 1st | 0 | 0 | 0 | M | M | M | M |
| | 2nd | 0 | M | 300 | M | M | M | M |

*Number of bacteria growing after 24 hours per ml of sample (CFU/ml);
M = many bacteria growing on the plate (too many to count)

NCL812 was found to be bactericidal against Gram-positive bacteria at concentrations equivalent to the MIC.

Kill Kinetics Assays (MRSA & VRE)

In preliminary experiments, colony counts were performed at t=15, 30, 45 and 60 min. No significant changes in the bacterial concentration were observed at these time points, suggesting that NCL812 is not rapidly bactericidal (by comparison, the lipoglycopeptide oritavancin (McKay et al. (2009) *J. Antimicrob. Chemother.* 63 (6): 1191-1199) caused a 3 $\log_{10}$ reduction in viable count within an hour of exposure to a concentration equivalent to the $C_{max}$). Therefore, for future experiments, sampling time points were extended out to one and then two hour intervals.

In the initial experiments, for MRSA, at 4 h a reduction of at least 2.5 $\log_{10}$ CFU/mL was observed in comparison to the growth control. At 8 h there was at least a 3.5 $\log_{10}$ CFU/mL difference between the control and the bacteria exposed to NCL812. After 24 h the numbers of bacteria present in all NCL812 concentrations was not significantly different to the control. There was a consistent reduction in bacterial numbers at NCL812 concentrations from 4-16 μg/mL, up to 8 h, but the same was not observed for concentrations greater than 16 μg/mL. By comparison, most bactericidal antimicrobial agents, used or being developed for the treatment of MRSA and VRE (oritavancin, daptomycin, vancomycin) are rapidly bactericidal achieving similar log reductions within 1 h of exposure in a concentration dependent manner (McKay et al., 2009). In kill kinetics experiments bacteriostatic antimicrobials recommended for the treatment of MRSA and VRE infections (teicoplanin and linezolid only marginally decrease the viable count and growth).

For VRE the observed decrease in the CFU/mL of bacteria exposed to NCL812 was less than for MRSA. At 4 h there was approximately a 2 $\log_{10}$ reduction in the viable count compared to the control, and at 8 h there was approximately a 2.5 $\log_{10}$ reduction. However, at 24 h the growth of bacteria was no longer as significantly reduced in comparison to the control. Bacterial numbers increased after 8 h incubation and this affect appeared to be more pronounced with increasing concentrations of NCL812.

Figure 34:
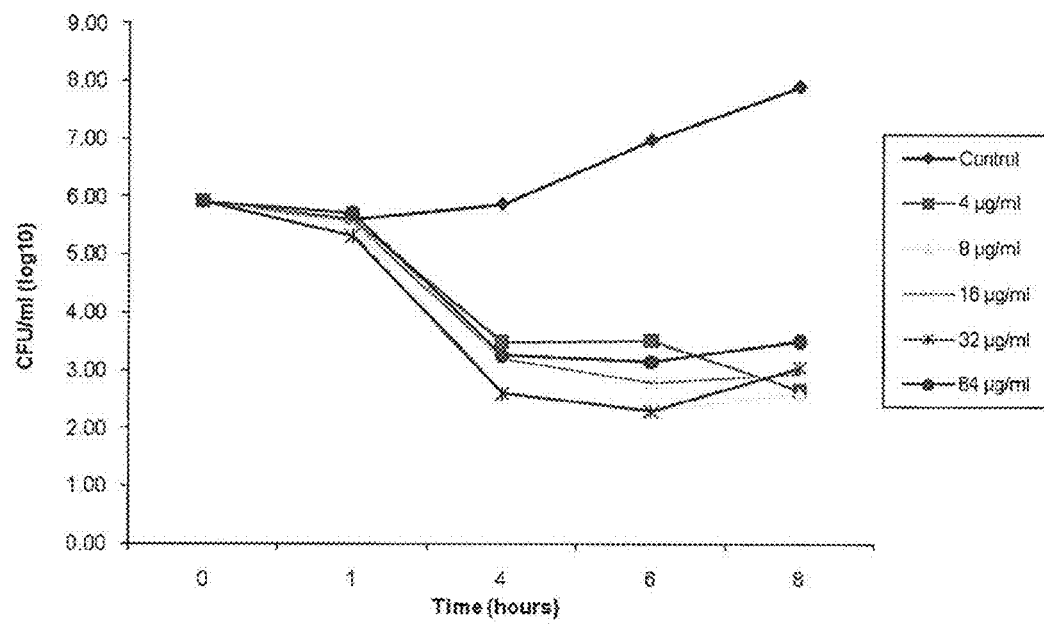
FIG. 34 shows the kill kinetics of MRSA 580 isolate obtained at different concentrations of NCL812 over a period of 8 hours according to example 7.
Figure 35:
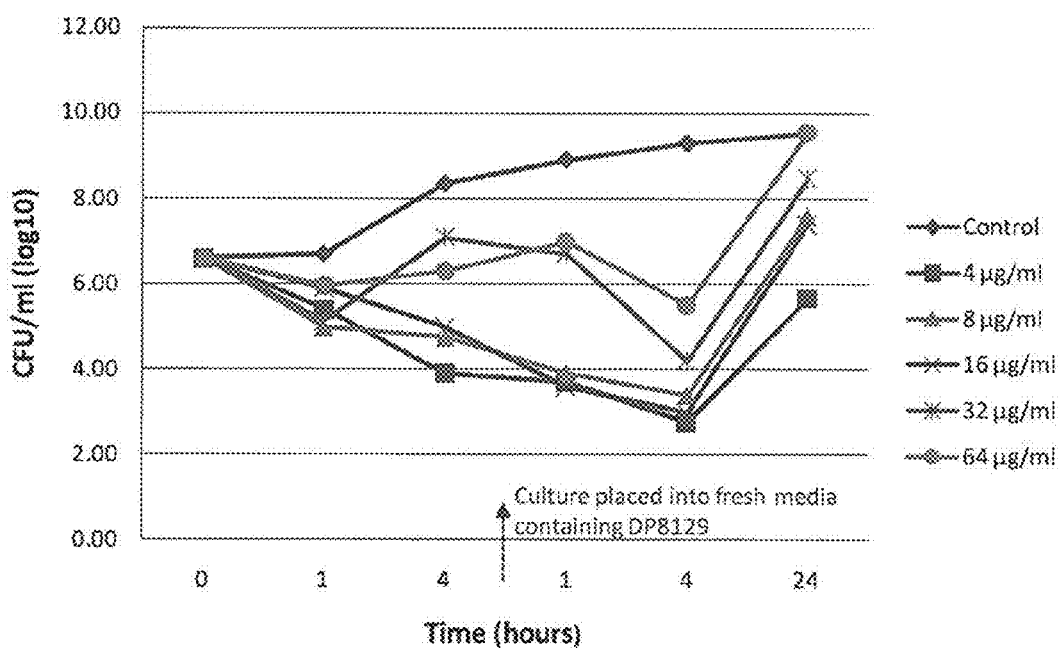
FIG. 35 shows the kill kinetics of MRSA 580 in different concentrations of NCL812 over a period of 24 h according to example 7.

The kill kinetics of MRSA 580 were obtained at different concentrations of NCL812 over a period of 8 h, as shown in FIG. 34 The kill kinetics of MRSA 580 in different concentrations of NCL812 over a period of 24 h are shown in FIG. 35 After 4 h of incubation the media was changed to fresh media containing the same concentration of NCL812.

Figure 36:
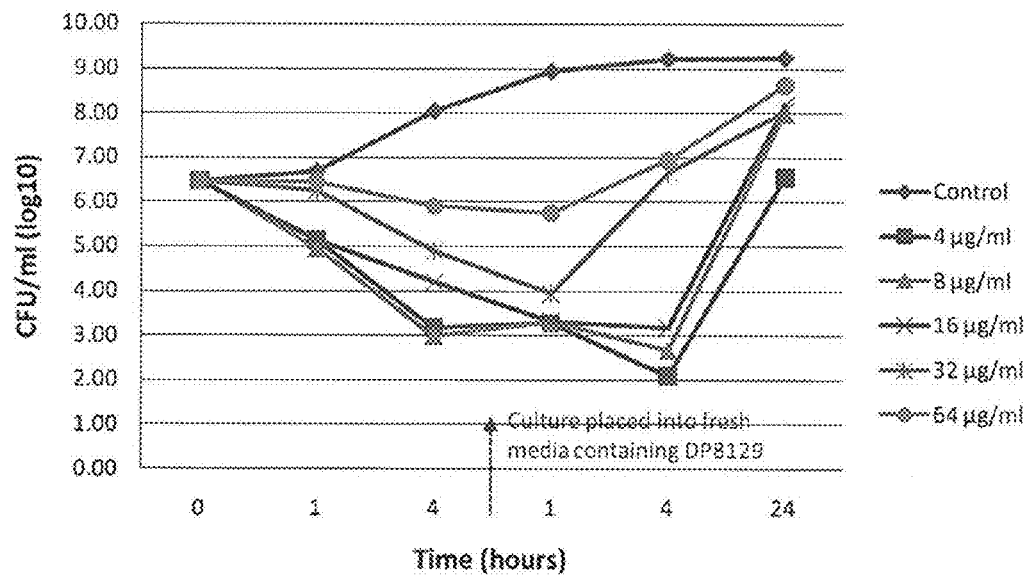
FIG. 36 shows the kill kinetics of MRSA 698 in different concentrations of NCL812 over a period of 24 h according to example 7.

The kill kinetics of MRSA 698 in different concentrations of NCL812 over a period of 24 h is shown in FIG. 36 After 4 h of incubation the media was changed to fresh media containing the same concentration of NCL812.

Figure 37:
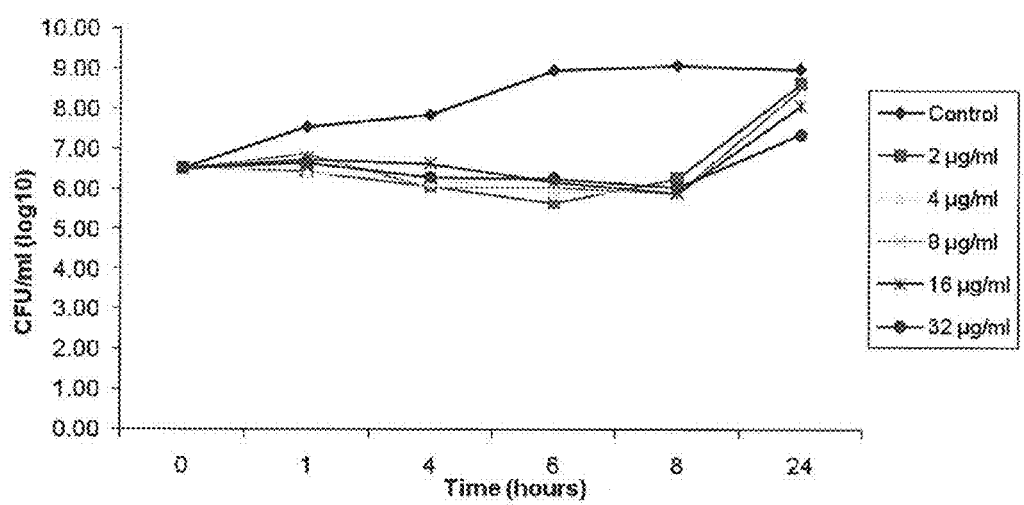
FIG. 37 shows the kill kinetics of VRE 26c(dc) at different concentrations of NCL812 over a period of 24 h according to example 7.

The kill kinetics of VRE 26c(dc) at different concentrations of NCL812 over a period of 24 h are shown in FIG. 37.

Figure 38:
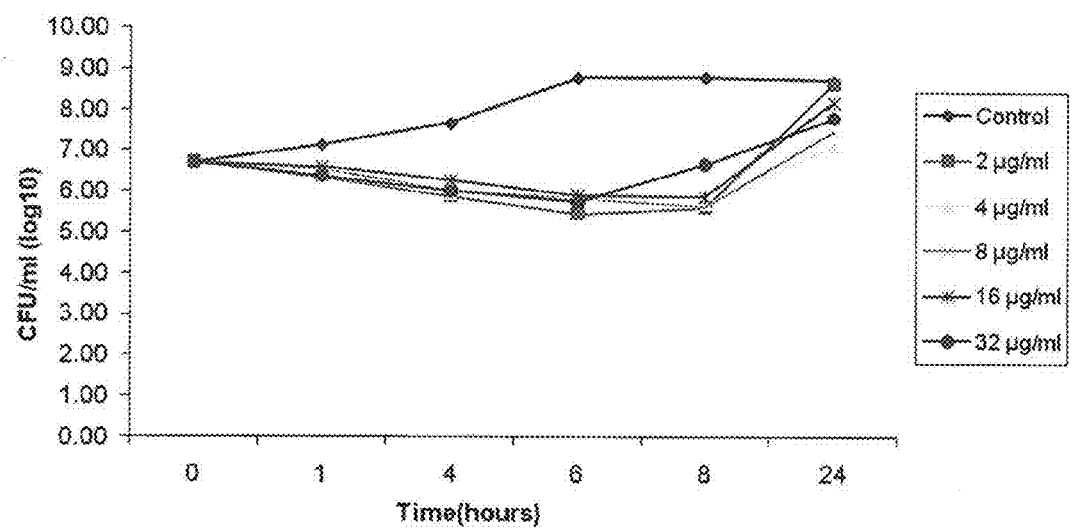
FIG. 38 shows the kill kinetics of VRE 16c(dc) at different concentrations of NCL812 over a period of 24 h according to example 8.

The kill kinetics of VRE 16c(dc) at different concentrations of NCL812 over a period of 24 h are shown in FIG. 38.

Test for Bacterial Resistance to NCL812

Preliminary tests were carried out to determine whether bacterial resistance may account for the observations of bacterial growth at higher concentrations of NCL812 and the increase in bacterial numbers in kill kinetics experiments at 24 h incubation. Bacteria (MRSA) growing at high concentrations of NCL812, in the 96 well micro titre tray, were subcultured on to SBA and incubated for 24 h, then MIC testing was performed. There was no change in the MIC of these bacteria. Bacteria growing in broth used for kill kinetics experiments was also tested for any change in the MIC. No change was observed.

Additionally, bacteria exposed to NCL812 at high concentrations were then subcultured on to plate count agar containing NCL812 (64 μg/mL and 128 μg/mL) and incubated for 24 h at 37° C. Bacteria growing on the plate were then used for running an MIC test. There was still no change in the MIC of the bacteria.

In summary, NCL812 has bactericidal activity against MRSA which is less pronounced against VRE strains. The bactericidal effect is not rapid in comparison to bactericidal antimicrobials developed for MRSA and VRE infections (daptomycin, oratovancin, vancomycin). Aberrant bactericidal results at higher concentrations of NCL812 are not indicative of resistance development, but may be suggestive of loss of activity. Stability testing of the compound in broth media should therefore be undertaken before exploring these interesting but currently unexplained results. This will include a detailed examination of the literature to determine if this phenomenon is observed in other classes of antimicrobial agent. In this case, closer examination of the kill kinetics between 8 and 24 h will be required. NCL812 kill curves for MRSA and VRE suggest more bactericidal activity in comparison to bacteriostatic antimicrobials (linezolid, teicoplanin). Kill curves should now be generated for *Streptococcus pneumoniae* once stability issues of NCL812 are investigated, as for example with linezolid, as some antibacterial agents can be bacteriostatic against some bacteria and bactericidal against others.

Synergy Studies with Other Classes of Antimicrobial Agent.

MICs, FICs, $FIC_I$ and the interaction between NCL812 and eight antibiotics is shown in Table 39. None of the eight tested compounds, representing distinct classes of antimicrobial agent showed either positive (synergism) or negative (antagonism) interaction with NCL812 consistent with an additive effect when antibacterial agents are added to NCL812.

TABLE 39

MICs, FICs, $FIC_I$ and the interaction between NCL812 and eight antibiotics according to Example 7.

| Antibiotic Name | Experiment | Repeat | Antibiotic MIC (μg/ml) With NCL812 | Alone | $FIC_1$ | NCL812 MIC (μg/ml) With Antibiotic | Alone | $FIC_2$ | $FIC_I$ | Result |
|---|---|---|---|---|---|---|---|---|---|---|
| Tetracycline[1] | 1 | 1st | 0.25 | 0.5 | 0.5 | 1 | 4 | 0.25 | 0.75 | NE |
|  |  | 2nd | 0.25 | 0.5 | 0.5 | 1 | 8 | 0.125 | 0.62 | NE |
|  | 2 | 1st | 0.031 | 0.25 | 0.125 | 4 | 8 | 0.5 | 0.625 | NE |
|  |  | 2nd | 0.031 | 0.25 | 0.125 | 4 | 8 | 0.5 | 0.625 | NE |
| Chloramphenicol[1] | 1 | 1st | 4 | 8 | 0.5 | 1 | 4 | 0.25 | 0.75 | NE |
|  |  | 2nd | 2 | 4 | 0.5 | 2 | 8 | 0.25 | 0.75 | NE |
|  | 2 | 1st | 4 | 8 | 0.5 | 2 | 8 | 0.25 | 0.75 | NE |
|  |  | 2nd | 0.5 | 8 | 0.0625 | 4 | 8 | 0.5 | 0.562 | NE |
| Erythromycin[1] | 1 | 1st | 0.031 | 0.125 | 0.25 | 2 | 4 | 0.5 | 0.75 | NE |
|  |  | 2nd | 0.007 | 0.125 | 0.063 | 2 | 4 | 0.5 | 0.562 | NE |
|  | 2 | 1St | 0.007 | 0.25 | 0.25 | 2 | 8 | 0.25 | 0.5 | NE |
|  |  | 2nd | 0.007 | 0.25 | 0.031 | 4 | 8 | 0.5 | 0.531 | NE |
| Ampicillin[1] | 1 | 1st | 0.125 | 0.25 | 0.5 | 1 | 4 | 0.25 | 0.75 | NE |
|  |  | 2nd | 0.25 | 0.5 | 0.5 | 0.125 | 4 | 0.031 | 0.53 | NE |
|  | 2 | 1st | 0.062 | 0.125 | 0.5 | 2 | 8 | 0.25 | 0.75 | NE |
|  |  | 2nd | 0.125 | 0.25 | 0.5 | 2 | 8 | 0.25 | 0.75 | NE |
| Gentamicin[2] | 1 | 1st | 0.062 | 0.125 | 0.5 | 0.5 | 4 | 0.125 | 0.625 | NE |
|  |  | 2nd | 0.062 | 0.125 | 0.5 | 1 | 4 | 0.25 | 0.75 | NE |
|  | 2 | 1st | 0.5 | 1 | 0.5 | 1 | 4 | 0.25 | 0.75 | NE |
|  |  | 2nd | 0.007 | 0.5 | 0.0156 | 2 | 4 | 0.5 | 0.515 | NE |
| Ciprofloxacin[2] | 1 | 1st | 0.062 | 0.125 | 0.5 | 2 | 4 | 0.5 | 0.75 | NE |
|  |  | 2nd | 0.003 | 0.125 | 0.025 | 4 | 2 | 0.5 | 0.525 | NE |
|  | 2 | 1st | 0.125 | 0.25 | 0.5 | 0.5 | 4 | 0.125 | 0.625 | NE |
|  |  | 2nd | 0.125 | 0.25 | 0.5 | 0.25 | 4 | 0.0625 | 0.562 | NE |
| Sulfamethoxazole[2] | 1 | 1st | 4 | 8 | 0.5 | 1 | 4 | 0.25 | 0.75 | NE |
|  |  | 2nd | 4 | 8 | 0.5 | 2 | 4 | 0.5 | 1 | NE |
|  | 2 | 1st | 4 | 8 | 0.5 | 1 | 4 | 0.25 | 0.75 | NE |
|  |  | 2nd | 4 | 8 | 0.5 | 2 | 4 | 0.5 | 1 | NE |
| Penicillin G[2] | 1 | 1st | 0.062 | 0.125 | 0.5 | 2 | 4 | 0.5 | 1 | NE |
|  |  | 2nd | 0.062 | 0.125 | 0.5 | 2 | 4 | 0.5 | 1 | NE |
|  | 2 | 1st | 0.062 | 0.125 | 0.5 | 2 | 4 | 0.5 | 1 | NE |
|  |  | 2nd | 0.031 | 0.25 | 0.125 | 2 | 4 | 0.5 | 0.625 | NE |

[1]*S. aureus* strain T3-29
[2]*Staphylococcus* spp. Strain MK1
$FIC_1$ = MIC of anitbiotic in combination with NCL812/MIC of antibiotic alone
$FIC_2$ = MIC of NCL812 in combination with antibiotic/MIC of NCL812 alone
$FIC_I$ = FIC index Testing of NCL812 Analogues The chemical structures of analogues NCL001 to NCL230 are shown in FIG. 1.

MICs for NCL812 and analogues NCL001-070 are shown in Table 40.

MICs for analogues NCL071 to 171 are shown in Table 41.

MICs for analogues NCL171 to 230 are shown in Table 42.

TABLE 40

MICs for NCL812 and analogues NCL001-070 according to Example 7.

| Compound | | MIC (μg/ml) at 24 hours | | | | | |
|---|---|---|---|---|---|---|---|
| | | MRSA 1 | MRSA 2 | VRE 1 | VRE 2 | E. coli | P. aeruginosa |
| Ampicillin | Amp | >128 | 16 | 0.5 | 0.25 | 4 | >128 |
| NCL812 | | 4 | 4 | 2 | 2 | >128 | >128 |
| NCL812 | 1st | 4 | 2 | 2 | 2 | >128 | >128 |
| | 2nd | 4 | 2 | 2 | 1 | >128 | >128 |
| NCL001 | 1st | >128 | >128 | >128 | >128 | >128 | >128 |
| | 2nd | >128 | >128 | >128 | >128 | >126 | >128 |
| NCL002 | 1st | >128 | >128 | >128 | >128 | >128 | >128 |
| | 2nd | >128 | >128 | >128 | >128 | >128 | >128 |
| NCL003 | 1st | >128 | >128 | >128 | >128 | >128 | >128 |
| | 2nd | >128 | >128 | >128 | >128 | >128 | >128 |
| NCL004 | 1st | >128 | >128 | >128 | >128 | >128 | >128 |
| | 2nd | >128 | >128 | >128 | >128 | >128 | >128 |
| NCL005 | 1st | >128 | >128 | >128 | >128 | >128 | >128 |
| | 2nd | >128 | >128 | >128 | >128 | >128 | >128 |
| NCL006 | 1st | >128 | >128 | >128 | >128 | >128 | >128 |
| | 2nd | >128 | >128 | >128 | >128 | >128 | >128 |
| NCL007 | 1st | >128 | >128 | >128 | >128 | >128 | >128 |
| | 2nd | >128 | >128 | >128 | >128 | >128 | >128 |
| NCL008 | 1st | >128 | >128 | >128 | >128 | >128 | >128 |
| | 2nd | >128 | >128 | >128 | >128 | >128 | >128 |
| NCL009 | 1st | >128 | >128 | >128 | >128 | >128 | >128 |
| | 2nd | >128 | >128 | >128 | >128 | >128 | >128 |
| NCL010 | 1st | >128 | >128 | >128 | >128 | >128 | >128 |
| | 2nd | >128 | >128 | >128 | >128 | >128 | >128 |
| NCL011 | 1st | >128 | >128 | >128 | 32 | >128 | >128 |
| | 2nd | >128 | >128 | >128 | 32 | >128 | >128 |
| NCL012 | 1st | >128 | >128 | >128 | >128 | >128 | >128 |
| | 2nd | >128 | >128 | >128 | >128 | >128 | >128 |
| NCL013 | 1st | >128 | >128 | >128 | >128 | >128 | >128 |
| | 2nd | >128 | >128 | >128 | >128 | >128 | >128 |
| NCL014 | 1st | >128 | >128 | >128 | >128 | >128 | >128 |
| | 2nd | >128 | >128 | >128 | >128 | >128 | >128 |
| NCL015 | 1st | >128 | >128 | >128 | 128 | >128 | >128 |
| | 2nd | >128 | >128 | >128 | 128 | >128 | >128 |
| NCL016 | 1st | >128 | >128 | >128 | >128 | >128 | >128 |
| | 2nd | >128 | >128 | >128 | >128 | >128 | >128 |
| NCL017 | 1st | >128 | >128 | >128 | >128 | >128 | >128 |
| | 2nd | >128 | >128 | >128 | >128 | >128 | >128 |
| NCL018 | 1st | >128 | >128 | >128 | >128 | >128 | >128 |
| | 2nd | >128 | >128 | >128 | >128 | >128 | >128 |
| NCL019 | 1st | >128 | >128 | >128 | >128 | >128 | >128 |
| | 2nd | >128 | >128 | >128 | >128 | >128 | >128 |
| NCL020 | 1st | >128 | >128 | >128 | >128 | >128 | >128 |
| | 2nd | >128 | >128 | >128 | >128 | >128 | >128 |
| NCL021 | 1st | 16 | 16 | 8 | 8 | >128 | >128 |
| | 2nd | 16 | 16 | 8 | 8 | >128 | >128 |
| NCL022 | 1st | >128 | >128 | >128 | >128 | >128 | >128 |
| | 2nd | >128 | >128 | >128 | >128 | >128 | >128 |
| NCL023 | 1st | 16 | 16 | 32 | 16 | >128 | >128 |
| | 2nd | 16 | 16 | 32 | 16 | >128 | >128 |
| NCL024 | 1st | >128 | >128 | >128 | >128 | >128 | >128 |
| | 2nd | >128 | >128 | >128 | >128 | >128 | >128 |
| NCL025 | 1st | >128 | >128 | >128 | >128 | >128 | >128 |
| | 2nd | >128 | >128 | >128 | >128 | >128 | >128 |
| NCL026 | 1st | >128 | >128 | >128 | >128 | >128 | >128 |
| | 2nd | >128 | >128 | >128 | >128 | >128 | >128 |
| NCL027 | 1st | >128 | >128 | >128 | >128 | >128 | >128 |
| | 2nd | >128 | >128 | >128 | >128 | >128 | >128 |
| NCL028 | 1st | >128 | >128 | >128 | 128 | >128 | >128 |
| | 2nd | >128 | >128 | >128 | 128 | >128 | >128 |
| NCL029 | 1st | 32 | 32 | 32 | 32 | >128 | >128 |
| | 2nd | 32 | 32 | 32 | 32 | >128 | >128 |
| NCL030 | 1st | 128 | 128 | 64 | 64 | >128 | 128 |
| | 2nd | 128 | 128 | 64 | 64 | >128 | 128 |
| NCL031 | 1st | >128 | >128 | >128 | >128 | >128 | >128 |
| | 2nd | >128 | >128 | >128 | >128 | >128 | >128 |
| NCL032 | 1st | >128 | >128 | >128 | >128 | >128 | >128 |
| | 2nd | >128 | >128 | >128 | >128 | >128 | >128 |
| NCL033 | 1st | >128 | >128 | >128 | >128 | >128 | >128 |
| | 2nd | >128 | >128 | >128 | >128 | >128 | >128 |
| NCL034 | 1st | >128 | >128 | >128 | >128 | >128 | >128 |
| | 2nd | >128 | >128 | >128 | >128 | >128 | >128 |
| NCL035 | 1st | 16 | 16 | 8 | 4 | >128 | >128 |
| | 2nd | 16 | 16 | 4 | 4 | >128 | >128 |

TABLE 40-continued

MICs for NCL812 and analogues NCL001-070 according to Example 7.

| | | MIC (µg/ml) at 24 hours | | | | | |
|---|---|---|---|---|---|---|---|
| Compound | | MRSA 1 | MRSA 2 | VRE 1 | VRE 2 | E. coli | P. aeruginosa |
| NCL036 | 1st | >128 | >128 | >128 | >128 | >128 | >128 |
| | 2nd | >128 | >128 | >128 | >128 | >128 | >128 |
| NCL037 | 1st | >128 | >128 | >126 | >128 | >128 | >128 |
| | 2nd | >128 | >128 | >128 | >128 | >128 | >128 |
| NCL038 | 1st | 8** | 8** | 8** | 8** | >128 | >128 |
| | 2nd | 8** | 8** | 16** | 8** | >128 | >128 |
| NCL039 | 1st | 32 | 32 | 32 | 8 | >128 | >128 |
| | 2nd | 64 | 32 | 32 | 8 | >128 | >188 |
| NCL040 | 1st | 8 | 8 | 8 | 8 | >128 | >128 |
| | 2nd | 8 | 8 | 8 | 8 | >128 | >128 |
| NCL041 | 1st | 64 | 64 | 64 | 64 | 128 | 128 |
| | 2nd | 64 | 64 | 64 | 64 | 64 | 128 |
| NCL042 | 1st | >128 | >128 | >128 | >128 | >128 | >128 |
| | 2nd | >128 | >128 | >128 | >128 | >128 | >128 |
| NCL043 | 1st | 128 | 128 | 128 | 128 | 128 | 128 |
| | 2nd | 128 | 128 | 128 | 64 | 128 | 128 |
| NCL044 | 1st | 128 | 128 | 128 | 128 | >128 | 128 |
| | 2nd | 128 | 128 | 128 | 128 | >128 | 128 |
| NCL045 | 1st | >128 | >128 | >128 | >128 | >128 | >128 |
| | 2nd | >128 | >128 | >128 | >128 | >128 | >128 |
| NCL046 | 1st | >128 | >128 | >128 | >128 | >128 | >128 |
| | 2nd | >128 | >128 | >128 | >128 | >128 | >128 |
| NCL047 | 1st | >128 | >128 | >128 | >128 | >128 | >128 |
| | 2nd | >128 | >128 | >128 | >128 | >128 | >128 |
| NCL048 | 1st | >128 | >128 | >128 | >128 | >128 | >128 |
| | 2nd | >128 | >128 | >128 | >128 | >128 | >128 |
| NCL049 | 1st | >128 | >128 | >128 | >128 | >128 | >128 |
| | 2nd | >128 | >128 | >128 | >128 | >128 | >128 |
| NCL050 | 1st | >128 | >128 | >128 | >128 | >128 | >128 |
| | 2nd | >128 | >128 | >128 | >128 | >128 | >128 |
| NCL051 | 1st | >128 | >128 | >128 | >128 | >128 | >128 |
| | 2nd | >128 | >128 | >128 | >128 | >128 | >128 |
| NCL052 | 1st | 128 | 128 | 128 | 128 | >128 | 128 |
| | 2nd | 128 | 128 | 128 | 128 | >128 | 128 |
| NCL053 | 1st | >128 | >128 | >128 | >128 | >128 | 128 |
| | 2nd | >128 | >128 | >128 | >128 | >128 | 128 |
| NCL054 | 1st | 4 | 2 | 4 | 4 | >128 | >128 |
| | 2nd | 2 | 4 | 4 | 4 | >128 | >128 |
| NCL055 | 1st | >128 | >128 | >128 | >128 | >128 | >128 |
| | 2nd | >128 | >128 | >128 | >128 | >128 | >128 |
| NCL056 | 1st | >128 | >128 | >128 | >128 | >128 | >128 |
| | 2nd | >128 | >128 | >128 | >128 | >128 | >128 |
| NCL057 | 1st | >128 | >128 | >128 | >128 | >128 | >128 |
| | 2nd | >128 | >128 | >128 | >128 | >128 | >128 |
| NCL058 | 1st | >128 | >128 | >128 | >128 | >128 | >128 |
| | 2nd | >128 | >128 | >128 | >128 | >128 | >128 |
| NCL059 | 1st | >128 | >128 | >128 | >128 | >128 | >128 |
| | 2nd | >128 | >128 | >128 | >128 | >128 | >128 |
| NCL060 | 1st | >128 | >128 | >128 | >128 | >128 | >128 |
| | 2nd | >128 | >128 | >128 | >128 | >128 | >128 |
| NCL061 | 1st | >128 | >128 | >128 | 8 | >128 | >128 |
| | 2nd | >128 | >128 | >128 | 8 | >128 | >128 |
| NCL062 | 1st | 2 | 4 | 2 | 1 | >128 | >128 |
| | 2nd | 2 | 4 | 2 | 1 | >128 | >128 |
| NCL063 | 1st | >128 | >128 | >128 | >128 | >128 | >128 |
| | 2nd | >128 | >128 | >128 | >128 | >128 | >128 |
| NCL064 | 1st | >128 | >128 | >128 | >128 | >128 | >128 |
| | 2nd | >128 | >128 | >128 | >128 | >128 | >128 |
| NCL065 | 1st | >128 | >128 | >128 | >128 | >128 | >128 |
| | 2nd | >128 | >128 | >128 | >128 | >128 | >128 |
| NCL066 | 1st | >128 | >128 | >128 | >128 | >128 | >128 |
| | 2nd | >128 | >128 | >128 | >128 | >128 | >128 |
| NCL067 | 1st | >128 | >128 | >128 | >128 | >128 | >128 |
| | 2nd | >128 | >128 | >128 | >128 | >128 | >128 |
| NCL068 | 1st | >128 | >128 | >128 | >128 | >128 | >128 |
| | 2nd | >128 | >128 | >128 | >128 | >128 | >128 |
| NCL069 | 1st | 128 | 128 | 128 | 64 | >128 | >128 |
| | 2nd | 128 | 128 | 128 | 64 | >128 | >128 |
| NCL070 | 1st | >128 | >128 | >128 | 32 | >128 | >128 |
| | 2nd | >128 | >128 | >128 | 32 | >128 | >128 |

TABLE 41

MICs for analogues NCL071-170 according to Example 7.

| NCL Compound | MIC (µg/ml) at 24 hours | | | | | |
|---|---|---|---|---|---|---|
| Code | MRSA 1 | MRSA 2 | VRE 1 | VRE 2 | E. coli | P. aeruginosa |
| NCL071 | >128 | >128 | >128 | >128 | >128 | >128 |
|  | >128 | >128 | >128 | >128 | >128 | >128 |
| NCL072 | 32 | 64 | 64 | 64 | >128 | >128 |
|  | 32 | 64 | 64 | 64 | >128 | >128 |
| NCL073 | 128 | 128 | 16 | 64 | >128 | >128 |
|  | 128 | 128 | 16 | 64 | >128 | >128 |
| NCL074 | 16 | 16 | 2 | 8 | >128 | >128 |
|  | 16 | 16 | 1 | 4 | >128 | >128 |
| NCL075 | >128 | >128 | >128 | >128 | >128 | >128 |
|  | >128 | >128 | >128 | >128 | >128 | >128 |
| NCL076 | >128 | >128 | >128 | >128 | >128 | >128 |
|  | >128 | >128 | >128 | >128 | >128 | >128 |
| NCL077 | >128 | >128 | >128 | >128 | >128 | >128 |
|  | >128 | >128 | >128 | >128 | >128 | >128 |
| NCL078 | 4 | 16 | 4 | 4 | >128 | >128 |
|  | 4 | 8 | 2 | 2 | >128 | >128 |
| NCL079 | 4 | 4 | 2 | 4 | >128 | >128 |
|  | 4 | 8 | 2 | 4 | >128 | >128 |
| NCL080 | 4 | 4 | 2 | 4 | >128 | >128 |
|  | 4 | 8 | 2 | 4 | >128 | >128 |
| NCL081 | 4 | 8 | 1 | 4 | >128 | >128 |
|  | 4 | 4 | 1 | 4 | >128 | >128 |
| NCL082 | 8 | 8 | 4 | 2 | >128 | >128 |
|  | 4 | 8 | 4 | 4 | >128 | >128 |
| NCL083 | >128 | >128 | >128 | >128 | >128 | >128 |
|  | >128 | >128 | >128 | >128 | >128 | >128 |
| NCL084 | 2 | 8 | 2 | 2 | >128 | >128 |
|  | 2 | 4 | 2 | 2 | >128 | >128 |
| NCL085 | >128 | >128 | >128 | >128 | >128 | >128 |
|  | >128 | >128 | >128 | >128 | >128 | >128 |
| NCL086 | >128 | >128 | >128 | 128 | >128 | >128 |
|  | >128 | >128 | >128 | 128 | >128 | >128 |
| NCL087 | >128 | >128 | >128 | >128 | >128 | >128 |
|  | >128 | >128 | >128 | >128 | >128 | >128 |
| NCL088 | 16 | 8 | 4 | 4 | >128 | >128 |
|  | 8 | 8 | 4 | 4 | >128 | >128 |
| NCL089 | 4 | 4 | 0.5 | 1 | >128 | >128 |
|  | 8 | 4 | 0.5 | 1 | >128 | >128 |
| NCL090 | >128 | >128 | >128 | >128 | >128 | >128 |
|  | >128 | >128 | >128 | >128 | >128 | >128 |
| NCL091 | >128 | >128 | >128 | >128 | >128 | >128 |
|  | >128 | >128 | >128 | >128 | >128 | >128 |
| NCL092 | >128 | >128 | >128 | >128 | >128 | >128 |
|  | >128 | >128 | >128 | >128 | >128 | >128 |
| NCL093 | 64 | 128 | 64 | >128 | >128 | >128 |
|  | 64 | 128 | 64 | >128 | >128 | >128 |
| NCL094 | 128 | 128 | 64 | 128 | >128 | >128 |
|  | 128 | 128 | 64 | 128 | >128 | >128 |
| NCL095 | >128 | >128 | >128 | >128 | >128 | >128 |
|  | >128 | >128 | >128 | >128 | >128 | >128 |
| NCL096 | >128 | >128 | >128 | >128 | >128 | >128 |
|  | >128 | >128 | >128 | >128 | >128 | >128 |
| NCL097 | 128 | 32 | 32 | 32 | >128 | 128 |
|  | 128 | 32 | 32 | 32 | >128 | >128 |
| NCL098 | >128 | >128 | >128 | >128 | >128 | >128 |
|  | >128 | >128 | >128 | >128 | >128 | >128 |
| NCL099 | 8 | 4 | 8 | 8 | >128 | >128 |
|  | 8 | 4 | 8 | 8 | >128 | >128 |
| NCL100 | >128 | >128 | >128 | >128 | >128 | >128 |
|  | >128 | >128 | >128 | >128 | >128 | >128 |
| NCL101 | 32 | 32 | 64 | 128 | >128 | >128 |
|  | 32 | 32 | 64 | 128 | >128 | >128 |
| NCL102 | >128 | >128 | >128 | >128 | >128 | >128 |
|  | >128 | >128 | >128 | >128 | >128 | >128 |
| NCL103 | >128 | >128 | >128 | >128 | >128 | >128 |
|  | >128 | >128 | >128 | >128 | >128 | >128 |
| NCL104 | 64 | 64 | 128 | >128 | >128 | >128 |
|  | 64 | 64 | 128 | >128 | >128 | >128 |
| NCL105 | 64 | >128 | 64 | >128 | >128 | >128 |
|  | 64 | >128 | 64 | >128 | >128 | >128 |
| NCL106 | >128 | >128 | >128 | >128 | >128 | >128 |
|  | >128 | >128 | >128 | >128 | >128 | >128 |
| NCL107 | 8 | 16 | 32 | 128 | >128 | >128 |
|  | 8 | 16 | 32 | 128 | >128 | >128 |

TABLE 41-continued

MICs for analogues NCL071-170 according to Example 7.

| NCL Compound Code | MIC (µg/ml) at 24 hours | | | | | |
|---|---|---|---|---|---|---|
| | MRSA 1 | MRSA 2 | VRE 1 | VRE 2 | E. coli | P. aeruginosa |
| NCL108 | 64 | 64 | 64 | 128 | >128 | >128 |
| | 64 | 64 | 64 | 128 | >128 | >128 |
| NCL109 | >128 | >128 | >128 | >128 | >128 | >128 |
| | >128 | >128 | >128 | >128 | >128 | >128 |
| NCL110 | >128 | >128 | >128 | >128 | >128 | >128 |
| | >128 | >128 | >128 | >128 | >128 | >128 |
| NCL111 | 64 | 64 | 64 | >128 | >128 | >128 |
| | 64 | 64 | 64 | >128 | >128 | >128 |
| NCL112 | >128 | 128 | 64 | 32 | >128 | >128 |
| | >128 | 128 | 64 | 32 | >128 | >128 |
| NCL113 | 16 | 8 | 8 | 16 | >128 | >128 |
| | 16 | 8 | 8 | 16 | >128 | >128 |
| NCL114 | >128 | >128 | >128 | >128 | >128 | >128 |
| | >128 | >128 | >128 | >128 | >128 | >128 |
| NCL 115 | >128 | >128 | >128 | >128 | >128 | >128 |
| | >128 | >128 | >128 | >128 | >128 | >128 |
| NCL 116 | >128 | >128 | >128 | >128 | >128 | >128 |
| | >128 | >128 | >128 | >128 | >128 | >128 |
| NCL 117 | 64 | 128 | 64 | 64 | >128 | >128 |
| | 64 | 128 | 64 | 64 | >128 | >128 |
| NCL 118 | >128 | >128 | >128 | >128 | >128 | >128 |
| | >128 | >128 | >128 | >128 | >128 | >128 |
| NCL 119 | >128 | >128 | >128 | >128 | >128 | >128 |
| | >128 | >128 | >128 | >128 | >128 | >128 |
| NCL 120 | 8 | 4 | 2 | 8 | >128 | >128 |
| | 8 | 8 | 2 | 8 | >128 | >128 |
| NCL 121 | 32 | 32 | 8 | 32 | >128 | >128 |
| | 32 | 32 | 8 | 64 | >128 | >128 |
| NCL 122 | >128 | >128 | >128 | >128 | >128 | >128 |
| | >128 | >128 | >128 | >128 | >128 | >128 |
| NCL 123 | 16 | 4 | 4 | 4 | >128 | >128 |
| | 32 | 8 | 4 | 4 | >128 | >128 |
| NCL 124 | >128 | >128 | >128 | >128 | >128 | >128 |
| | >128 | >128 | >128 | >128 | >128 | >128 |
| NCL 125 | >128 | >128 | >128 | >128 | >128 | >128 |
| | >128 | >128 | >128 | >128 | >128 | >128 |
| NCL 126 | >128 | >128 | 4 | >128 | >128 | >128 |
| | >128 | >128 | 8 | >128 | >128 | >128 |
| NCL 127 | >128 | >128 | >128 | >128 | >128 | >128 |
| | >128 | >128 | >128 | >128 | >128 | >128 |
| NCL 128 | >128 | >128 | >128 | >128 | >128 | >128 |
| | >128 | >128 | >128 | >128 | >128 | >128 |
| NCL 129 | >128 | >128 | >128 | >128 | >128 | >128 |
| | >128 | >128 | >128 | >128 | >128 | >128 |
| NCL 130 | >128 | >128 | >128 | >128 | >128 | >128 |
| | >128 | >128 | >128 | >128 | >128 | >128 |
| NCL 131 | >128 | >128 | 4 | >128 | >128 | >128 |
| | >128 | >128 | 4 | >128 | >128 | >128 |
| NCL 132 | >128 | >128 | >128 | >128 | >128 | >128 |
| | >128 | >128 | >128 | >128 | >128 | >128 |
| NCL 133 | >128 | >128 | >128 | >128 | >128 | >128 |
| | >128 | >128 | >128 | >128 | >128 | >128 |
| NCL 134 | >128 | >128 | >128 | >128 | >128 | >128 |
| | >128 | >128 | >128 | >128 | >128 | >128 |
| NCL 135 | >128 | >128 | >128 | >128 | >128 | >128 |
| | >128 | >128 | >128 | >128 | >128 | >128 |
| NCL 136 | 64 | 128 | 32 | 128 | >128 | >128 |
| | 64 | 128 | 32 | 128 | >128 | >128 |
| NCL 137 | >128 | >128 | >128 | >128 | >128 | >128 |
| | >128 | >128 | >128 | >128 | >128 | >128 |
| NCL 138 | >128 | 32 | >128 | >128 | >128 | >128 |
| | >128 | 32 | >128 | >128 | >128 | >128 |
| NCL 139 | >128 | >128 | >128 | >128 | >128 | >128 |
| | >128 | >128 | >128 | >128 | >128 | >128 |
| NCL 140 | >128 | 16 | 2 | 8 | >128 | >128 |
| | >128 | 32 | 2 | 8 | >128 | >128 |
| NCL 141 | >128 | >128 | 16 | >128 | >128 | >128 |
| | >128 | >128 | 16 | >128 | >128 | >128 |
| NCL 142 | >128 | >128 | >128 | >128 | >128 | >128 |
| | >128 | >128 | >128 | >128 | >128 | >128 |
| NCL 143 | 16 | 16 | 8 | 8 | >128 | >128 |
| | 16 | 16 | 8 | 8 | >128 | >128 |
| NCL 144 | >128 | >128 | >128 | >128 | >128 | >128 |
| | >128 | >128 | >128 | >128 | >128 | >128 |

TABLE 41-continued

MICs for analogues NCL071-170 according to Example 7.

| NCL Compound Code | MIC (µg/ml) at 24 hours | | | | | |
|---|---|---|---|---|---|---|
| | MRSA 1 | MRSA 2 | VRE 1 | VRE 2 | E. coli | P. aeruginosa |
| NCL 145 | >128 | >128 | >128 | >128 | >128 | >128 |
| | >128 | >128 | >128 | >128 | >128 | >128 |
| NCL 146 | 8 | 16 | 16 | 16 | >128 | >128 |
| | 8 | 16 | 16 | 16 | >128 | >128 |
| NCL 147 | >128 | >128 | >128 | >128 | >128 | >128 |
| | >128 | >128 | >128 | >128 | >128 | >128 |
| NCL 148 | >128 | >128 | >128 | >128 | >128 | >128 |
| | >128 | >128 | >128 | >128 | >128 | >128 |
| NCL 149 | >128 | >128 | >128 | >128 | >128 | >128 |
| | >128 | >128 | >128 | >128 | >128 | >128 |
| NCL 150 | 128 | 128 | >128 | >128 | >128 | >128 |
| | 128 | 128 | >128 | >128 | >128 | >128 |
| NCL 151 | 64 | 64 | 128 | 64 | >128 | >128 |
| | 64 | 64 | 128 | 64 | >128 | >128 |
| NCL 152 | >128 | >128 | >128 | >128 | >128 | >128 |
| | >128 | >128 | >128 | >128 | >128 | >128 |
| NCL 153 | 32 | 16 | 8 | 8 | >128 | >128 |
| | 32 | 16 | 8 | 8 | >128 | >128 |
| NCL 154 | >128 | >128 | >128 | >128 | >128 | >128 |
| | >128 | >128 | >128 | >128 | >128 | >128 |
| NCL 155 | 8 | 8 | 16 | 8 | >128 | >128 |
| | 8 | 8 | 16 | 8 | >128 | >128 |
| NCL 156 | >128 | >128 | >128 | >128 | >128 | >128 |
| | >128 | >128 | >128 | >128 | >128 | >128 |
| NCL 157 | 2 | 2 | 2 | 2 | >128 | >128 |
| | 2 | 2 | 2 | 4 | >128 | >128 |
| NCL 140 | 8 | 16 | 16 | 16 | >128 | >128 |
| | 8 | 16 | 16 | 16 | >128 | >128 |
| NCL 038 | 8 | 8 | 8 | 8 | >128 | >128 |
| | 8 | 8 | 8 | 8 | >128 | >128 |
| NCL 158 | 4 | 4 | 4 | 4 | >128 | >128 |
| | 4 | 4 | 4 | 4 | >128 | >128 |
| NCL 159 | 64 | 128 | 16 | 128 | >128 | >128 |
| | 64 | 128 | 16 | 128 | >128 | >128 |
| NCL 160 | 32 | 128 | 16 | 64 | >128 | >128 |
| | 64 | 128 | 16 | 64 | >128 | >128 |
| NCL 161 | 64 | 128 | 128 | 128 | >128 | >128 |
| | 128 | 128 | 128 | 128 | >128 | >128 |
| NCL 162 | >128 | 128 | >128 | >128 | >128 | >128 |
| | >128 | 128 | >128 | >128 | >128 | >128 |
| NCL 163 | >128 | >128 | >128 | >128 | >128 | >128 |
| | >128 | >128 | >128 | >128 | >128 | >128 |
| NCL 164 | >128 | >128 | >128 | >128 | >128 | >128 |
| | >128 | >128 | >128 | >128 | >128 | >128 |
| NCL 165 | >128 | >128 | >128 | >128 | >128 | >128 |
| | >128 | >128 | >128 | >128 | >128 | >128 |
| NCL 166 | 32 | 64 | 8 | 128 | >128 | >128 |
| | 32 | 64 | 8 | 128 | >128 | >128 |
| NCL 167 | >128 | >128 | >128 | >128 | >128 | >128 |
| | >128 | >128 | >128 | >128 | >128 | >128 |
| NCL 168 | 32 | 32 | 64 | 32 | >128 | >128 |
| | 32 | 32 | 64 | 32 | >128 | >128 |
| NCL 169 | 32 | 64 | 32 | 32 | >128 | >128 |
| | 32 | 64 | 32 | 32 | >128 | >128 |
| NCL 170 | >128 | >128 | >128 | >128 | >128 | >128 |
| | >128 | >128 | >128 | >128 | >128 | >128 |

TABLE 42

MICs for analogues NCL171-230 according to Example 7.

| NCL Compound Code | MIC (µg/ml) at 24 hours | | | | | |
|---|---|---|---|---|---|---|
| | MRSA 1 | MRSA 2 | VRE 1 | VRE 2 | E. coli | P. aeruginosa |
| NCL171 | 128 | 64 | 32 | >128 | >128 | >128 |
| | 128 | 64 | 32 | >128 | >128 | >128 |
| NCL 172 | 128 | 64 | >128 | >128 | >128 | >128 |
| | 128 | 64 | >128 | >128 | >128 | >128 |
| NCL 173 | 16 | 16 | 4 | 32 | >128 | >128 |
| | 16 | 16 | 4 | 32 | >128 | >128 |

TABLE 42-continued

MICs for analogues NCL171-230 according to Example 7.

| | | | | | | |
|---|---|---|---|---|---|---|
| NCL 174 | 32 | 32 | 4 | 32 | >128 | >128 |
| | 32 | 32 | 4 | 32 | >128 | >128 |
| NCL 175 | 64 | >128 | 32 | >128 | >128 | >128 |
| | 64 | >128 | 32 | >128 | >128 | >128 |
| NCL 176 | >128 | >128 | >128 | >128 | >128 | >128 |
| | >128 | >128 | >128 | >128 | >128 | >128 |
| NCL 177 | 8 | 8 | 4 | 8 | >128 | >128 |
| | 8 | 8 | 4 | 8 | >128 | >128 |

| NCL Compound Code | MIC (µg/ml) at 24 hours | | | |
|---|---|---|---|---|
| | S. aureus ATCC29213 | E. faecalis #32 | E. coli ATCC25922 | Pseudomonas #008 |
| NCL 178 | >64 | >64 | >64 | >64 |
| | >64 | >64 | >64 | >64 |
| NCL 179 | 4 | 8 | >64 | >64 |
| | 4 | 8 | >64 | >64 |
| NCL 180 | >64 | 64 | >64 | >64 |
| | >64 | 64 | >64 | >64 |
| NCL 181 | >64 | >64 | >64 | >64 |
| | >64 | >64 | >64 | >64 |
| NCL 182 | >64 | >64 | >64 | >64 |
| | >64 | >64 | >64 | >64 |
| NCL 183 | >64 | >64 | >64 | >64 |
| | >64 | >64 | >64 | >64 |
| NCL 184 | >64 | 64 | >64 | >64 |
| | >64 | 64 | >64 | >64 |
| NCL 185 | >64 | >64 | >64 | >64 |
| | >64 | >64 | >64 | >64 |
| NCL 186 | >64 | >64 | >64 | >64 |
| | >64 | >64 | >64 | >64 |
| NCL 187 | >64 | >64 | >64 | >64 |
| | >64 | >64 | >64 | >64 |
| NCL 188 | 32 | 32 | 64 | >64 |
| | 32 | 32 | 64 | >64 |
| NCL 189 | >64 | >64 | >64 | >64 |
| | >64 | >64 | >64 | >64 |
| NCL 190 | 32 | 64 | >64 | >64 |
| | 64 | 64 | >64 | >64 |
| NCL 191 | >64 | >64 | >64 | >64 |
| | >64 | >64 | >64 | >64 |
| NCL 192 | >64 | >64 | >64 | >64 |
| | >64 | >64 | >64 | >64 |

| NCL Compound Code | MIC (µg/ml) at 24 hours | | | | | |
|---|---|---|---|---|---|---|
| | MRSA 1 | MRSA 2 | VRE 1 | VRE 2 | E. coli | P. aeruginosa |
| NCL193 | 2 | 2 | 4 | 4 | >128 | >128 |
| | 2 | 4 | 4 | 8 | >128 | >128 |
| NCL194 | >128 | >128 | >128 | >128 | >128 | >128 |
| | >128 | >128 | >128 | >128 | >128 | >128 |
| NCL195 | 2 | 2 | 4 | 2 | >128 | >128 |
| | 2 | 2 | 4 | 4 | >128 | >128 |
| NCL196 | 32 | 64 | 32 | 64 | 64 | 64 |
| | 32 | 32 | 64 | 64 | 64 | 128 |
| NCL197 | 8 | 8 | 8 | 8 | >128 | >128 |
| | 8 | 8 | 4 | 8 | >128 | >128 |
| NCL198 | >128 | >128 | >128 | >128 | >128 | >128 |
| | >128 | >128 | >128 | >128 | >128 | >128 |
| NCL199 | 2 | 4 | >128 | >128 | >128 | >128 |
| | 4 | 4 | >128 | >128 | >128 | >128 |
| NCL200 | >128 | >128 | >128 | >128 | >128 | >128 |
| | >128 | >128 | >128 | >128 | >128 | >128 |
| NCL201 | 32 | 16 | >128 | >128 | >128 | >128 |
| | 64 | 32 | >128 | >128 | >128 | >128 |
| NCL202 | 8 | 8 | 8 | 8 | >128 | >128 |
| | | 8 | 8 | 8 | >128 | >128 |
| NCL203 | 32 | 64 | 32 | 32 | >128 | >128 |
| | 32 | 64 | 64 | 32 | >128 | >128 |
| NCL204 | 4 | 4 | 64 | >128 | >128 | >128 |
| | 8 | 8 | 64 | >128 | >128 | >128 |
| NCL205 | 4 | 4 | 64 | >128 | >128 | >128 |
| | 8 | 8 | 64 | >128 | >128 | >128 |
| NCL206 | >128 | >128 | >128 | >128 | >128 | >128 |
| | >128 | >128 | >128 | >128 | >128 | >128 |

TABLE 42-continued

MICs for analogues NCL171-230 according to Example 7.

| | | | | | | |
|---|---|---|---|---|---|---|
| NCL207 | 16 | 32 | >128 | >128 | >128 | >128 |
| | 32 | 32 | >128 | >128 | >128 | >128 |
| NCL208 | >128 | >128 | >128 | >128 | >128 | >128 |
| | >128 | | >128 | >128 | >128 | >128 |
| NCL209 | >128 | >128 | >128 | >128 | >128 | >128 |
| | >128 | >128 | >128 | >128 | >128 | >128 |
| NCL210 | >128 | >128 | 128 | 32 | >128 | >128 |
| | >128 | >128 | 128 | 64 | >128 | >128 |
| NCL211 | >128 | >128 | >128 | >128 | >128 | >128 |
| | >128 | >128 | >128 | >128 | >128 | >128 |
| NCL212 | >128 | >128 | 32 | 16 | >128 | >128 |
| | >128 | 128 | 32 | 16 | >128 | >128 |
| NCL213 | >128 | >128 | >128 | >128 | >128 | >128 |
| | >128 | >128 | >128 | >128 | >128 | >128 |
| NCL214 | >128 | >128 | >128 | >128 | >128 | >128 |
| | >128 | >128 | >128 | >128 | >128 | >128 |
| NCL215 | 8 | 8 | 2 | 4 | >128 | >128 |
| | 16 | 8 | 4 | 8 | >128 | >128 |
| NCL216 | 2 | 2 | 2 | 4 | >128 | >128 |
| | 4 | | 2 | 4 | >128 | >128 |
| NCL217 | 4 | 4 | 2 | 4 | >128 | >128 |
| | 4 | 4 | 2 | 4 | >128 | >128 |
| NCL218 | >128 | >128 | 16 | >128 | >128 | >128 |
| | >128 | >128 | 16 | >128 | >128 | >128 |
| NCL219 | 2 | 2 | 16 | 16 | >128 | >128 |
| | 2 | 2 | 16 | 16 | >128 | >128 |
| NCL220 | 16 | 16 | 32 | 32 | >128 | >128 |
| | 16 | 16 | 32 | 32 | >128 | >128 |
| NCL221 | 4 | 2 | 64 | 64 | >128 | >128 |
| | 4 | 2 | 64 | 64 | >128 | >128 |
| NCL222 | >128 | >128 | >128 | >128 | >128 | >128 |
| | >128 | >128 | >128 | >128 | >128 | >128 |
| NCL223 | >128 | >128 | >128 | >128 | >128 | >128 |
| | >128 | >128 | >128 | >128 | >128 | >128 |
| NCL224 | >128 | >128 | >128 | >128 | >128 | >128 |
| NCL225 | >128 | >128 | >128 | >128 | >128 | >128 |
| NCL226 | >128 | >128 | >128 | >128 | >128 | >128 |
| NCL227 | >128 | >128 | >128 | >128 | >128 | >128 |
| NCL228 | >128 | >128 | >128 | >128 | >128 | >128 |
| NCL229 | >128 | >128 | >128 | >128 | >128 | >128 |
| NCL230 | >128 | >128 | >128 | >128 | >128 | >128 |

The NCL analogues showing the highest level of Gram-negative antibacterial activity included NCL030 (especially *Pseudomonas*), NCL041, NCL043, NCL044 (especially *Pseudomonas*), NCL052 (especially *Pseudomonas*), and NCL053 (especially *Pseudomonas*), NCL097 (especially *Pseudomonas*), NCL196 and NCL188 (especially *E. coli*).

The NCL analogues showing greatest activity against MRSA included: NCL021; NCL023; NCL029; NCL030; NCL035; NCL038; NCL039; NCL040; NCL041; NCL043; NCL044; NCL052; NCL054; NCL062; NCL069; NCL072; NCL073; NCL074; NCL078; NCL079; NCL080; NCL081; NCL082; NCL084; NCL088; NCL089; NCL093; NCL094; NCL097; NCL099; NCL101; NCL104; NCL107; NCL108; NCL111; NCL113; NCL117; NCL120; NCL121; NCL123; NCL136; NCL138; NCL140; NCL143; NCL146; NCL150; NCL151; NCL153; NCL155; NCL157; NCL158; NCL159; NCL160; NCL161; NCL166; NCL168; NCL169; NCL171; NCL172; NCL173; NCL174; NCL177; NCL178; NCL179; NCL180; NCL181; NCL182; NCL183; NCL184; NCL185; NCL186; NCL187; NCL188; NCL189; NCL190; NCL191; NCL192; NCL193; NCL195; NCL196; NCL197; NCL199; NCL201; NCL202; NCL203; NCL204; NCL205; NCL207; NCL215; NCL216; NCL217; NCL219; NCL220; and NCL221.

The NCL analogues showing greatest activity against VRE included: NCL011; NCL021; NCL023; NCL029; NCL030; NCL035; NCL038; NCL039; NCL040; NCL041; NCL043; NCL044; NCL052; NCL054; NCL061; NCL062; NCL069; NCL070; NCL072; NCL073; NCL074; NCL078; NCL079; NCL080; NCL081; NCL082; NCL084; NCL088; NCL093; NCL094; NCL097; NCL099; NCL101; NCL105; NCL107; NCL108; NCL111; NCL112; NCL113; NCL117; NCL120; NCL121; NCL123; NCL126; NCL131; NCL136; NCL140; NCL141; NCL143; NCL146; NCL151; NCL153; NCL155; NCL157; NCL158; NCL159; NCL160; NCL161; NCL166; NCL168; NCL169; NCL171; NCL173; NCL174; NCL175; NCL177; NCL178; NCL179; NCL180; NCL181; NCL182; NCL183; NCL184; NCL185; NCL186; NCL187; NCL188; NCL189; NCL190; NCL191; NCL192; NCL193; NCL195; NCL196; NCL197; NCL202; NCL203; NCL204; NCL205; NCL210; NCL212; NCL215; NCL216; NCL217; NCL218; NCL219; NCL220; and NCL221.

The bioassay ranking of the analogues tested is shown in Table 43.

TABLE 43

The bioassay ranking of the analogues tested according to Example 7.

| NCL ID | G-Rank | NCL ID | M + R mcg/ml | M + R rank | NCL ID | MRSA mcg/ml | MRSA rank | NCL ID | VRE mcg/ml | VRE rank |
|---|---|---|---|---|---|---|---|---|---|---|
| NCL097 | 1 | NCL062 | 2.25 | 1 | NCL157 | 2 | 1 | NCL089 | 0.75 | 1 |
| NCL196 | 1 | NCL157 | 2.25 | 2 | NCL195 | 2 | 2 | NCL062 | 1.5 | 2 |
| NCL030 | 1 | NCL812 | 2.375 | 3 | NCL179 | 2 | 3 | NCL812 | 1.75 | 3 |
| NCL041 | 1 | NCL195 | 2.75 | 4 | NCL219 | 2 | 4 | NCL084 | 2 | 4 |
| NCL043 | 1 | NCL216 | 2.75 | 5 | NCL216 | 2.5 | 5 | NCL157 | 2.5 | 5 |
| NCL044 | 1 | NCL089 | 2.875 | 6 | NCL193 | 2.5 | 6 | NCL081 | 2.5 | 6 |
| NCL052 | 1 | NCL084 | 3 | 7 | NCL062 | 3 | 7 | NCL216 | 3 | 7 |
| NCL053 | 1 | NCL179 | 3 | 8 | NCL812 | 3 | 8 | NCL217 | 3 | 8 |
|  |  | NCL054 | 3.5 | 9 | NCL054 | 3 | 9 | NCL079 | 3 | 9 |
|  |  | NCL217 | 3.5 | 10 | NCL221 | 3 | 10 | NCL080 | 3 | 10 |
|  |  | NCL081 | 3.75 | 11 | NCL199 | 3.5 | 11 | NCL078 | 3 | 11 |
|  |  | NCL193 | 3.75 | 12 | NCL084 | 4 | 12 | NCL195 | 3.5 | 12 |
|  |  | NCL079 | 4 | 13 | NCL217 | 4 | 13 | NCL082 | 3.5 | 13 |
|  |  | NCL080 | 4 | 14 | NCL158 | 4 | 14 | NCL074 | 3.75 | 14 |
|  |  | NCL158 | 4 | 15 | NCL089 | 5 | 15 | NCL179 | 4 | 15 |
|  |  | NCL082 | 5.25 | 16 | NCL081 | 5 | 16 | NCL054 | 4 | 16 |
|  |  | NCL078 | 5.5 | 17 | NCL079 | 5 | 17 | NCL158 | 4 | 17 |
|  |  | NCL120 | 6 | 18 | NCL080 | 5 | 18 | NCL088 | 4 | 18 |
|  |  | NCL088 | 7 | 19 | NCL099 | 6 | 19 | NCL123 | 4 | 19 |
|  |  | NCL099 | 7 | 20 | NCL204 | 6 | 20 | NCL215 | 4.5 | 20 |
|  |  | NCL177 | 7 | 21 | NCL205 | 6 | 21 | NCL193 | 5 | 21 |
|  |  | NCL215 | 7.25 | 22 | NCL082 | 7 | 22 | NCL120 | 5 | 22 |
|  |  | NCL197 | 7.5 | 23 | NCL120 | 7 | 23 | NCL035 | 5 | 23 |
|  |  | NCL040 | 8 | 24 | NCL078 | 8 | 24 | NCL140 | 5 | 24 |
|  |  | NCL038 | 9 | 25 | NCL177 | 8 | 25 | NCL177 | 6 | 25 |
|  |  | NCL202 | 9 | 26 | NCL197 | 8 | 26 | NCL197 | 7 | 26 |
|  |  | NCL219 | 9 | 27 | NCL040 | 8 | 27 | NCL099 | 8 | 27 |
|  |  | NCL123 | 9.5 | 28 | NCL038 | 8 | 28 | NCL040 | 8 | 28 |
|  |  | NCL074 | 9.875 | 29 | NCL155 | 8 | 29 | NCL202 | 8 | 29 |
|  |  | NCL155 | 10 | 30 | NCL088 | 10 | 30 | NCL021 | 8 | 30 |
|  |  | NCL035 | 10.5 | 31 | NCL215 | 10 | 31 | NCL143 | 8 | 31 |
|  |  | NCL021 | 12 | 32 | NCL202 | 10 | 32 | NCL153 | 8 | 32 |
|  |  | NCL113 | 12 | 33 | NCL113 | 12 | 33 | NCL038 | 10 | 33 |
|  |  | NCL143 | 12 | 34 | NCL146 | 12 | 34 | NCL155 | 12 | 34 |
|  |  | NCL146 | 14 | 35 | NCL107 | 12 | 35 | NCL113 | 12 | 35 |
|  |  | NCL153 | 16 | 36 | NCL123 | 15 | 36 | NCL219 | 16 | 36 |
|  |  | NCL188 | 16 | 37 | NCL074 | 16 | 37 | NCL146 | 16 | 37 |
|  |  | NCL173 | 17 | 38 | NCL035 | 16 | 38 | NCL188 | 16 | 38 |
|  |  | NCL023 | 20 | 39 | NCL021 | 16 | 39 | NCL173 | 18 | 39 |
|  |  | NCL220 | 24 | 40 | NCL143 | 16 | 40 | NCL174 | 18 | 40 |
|  |  | NCL174 | 25 | 41 | NCL188 | 16 | 41 | NCL039 | 20 | 41 |
|  |  | NCL190 | 28 | 42 | NCL173 | 16 | 42 | NCL023 | 24 | 42 |
|  |  | NCL039 | 30 | 43 | NCL023 | 16 | 43 | NCL212 | 24 | 43 |
|  |  | NCL121 | 30 | 44 | NCL220 | 16 | 44 | NCL121 | 28 | 44 |
|  |  | NCL029 | 32 | 45 | NCL153 | 24 | 45 | NCL220 | 32 | 45 |
|  |  | NCL221 | 33.5 | 46 | NCL190 | 24 | 46 | NCL190 | 32 | 46 |
|  |  | NCL168 | 40 | 47 | NCL207 | 28 | 47 | NCL029 | 32 | 47 |
|  |  | NCL169 | 40 | 48 | NCL174 | 32 | 48 | NCL169 | 32 | 48 |
|  |  | NCL203 | 44 | 49 | NCL121 | 32 | 49 | NCL180 | 32 | 49 |
|  |  | NCL107 | 46 | 50 | NCL029 | 32 | 50 | NCL184 | 32 | 50 |

Example 8: The Effects of NCL812 on Antimicrobial Sensitive Isolates of *Staphylococcus aureus* and *Enterococcus faecalis*

Materials and Methods

Strain Information

Two *Staphylococcus aureus* isolates were used in the following experiments; *S. aureus* MK01 a human skin strain, and *S. aureus* KC01 an equine skin strain. These isolates were identified by Gram stain and biochemical methods, including the Remel Staphaurex commercial kit. One *Enterococcus faecalis* isolate (USA01), was not identified as a VRE strain. As this isolate has previously been speciated, it was not subjected to further testing, except for observation of pure, characteristic growth on blood agar.

Investigation of Minimum Bactericidal Concentration (MBC)

CLSI Methodology

As in previous experiments, 10 μL of the contents of each well starting at the MIC was inoculated on to a Columbia SBA plate and incubated at 37° C. for 48 h. Plates were examined at 24 and 48 h and the MBC was recorded as the lowest concentration of NCL812 at which no colonies of bacteria were observed on the plate (or significant inhibition of growth was observed compared to the control) (CLSI 2005).

Kill Kinetics Assays for *S. aureus* KC01 & *E. faecalis* USA01 Method

*S. aureus* KC01 and *E. faecalis* USA01, not determined to be MRSA or VRE, respectively, were grown overnight on Columbia SBA at 37° C. A few colonies of bacteria were then suspended in CAMHB (cation-adjusted Mueller Hinton broth) and adjusted to $OD_{600}$ of 0.08 to 0.10. The bacterial suspension was diluted 1:10. One milliliter of the bacteria were added to 9 mL of CAMHB containing various concentrations (up to 4×MIC) of NCL, to achieve a final bacterial concentration of 1 to 3×106 CFU/mL. The tubes were incubated at 37° C., with constant shaking. In order to determine the number of viable bacteria present at various time points, a 100 µL aliquot was removed from each tube and diluted. Then, 100 µL of each dilution were spread onto colony count agar, in duplicate, and incubated for 48 h at 37° C. After 24 h the numbers of colonies present on each plate were counted and therefore the number of viable bacteria present in the original suspension enumerated. Plates were re-checked after 48 hours.

Results

Minimum Inhibitory Concentration (MIC)

The NCL812 MIC for isolates *S. aureus* MK01 and KC01, and *E. faecalis* USA01 was investigated. The results were: *S. aureus* MK01=4-8 µg/mL, *S. aureus* KC01=2 µg/mL, *E. faecalis* USA 01=4 µg/mL. *S. aureus* isolates MK01 and KC01 were investigated and no growth, or growth only at low concentrations of NCL812 (2 µg/ml), was observed, indicating that NCL812 is bactericidal against *S. aureus*. For the *E. faecalis* isolate tested (USA01) however, growth of bacteria was observed at all concentrations of NCL812 tested. There was an obvious reduction in the number of bacteria with increasing concentration, but growth was present compared with no growth for *S. aureus*. A summary of these results can be seen in Table 45. Table 45 shows the results for NCL812 MBC tests on two non-MRSA *S. aureus* isolates and one non-VRE *E. faecalis* isolate. Each MBC test was performed in duplicate. No change in the results was observed at 48 h. Table 37 shows NCL812 MBC values (µg/mL) for 20 MRSA isolates. Each MBC test was performed in duplicate starting from NCL812 MIC concentration to 16 times of MIC. Table 38 shows NCL812 MBC values (µg/ml) for 10 VRE isolates. Each MBC test was performed in duplicate starting from NCL812 MIC concentration to 32 times the MIC.

TABLE 45

NCL812 MBC tests on two non-MRSA *Staphylococcus aureus* isolates and one non-VRE *Enterococcus faecalis* isolate according to Example 8.

| Organism/ Sample No. | | NCL812 MBC | | | | | | |
|---|---|---|---|---|---|---|---|---|
| | | 2 µg/ml | 4 µg/ml | 8 µg/ml | 16 µg/ml | 32 µg/ml | 64 µg/ml | 128 µg/ml |
| S. aureus (KC01) | 1st | + | 0 | 0 | 0 | 0 | 0 | 0 |
| | 2nd | + | + | + | 0 | 0 | 0 | 0 |
| S. aureus (MK01) | 1st | 0 (5) | 0 | 0 | 0 (N) | 0 (N) | 0 (N) | 0 (N) |
| | 2nd | 0 | 0 | 0 | 0 | 0 | 0 | 0 |
| E. faecalis (USA01) | 1st | N | + (488) | + | + | + (7) | + (1) | + |
| | 2nd | N | + | + | + | + | + | + |

+ = Growth on Sheep Blood Agar;
0 = No Growth on Sheep Blood Agar;
N = Not Cultured;
Numbers in Parenthesis are the Number of Bacteria Growing after 24 hours per ml of sample (CFU/ml)

Kill Kinetics Assays for *S. aureus* KC01 & *E. faecalis* USA01

Method

Colony counts were performed at t=0, 120, 240, and 360 min, then again at 24 h. At the 2 h time point *S. aureus* KC01 showed a minimum of a 2.5 $log_{10}$ reduction in bacterial numbers from initial numbers, and greater than a 3 $log_{10}$ reduction in comparison to the control at the same time point. A minimum of a 2 $log_{10}$ reduction was still evident at 6 h incubation, however after 24 h the numbers of bacteria present had increased and this was not significantly different to the control.

Similar results were obtained with *E. faecalis* USA01, however the reduction in bacterial numbers observed was less than for *S. aureus* KC01. A 2 $log_{10}$ reduction in CFU/mL was observed at 2 h, compared to the growth control. However, the reduction in CFU/mL compared to the original bacterial numbers was only just greater than 1 $log_{10}$. At concentrations of 4-16 µg/mL of NCL812 this reduction in bacterial numbers remained consistent until the 6 h time point. At concentrations of 32 and 64 µg/mL however, there was approximately a 1 $log_{10}$ rise in bacterial numbers over the same time period. At 24 h bacterial numbers at all concentrations had increased to almost the same level as the growth control.

Figure 39:
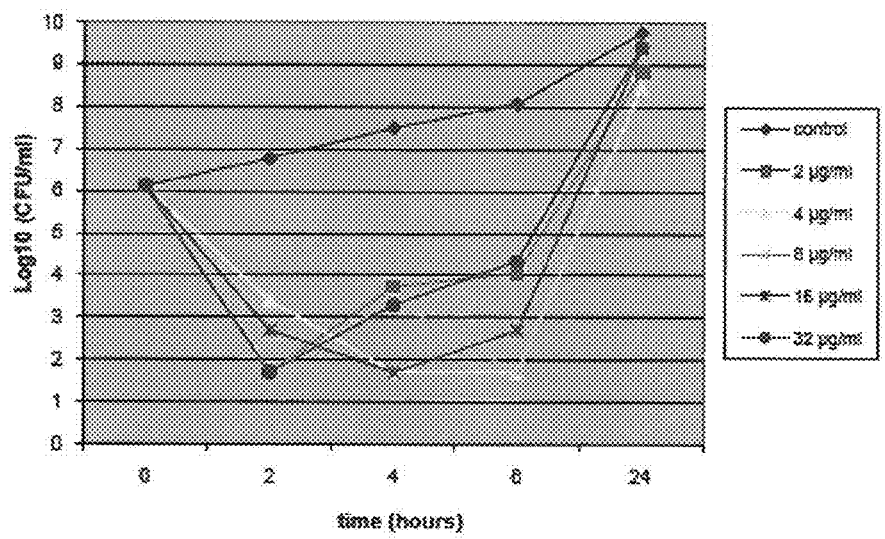
FIG. 39 shows the kill kinetics assay of *Staphylococcus aureus* KC01 at different concentrations of NCL812, up to 24 h incubation according to example 8.
Figure 40:
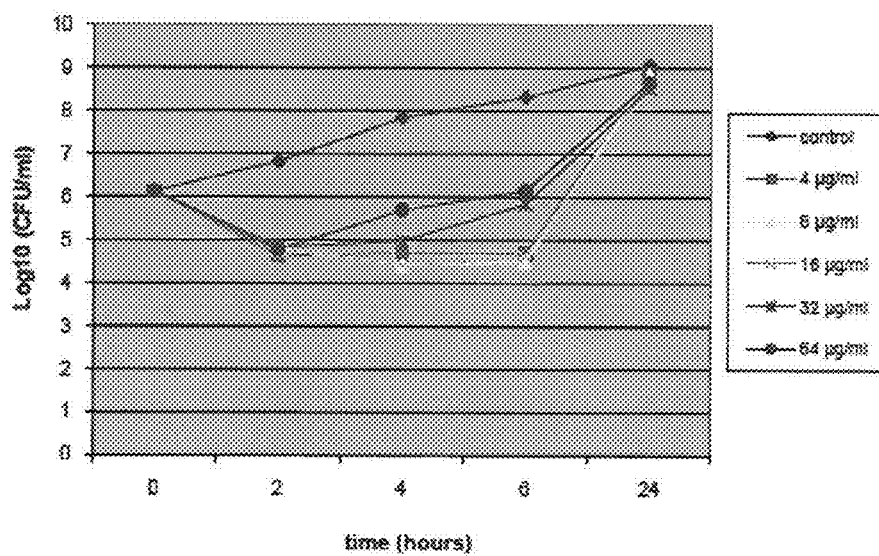
FIG. 40 shows the kill kinetics assay of *Enterococcus faecalis* USA01 at different concentrations of NCL812, up to 24 h incubation according to example 8.

The results observed with these strains of *S. aureus* and *E. faecalis* are consistent with the results observed for the kill kinetics assay for all MRSA and VRE isolates tested. The kill kinetics assay of *Staphylococcus aureus* KC01 at different concentrations of NCL812, up to 24 h incubation are shown in FIG. 39. The kill kinetics assay of *Enterococcus faecalis* USA01 at different concentrations of NCL812, up to 24 h incubation are shown in FIG. 40.

Example 9: Formulations of Compounds

The following formulations were prepared using standard methods in the art.

Formulation A—Topical Formulation—PEG-Based Gel with Compounds of the Invention
 4.0 g PEG 4000;
 3.5 g PEG 200;
 0.6 g propylene glycol;
 1.9 g water; and
 0.204 g of Compound (for example, NCL099)

PEG 4000, PEG 200 and propylene glycol were mixed and heated to 150° C. and until all solid crystals were dissolved. Compound was added to water and sonicated for 30 minutes until fully suspended. The Compound solution and gel solutions were mixed and allowed to cool and solidify. Formulation A will likely demonstrate acceptable viscosity, ease of skin application, uniform suspension and consistent and fine texture.

Formulation B—Topical Formulation—PEG-Based Gel with Compounds of the Invention
 3.0 g PEG 4000;
 1.0 g PEG 8000;
 3.0 g PEG 200;
 1.0 g propylene glycol;
 1.9 g water; and
 0.202 g of Compound (for example, NCL099)

PEG 4000, PEG 8000, PEG 200 and propylene glycol were mixed and heated to 150° C. and until all solid crystals were dissolved. Compound (for example, NCL099) was added to water and sonicated for 30 minutes until fully suspended. The Compound solution and gel solutions were mixed and allowed to cool and solidify. Formulation B demonstrated acceptable viscosity, ease of skin application, uniform suspension and consistent and fine texture.

Formulation C—Topical Formulation—PEG-Based Gel with Compound-Soluplus
 2.5 g PEG 4000;
 4.0 g PEG 200;
 2.5 g propylene glycol;

1.0 g water; and
1.8 g solid dispersion of Compound-SoluPlus.

Soluplus was purchased from BASF (www.soluplus.com). Compound-SoluPlus was prepared using standard methods in the art. PEG 4000, PEG 200, Compound-SoluPlus and propylene glycol were mixed and heated to 150° C. and until all solid crystals were dissolve. Water was added and then the solution was sonicated. The solution was allowed to cool and solidify. Formulation C demonstrated acceptable viscosity, ease of skin application, uniform suspension and consistent and fine texture.

Formulation D—Tablet Formulation
  30 mg Calcium hydrogen phosphate dehydrate;
  80 mg Microcrystalline cellulose;
  50 mg Lactose;
  8 mg Hydroxypropyl methyl cellulose
  1.5 mg Talc
  10 mg of compound (for example NCL099)

The excipients were weighed and mixed for 5 minutes. The mixture was fed into a feed hopper of a tablet press machine and the machine was operated according to standard procedures in the art. Formulation D demonstrated acceptable tablet hardness, disintegration and frability.

Formulation E—Oral Suspension
  2.0 ml Glycerol;
  1.5 ml Absolute ethanol;
  600 mg NCL812; and
  To 60 ml Vehicle (Ora Sweet and Ora Plus, 1:1).

NCL 812 powder was sieved through a 75 μm sieve. 600 mg of sieved NCL 812 was mixed with 2.0 ml glycerol and 1.5 ml absolute ethanol. The mixture was placed in a mortar and manually milled until all NCL 812 was suspended uniformly. The suspension was sonicated for 30 minutes. Vehicle (55 ml of Ora Sweet and Ora Plus mixture) was then added to the suspension and milled for another 10 minutes. Volume was made up with the Ora plus and Ora sweet mixture to 60 ml by transferring to a measuring cylinder Formulation E demonstrated acceptable suspension and demonstrated acceptable short term stability.

Formulation F—Intramuscular Injection
  20 mg/ml Polyvinylpyrrolidone K30 (PVPK30);
  0.09 mg/ml NCL812; and
  50 ml water.

Two percent of w/v PVP K30 solution was prepared by the addition of 1.0 g of PVP K30 to 50 ml of MilliQ water. The solution was then placed in a sonicator for 30 minutes to equilibrate and 4.5 mg of NCL 812 was added to the PVP solution and placed on an incubator shaker at a maximum speed of 10 rpm over a period of 24 hours, with controlled temperature of 25±1° C. Solution was transferred to 5 ml vials and checked for clarity, appearance, pH and short-term stability. The pH of solution was 7.25.

Formulation F demonstrated acceptable transparency and short term stability.

Example 10: Release of NCL812 and NCL099 from Formulation B

The objective of this study was to measure the release of NCL812 and NCL099 from Formulation B prepared in Example 9.

Franz diffusion cells were utilized to quantify the release rate of NCL 812 and NCL099 from its topical formulations. Five milliliters of absolute ethanol, which was chosen as the desired release medium, was loaded into the receptor chamber. Temperature of the receptor fluid was kept constant, at 32±1° C. using a water jacket. Acetyl cellulose membranes, with pore size of 0.45 μm (Pall Corporation) was selected and placed between donor and receptor chamber. Followed by that, a number of test samples (Formulation B) was loaded into the donor chamber. One milliliter of receptor fluid was collected at regular time intervals of 0.25, 0.50, 0.75, 1, 2, 3, 4, 5, 6, 7, 8 and 24 hours through the sampling port. One milliliter of fresh absolute ethanol was immediately returned to the receptor chamber. UV-HPLC was utilized to analyse the content of the receptor fluids attained.

Figure 41:
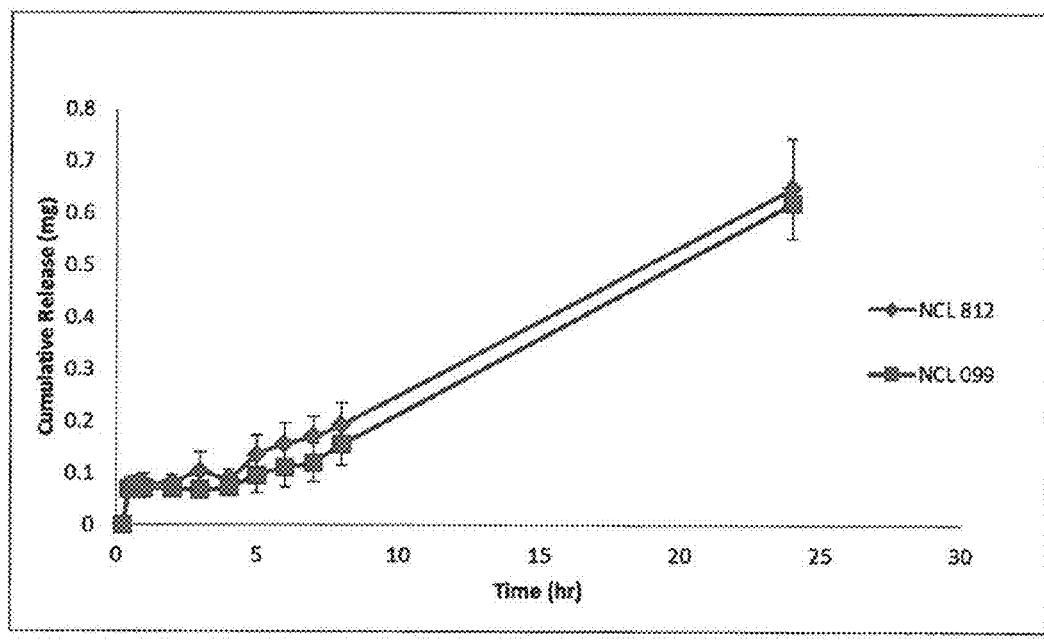
FIG. 41 is a graph illustrating the cumulative release of NCL812 and NCL099 from Formulation B according to example 10.

FIG. 41 presents the cumulative release of NCL812 and NCL099 over time. This study demonstrates that Formulation B provides an acceptable release profile for NCL812 and NCL099.

Example 11: NMR Spectroscopy Lists of Compounds NCL812, NCL001-NCL230

NMR Spectroscopy was performed on compounds NCL812, NCL001-NCL230 using standard methods in the art. The lists of the NMR spectroscopy are presented in Table 46.

TABLE 46

NMR Specroscopy Lists of Compounds NCL812, NCL001-NCL230

| NCL Code | NMR |
|---|---|
| NCL812 | 1H NMR (400 MHz, DMSO) δ 12.04 (br. s, 2H) 8.48 (br. s, 1H), 8.37 (br. s, 2H), 7.97 (d, J = 8.6 Hz, 4H) 7.57 (d, J = 8.6 Hz 4H) |
| NCL001 | 1H NMR (400 MHz, DMSO) δ 10.84 (br. s, 2H), 8.17 (br. s, 2H), 7.77 (d, J = 8.2 Hz, 4H), 7.50 (d, J = 8.6 Hz, 4H) |
| NCL002 | 1H NMR (400 MHz, DMSO) δ 11.06 (s, 2H), 8.58 (br. s, 2H), 8.17 (br. s, 2H), 7.50-7.52 (m, 2H), 7.41-7.45 (m, 4H) |
| NCL003 | 1H NMR (400 MHz, DMSO) δ 10.71 (s, 2H), 8.17 (br. s, 2H), 7.73-7.88 (m, 4H), 7.28 (t, J = 8.8 Hz, 4H) |
| NCL004 | 1H NMR (400 MHz, DMSO) δ 10.89 (br. s, 2H), 8.19 (br. s, 2H), 7.65 (br. s, 2H), 7.43-7.56 (m, 4H), 7.19-7.27 (m, 2H) |
| NCL005 | 1H NMR (400 MHz, DMSO) δ 10.94 (br. s, 2H), 8.43 (br. s, 2H), 8.10 (br. s, 2H), 7.39-7.52 (m, 2H), 7.21-7.35 (m, 4H) |
| NCL006 | 1H NMR (400 MHz, DMSO) δ 10.50 (s, 2H), 8.11 (br. s, 2H), 7.68 (d, J = 8.6 Hz, 4H), 6.99 (d, J = 8.6 Hz, 4H), 3.80 (s, 6H) |
| NCL007 | 1H NMR (400 MHz, DMSO) δ 11.10 (br. s, 2H), 8.24 (br. s, 2H), 7.81-8.03 (m, 8H) |
| NCL008 | 1H NMR (400 MHz, DMSO) δ 11.24 (br. s, 2H), 8.51 (br. s, 2H), 8.18-8.29 (m, 2H), 7.90 (d, J = 7.4 Hz, 2H), 7.80 (t, J = 7.6 Hz, 2H), 7.59 (t, J = 7.0 Hz, 2H) |
| NCL009 | 1H NMR (400 MHz, DMSO) δ 11.02 (s, 2H), 8.26 (br. s, 4H), 8.07 (d, J = 7.8 Hz, 2H), 7.85 (d, J = 7.8 Hz, 2H), 7.65 (t, J = 7.8 Hz, 2H) |

TABLE 46-continued

NMR Specroscopy Lists of Compounds NCL812, NCL001-NCL230

| NCL Code | NMR |
|---|---|
| NCL010 | 1H NMR (400 MHz, DMSO) δ 10.74 (br. s, 2H), 8.15 (br. s, 2H), 7.25-7.39 (m, 6H), 6.94-7.01 (m, 2H), 3.82 (s, 6H) |
| NCL011 | 1H NMR (400 MHz, DMSO) δ 11.02 (s, 2H), 8.28 (br. s, 2H), 8.13 (s, 2H), 8.04 (d, J = 7.4 Hz, 2H), 7.75 (d, J = 8.0 Hz, 2H), 7.68 ( t, J = 8.0 Hz, 2H) |
| NCL012 | 1H NMR (400 MHz, DMSO) δ 11.04 (br. s, 2H), 8.27 (br. s, 2H), 7.97 (d, J = 7.8 Hz, 4H), 7.80 (d, J = 8.2 Hz, 4H) |
| NCL013 | 1H NMR (400 MHz, DMSO) δ 11.22 (br. s, 2H), 8.55 (br. s, 2H), 8.35 (d, J = 7.0 Hz, 2H), 7.73-7.82 (m, 4H), 7.57-7.65 (m, 2H) |
| NCL014 | 1H NMR (400 MHz, DMSO) δ 10.30 (s, 1H), 7.81 (s, 1H), 7.76 (d, J = 8.6 Hz, 2H), 7.43 (d, J = 8.6 Hz, 2H), 6.53 (br. s, 2H) |
| NCL015 | 1H NMR (400 MHz, DMSO) δ 12.02 (br. s, 1H), 8.55 (s, 1H), 8.27-8.33 (m, 1H), 7.79 (br. s, 3H), 7.51-7.56 (m, 1H), 7.39-7.51 (m, 2H) |
| NCL016 | 1H NMR (400 MHz, DMSO) δ 11.98 (br. s, 1H), 8.39 (s, 1H), 8.19-8.26 (m, 1H), 7.80 (br. s, 3H), 7.46-7.58 (m, 1H), 7.20-7.38 (m, 2H) |
| NCL017 | 1H NMR (400 MHz, DMSO) δ 11.79 (br. s, 1H), 8.17 (s, 1H), 7.87 (d, J = 9.8 Hz, 1H), 7.71 (br. s, 3H), 7.62 (d, J = 7.4 Hz, 1H), 7.45-7.54 (m, 1H), 7.25-7.32 (m, 1H) |
| NCL018 | 1H NMR (400 MHz, DMSO) δ 10.66 (s, 2H), 8.47 (br. s, 2H), 7.91-8.00 (m, 2H), 7.19-7.32 (m, 6H), 2.42 (s, 6H) |
| NCL019 | 1H NMR (400 MHz, DMSO) δ 10.68 (br. s, 2H), 8.15 (br. s, 2H), 7.57 (s, 2H), 7.52 (d, J = 7.4 Hz, 2H), 7.32 (t, J = 7.6 Hz, 2H), 7.21 (d, J = 7.4 Hz, 2H), 2.36 (s, 6H) |
| NCL020 | 1H NMR (400 MHz, DMSO) δ 12.37 (br. s, 2H), 8.83 (br. s, 2H), 8.63 (br. s, 2H), 8.39-8.44 (m, 2H), 7.55-7.60 (m, 2H), 7.44-7.55 (m, 4H) |
| NCL021 | 1H NMR (400 MHz, DMSO) δ 12.11 (br. s, 1H), 8.52 (br. s, 2H), 8.40 (br. s, 2H), 8.02 (t, J = 8.6 Hz, 4H), 7.35 (t, J = 8.8 Hz, 4H) |
| NCL022 | 1H NMR (400 MHz, DMSO) δ 12.19 (br. s, 2H), 8.65 (br. s, 2H), 8.58 (br. s, 1H), 8.34 (t, J = 7.6 Hz, 2H), 7.51-7.60 (m, 2H), 7.34 (t, J = 8.2 Hz 4H) |
| NCL023 | 1H NMR (400 MHz, DMSO) δ 12.08 (br. s, 2H), 8.38 (br. s, 2H), 7.92-8.00 (m, 2H), 7.65-7.71 (m, 2H), 7.50-7.58 (m, 2H), 7.29-7.37 (m, 2H) |
| NCL024 | 1H NMR (400 MHz, DMSO) δ 12.32 (br. s, 2H), 8.67 (br. s, 2H), 8.44 (br. s, 2H), 8.15 (d, J = 8.6 Hz, 4H), 7.98 (d, J = 8.6 Hz, 4H) |
| NCL025 | 1H NMR (400 MHz, DMSO) δ 8.75 (br. s, 2H), 8.50 (d, J = 8.2 Hz, 2H), 7.97 (d, J = 7.4 Hz, 2H), 7.85 (t, J = 7.6 Hz, 2H), 7.68 (t, J = 7.6 Hz, 2H) |
| NCL026 | 1H NMR (400 MHz, DMSO) δ 12.26 (br. s, 1H), 8.66 (br. s, 1H), 8.55 (s, 2H), 8.43 (br. s, 2H), 8.21 (d, J = 7.8 Hz, 2H), 7.94 (d, J = 7.8 Hz, 2H), 7.71 (t, J = 7.8 Hz, 2H) |
| NCL027 | 1H NMR (400 MHz, DMSO) δ 11.78 (br. s, 2H), 8.31 (br. s, 3H), 7.87 (d, J = 8.6 Hz, 4H), 7.04 (d, J = 8.6 Hz, 4H), 3.83 (s, 6H) |
| NCL028 | 1H NMR (400 MHz, DMSO) δ 12.00 (br. s, 2H), 8.75 (br. s, 2H), 8.39 (br. s, 2H), 8.22 (d, J = 6.7 Hz, 2H), 7.44-7.52 (m, 2H), 7.14 (d, J = 8.2 Hz, 2H), 7.05 (t, J = 7.6 Hz, 2H), 3.89 (s, 6H) |
| NCL029 | 1H NMR (400 MHz, DMSO) δ 11.98 (br. s, 2H), 8.48 (br. s, 2H), 8.36 (br. s, 2H), 7.56 (s, 2H), 7.35-7.49 (m, 4H),7.04-7.10 (m, 2H), 3.84 (s, 6H) |
| NCL030 | 1H NMR (400 MHz, DMSO) δ 11.83 (br. s, 1H), 8.16 (s, 1H), 7.91 (d, J = 8.2 Hz, 2H), 7.75 (br. s, 1H), 7.53 (d, J = 8.2 Hz, 2H) |
| NCL031 | 1H NMR (400 MHz, DMSO) δ 11.91 (br. s, 1H), 8.22 (s, 1H), 8.09 (d, J = 8.2 Hz, 2H), 7.93 (d, J = 8.2 Hz, 2H) |
| NCL032 | 1H NMR (400 MHz, DMSO) δ 12.12 (s, 1H), 8.48 (s, 1H), 8.38 (d, J = 7.8 Hz, 1H), 7.94 (d, J = 7.8 Hz, 1H), 7.86 (br. s, 2H), 7.80 (t, J = 7.8 Hz, 2H), 7.64 (t, J = 7.6 Hz, 1H) |
| NCL033 | 1H NMR (400 MHz, DMSO) δ 11.93 (s, 1H), 8.50 (s, 1H), 8.20 (s, 1H), 8.14 (d, J = 7.8 Hz, 1H), 7.90 (d, J = 7.8 Hz, 1H), 7.66 (t, J = 7.8 Hz, 1H) |
| NCL034 | 1H NMR (400 MHz, DMSO) δ 11.87 (br. s, 1H), 8.48 (s, 1H), 8.09 (d, J = 7.8 Hz, 1H), 7.70 (br. s, 2H), 7.38-7.49 (m, 1H), 7.11 (d, J = 8.6 Hz, 1H), 7.01 (t, J = 7.4 Hz, 1H), 3.86 (s, 3H) |
| NCL035 | 1H NMR (400 MHz, DMSO) δ 12.32 (br. s, 2H), 8.69 (br. s, 2H), 8.49 (br. s, 2H), 8.18 (d, J = 7.8 Hz, 4H), 7.86 (d, J = 8.2 Hz, 4H) |
| NCL036 | 1H NMR (400 MHz, DMSO) δ 12.51 (br. s, 1H), 8.80 (br. s, 2H), 8.72 (br. s, 1 H), 8.59 (d, J = 7.8 Hz, 2H), 7.78-7.91 (m, 4H), 7.71 (t, J = 8.0 Hz, 2H) |
| NCL037 | 1H NMR (400 MHz, DMSO) δ 12.28 (br. s, 2H), 8.70 (br. s, 2H), 8.50 (br. s, 2H), 8.38 (s, 2H), 8.22 (d, J = 7.8 Hz, 2H), 7.85 (d, J = 7.8 Hz, 2H), 7.74 (t, J = 7.8 Hz, 2H) |
| NCL038 | 1H NMR (400 MHz, DMSO) δ 11.92 (br. s, 2H), 8.41 (br. s, 2H), 8.36 (br. s, 2H), 7.83 (d, J = 8.2 Hz, 4H), 7.31 (d, J = 7.8 Hz, 4H), 2.37 (s, 6H) |
| NCL039 | 1H NMR (400 MHz, DMSO) δ 11.99 (br. s, 2H), 8.73 (br. s, 2H), 8.41 (br. s, 2H), 8.19 (d, J = 7.8 Hz, 2H), 7.37 (t, J = 8.0 Hz, 2H), 7.30 (t, J = 7.8 Hz, 4H), 2.46 (s, 6H) |
| NCL040 | 1H NMR (400 MHz, DMSO) δ 11.97 (br. s, 2H), 8.44 (br. s, 2H), 8.37 (br. s, 2H), 7.76 (s, 2H), 7.71 (d, J = 7.8 Hz, 2H), 7.38 (t, J = 7.8 Hz, 2H), 7.31 (d, J = 7.8 Hz, 2H), 2.38 (s, 6H) |
| NCL041 | 1H NMR (400 MHz, DMSO) δ 11.94 (s, 1H), 8.25 (s, 1H), 8.11 (d, J = 7.8 Hz, 2H), 7.71-7.91 (m, 4H) |
| NCL042 | 1H NMR (400 MHz, DMSO) δ 12.04 (s, 1H), 8.46-8.56 (m, 2H), 7.70-7.93 (m, 5H), 7.66 (t, J = 7.8 Hz, 1H) |
| NCL043 | 1H NMR (400 MHz, DMSO) δ 11.88 (s, 1H), 8.33 (s, 1H), 8.26 (s, 1H), 8.14 (d, J = 7.8 Hz, 1H), 7.80 (d, J = 7.8 Hz, 1H), 7.69 (t, J = 7.8 Hz, 1H) |
| NCL044 | 1H NMR (400 MHz, DMSO) δ 11.71 (br. s, 1H), 8.13 (s, 1H), 7.76 (d, J = 8.2 Hz, 2H), 7.27 (d, J = 7.8 Hz, 2H), 2.35 (s, 3H) |
| NCL045 | 1H NMR (400 MHz, DMSO) δ 11.69 (br. s, 1H), 8.45 (s, 1H), 8.06 (d, J = 7.4 Hz, 1H), 7.67 (br. s, 2H), 7.30-7.39 (m, 1H), 7.20-7.29 (m, 2H), 2.42 (s, 3H) |
| NCL046 | 1H NMR (400 MHz, DMSO) δ 11.64 (br. s, 1H), 8.12 (s, 1H), 7.53-7.77 (m, 4H), 7.34 (t, J = 7.8 Hz, 1H), 7.27 (d, J = 7.8 Hz, 1H), 2.35 (s, 3H) |
| NCL047 | 1H NMR (400 MHz, DMSO) δ 10.47 (s, 1H), 8.23 (s, 1H), 8.16-8.21 (m, 1H), 7.42-7.50 (m, 1H), 7.30-7.40 (m, 2H), 6.57 (br. s, 2H) |

TABLE 46-continued

NMR Specroscopy Lists of Compounds NCL812, NCL001-NCL230

| NCL Code | NMR |
|---|---|
| NCL048 | 1H NMR (400 MHz, DMSO) δ 10.40 (s, 1H), 8.08-8.15 (m, 1H), 8.05 (s, 1H), 7.34-7.44 (m, 1H), 7.17-7.28 (m, 2H), 6.54 (br. s, 2H) |
| NCL049 | 1H NMR (400 MHz, DMSO) δ 10.51 (s, 1H), 7.93 (d, J = 8.2 Hz, 1H), 7.86 (s, 1H), 7.83 (d, J = 8.2 Hz, 1H), 6.63 (br. s, 2H) |
| NCL050 | 1H NMR (400 MHz, DMSO) δ 10.66 (s, 1H), 8.13 (d, J = 8.0 Hz, 1H), 8.11 (s, 1H), 7.85 (d, J = 7.4 Hz, 1H), 7.71 (t, J = 7.8 Hz, 1H), 7.52 (t, J = 7.0 Hz, 1H), 6.60 (br. s, 2H) |
| NCL051 | 1H NMR (400 MHz, DMSO) δ 10.43 (s, 1H), 8.37 (s, 1H), 7.98 (d, J = 7.8 Hz, 1H), 7.84 (s, 1H), 7.77 (d, J = 7.8 Hz, 1H), 7.57 (t, J = 7.8 Hz, 1H) |
| NCL052 | 1H NMR (400 MHz, DMSO) δ 11.95 (s, 1H), 8.16 (s, 1H), 8.10 (s, 1H), 7.80 (br. s, 2H), 7.76 (d, J = 7.0 Hz, 1H), 7.40-7.55 (m, 2H) |
| NCL053 | 1H NMR (400 MHz, DMSO) δ 11.88 (s, 1H), 8.17 (s, 1H), 7.95 (dd, J = 8.8, 5.7 Hz, 2H), 7.76 (br. s, 1 H), 7.30 (t, J = 9.0 Hz, 2H) |
| NCL054 | 1H NMR (400 MHz, DMSO) δ 12.17 (br. s, 2H), 8.61 (br. s, 2H), 8.39 (br. s, 2H), 8.16 (s, 2H), 7.83 (d, J = 7.0 Hz, 2H), 7.45-7.61 (m, 4H) |
| NCL055 | 1H NMR (400 MHz, DMSO) δ 10.34 (s, 1H), 7.93 (s, 1H), 7.80 (s, 1H), 7.54-7.67 (m, 1H), 7.32-7.46 (m, 2H), 6.58 (br. s, 1H) |
| NCL056 | 1H NMR (400 MHz, DMSO) δ 10.23 (s, 1H), 7.82 (s, 1H), 7.78 (dd, J = 8.8, 5.7 Hz, 2H), 7.21 (t, J = 8.8 Hz, 1H), 6.49 (br. s, 2H) |
| NCL057 | 1H NMR (400 MHz, DMSO) δ 10.33 (s, 1H), 7.82 (s, 1H), 7.71 (d, J = 9.8 Hz, 1H), 7.35-7.53 (m, 2H), 7.10-723 (m, 1H), 6.57 (br. s, 1H) |
| NCL058 | 1H NMR (400 MHz, DMSO) δ 10.08 (s, 1H), 7.78 (s, 1H), 7.65 (d, J = 9.0 Hz, 2H), 6.94 (d, J = 8.6 Hz, 2H), 6.40 (br. s, 2H), 3.78 (s, 3H) |
| NCL059 | 1H NMR (400 MHz, DMSO) δ 10.23 (s, 1H), 7.80 (s, 1H), 7.34 (s, 1H), 7.29 (t, J = 7.8 Hz, 1H), 7.21 (d, J = 7.8 Hz, 1H), 6.91 (dd, J = 7.8, 2.0 Hz, 1H), 6.51 (br. s, 2H), 3.79 (s, 3H) |
| NCL060 | 1H NMR (400 MHz, DMSO) δ 10.56 (s, 1H), 8.41 (d, J = 7.8 Hz, 1H), 8.19 (br. s, 1H), 7.74 (d, J = 7.8 Hz, 1H), 7.67 (t, J = 7.6 Hz, 1H), 7.54 (t, J = 7.8 Hz, 1H), 6.62 (br. s, 2H) |
| NCL061 | 1H NMR (400 MHz, DMSO) δ 11.71 (br. s, 2H), 8.91 (br. s, 1H), 8.28 (d, J = 7.8 Hz, 4H), 7.82 (d, J = 8.2 Hz, 4H), 2.49 (br. s, 6H) |
| NCL062 | 1H NMR (400 MHz, DMSO) δ 11.68 (br. s, 2H), 8.78 (br. s, 1H), 8.10 (d, J = 8.6 Hz, 4H), 7.52 (d, J = 8.6 Hz, 4H), 2.43 (s, 6H) |
| NCL063 | 1H NMR (400 MHz, DMSO) δ 7.99 (br. s, 4H), 7.83 (d, J = 7.8 Hz, 6H) |
| NCL064 | 1H NMR (400 MHz, DMSO) δ 7.94 (d, J = 7.8 Hz, 4H), 7.84 (t, J = 7.6 Hz, 4H), 7.64 (t, J = 7.6 Hz, 4H) |
| NCL065 | 1H NMR (400 MHz, DMSO) δ 12.20 (br. s, 1H), 11.86 (br. s, 1H), 8.65 (br. s, 1H), 8.50 (br. s, 1H), 2H) 8.03-8.27 (m, 3H), 7.90 (d, J = 7.8 Hz, 2H), 7.68 (t, J = 7.6 Hz) |
| NCL066 | 1H NMR (400 MHz, DMSO) δ 7.43-7.67 (m, 7H), 7.23-7.34 (m, 2H) |
| NCL067 | 1H NMR (400 MHz, DMSO) δ 10.40 (s, 1H), 8.16 (s, 1H), 7.98 (d, J = 7.4 Hz, 1 H), 7.90 (s, 1H), 7.67 (d, J = 7.3 Hz, 1H), 7.60 (t, J = 7.4 Hz, 1H) |
| NCL068 | 1H NMR (400 MHz, DMSO) δ 8.47 (br. s, 1H), 8.18 (d, J = 7.8 Hz, 3H), 8.07 (d, J = 8.6 Hz, 2H), 7.85 (d, J = 7.8 Hz, 2H), 7.53 (d, J = 8.6 Hz, 2H), 2.40 (s, 3H) |
| NCL069 | 1H NMR (400 MHz, DMSO) δ 9.44 (br. s, 1H), 8.03 (d, J = 8.2 Hz, 2H), 7.94 (br. s, 2H), 7.48 (d, J = 8.6 Hz, 2H), 2.31 (s, 3H) |
| NCL070 | 1H NMR (400 MHz, DMSO) δ 8.12 (br. s, 1 H), 7.71 (br. s, 3H), 7.49 (br. s, 6H) |
| NCL071 | 1H NMR (400 MHz, DMSO) δ 11.43 (s, 1H), 8.40 (s, 1H), 8.16 (br. s, 1H), 8.10 (d, J = 7.4 Hz, 1H), 7.95 (br. s, 1H), 7.37 (t, J = 7.8 Hz, 1H), 7.06 (d, J = 8.2 Hz, 1H), 6.95 (t, J = 7.4 Hz, 1H), 3.82 (s, 3H) |
| NCL072 | 1H NMR (400 MHz, DMSO) δ 7.91 (br. d, J = 8.2 Hz, 3H), 7.52 (d, J = 8.6 Hz, 2H) |
| NCL073 | 1H NMR (400 MHz, DMSO) δ 9.51 (br. s, 1H), 8.22 (d, J = 8.3 Hz, 2H), 8.01 (br. s, 2H), 7.77 (d, J = 8.3 Hz, 2H), 2.36 (s, 3H) |
| NCL074 | 1H NMR (400 MHz, DMSO) δ 12.46 (br. s, 1 H), 8.79 (br. s, 1H), 8.66 (br. s, 2H), 8.46 (d, J = 8.2 Hz, 2H), 7.99 (d, J = 7.0 Hz, 2H), 7.77 (br. s, 1H), 7.58 (d, J = 6.7 Hz, 3H) |
| NCL075 | 1H NMR (400 MHz, DMSO) δ 8.48 (br. s, 1H), 8.26 (d, J = 7.4 Hz, 2H), 8.19 (d, J = 7.4 Hz, 2H), 7.75-7.93 (m, 4H), 2.46 (s, 3H) |
| NCL076 | 1H NMR (400 MHz, DMSO) δ 8.53 (br. s, 2H), 8.29-8.46 (m, 2H), 7.99 (d, J = 7.8 Hz, 2H), 7.83 (d, J = 7.8 Hz, 2H), 7.57 (d, J = 7.8 Hz, 2H), 7.31 (d, J = 7.8 Hz, 2H), 2.37 (s, 3H) |
| NCL077 | 1H NMR (400 MHz, DMSO) δ 12.28 (br. s, 1H), 8.67 (br. s, 1H), 8.49 (br. s, 1H), 8.42 (br. s, 1H), 8.18 (d, J = 7.8 Hz, 2H), 8.00 (d, J = 8.2 Hz, 2H), 7.86 (d, J = 8.2 Hz, 2H), 7.58 (d, J = 7.8 Hz, 2H) |
| NCL078 | 1H NMR (400 MHz, DMSO) δ 12.33 (br. s, 1H), 8.74 (br. s, 2H), 8.58 (t, J = 7.6 Hz, 1H), 8A2 (br. s, 1H), 8.00 (d, J = 8.2 Hz, 2H), 7.87 (d, J = 10.2 Hz, 1H), 7.74 (d, J = 8.2 Hz, 1H), 7.58 (d, J = 8.2 Hz, 2H) |
| NCL079 | 1H NMR (400 MHz, DMSO) δ 12.08 (br. s, 1H), 8.54 (br. s, 1H), 8.39 (br. s, 2H), 7.93-8.09 (m, 4H), 7.57 (d, J = 8.2 Hz, 2H), 7.35 (t, J = 8.6 Hz, 2H) |
| NCL080 | 1H NMR (400 MHz, DMSO) δ 12.04 (br. s, 1H), 11.36 (br. s, 1H), 8.40 (br. s, 1H), 8.25 (d, J = 8.2 Hz, 1H), 8.00 (d, J = 7.0 Hz, 2H), 7.82 (d, J = 7.4 Hz, 2H), 7.57 (d, J = 6.7 Hz, 2H), 2.44 (s, 3H) |
| NCL081 | 1H NMR (400 MHz, DMSO) δ 8.39 (br. s, 1H), 8.07 (d, J = 8.6 Hz, 2H), 7.99 (d, J = 8.6 Hz, 2H), 7.57 (d, J = 8.2 Hz, 2H), 7.53 (d, J = 8.6 Hz, 2H), 2.39 (s, 3H) |
| NCL082 | 1H NMR (400 MHz, DMSO) δ 12.40 (br. s, 1H), 8.84 (br. s, 1H), 8.63 (br. s, 2H), 8.42 (d, J = 7.8 Hz, 2H), 7.99 (d, J = 8.6 Hz, 2H), 7.58 (d, J = 8.2 Hz, 3H), 7.43-7.54 (m, 2H) |
| NCL083 | 1H NMR (400 MHz, DMSO) δ 12.30 (br. s, 1H), 8.64 (br. s, 2H), 8.41 (br. s, 2H), 8.17 (s, 1H), 7.99 (d, J = 8.6 Hz, 2H), 7.82 (d, J = 6.7 Hz, 1H), 7.45-7.64 (m, 4H) |
| NCL084 | 1H NMR (400 MHz, DMSO) δ 12.38 (br. s, 1H), 8.64 (br. s, 2H), 8.30-8.50 (m, 2H), 7.99 (d, J = 8.6 Hz, 2H), 7.62 (d, J = 10.4, 1.4 Hz, 1H), 7.57 (d, J = 8.6 Hz, 2H), 7.46 (d, J = 8.6 Hz, 1H) |
| NCL085 | 1H NMR (400 MHz, DMSO) δ 8.77 (br. s, 1H), 8.68 (br. s, 2H), 8.52 (d, J = 8.2 Hz, 1H), 8.46 (br. s, 1H), 7.92-8.06 (m, 3H), 7.84 (t, J = 7.6 Hz, 1H), 7.68 (t, J = 7.6 Hz, 1H), 7.58 (d, J = 8.2 Hz, 2H) |

TABLE 46-continued

NMR Specroscopy Lists of Compounds NCL812, NCL001-NCL230

| NCL Code | NMR |
|---|---|
| NCL086 | 1H NMR (400 MHz, DMSO) δ 12.39 (br. s, 1H), 8.68 (br. s, 2H), 8.57 (s, 1H), 8.43 (br. s, 2H), 8.21 (d, J = 7.4 Hz, 1H), 8.00 (d, J = 8.2 Hz, 2H), 7.94 (d, J = 7.0 Hz, 1H), 7.70 (t, J = 7.2 Hz, 1H), 7.58 (d, J = 7.8 Hz, 2H) |
| NCL087 | 1H NMR (400 MHz, DMSO) δ 8.71 (br. s, 2H), 8.48 (br. s, 1H), 8.43 (br. s, 1H), 8.16 (d, J = 8.2 Hz, 2H), 7.99 (t, J = 8.0 Hz, 4H), 7.58 (d, J = 8.6 Hz, 2H) |
| NCL088 | 1H NMR (400 MHz, DMSO) δ 12.33 (br. s, 1H), 8.68 (br. s, 1H), 8.61 (br. s, 2H), 8.42 (br. s, 1H), 8.35 (t, J = 7.4 Hz, 1H), 7.99 (d, J = 8.2 Hz, 2H), 7.49-7.64 (m, 3H), 7.27-7.41 (m, 2H) |
| NCL089 | 1H NMR (400 MHz, DMSO) δ 11.45 (br. s, 1H), 8.76-8.94 (m, 1H), 8.11 (d, J = 8.0 Hz, 4H), 7.53 (d, J = 8.0 Hz, 4H), 2.42 (br. s, 6H) |
| NCL090 | 1H NMR (400 MHz, DMSO) δ 10.60 (br. s, 1H), 8.68 (s, 1H), 8.09 (br. s, 1H), 7.95 (br. s, 4H), 7.32-7.71 (m, 10H) |
| NCL091 | 1H NMR (400 MHz, DMSO) δ 9.61 (br. s, 1H), 8.19 (d, J = 6.3 Hz, 2H), 7.90 (br. s, 2H), 7.56-7.73 (m, 2H), 7.26-7.40 (m, 2H) |
| NCL092 | 1H NMR (400 MHz, DMSO) δ 12.38 (br. s, 1H), 7.82-7.94 (m, 2H), 7.18-7.63 (m, 7H), 4.39 (br. s, 2H) |
| NCL 093 | 1H NMR (300 MHz, DMSO) δ 8.64 (s, 4H), 8.35-8.24 (m, 4H), 8.06-7.93 (m, 6H), 7.64-7.54 (m, 4H). |
| NCL 094 | 1H NMR (300 MHz, CDCl3) δ 7.16 (d, J = 4.7 Hz, 2H), 6.10 (br s, 3H), 2.27-2.14 (m, 2H), 1.84-1.61 (m, 10H), 1.37-1.13 (m, 10H) |
| NCL 095 | 1H NMR (300 MHz, DMSO) δ 8.39 (s, 2H), 8.36-8.11 (m, 4H), 7.78 (s, 2H), 7.12 (d, J = 1.4 Hz, 2H). |
| NCL 096 | 1H NMR (300 MHz, MeOD) δ 8.08 (d, J = 8.2 Hz, 2H), 7.61-7.53 (m, 4H), 7.45-7.30 (m, 6H), 7.17-6.97 (m, 4H). 1H NMR (300 MHz, DMSO) δ 9.06 (br s, 6H), 8.25-8.01 (m, 4H), 6.83 (s, 4H). |
| NCL 097 | 13C NMR (75 MHz, DMSO) δ 152.2, 149.7, 146.2, 136.5, 123.7, 107.4. |
| NCL 098 | 1H NMR (300 MHz, DMSO) δ 8.65 (s, 2H), 8.53 (s, 2H), 8.40 (s, 2H), 8.24 (d, J = 7.3 Hz, 2H), 8.09-7.98 (m, 2H), 7.62 (t, J = 7.7 Hz, 2H). |
| NCL 099 | 1H NMR (300 MHz, DMSO) δ 8.56-8.32 (m, 4H), 7.85 (d, J = 8.3 Hz, 4H), 7.49 (d, J = 8.3 Hz, 4H), 1.31 (s, 18H). 13C NMR (75 MHz, DMSO) δ 153.7, 152.7, 148.8, 130.7, 127.8, 125.6, 34.7, 31.0. |
| NCL 100 | 1H NMR (300 MHz, DMSO) δ 12.39 (br s, 2H), 8.55 (s, 2H), 8.46 (s, 2H), 8.01-7.88 (m, 4H), 7.55-7.41 (m, 6H). |
| NCL 101 | 1H NMR (300 MHz, DMSO) δ 12.06 (br s, 2H), 9.71 (br s, 2H), 9.21 (s, 2H), 8.70 (s, 2H), 8.30 (s, 2H), 7.50 (d, J = 7.9 Hz, 2H), 6.90 (d, J = 7.7 Hz, 2H), 6.70 (t, J = 7.7 Hz, 2H). |
| NCL 102 | 1H NMR (300 MHz, DMSO) δ 12.86 (br s, 2H), 8.89 (s, 2H), 8.77 (s, 2H), 8.52 (d, J = 7.9 Hz, 2H), 8.11 (d, J = 8.1 Hz, 2H), 7.91-7.78 (m, 2H), 7.77-7.65 (m, 2H). |
| NCL 103 | 1H NMR (300 MHz, DMSO) δ 11.81 (br s, 2H), 10.32-9.85 (m, 4H), 8.52 (s, 2H), 8.12 (s, 2H), 7.85 (d, J = 8.4 Hz, 2H), 6.43 (s, 2H), 8.33 (d, J = 8.5 Hz, 2H). |
| NCL 104 | 1H NMR (300 MHz, DMSO) δ 11.72 (br s, 2H), 9.78 (br s, 2H), 9.45 (s, 2H), 8.48 (s, 2H), 8.34 (br s, 2H), 8.04 (s, 2H), 7.33 (s, 2H), 6.44 (s, 2H). |
| NCL 105 | 1H NMR (300 MHz, DMSO) δ 11.75 (br s, 2H), 9.71 (br s, 2H), 9.15 (br s, 2H), 8.86 -8.40 (m, 4H), 8.13 (s, 2H), 7.33 (d, J = 8.6 Hz, 2H), 6.42 (d, J = 8.6 Hz, 2H). |
| NCL 106 | 1H NMR (300 MHz, DMSO) δ 9.12 (br s, 4H), 8.29 (s, 2H), 8.20 (s, 2H), 7.10 (s, 2H), 6.93 (s, 2H), 3.84 (s, 6H). |
| NCL 107 | 1H NMR (300 MHz, DMSO) δ 12.19 (s, 2H), 10.25 (s, 2H), 8.70 (s, 2H), 8.34 (s, 2H), 8.06 (d, J = 7.8 Hz, 2H), 7.35-7.23 (m, 2H), 7.00 (d, J = 8.2 Hz, 2H), 6.87 (t, J = 7.5 Hz, 2H). |
| NCL 108 | 1H NMR (300 MHz, DMSO) δ 8.00 (s, 2H), 7.26-7.08 (m, 6H), 6.98-6.43 (m, 4H). |
| NCL 109 | 1H NMR (300 MHz, DMSO) δ 8.60 (d, J = 1.2 Hz, 2H), 8.33-8.19 (m, 4H), 8.15 (d, J = 8.0 Hz, 2H), 7.74-7.61 (m, 2H), 7.12 (s, 2H). |
| NCL 110 | 1H NMR (300 MHz, DMSO) δ 8.85 (s, 2H), 8.58 (s, 2H), 8.31 (d, J = 8.7 Hz, 4H), 8.23 (d, J = 8.9 Hz, 4H). |
| NCL 111 | 1H NMR (300 MHz, DMSO) δ 11.80 (br s, 2H), 10.30-9.80 (m, 4H), 8.52 (s, 2H), 8.12 (s, 2H), 7.84 (d, J = 8.6 Hz, 2H), 6.42 (d, J = 1.8 Hz, 2H), 6.33 (d, J = 8.6 Hz, 2H). |
| NCL 112 | 1H NMR (300 MHz, DMSO) δ12.48 (br s, 2H), 8.62 (s, 2H), 8.51 (s, 2H), 8.04 (d, J = 7.5 Hz, 4H), 7.85-7.69 (m, 8H), 7.54-7.36 (m, 6H). |
| NCL 113 | 1H NMR (400 MHz, DMSO) δ 11.92 (br s, 2H), 8.24 (s, 2H), 8.16 (s, 2H), 7.71 (d, J = 8.9 Hz, 4H), 6.74 (d, J = 8.9 Hz, 4H), 2.98 (s, 12H). |
| NCL 114 | 1H NMR (400 MHz, DMSO) δ 12.67 (br s, 2H), 8.81 (s, 2H), 8.40 (s, 2H), 8.06 (d, J = 1.8 Hz, 4H), 7.68 (t, J = 1.8 Hz, 2H). |
| NCL 115 | 1H NMR (400 MHz, DMSO) δ 12.09 (br s, 2H), 8.44 (s, 2H), 8.34 (s, 2H), 7.63 (d, J = 1.4 Hz, 2H), 7.33 (dd, J = 8.3, 1.6 Hz, 2H), 7.03 (d, J = 8.4 Hz, 2H), 3.86 (s, 6H), 3.81 (s, 6H). |
| NCL 116 | 1H NMR (400 MHz, DMSO) δ 12.27 (br s, 2H), 8.49 (s, 2H), 8.44-8.27 (m, 4H), 7.57-7.44 (m, 10H), 7.41-7.33 (m, 6H). |
| NCL 117 | 1H NMR (400 MHz, DMSO) δ 9.77 (br s, 2H), 8.36 (s, 2H), 8.29 (s, 2H), 7.58 (d, J = 1.5 Hz, 2H), 7.23 (dd, J = 8.1, 1.2 Hz, 2H), 6.87 (d, J = 8.1 Hz, 2H), 3.86 (s, 6H). |
| NCL 118 | 1H NMR (400 MHz, DMSO) δ 12.83 (br s, 2H), 8.76 (s, 2H), 8.69 (s, 2H), 8.31-8.21 (m, 2H), 7.45-7.31 (m, 4H). |
| NCL 119 | 1H NMR (400 MHz, DMSO) δ 12.13 (br s, 2H), 10.35 (s, 2H), 8.39 (s, 2H), 8.35 (s, 2H), 7.85 (d, J = 8.7 Hz, 4H), 7.72 (d, J = 8.6 Hz, 4H), 2.08 (s, 6H). |
| NCL 120 | 1H NMR (400 MHz, DMSO) δ 8.62-8.29 (m, 4H), 7.85 (d, J = 8.2 Hz, 4H), 7.33 (d, J = 8.2 Hz, 4H), 2.98-2.87 (m, 2H), 1.21 (d, J = 6.9 Hz, 12H). |
| NCL 121 | 1H NMR (400 MHz, DMSO) δ 8.60-8.30 (m, 4H), 7.84 (d, J = 8.1 Hz, 4H), 7.28 (d, J = 8.1 Hz, 4H), 2.59 (t, J = 7.5 Hz, 4H), 1.64-1.54 (m, 4H), 0.88 (t, J= 7.3 Hz, 6H) |
| NCL 122 | 1H NMR (400 MHz, DMSO) δ 8.56 (s, 2H), 8.42 (d, J = 2.0 Hz, 2H), 8.38 (s, 2H), 8.09 (dd, J = 8.7, 2.0 Hz, 2H), 7.29 (d, J = 8.7 Hz, 2H). |
| NCL 123 | 1H NMR (400 MHz, DMSO) δ 8.68 (s, 2H), 8.43 (s, 2H), 8.28-8.16 (m, 2H), 7.77-7.64 (m, 2H), 7.58-7.46 (m, 2H), 13C NMR (101 MHz, DMSO) δ 153.0, 150.8 (dd, J = 250.6, 13.0 Hz), 149.9 (dd, J = 245.9, 13.2 Hz), 146.6, 131.2 (dd, J = 6.4, 3.4 Hz), 126.0 (dd, J = 6.4, 2.8 Hz), 117.8 (d, J = 17.7 Hz), 115.7 (d, J = 18.5 Hz). |

TABLE 46-continued

NMR Specroscopy Lists of Compounds NCL812, NCL001-NCL230

| NCL Code | NMR |
|---|---|
| NCL 124 | 1H NMR (400 MHz, DMSO) δ 10.84 (br s, 2H), 9.29 (s, 2H), 8.80 (d, J = 8.6 Hz, 2H), 8.43 (s, 2H), 7.94 (d, J = 9.0 Hz, 2H), 7.87 (d, J = 7.9 Hz, 2H), 7.64-7.56 (m, 2H), 7.43-7.36 (m, 2H), 7.34 (d, J = 8.9 Hz, 2H). |
| NCL 125 | 1H NMR (400 MHz, DMSO) δ 9.21 (br s, 2H), 8.42-8.17 (m, 4H), 7.43 (d, J = 1.9 Hz, 2H), 7.25 (dd, J = 8.4, 1.9 Hz, 2H), 6.99 (d, J = 8.4 Hz, 2H), 3.83 (s, 6H). |
| NCL 126 | 1H NMR (400 MHz, DMSO) δ 12.27 (br s, 2H), 8.58 (s, 2H), 8.42 (s, 2H), 7.96 (d, J = 8.3 Hz, 4H), 7.58 (d, J = 8.2 Hz, 4H), 4.39 (s, 2H). |
| NCL 127 | 1H NMR (400 MHz, DMSO) δ12.84 (br s, 2H), 8.84 (s, 2H), 8.74 (s, 2H), 8.46 (d, J = 8.6 Hz, 2H), 7.71 (d, J = 1.6 Hz, 2H), 7.54 (dd, J = 8.6, 1.2 Hz, 2H). |
| NCL 128 | 1H NMR (400 MHz, DMSO) δ 8.64 (s, 2H), 8.36 (s, 2H). |
| NCL 129 | 1H NMR (400 MHz, DMSO) δ 8.84 (s, 2H), 8.69 (s, 2H), 8.41 (dd, J = 7.8, 1.7 Hz, 2H), 7.70 (dd, J = 8.0, 1.0 Hz, 2H), 7.48 (t, J = 7.3 Hz, 2H)*, 7.44-7.37 (m, 2H)*. |
| NCL 130 | 1H NMR (400 MHz, DMSO) δ 8.66 (s, 2H), 8.37 (s, 2H), 7.79 (d, J = 1.6 Hz, 2H), 7.68-7.62 (m, 2H), 3.92 (s, 6H), 3.78 (s, 6H). |
| NCL 131 | 1H NMR (400 MHz, DMSO) δ 12.45 (br s, 2H), 8.68 (s, 2H), 8.41 (s, 2H), 8.29 (s, 2H), 7.87 (d, J = 7.8 Hz, 2H), 7.70-7.63 (m, 2H), 7.44 (t, J = 7.9 Hz, 2H). |
| NCL 132 | 1H NMR (400 MHz, DMSO) δ 12.69 (br s, 2H), 8.61 (s, 4H), 7.34 (dd, J = 9.0, 2.8 Hz, 2H), 7.22 (td, J = 8.6, 2.9 Hz, 2H), 7.03 (dd, J = 8.8, 4.6 Hz, 2H), 5.29 (s, 4H). |
| NCL 133 | 1H NMR (400 MHz, DMSO) δ 12.51 (br s, 2H), 8.49-8.28 (m, 4H), 8.16 (s, 2H), 7.35 (s, 2H). |
| NCL 134 | 1H NMR (400 MHz, DMSO) δ 12.42 (br s, 2H), 8.60 (s, 2H), 8.42 (s, 2H), 7.91 (d, J = 8.5 Hz, 4H), 7.69 (d, J = 8.5 Hz, 4H). |
| NCL 135 | 1H NMR (400 MHz, DMSO) δ 12.24 (br s, 2H), 8.66 (s, 2H), 8.49 (br s, 2H), 7.79 (s, 2H), 7.24 (s, 2H), 3.88 (s, 6H), 3.85 (s, 6H). |
| NCL 136 | 1H NMR (400 MHz, DMSO) δ 12.21 (br s, 2H), 8.44 (s, 2H), 8.39 (s, 2H), 7.83 (d, J = 8.2 Hz, 4H), 7.30 (d, J = 8.2 Hz, 4H), 2.63 (t, J = 7.7 Hz, 4H), 1.61-1.52 (m, 4H), 1.36-1.26 (m, 4H), 0.90 (t, J = 7.3 Hz, 6H). |
| NCL 137 | 1H NMR (400 MHz, DMSO) δ 12.94 (br s, 2H), 8.68 (s, 2H), 8.33 (s, 2H), 7.60 (d, J = 7.9 Hz, 4H)*, 7.49 (dd, J = 8.7, 7.4 Hz, 2H)*. |
| NCL 138 | 1H NMR (400 MHz, DMSO) δ 12.12 (br s, 2H), 8.21 (s, 2H), 7.97 (s, 2H), 7.54-7.47 (nu, 6H), 7.42-7.36 (m, 6H), 7.31-7.21 (m, 8H), 6.84 (d, J = 9.8 Hz, 2H). |
| NCL 139 | 1H NMR (400 MHz, DMSO) δ 12.65 (br s, 2H), 9.63 (d, J = 1.8 Hz, 2H), 8.88-8.58 (m,6H), 8.13-8.01 (m, 4H), 7.88-7.79 ((m, 2H), 7.68 (t, J = 7.4 Hz, 2H). |
| NCL 140 | 1H NMR (400 MHz, DMSO) δ 12.17 (br s, 2H), 8.46 (s, 2H), 8.37 (s, 2H), 7.86 (d, J = 8.2 Hz, 4H), 7.34 (d, J = 8.2 Hz, 4H), 2.53 (s, 6H). |
| NCL 141 | 1H NMR (400 MHz, DMSO) δ 8.66 (s, 2H), 8.60 (d, J = 1.9 Hz, 2H), 8.52 (br s, 2H), 8.49 (s, 2H), 8.09 (d, J = 8.6 Hz, 2H), 7.50 (dd, J = 8.6, 2.0 Hz, 2H). |
| NCL 142 | 1H NMR (400 MHz, DMSO) δ 8.80 (s, 2H), 7.41-7.20 (m, 12H), 5.56 (s, 2H), 3.79 (d, J = 3.4 Hz, 4H). |
| NCL 143 | 1H NMR (400 MHz, DMSO) δ 11.91 (br s, 2H), 8.66 (br s, 2H), 8.10-8.00 (m, 4H), 7.51-7.41 (m, 6H), 2.45 (s, 6H). |
| NCL 144 | 1H NMR (400 MHz, DMSO) δ 12.36 (br s, 2H), 8.38-8.23 (m, 4H), 7.16 (d, J = 3.5 Hz, 2H), 6.82 (d, J = 3.5 Hz, 2H). |
| NCL 145 | 1H NMR (400 MHz, DMSO) δ12.41 (br s, 2H), 8.41-8.21 (m, 4H), 7.20 (d, J = 3.5 Hz, 2H), 6.73 (d, J = 3.5 Hz, 2H). |
| NCL 146 | 1H NMR (400 MHz, DMSO) δ 11.97 (br s, 2H), 11.45 (s, 2H), 8.47 (s, 2H), 8.30 (s, 2H), 8.02 (s, 2H), 7.80 (dd, J = 8.6, 0.9 Hz, 2H), 7.48 (d, J = 8.5 Hz, 2H), 7.45-7.40 (m, 2H), 6.53 (s, 2H) 13C NMR (101 MHz, DMSO) δ 152.4, 150.6, 137.4, 127.6, 126.7, 124.5, 121.8, 120.3, 111.9, 102.0. |
| NCL 147 | 1H NMR (400 MHz, DMSO) δ 13.09 (br s, 2H), 9.97 (s, 2H), 9.01 (s, 2H), 8.73 (s, 2H), 8.19-8.09 (m, 4H), 7.95-7.84 (m, 4H). |
| NCL 148 | 1H NMR (400 MHz, DMSO) δ 12.44 (s, 4H), 8.60 (s, 2H), 8.44 (s, 2H), 7.99 (d, J = 8.3 Hz, 4H), 7.81 (d, J = 8.3 Hz, 4H), 7.63 (d, J = 16.0 Hz, 2H), 6.66 (d, J = 16.0 Hz, 2H). |
| NCL 149 | 1H NMR (400 MHz, DMSO) δ 8.75 (d, J = 6.1 Hz, 4H), 8.68 (s, 2H), 8.47 (s, 2H), 8.07 (d, J = 6.1 Hz, 4H). |
| NCL 150 | 1H NMR (400 MHz, DMSO) δ 12.10 (br s, 2H), 8.23-8.07 (m, 4H), 7.55 (d, J = 8.7 Hz, 4H), 7.13 (d, J = 16.0 Hz, 2H), 6.99 (d, J = 8.7 Hz, 4H), 6.81 (dd, J = 16.0, 9.4 Hz, 2H), 3.79 (s, 6H). |
| NCL 151 | 1H NMR (400 MHz, DMSO) δ 11.92 (br s, 2H), 10.13 (br s, 2H), 8.28 (s, 4H), 7.75 (d, J = 8.5 Hz, 4H), 6.86 (d, J = 8.5 Hz, 4H). |
| NCL 152 | 1H NMR (400 MHz, DMSO) δ 12.08 (br s, 2H), 9.35 (s, 2H), 8.66 (s, 2H), 8.48 (s, 2H), 7.67 (d, J = 7.2 Hz, 2H), 7.25 (d, J = 7.2 Hz, 2H), 6.88 (t, J = 7.6 Hz, 2H), 2.23 (s, 6H). |
| NCL 153 | 1H NMR (400 MHz, DMSO) δ 11.68 (s, 2H), 8.78 (s, 2H), 8.09 (d, J = 8.4 Hz, 4H), 7.52 (d, J = 8.6 Hz, 4H), 2.92 (q, J = 7.5 Hz, 4H), 1.12 (t, J = 7.4 Hz, 6H). |
| NCL 154 | 1H NMR (400 MHz, DMSO) δ 12.09 (s, 2H), 8.69 (s, 2H), 8.07 (d, J = 8.6 Hz, 4H), 7.50 (d, J = 8.6 Hz, 4H), 3.01-2.88 (m, 4H), 1.49-1.39 (m, 8H), 0.88 (t, J = 6.6 Hz, 6H). |
| NCL 155 | 1H NMR (400 MHz, DMSO) δ 11.63 (s, 2H), 8.76 (s, 2H), 8.01 (d, J = 8.6 Hz, 4H), 7.65 (d, J = 8.6 Hz, 4H), 2.41 (s, 6H). |
| NCL 156 | 1H NMR (400 MHz, DMSO) δ 12.18 (s, 2H), 8.71 (s, 2H), 8.08 (d, J = 8.0 Hz, 4H), 7.50 (d, J = 8.3 Hz, 4H), 3.01-2.87 (m, 4H), 1.58-1.46 (m, 4H), 1.01 (t, J = 7.1 Hz, 6H). |
| NCL 157 | 1H NMR (400 MHz, DMSO) δ 11.71 (br s, 2H), 8.40 (s, 2H), 8.37 (s, 2H), 7.29 (d, J = 8.4 Hz, 2H), 6.87 (d, J = 2.0 Hz, 2H), 6.73 (br s, 4H), 6.59 (dd, J = 8.3, 2.0 Hz, 2H). |
| NCL 158 | 13C NMR (101 MHz, DMSO) δ 152.1, 151.5, 148.9, 136.0, 134.7, 115.1, 114.5, 112.8. 1H NMR (400 MHz, DMSO) δ 13.03 (br s, 1H), 10.49 (br s, 1H), 9.35 (br s, 1H), 7.24 (d, J = 7.6 Hz, 2H), 7.11-6.61 (m, 6H), 2.5 (Contains CH2 groups determined by COSY, however eclipsed by solvent signal), 0.93 (s, 6H). 13C NMR (101 MHz, DMSO) δ 157.8, 155.4, 152.9, 134.4, 130.1, 118.7, 115.6, 29.9, 10.8. |

*COSY was used to determine that the signal due to the methylene protons appears under the DMSO signal. Line broadening is apparent in the 13C-NMR (due to tautomerisation effects) making carbon allocation difficult.

TABLE 46-continued

NMR Specroscopy Lists of Compounds NCL812, NCL001-NCL230

| NCL Code | NMR |
|---|---|
| NCL 159 | 1H NMR (400 MHz, DMSO) δ 12.69 (br s, 1H), 10.44 (br s, 1H), 9.15 (br s, 1H), 7.21 (s, 2H), 7.09-6.60 (m, 6H), 2.98 (p, J = 7.7 Hz, 2H), 1.84-1.01 (m, 16H). |
| NCL 160 | 1H NMR (400 MHz, DMSO) δ 12.49 (br s, 2H), 8.65 (s, 2H), 8.49 (s, 2H), 8.10 (d, J = 8.7 Hz, 4H)*, 7.47 (d, J = 8.3 Hz, 4H)*. |
| NCL 161 | 1H NMR (400 MHz, DMSO) δ 7.73 (d, J = 8.8 Hz, 2H), 6.92 (d, J = 8.9 Hz, 2H), 3.22-3.13 (m, 4H), 2.99-2.86 (m, 4H), 2.24 (s, 3H). |
| NCL162 | 1H NMR (400 MHz, CDCl3) δ 7.76-7.70 (m, 2H), 7.35-7.30 (m, 21-1), 4.99 (s, 2H), 4.34 (q, J = 7.1 Hz, 2H), 2.39 (s, 3H), 1.35 (t, J = 7.1 Hz, 3H). |
| NCL 163 | 1H NMR (400 MHz, DMSO) δ 13.88 (s, 1H), 13.21 (s, 1H), 11.50 (s, 2H), 9.70 (s, 2H), 7.70 (s, 2H), 7.43 (t, J = 7.7 Hz, 2H), 7.14 (t, J = 7.5 Hz, 2H), 7.00 (d, J = 7.8 Hz, 2H). |
| NCL164 | 1H NMR (400 MHz, DMSO) δ 10.85 (s, 2H), 9.38 (s, 2H), 8.64 (s, 3H), 7.90 (s, 3H), 7.34 (d, J = 8.5 Hz, 2H), 7.19 (s, 3H), 6.83 (d, J = 2.1 Hz, 2H), 6.57 (dd, J = 8.5, 2.1 Hz, 2H). |
| NCL165 | 1H NMR (400 MHz, DMSO) δ 10.87 (br s, 1H), 9.53 (br s, 1H), 8.77 (br s, 3H), 7.61-7.44 (m, 8H), 7.40 (br s, 3H), 7.27 (br s, 3H), 4.07 (br s, 2H). |
| NCL166 | 1H NMR (400 MHz, DMSO) δ 12.70 (br s, 2H), 8.75 (br s, 2H), 8.55 (br s, 2H), 8.13 (d, J = 8.2 Hz, 4H), 7.81 (d, J = 8.1 Hz, 4H). |
| NCL167 | 1H NMR (400 MHz, DMSO) δ 14.09 (s, 1H), 8.12 (d, J = 6.9 Hz, 2H), 7.97 (dd, J = 6.4, 3.0 Hz, 2H), 7.56 (ddd, J = 8.2, 6.7, 2.9 Hz, 7H). |
| NCL168 | 1H NMR (400 MHz, DMSO) δ 11.86 (br s, 2H), 8.42 (br s, 4H), 7.35 (d, J = 6.8 Hz, 4H), 6.75 (s, 2H), 6.67 (d, J = 7.9 Hz, 2H), 3.44 (d, J = 6.9 Hz, 2H)*, 1.24 (t, J = 5.3 Hz, 6H). *Signal partly eclipsed by H2O in DMSO |
| NCL170 | 1H NMR (400 MHz, DMSO) δ 12.29 (s, 2H), 10.29 (s, 2H), 8.55 (s, 2H), 8.45 (s, 2H), 8.13 (d, J = 8.5 Hz, 2H), 7.71 (s, 2H), 7.35 (dd, J = 8.5, 1.8 Hz, 2H), 2.12 (s, 6H). |
| NCL171 | 1H NMR (400 MHz, DMSO) δ 11.63 (s, 2H), 9.84 (s, 2H), 8.46 (s, 2H), 8.02 (s, 2H), 7.74 (d, J = 8.8 Hz, 2H), 6.30 (d, J = 7.4 He, 2H), 6.17 (s, 2H), 2.94 (s, 12H). *Poorly resolved doublet gives reduced coupling constant. |
| NCL172 | 1H NMR (400 MHz, DMSO) δ 12.00 (s, 2H), 8.92 (s, 2H), 8.64 (dd, J = 4.7, 0.6 Hz, 2H), 8.57 (d, J = 8.1 Hz, 2H), 7.89 (td, J = 8.0, 1.6 Hz, 2H), 7.50-7.41 (m, 2H), 2.52 (s, 6H). |
| NCL173 | 1H NMR (400 MHz, DMSO) δ 11.49 (br s, 2H), 10.62 (br s, 2H), 8.55 (br s, 2H), 7.59 (d, J = 8.3 Hz, 2H), 6.98 (d, J = 1.9 Hz, 2H), 6.92 (dd, J = 8.4, 2.0 Hz, 2H), 2.37 (s, 6H). |
| NCL174 | 1H NMR (400 MHz, DMSO) δ 12.02 (s, 2H), 10.81 (s, 2H), 8.63 (s, 2H), 8.38 (s, 2H), 8.12 (d, J = 8.3 Hz, 2H), 7.13-6.84 (m, 4H). |
| NCL175 | 1H NMR (400 MHz, DMSO) δ 12.63 (br s, 2H), 8.90 (d, J = 2.1 Hz, 2H), 8.74 (s, 2H), 8.56-8.42 (m, 4H), 7.66 (d, J = 8.4 Hz, 2H). |
| NCL176 | 1H NMR (400 MHz, DMSO) δ 11.94 (br s, 2H), 8.44 (s, 2H), 8.36 (s, 2H), 8.07 (dd, J = 4.8, 1.7 Hz, 2H), 7.72 (dd, J = 7.6, 1.4 Hz, 2H), 7.19 (s, 4H), 6.67 (dd, J = 7.5, 4.9 Hz, 2H). |
| NCL177 | 1H NMR (400 MHz, DMSO) δ 8.67 (s, 2H), 7.97 (s, 4H), 7.50 (d, J = 8.6 Hz, 4H), 4.81 (s, 4H). |
| NCL178 | 1H NMR (400 MHz, DMSO) δ 10.17 (s, 2H), 8.24 (s, 1H), 7.83 (d, J = 8.6 Hz, 4H), 7.50 (d, J = 8.6 Hz, 4H), 6.97 (s, 1H), 2.32 (s, 6H). |
| NCL179 | 1H NMR (400 MHz, DMSO) δ 10.70 (s, 2H), 8.02 (s, 2H), 7.67 (d, J = 8.4 Hz, 4H), 7.52 (d, J = 8.4 Hz, 4H), 6.28 (s, 1H), 5.85 (s, 2H). 13C NMR (101 MHz, DMSO) δ 162.8, 162.6, 138.8, 134.1, 133.1, 128.9, 127.6, 73.5. |
| NCL180 | 1H NMR (400 MHz, DMSO) δ 10.62 (s, 2H), 8.22 (d, J = 0.9 Hz, 1H), 7.82-7.74 (m, 4H), 7.53-7.47 (m, 4H), 6.93 (d, J = 0.6 Hz, 1H), 5.85 (t, J = 5.3 Hz, 2H), 4.74 (d, J = 5.2 Hz, 4H). |
| NCL181 | 1H NMR (400 MHz, DMSO) δ 11.20 (s, 2H), 8.17 (s, 1H), 8.09 (s, 2H), 7.72 (d, J = 7.4 Hz, 4H), 7.54 (d, J = 7.6 Hz, 4H), 6.83 (s, 1H). |
| NCL182 | 1H NMR (400 MHz, CDCl3) δ 7.44-7.19 (m, 6H), 5.67 (s, 1H), 5.42 (s, 1H), 5.06 (s, 2H), 4.95-4.93 (m, 1H), 1.52 (d, J = 6.8 Hz, 3H) |
| NCL183 | 1H NMR (400 MHz, CDCl3) δ 8.28 (s, 1H), 7.43-7.13 (m, 10H), 6.19 (s, 1H), 5.94 (s, 1H), 4.95-4.48 (m, 2H), 1.56 (d, J = 6.8 Hz, 4H), 1.50 (d, J = 6.5 Hz, 2H). |
| NCL184 | 1H NMR (400 MHz, MeOD) δ 7.44-7.04 (m, 10H), 5.26-4.56 (m, 7H), 1.51-1.35 (m, 6H). |
| NCL188 | 1H NMR (400 MHz, DMSO) δ 11.54 (s, 1 H), 7.99 (d, J = 8.7 Hz, 2H), 7.90 (s, 3H), 7.47 (d, J = 8.6 Hz, 2H), 2.91-2.82 (m, 2H), 1.48-1.32 (m, 4H), 0.89-0.84 (m, 3H). 13C NMR (101 MHz, DMSO) δ 156.2, 153.8, 134.8, 134.4, 128.7, 128.4, 28.1, 26.6, 22.0, 13.8. |
| NCL190 | 1H NMR (400 MHz, DMSO) δ 11.42 (s, 1H), 8.06 (d, J = 8.7 Hz, 3H), 8.01-7.71 (m, 5H), 7.53 (d, J = 8.7 Hz, 3H), 4.90 (s, 2H), 3.69 (br s, 3H). |
| NCL191 | 1H NMR (400 MHz, DMSO) δ 11.51 (s, 1 H), 8.85 (s, 3H), 7.99 (d, J = 8.6 Hz, 7H), 7.46 (d, J = 8.6 Hz, 4H), 2.35 (s, 3H). |
| NCL192 | 1H NMR (400 MHz, DMSO) δ 11.65 (s, 1H), 8.21 (s, 4H), 7.82 (dd, J = 7.6, 1.9 Hz, 2H), 7.53-7.39 (m, 3H). |
| NCL193 | 1H NMR (400 MHz, DMSO) δ 10.71 (s, 2H), 8.00 (s, 2H), 7.66 (d, J = 8.5 Hz, 4H), 7.60 (d, J = 8.6 Hz, 4H), 6.27 (s, 1H), 5.86 (s, 2H). 13C NMR (101 MHz, DMSO) δ 162.7, 162.6, 138.8, 134.5, 131.8, 127.9, 121.7, 73.5. |
| NCL194 | 1H NMR (400 MHz, DMSO) δ 12.01 (br s, 1H), 10.84 (s, 2H), 9.98 (br s, 1H), 9.79 (br s, 1H), 7.96 (br s, 3H), 7.79 (br s, 2H), 7.67-7.37 (m, 6H), 5.37 (br s, 1H). |
| NCL195 | 1H NMR (400 MHz, DMSO) δ 10.51 (s, 2H), 8.00 (s, 2H), 7.54 (d, J = 8.0 Hz, 4H), 7.26 (d, J = 7.9 Hz, 4H), 6.26 (s, 1H), 5.77 (s, 2H), 2.34 (s, 6H). 13C NMR (101 MHz, DMSO) δ 162.8, 162.6, 140.1, 138.4, 132.5, 129.4, 126.0, 73.3, 21.0. |
| NCL196 | 1H NMR (400 MHz, CDCl3) δ 10.31 (s, 2H), 9.74 (s, 2H), 7.94 (s, 2H), 7.48 (d, J = 8.6 Hz, 4H), 6.83 (d, J = 8.6 Hz, 4H), 6.20 (s, 1H), 5.70 (s, 2H). 13C NMR (101 MHz, CDCl3) δ 162.7, 162.5, 158.3, 140.5, 127.7, 126.3, 115.7, 73.0. |
| NCL197 | 1H NMR (400 MHz, DMSO) δ 10.51 (s, 2H), 9.55 (s, 2H), 7.95 (s, 2H), 7.22 (t, J = 7.9 Hz, 2H), 7.11-7.04 (m, 4H), 6.76 (d, J = 8.4 Hz, 2H), 6.23 (s, 1H), 5.80 (s, 2H). 13C NMR (101 MHz, DMSO) δ 162.8, 162.6, 157.7, 140.4, 136.4, 129.9, 117.4, 116.1, 112.4, 73.3. |

TABLE 46-continued

NMR Specroscopy Lists of Compounds NCL812, NCL001-NCL230

| NCL Code | NMR |
|---|---|
| NCL199 | 1H NMR (400 MHz, DMSO) δ 10.60 (s, 2H), 8.04 (s, 2H), 7.66 (d, J = 7.5 Hz, 4H), 7.45 (t, J = 7.1 Hz, 4H), 7.40-7.34 (m, 2H), 6.30 (s, 1H), 5.82 (s, 2H). 13C NMR (101 MHz, DMSO) δ 163.3, 163.1, 140.5, 135.7, 129.3, 129.2, 126.5, 73.9. |
| NCL200 | 1H NMR (400 MHz, DMSO) δ 10.51 (s, 2H), 8.02 (s, 2H), 7.58 (d, J = 8.3 Hz, 4H), 7.47 (d, J = 8.3 Hz, 4H), 6.25 (s, 1H), 5.77 (s, 2H), 1.31 (s, 18H). |
| NCL201 | 1H NMR (400 MHz, DMSO) δ 10.19 (s, 2H), 7.91 (s, 2H), 7.47 (d, J = 8.8 Hz, 4H), 6.77 (d, J = 8.9 Hz, 4H), 6.16 (s, 1H), 5.63 (s, 2H). |
| NCL202 | 1H NMR (600 MHz, DMSO) δ 13.43 (s, 1H), 11.45 (s, 2H), 10.28 (br. s, 1H), 9.47 (s, 1H), 8.38 (s, 2H), 7.71 (dd, J = 7.7, 1.3 Hz, 1H), 7.67 (br d, J = 7.0 Hz, 2H), 7.53-7.48 (m, 1H), 7.28-7.23 (m, 2H), 7.03-6.98 (m, 2H), 6.96-6.90 (m, 4H), 6.56 (br s, 1H). *Due to tautomers and rotamers associated with proximity of the phenol to the hydrazone >17 protons are observed. 13C NMR (151 MHz, DMSO) δ 167.7, 163.2, 162.6, 156.7*, 141.4*, 135.3, 133.9, 131.0, 130.5, 120.7*, 119.95, 119.8, 118.9, 117.6, 116.7, 116.6*. *Line broadening due to tautomers and rotamers made signals difficult to assign. |
| NCL203 | 1H NMR (400 MHz, DMSO) δ 12.60-10.94 (m, 3H), 7.79-7.39 (m, 3H), 2.25 (s, 2H), 1.82-1.59 (m, 10H). |
| NCL204 | 1H NMR (400 MHz, DMSO) δ 9.58 (d, J = 7.6 Hz, 2H), 7.82 (s, 4H), 7.50 (s, 4H), 6.45 (d, J = 9.6 Hz, 1H), 5.75 (s, 2H), 2.28 (d, J = 9.3 Hz, 6H). 13C NMR (101 MHz, DMSO) δ 163.48, 162.11, 143.34, 137.68, 132.88, 128.34, 127.16, 75.15, 13.01. |
| NCL205 | 1H NMR (600 MHz, DMSO) δ 10.92 (s, 2H), 8.42 (s, 2H), 7.98 (d, J = 7.5 Hz, 2H), 7.50 (d, J = 7.8 Hz, 2H), 7.44 (1, J = 7.4 Hz, 2H), 7.38 (t, J = 7.3 Hz, 2H), 6.35 (s, 1H), 5.95 (s, 2H). 13C NMR (151 MHz, DMSO) δ 162.75, 162.68, 136.0, 132.4, 132.0, 130.1, 129.9, 127.6, 126.2, 73.7. |
| NCL206 | 1H NMR (400 MHz, DMSO) δ 10.75 (s, 2H), 8.09 (s, 2H), 7.52 (d, J = 8.1 Hz, 4H), 7.24 (d, J = 8.0 Hz, 4H), 6.71 (s, 1H), 2.33 (s, 6H). |
| NCL207 | 1H NMR (400 MHz, DMSO) δ 11.43 (s, 2H), 11.05 (s, 2H), 8.31 (s, 2H), 7.42 (s, 2H), 7.29-7.18 (m, 2H), 6.89 (t, J = 7.7 Hz, 4H), 6.74 (s, 2H). |
| NCL208 | 1H NMR (400 MHz, DMSO) δ 9.63 (s, 2H), 7.82 (d, J = 8.5 Hz, 4H), 7.46 (d, J = 8.5 Hz, 4H), 6.73 (s, 2H), 2.29 (s, 6H). |
| NCL209 | 1H NMR (400 MHz, DMSO) δ 10.75 (s, 2H), 9.55 (s, 2H), 8.04 (s, 2H), 7.21 (t, J = 7.8 Hz, 2H), 7.06 (s, 2H), 7.02 (d, J = 7.6 Hz, 2H), 6.84-6.57 (m, 4H). |
| NCL210 | 1H NMR (400 MHz, DMSO) δ 11.16 (s, 2H), 8.22 (s, 2H), 7.85 (d, J = 8.3 Hz, 4H), 7.80 (d, J = 8.5 Hz, 4H), 6.92 (s, 2H). |
| NCL211 | 1H NMR (400 MHz, DMSO) δ 10.56 (s, 2H), 9.78 (s, 2H), 8.02 (s, 2H), 7.45 (d, J = 8.6 Hz, 4H), 6.80 (d, J = 8.6 Hz, 4H), 6.62 (s, 2H). |
| NCL212 | 1H NMR (400 MHz, DMSO) δ 10.94 (s, 2H), 8.10 (s, 2H), 7.67-7.60 (m, 4H), 7.61-7.54 (m, 4H), 6.80 (s, 2H). |
| NCL213 | 1H NMR (400 MHz, DMSO) δ 10.23 (br s, 2H), 7.27 (s, 2H), 2.27-1.98 (m, 2H), 1.78-1.42 (m, 10H), 1.33-1.00 (m, 10H). |
| NCL214 | 1H NMR (400 MHz, DMSO) δ 10.84 (s, 2H), 8.14 (s, 2H), 7.63 (d, J = 7.4 Hz, 4H), 7.46-7.33 (m, 3H), 6.76 (s, 2H). |
| NCL215 | 1H NMR (600 MHz, DMSO) δ 12.06 (s, 2H), 8.72 (s, 2H), 7.97 (t, J = 8.4 Hz, 2H), 7.56 (dd, J = 11.1, 1.9 Hz, 2H), 7.38 (dd, J = 8.5, 1.9 Hz, 2H), 2.42 (d, J = 2.9 Hz, 6H). |
| NCL216 | 1H NMR (400 MHz, DMSO) δ 12.43 (br s, 2H), 8.66 (br s, 2H), 8.62 (br s, 2H), 8.38 (t, J = 8.3 Hz, 2H), 7.61 (dd, J = 10.5, 1.9 Hz, 2H), 7.45 (dd, J = 8.6, 1.6 Hz, 2H). 13C NMR (101 MHz, DMSO) δ 160.7 (d, J = 254.5 Hz), 152.8*, 140.8*, 136.3 (d, J = 10.8 Hz), 128.5, 125.3, 120.2 (d, J = 10.0 Hz), 116.7 (d, J = 24.7 Hz). *Broad signals |
| NCL217 | 1H NMR (400 MHz, DMSO) δ 11.66 (s, 2H), 8.61 (s, 2H), 7.94 (d, J = 8.2 Hz, 4H), 7.25 (d, J = 8.1 Hz, 4H), 2.41 (s, 6H), 2.35 (s, 6H). 13C NMR (101 MHz, DMSO) δ 154.0, 153.3, 139.7, 133.9, 129.0, 127.0, 21.0, 14.9. |
| NCL218 | 1H NMR (400 MHz, DMSO) δ 10.73 (s, 2H), 8.05 (s, 2H), 7.70 (d, J = 8.58 Hz, 4H), 7.31-7.27 (m, 4H), 6.24 (s, 1H), 5.92 (s, 2H), 4.17 (dq, J = 7.06, 8.70 Hz, 8H), 1.28 (td, J = 1.01, 7.05 Hz, 12H). |
| NCL219 | 1H NMR (400 MHz, DMSO) δ 11.74 (s, 2H), 8.60 (s, 2H), 7.95 (d, J = 8.6 Hz, 4H), 7.45 (d, J = 8.6 Hz, 4H), 2.42 (s, 6H), 1.31 (s, 18H). 13C NMR (101 MHz, DMSO) δ 154.1, 153.3, 152.6, 134.0, 126.8, 125.0, 34.5, 31.0, 14.9. |
| NCL220 | 1H NMR (400 MHz, DMSO) δ 10.61 (s, 2H), 8.03 (s, 2H), 7.70 (dd, J = 8.7, 5.6 Hz, 4H), 7.29 (t*, J = 8.9 Hz, 4H), 6.27 (s, 1H), 5.82 (s, 2H). |
| NCL221 | 1H NMR (600 MHz, DMSO) δ10.89 (s, 2H), 8.11 (s, 2H), 7.86 (d, J = 8.2 Hz, 4H), 7.81 (d, J = 8.4 Hz, 4H), 6.34 (s, 1H), 5.94 (s, 2H). |
| NCL222 | 1H NMR (400 MHz, DMSO) δ 10.76 (s, 2H), 7.99 (s, 2H), 7.70 (td, J = 1.7, 9.2 Hz, 2H), 7.54-7.41 (m, 4H), 6.30 (s, 1H), 5.87 (s, 2H). |
| NCL223 | 1H NMR (400 MHz, DMSO) δ 10.48 (s, 2H), 10.07 (s, 2H), 7.98 (s, 2H), 7.65 (d, J = 8.7 Hz, 4H), 7.58 (d, J = 8.7 Hz, 4H), 6.24 (s, 1H), 5.76 (s, 2H), 2.07 (s, 6H). |
| NCL224 | 1H NMR (400 MHz, DMSO) δ 8.36 (s, 1H), 7.96-7.90 (m, 2H), 7.86 (s, 1H), 7.79-7.73 (m, 2H), 7.54-7.47 (m, 6H), 4.26 (q, J = 7.1 Hz, 2H), 1.27 (t, J = 7.1 Hz, 3H). |
| NCL225 | 1H NMR (400 MHz, DMSO) δ 8.35 (s, 1H), 7.98-7.91 (m, 2H), 7.87 (s, 1H), 7.79-7.74 (m, 2H), 7.51 (dd, J = 2.8, 8.5 Hz, 6H), 3.99 (d, J = 6.5 Hz, 2H), 1.95 (hept, J = 6,7 Hz, 1H), 0.93 (d, J = 6,7 Hz, 6H). |
| NCL226 | 1H NMR (400 MHz, DMSO) δ 10.95 (s, 1H), 9.18 (t, J = 5.6 Hz, 1H), 8.38 (d, J = 10.1 Hz, 2H), 8.32 (s, 1H), 7.99-7.92 (m, 2H), 7.83 (d, J = 8.5 Hz, 2H), 7.57-7.46 (m, 5H), 3.30-3.20 (m, 2H), 1.14 (t, J = 7.2 Hz, 3H). |
| NCL227 | 1H NMR (400 MHz, DMSO) δ 11.00 (s, 1H), 9.68 (s, 1H), 8.52 (s, 1H), 8.41 (s, 1H), 8.32 (s, 1H), 8.01-7.80 (m, 4H), 7.56-7.46 (m, 4H), 7.36 (d, J = 6.00 Hz, 1H), 7.30-7.21 (m, 1H), 4.56-4.33 (m, 4H). |
| NCL228 | 1H NMR (400 MHz, DMSO) δ 10.95 (s, 1H), 9.22 (t, J = 5.6 Hz, 1H), 8.40 (s, 1H), 8.34 (s, 1H), 8.32 (s, 1H), 7.98-7.90 (m, 2H), 7.87-7.80 (m, 2H), 7.55-7.48 (m, 4H), 3.22 (q, J = 6.6 Hz, 2H), 1.56-1.46 (m, 2H), 1.39-1.25 (m, 6H), 0.88 (t, J = 6.6 Hz, 3H) |
| NCL229 | 1H NMR (400 MHz, DMSO) δ 10.98 (s, 1H), 9.60 (s, 1H), 8.54 (s, 1H), 8.40 (s, 1H), 8.30 (s, 1H), 8.01-7.89 (m, 2H), 7.85 (d, J = 8.4 Hz, 2H), 7.64-7.59 (m, 1H), 7.54-7.47 (m, 4H), 6.42 (dd, J = 1.8, 3.3 Hz, 1H), 6.31 (m, 1H), 4.44 (d, J = 5.5 Hz, 2H). |

TABLE 46-continued

NMR Specroscopy Lists of Compounds NCL812, NCL001-NCL230

| NCL Code | NMR |
|---|---|
| NCL230 | 1H NMR (400 MHz, DMSO) δ 10.41 (s, 2H), 7.98 (s, 2H), 7.59 (d, J = 8.9 Hz, 4H), 7.02 (d, J = 8.9 Hz, 4H), 6.23 (s, 1H), 5.73 (s, 2H), 3.80 (s, 6H). |

Example 12: Treatment of a Bacterial Infection In Vivo by the Administration of NCL812 or NCL099

The objective of this study was to determine the efficacy of an Investigational Veterinary Product containing NCL812 or NCL099 in the treatment of a skin infection in mice Summary of the Model:

A useful animal model system should be clinically relevant, experimentally robust, ethically acceptable, convenient to perform and should provide reliable and reproducible results. There are many animal models of topical skin infection that have been described including the croton oil-inflamed skin model (Akiyama, H., H. Kanzaki, Y. Abe, J. Tada and J. Arata (1994). "Staphylococcus aureus infection on experimental croton oil-inflamed skin in mice." Journal of Dermatological Science 8(1): 1-10), the burnt skin model (Stieritz, D. D., A. Bondi, D. McDermott and E. B. Michaels (1982). "A burned mouse model to evaluate anti-pseudomonas activity of topical agents." Journal of Antimicrobial Chemotherapy 9(2): 133-140), the skin suture-wound model (McRipley, R. J. and R. R. Whitney (1976). "Characterization and Quantitation of Experimental Surgical-Wound Infections Used to Evaluate Topical Antibacterial Agents." Antimicrobial Agents and Chemotherapy 10(1): 38-44), the skin tape-stripping model (Kugelberg, E., T. Norström, T. K. Petersen, T. Duvold, D. I. Andersson and D. Hughes (2005). "Establishment of a Superficial Skin Infection Model in Mice by Using Staphylococcus aureus and Streptococcus pyogenes." Antimicrobial Agents and Chemotherapy 49(8): 3435-3441) and the linear full thickness scalpel cut method (Guo, Y., R. I. Ramos, J. S. Cho, N. P. Donegan, A. L. Cheung and L. S. Miller (2013). "In Vivo Bioluminescence Imaging To Evaluate Systemic and Topical Antibiotics against Community-Acquired Methicillin-Resistant Staphylococcus aureus-Infected Skin Wounds in Mice." Antimicrobial Agents and Chemotherapy 57(2): 855-863)

Preliminary studies prior to the conduct of the current study established a new method of skin infection arising from a detailed study of the models mentioned above. Briefly, study mice are anaesthetised, a patch of dorsal skin is clipped to reveal the skin and a circular area of skin is removed with a hand held punch, leaving a wound on the dorsum with a central cavity. The wound is infected with a known number of the challenge organism. Approximately four to six hours after infection, the wound is either treated topically with a vehicle formulation or an active formulation. The infected skin wound is retreated every 12 hours for a total of 14 treatments. Mice are humanely euthanased, the area of the original infected wound is dissected and removed and its bacterial content quantified by standard microbiologic tests. In this way, the change in bacterial concentration due to treatment with the active formulation can be readily determined by examining the reduction in bacterial burden compared with the vehicle control.

Materials and Methods

Preparation of Infection Inoculum

Fresh cultures of bacteria (Staphylococcus aureus) were grown on Sheep Blood Agar at 37° C. for 16-18 hours. A few typical colonies were selected and suspended in 10 ml of Tryptic Soy Broth and incubated overnight in a shaking incubator (240 rpm) at 37° C. The overnight suspension was vortexed and diluted (1:100) in fresh Tryptic soy broth (100 µl [0.1 ml] in 9.9 ml broth). The fresh suspension was incubated for 3 hours in a shaking incubator (as above) in order to obtain mid-logarithmic phase bacteria. Bacteria were pelleted through centrifugation at 7,500 rpm for 10 mins. Broth supernatant was removed and bacteria suspended in 10 ml Phosphate Buffered Saline (PBS). These steps were repeated a further two times. The density of the suspension was checked by measuring absorbance at 600 nm, using a spectrophotometer with saline as a blank, to confirm the target density at a reading of approximately 0.100, consistent with a bacterial density of $2.5 \times 10^7$ CFU/ml. The suspension was placed into a rack placed into a lockable transport box with an ice brick to maintain refrigeration during transport, followed by storage in cool room upon arrival at the mouse skin infection laboratory. Final suspension was mixed thoroughly before inoculating the skin wounds created in mice.

In order to ensure the purity and accuracy of the suspension, the following steps were performed prior to placement into lock box.

Purity of bacterial suspension ensured by spreading 100 µl of the final suspension onto a SBA (sheep blood agar) plate which was incubated at 37° C. for 18 hours and examined to confirm uniform growth of one colony type. Viable counts were performed on final suspension by prepping saline in Eppendorf tubes (approximately 900 µl per tube), removing 100 µl sample and adding to first Eppendorf tube, vortexing the mixture and repeating using $2^{nd}$ Eppendorf tube containing saline. This process was continued for 5-6 tubes. Finally, 100 µl of $5^{th}$ and $6^{th}$ dilutions were plated out on plate count agar, incubated at 37° C. for 18 hours and colony counts performed to confirm that the CFU/ml was approximately $2.5 \times 10^7$. Following inoculation of the wounds, this process was repeated to ensure that no contamination or decrease in viable counts had occurred during the time of the surgery.

Skin Wound Surgical Procedure

Each mouse was placed into induction chamber and anaesthesia induced using 2% isoflurane. Eyes of each anaesthetised mouse were covered with veterinary eye lubricant in order to prevent corneal dehydration. Each mouse removed from induction chamber and placed onto surgical area, in front of individual aesthetic nose cone. While under anaesthesia each mouse was monitored for assessment of depth of anaesthesia (response to pain, blink reflex, skeletal muscle tone) and respiratory and cardiac function. Back skin hair was shaved from surgical area with mechanical clippers. Shaved area was cleaned using 70% ethanol applied to paper towel followed by 10% w/v povidone-iodine solution. Once the iodine solution was dry, a subcutaneous injection of the nonsteroidal anti-inflammatory agent meloxicam was administered. Dorsal skin was pinched gently to allow creation of a circular full-thickness wound using ear punch/biopsy punch. Vehicle control and NCL812 and NCL099 mice had wounds inoculated with 10 μl of bacterial suspension using a micropipette ($2.5 \times 10^5$ CFU/10 μl). Once the bacterial suspension was dry, mice were placed into individual recovery boxes labelled with the mouse number. The time of inoculation was recorded. Initial body weights of each mouse were recorded on the appropriate score sheet. Mice recovered to full consciousness within 5 minutes. Recovered mice were returned to individual housing and monitored hourly for post-surgical or anaesthetic complications.

Post-Surgical Care (4 Hours Post-Surgery)

Mice were assessed for post-surgical complications and observations were recorded on clinic record sheet. Each mouse was carefully removed from IVC and placed into an assessment container, avoiding excessive handling or touching of the surgical site. Once the mouse was inside assessment container, it was assessed and the observations recorded on the post-surgical clinical record sheet. Whenever the suggested wellness breakpoints were reached, post-operative analgesia was administered and recorded on the clinical record sheet.

Animal Monitoring and Daily Care

Antibiotic Administration (7 am and 6 pm). The first administration of vehicle or NCL812 or NCL099 ointment occurred 4 hours post-surgically. Each ointment container was weighted prior to administration and the weight recorded. Each mouse was carefully restrained. Ointment (vehicle or NCL812 or NCL099) was applied to the lesion area and the treated mouse was returned to IVC where each mouse was observed to ensure ointment was not immediately removed by grooming. The weight of the ointment container post-administration was recorded. The vehicle and active NCL products were applied to the skin wound each 12 hours following the first administration for a total of 14 consecutive treatments. Both the NCL812 and NCL099 products (Formulation B, as presented in Example 9) contained their respective active ingredients at a concentration of 20 mg/g. Approximately 0.1-0.2 g of ointment was applied on each occasion, delivering a total topical dose of NCL812 or NCL099 between 28 and 56 mg to mice weighing between 18 g and 25 g.

Daily Monitoring.

Monitoring of each mouse took place once daily at around 12 μm. Each mouse carefully removed from IVC and placed into observation container, avoiding excessive handling or touching surgical site. The coat, posture, eyes, behaviour, vocalisation and activity whilst in the container were carefully assessed and observations recorded on assessment sheet. Mouse faeces (either on floor of cage or in container) were checked for consistency and observations recorded. The weight of each mouse was determined whilst it was in the container and change in body weight calculated and recorded. The observation container was disinfected with ethanol and set aside to dry while a fresh container was used for the next mouse. For every second day, mice were again anaesthetised using 2% isoflurane and photographed using a ruler for size referencing. These photos were used to assess lesion size and infection progression during the trial period.

Tissue Analysis and Assessment of Antibacterial Efficacy

At the end of the 7 day skin wound assessment period, all test mice were euthanased prior to wound collection for post mortem examination. The skin wound was dissected from the dorsum of each mouse. The sample was placed in a sample tube and weighed before 1 ml PBS and sterile tissue homogenisation beads were added. Tissue samples were homogenised for 10 mins using a tissue homogeniser (Next Advance Bullet Blender) and then vortexed for approximately 30 seconds. 100 μl of supernatant was removed and placed into an Eppendorf tube containing 900 μl of PBS. This procedure was repeated using serial dilutions for a total of 8 dilutions. Finally, 100 μl of each dilution was pipetted onto a plate count agar in duplicate and incubated overnight at 37° C. Ten microliters of original suspension was placed onto sheep blood agar to assess culture purity and incubated overnight at 37° C. The following day, viable counts were performed using incubated plate count agar plates and the identity of *Staphylococcus aureus* (the challenge organisms) as the harvested strain was confirmed.

Results

The mean colony count per g of tissue observed in vehicle treated group was 5,888,436 (6.77 log1c). The mean colony count per g of tissue observed in NCL812 group was 141,254 ($5.15 \log_{10}$). The mean colony count per g of tissue observed in NCL099 treated mice was 1,318 ($3.12 \log_{10}$). The $\log_{10}$ colony forming units per gram of tissue and % reduction are summarised in the following table.

TABLE 47

$\log_{10}$ colony forming units per gram of tissue and percentage reduction following topical administration of vehicle and treatment.

| Treatment | $\log_{10}$ (CFU/g) | % reduction |
|---|---|---|
| Vehicle | 6.77 | |
| NCL812 | 5.15 | 97.6 |
| NCL099 | 3.12 | 99.98 |

It is clear from this table that treatment with either NCL812 or NCL099 leads to high level reductions in the number of infecting *Staphylococcus aureus*. These results demonstrate effective treatment of a bacterial colonisation or infection in vivo by administration of compounds of the invention.

The invention claimed is:

1. A compound selected from the group consisting of: 2,2'-bis[(2-fluorophenyl)methylene]carbonimidic dihydrazide hydrochloride (NCL022); 2,2'-bis[(3-fluorophenyl)methylene]carbonimidic dihydrazide hydrochloride (NCL023); 2,2'-bis[(2-cyanophenyl)methylene]carbonimidic dihydrazide hydrochloride (NCL025); 2,2'-bis[(3-cyanophenyl)methylene]carbonimidic dihydrazide hydrochloride (NCL026); 2,2'-bis[(3-methoxyphenyl)methylene]carbonimidic dihydrazide hydrochloride (NCL029); 2,2'-bis{[3-(trifluoromethyl)phenyl]methylene}carbonimidic dihydrazide hydrochloride (NCL037); 2,2'-bis[(2-methylphenyl)methylene]carbonimidic dihydrazide hydrochloride (NCL039); 2,2'-bis[(3-methylphenyl)methylene]carbonimidic dihydrazide hydrochloride (NCL040); 2,2'-bis{1-[4-(trifluoromethyl)phenyl]ethylidene}carbonimidic dihydrazide hydrochloride (NCL061); 2-{[1-(4-trifluoromethyl)phenyl]ethylidene}carbonimidic dihydrazide hydrochloride (NCL073); 2-[(4-chlorophenyl)methylene]-2'-[(4-methylphenyl)methylene]carbonimidic dihydrazide hydrochloride (NCL076); 2-{[2-fluoro-4-(trifluoromethyl)phenyl]methylene}-2'-[(4-chlorophenyl)methylene]carbonimidic dihydrazide hydrochloride (NCL078); 2-[(4-chlorophenyl)methylene]-2'-[(4-fluorophenyl)methylene]carbonimidic dihydrazide hydrochloride (NCL079); 2-{1-[4-(trifluoromethyl)phenyl]ethylidene}-2'-[(4-chlorophenyl)methylene]carbonimidic dihydrazide hydrochloride (NCL080); 2-[(2-fluoro-4-chlorophenyl)methylene]-2'-[(4-chlorophenyl)methylene]carbonimidic dihydrazide hydrochloride (NCL084); 2-[(2-cyanophenyl)methylene]-2'-[(4-chlorophenyl)methylene]carbonimidic dihydrazide hydrochloride (NCL085); 2-[(3-cyanophenyl)methylene]-2'-[(4-chlorophenyl)methylene]carbonimidic dihydrazide hydrochloride (NCL086); 2-[(2-fluorophenyl)methylene]-2'-[(4-chlorophenyl)methylene]carbonimidic dihydrazide hydrochloride (NCL088); 2-[1-(4-chlorophenyl)ethylidene]-2'-{1-[4-(trifluoromethyl)phenyl]ethylidene}carbonimidic dihydrazide hydrochloride (NCL089); N-benzoyl-1-benzoyl-2-[(2-chlorophenyl)methylene]hydrazinecarboximidamide hydrochloride (NCL090); 2,2'-bis(cyclohexylmethylene)carbonimidic dihydrazide hydrochloride (NCL094); 2,2'-bis(3-furanylmethylene)carbonimidic dihydrazide hydrochloride (NCL095); 2,2'-bis[(3,4,5-trihydroxyphenyl)methylene]carbonimidic dihydrazide hydrochloride (NCL097); 2,2'-bis[(3-carboxyphenyl)methylene]carbonimidic dihydrazide hydrochloride (NCL098); 2,2'-bis{[4-(1,1-dimethylethyl)phenyl]methylene}carbonimidic dihydrazide hydrochloride (NCL099); 2,2'-bis[(2,3-dihydroxyphenyl)methylene]carbonimidic dihydrazide hydrochloride (NCL101); 2,2'-bis[(2,4,5-trihydroxyphenyl)methylene]carbonimidic dihydrazide hydrochloride (NCL104); 2,2'-bis[(2,3,4-trihydroxyphenyl)methylene]carbonimidic dihydrazide hydrochloride (NCL105); 2,2'-bis[(4,5-dihydroxy-3-methoxyphenyl)methylene]carbonimidic dihydrazide hydrochloride (NCL106); 2,2'-bis[(3-hydroxyphenyl)methylene]carbonimidic dihydrazide hydrochloride (NCL108); 2,2'-bis[(3,4-dihydroxyphenyl)methylene]carbonimidic dihydrazide hydrochloride (NCL111); 2,2'-bis([1,1'-biphenyl]-4-ylmethylene)carbonimidic dihydrazide hydrochloride (NCL112); 2,2'-bis[(3,5-dichlorophenyl)methylene]carbonimidic dihydrazide hydrochloride (NCL114); 2,2'-bis[(3,4-dimethoxyphenyl)methylene]carbonimidic dihydrazide hydrochloride (NCL115); 2,2'-bis([1,1'-biphenyl]-2-ylmethylene)carbonimidic dihydrazide hydrochloride (NCL116); 2,2'-bis[(2,5-fluorophenyl)methylene]carbonimidic dihydrazide hydrochloride (NCL118); 2,2'-bis[(4-acetamidophenyl)methylene]carbonimidic dihydrazide hydrochloride (NCL119); 2,2'-bis[(4-propylphenyl)methylene]carbonimidic dihydrazide hydrochloride (NCL121); 2,2'-bis[(4-hydroxy-3-nitrophenyl)methylene]carbonimidic dihydrazide hydrochloride (NCL122); 2,2'-bis[(3,4-difluorophenyl)methylene]carbonimidic dihydrazide hydrochloride (NCL123); 2,2'-bis[(2-hydroxy-1-naphthalenyl)methylene]carbonimidic dihydrazide hydrochloride (NCL124); 2,2'-bis[(3-hydroxy-4-methoxyphenyl)methylene]carbonimidic dihydrazide hydrochloride (NCL125); 2,2'-bis[(3-ethynylphenyl)methylene]carbonimidic dihydrazide hydrochloride (NCL126); 2,2'-bis[(3-bromo-4,5-dimethoxyphenyl)methylene]carbonimidic dihydrazide hydrochloride (NCL130); 2,2'-bis[(3-bromophenyl)methylene]carbonimidic dihydrazide hydrochloride (NCL131); 2,2'-bis[(4-chloro-6-fluoro-2H-1-benzopyran-3-yl)methylene]carbonimidic dihydrazide hydrochloride (NCL132); 2,2'-bis[(4-bromo-2-furanyl)methylene]carbonimidic dihydrazide hydrochloride (NCL133); 2,2'-bis[(2-bromo-4,5-dimethoxyphenyl)methylene]carbonimidic dihydrazide hydrochloride (NCL135); 2,2'-bis[(4-butylphenyl)methylene]carbonimidic dihydrazide hydrochloride (NCL136); 2,2'-bis[(2,6-dichlorophenyl)methylene]carbonimidic dihydrazide hydrochloride (NCL137); 2,2'-bis(2,3-diphenyl-2-propenylidene)carbonimidic dihydrazide hydrochloride (NCL138); 2,2'-bis(3-quinolinylmethylene)carbonimidic dihydrazide hydrochloride (NCL139); 2,2'-bis{[4-(methylsulfanyl)phenyl]methylene}carbonimidic dihydrazide hydrochloride (NCL140); 2,2'-bis[(5-chlorobenzo[b]thien-3-yl)methylene]carbonimidic dihydrazide hydrochloride (NCL141); 2,2'-bis[(5-bromo-2-furanyl)methylene]carbonimidic dihydrazide hydrochloride (NCL144); 2,2'-bis[(5-chloro-2-furanyl)methylene]carbonimidic dihydrazide hydrochloride (NCL145); 2,2'-bis(1H-indol-5-ylmethylene)carbonimidic dihydrazide hydrochloride (NCL146); 2,2'-bis(2-quinoxalinylmethylene)carbonimidic dihydrazide hydrochloride (NCL147); 2,2'-bis{[4-(carboxypropenyl)phenyl]methylene}carbonimidic dihydrazide hydrochloride (NCL148); 2,2'-bis[3-(4-methoxylphenyl)-2-propenylidene]carbonimidic dihydrazide hydrochloride (NCL150); 2,2'-bis[(2-hydroxy-3-methylphenyl)methylene]carbonimidic dihydrazide hydrochloride (NCL152); 2,2'-bis[1-(4-chlorophenyl)propylidene]carbonimidic dihydrazide hydrochloride (NCL153); 2,2'-bis[1-(4-chlorophenyl)pentylidene]carbonimidic dihydrazide hydrochloride (NCL154); 2,2'-bis[1-(4-chlorophenyl)butylidene]carbonimidic dihydrazide hydrochloride (NCL156); 2,2'-bis[(2-amino-4-chlorophenyl)methylene]carbonimidic dihydrazide hydrochloride (NCL157); 2,2'-bis[1-(2-hydroxy-4-chlorophenyl)propylidene]carbonimidic dihydrazide hydrochloride (NCL158); 2,2'-bis[(2-hydroxy-4-chlorophenylxcyclopentyl)methylene]carbonimidic dihydrazide hydrochloride (NCL159); 2,2'-bis[1-(4-piperazinylphenyl)ethylidene]carbonimidic dihydrazide hydrochloride (NCL161); 2,2'-bis[1-(2-amino-4-chlorophenyl)ethylidene]carbonimidic dihydrazide hydrochloride (NCL164); 2,2'-bis(1-phenyl-2-aminoethylidene)carbonimidic dihydrazide trihydrochloride (NCL165); 2,2'-bis{[4-(trifluoromethylsulfanyl)phenyl]methylene)carbonimidic dihydrazide hydrochloride (NCL166); 2,2'-bis(phenylcarboxymethylene)carbonimidic dihydrazide hydrochloride (NCL167); 2,2'-bis{[2-(1-hydroxyethylamino)-4-chlorophenyl]methylene}carbonimidic dihydrazide hydrochloride (NCL168); 2,2'-bis[(2-amino-4-chlorophenyl)methylene]carbonimidic dihydrazide (NCL169); 2,2'-bis[(2-acetamido-4-chlorophenyl)methylene]carbonimidic dihydrazide (NCL170); 2,2'-bis{[4-(dimethylamino)-2-hydroxyphenyl]methylene}carbonimidic dihydrazide (NCL171); 2,2'-Bis[1-(2-pyridinyl)ethylidene]Carbonimidic dihydrazide hydrochloride (NCL172); 2,2'-bis[1-(4-chloro-2-hydroxyphenyl)ethylidene]carbonimidic dihydrazide hydrochloride (NCL173); 2,2'-bis(4-chloro-2-hydroxyphenylmethylene)carbonimidic dihydrazide hydrochloride (NCL174); 2,2'-Bis(2-aminopyridin-3-ylmethylene)Carbonimidic dihydrazide hydrochloride (NCL176); 2,2'-bis[1-(4-chlorophenyl)-2-hydroxyethylidene]carbonimidic dihydrazide hydrochloride (NCL177); (E)-2-(1-(4-chlorophenyl)pentylidene)hydrazine-1-carboximidamide hydrochloride (NCL188); (Z)-2-(1-(4-chlorophenyl)-2-hydrazinylethylidene)hydrazine-1-carboximidamide hydrochloride (NCL190); 2,2'-bis[1-(4-chloro-2-fluorophenyl)ethylidene]carbonimidic dihydrazide hydrochloride (NCL215); N',2-bis((E)-4-chloro-2-fluorobenzylidene)hydrazine-1-carboximidhydrazide hydrochloride (NCL216); N',2-bis((E)-1-(p-tolyl)ethylidene)hydrazine-1-carboximidhydrazide hydrochloride (NCL217); 2,2'-bis(1-[4-(t-butyl)phenyl]ethylidene)carbonimidic dihydrazide hydrochloride (NCL219); 2-((E)-4-chlorobenzylidene)-1-((E)-N'-((E)-4-chlorobenzylidene)carbamohydrazonoyl)-N-ethylhydrazine-1-carboxamide (NCL226); N-benzyl-2-((E)-4-chlorobenzylidene)-1-((E)-N'-((E)-4-chlorobenzylidene)carbamohydrazonoyl)hydrazine-1-carboxamide (NCL227); 2-((E)-4-chlorobenzylidene)-1-((E)-N'-((E)-4-chlorobenzylidene)carbamohydrazonoyl)-N-hexylhydrazine-1-carboxamide (NCL228); and 2-((E)-4-chlorobenzylidene)-1-((E)-N'-((E)-4-chlorobenzylidene)carbamohydrazonoyl)-N-(furan-2-ylmethyl)hydrazine-1-carboxamide (NCL229).

2. The compound according to claim 1, wherein the compound is selected from the group consisting of: NCL040; NCL078; NCL079; NCL080; NCL084; NCL088; NCL089; NCL097; NCL099; NCL123; NCL146; NCL157; NCL158; NCL177; NCL188; NCL216; NCL217; and NCL219.

3. The compound according to claim 1, wherein the compound is selected from the group consisting of: NCL078; NCL079; NCL080; NCL084; NCL089; NCL097; NCL146; NCL157; NCL158; NCL177; NCL88; NCL216; NCL217; and NCL219.

4. The compound according to claim 1, wherein the compound is selected from the group consisting of: NCL089; NCL097; NCL146; NCL157; NCL158; NCL177; NCL216; NCL217; and NCL219.

5. The compound according to claim 1, wherein the compound is selected from the group consisting of: NCL089; NCL097; NCL146; NCL157; NCL158; NCL177; NCL188; NCL216; NCL217; and NCL219.

6. The compound according to claim 1, wherein the compound is selected from the group consisting of: NCL146; NCL157; NCL158; NCL177; NCL216; NCL217; and NCL219.

7. A compound selected from the group consisting of: 4,6-bis(2-((E)-1-(4-chlorophenyl)ethylidene)hydrazinyl)pyrimidine (NCL178); 4,6-bis(2-((E)-4-chlorobenzylidene)hydrazinyl)pyrimidin-2-amine (NCL179); (2Z,2'Z)-2,2'-(pyrimidine-4,6-diylbis(hydrazin-2-yl-1-ylidene))bis(2-(4-chlorophenyl)ethan-1-ol) (NCL180); 4,6-bis(2-((E)-4-chlorobenzylidene)hydrazinyl)pyrimidine (NCL181); N4,N6-bis(1-phenylethyl)pyrimidine-4,6-diamine (NCL183); N4,N6-bis(1-phenylethyl)pyrimidine-2,4,6-triamine (NCL184); 4,6-bis(2-((E)-1-(4-chlorophenyl)ethylidene)hydrazinyl)pyrimidine hydrochloride (NCL185); 4,6-bis(2-((E)-4-chlorobenzylidene)hydrazinyl)pyrimidine hydrochloride (NCL187); (2Z,2'Z)-2,2'-(pyrimidine-4,6-diylbis(hydrazin-2-yl-1-ylidene))bis(2-(4-chlorophenyl)ethan-1-ol) hydrochloride (NCL189); 4,6-bis(2-((E)-4-bromobenzylidene)hydrazinyl)pyrimidin-2-amine (NCL193); N',N'''-(2-aminopyrimidine-4,6-diyl)di(benzohydrazide) (NCL194); 4,6-bis(2-((E)-4-methylbenzylidene)hydrazinyl)pyrimidin-2-amine (NCL195); 4,4'-((1E,1'E)-((2-aminopyrimidine-4,6-diyl)bis(hydrazin-2-yl-1-ylidene))bis(methanylylidene))diphenol (NCL196); 3,3'-((1E,1'E)-((2-aminopyrimidine-4,6-diyl)bis(hydrazin-2-yl-1-ylidene))bis(methanylylidene))diphenol (NCL197); 4,6-bis(2-((E)-4-(tert-butyl)benzylidene)hydrazinyl)pyrimidin-2-amine dihydrochloride (NCL198); 4,6-bis(2-((E)-benzylidene)hydrazinyl)pyrimidin-2-amine (NCL199); 4,6-bis(2-((E)-4-(tert-butyl)benzylidene)hydrazinyl)pyrimidin-2-amine (NCL200); 4,4'-((1E,1'E)-((2-aminopyrimidine-4,6-diyl)bis(hydrazin-2-yl-1-ylidene))bis(methanylylidene))bis(N,N-dimethylaniline) (NCL201); 2,2'-((1E,1'E)-((2-aminopyrimidine-4,6-diyl)bis(hydrazin-2-yl-1-ylidene))bis(methanylylidene))diphenol (NCL202); 4,6-bis(2-((E)-cyclohexylmethylene)hydrazinyl)pyrimidin-2-amine dihydrochloride (NCL203); 4,6-bis(2-((E)-1-(4-chlorophenyl)ethylidene)hydrazinyl)pyrimidin-2-amine (NCL204); 4,6-bis(2-((E)-2-chlorobenzylidene)hydrazinyl)pyrimidin-2-amine (NCL205); 4,6-bis(2-((E)-4-methylbenzylidene)hydrazinyl)-1,3,5-triazin-2-amine (NCL206); 2,2'-((1E,1'E)-((6-amino-1,3,5-triazine-2,4-diyl)bis(hydrazin-2-yl-1-ylidene))bis(methanylylidene))diphenol (NCL207); 4,6-bis(2-((E)-1-(4-chlorophenyl)ethylidene)hydrazinyl)-1,3,5-triazin-2-amine (NCL208); 3,3'-((1E,1'E)-((6-amino-1,3,5-triazine-2,4-diyl)bis(hydrazin-2-yl-1-ylidene))bis(methanylylidene))diphenol (NCL209); 4,6-bis(2-((E)-4-(trifluoromethyl)benzylidene)hydrazinyl)-1,3,5-triazin-2-amine (NCL210); 4,4'-((1E,1'E)-((6-amino-1,3,5-triazine-2,4-diyl)bis(hydrazin-2-yl-1-ylidene))bis(methanylylidene))diphenol (NCL211); 4,6-bis(2-((E)-4-bromobenzylidene)hydrazinyl)-1,3,5-triazin-2-amine (NCL212); 4,6-bis(2-((E)-cyclohexylmiethylene)hydrazinyl)-1,3,5-triazin-2-amine (NCL213); 4-((E)-(2-(2-amino-6-(2-((E)-4-((diethoxyphosphoryl)oxy)benzylidene)hydrazinyl)pyrimidin-4-yl)hydrazono)methyl)phenyl diethyl phosphate (NCL218); 4,6-bis(2-((E)-4-fluorobenzylidene)hydrazinyl)pyrimidin-2-amine (NCL22O); 4,6-bis(2-((E)-4-(trifluoromethyl)benzylidene)hydrazinyl)pyrimidin-2-amine (NCL221); 4,6-bis(2-((E)-3,4-difluorobenzylidene)hydrazinyl)pyrimidin-2-amine (NCL222); N,N'-(((1E,1'E)-((2-aminopyrimidine-4,6-diyl)bis(hydrazin-2-yl-1-ylidene))bis(methanylylidene))bis(4,1-phenylene))diacetamide (NCL223); and 4,6-bis(2-((E)-4-methoxybenzylidene)hydrazinyl)pyrimidin-2-amine (NCL230).

8. The compound according to claim 7, wherein the compound is selected from the group consisting of: NCL179, NCL193, NCL195, NCL196, NCL197, NCL199, NCL202, NCL204, NCL205, and NCL221.

9. The compound according to claim 7, wherein the compound is selected from the group consisting of: NCL179, NCL193, NCL195, NCL197, NCL202, NCL204, NCL205, and NCL221.

\* \* \* \* \*

SEQUENCE LISTING

<160> NUMBER OF SEQ ID NOS: 4

<210> SEQ ID NO 1
<211> LENGTH: 20
<212> TYPE: DNA
<213> ORGANISM: Staphylococcus aureus

<400> SEQUENCE: 1
tgatacagta aatgacattg                    20

-continued

```
<210> SEQ ID NO 2
<211> LENGTH: 20
<212> TYPE: DNA
<213> ORGANISM: Staphylococcus aureus

<400> SEQUENCE: 2
ttcttatcaa caacaagttc                                              20

<210> SEQ ID NO 3
<211> LENGTH: 23
<212> TYPE: DNA
<213> ORGANISM: Staphylococcus aureus

<400> SEQUENCE: 3
ttcgtgtctt ttaataagtg agg                                          23

<210> SEQ ID NO 4
<211> LENGTH: 24
<212> TYPE: DNA
<213> ORGANISM: Staphylococcus aureus

<400> SEQUENCE: 4
atgaagtggt aaatggtaat atcg                                         24
```